US010442851B2

(12) United States Patent
Mitchell et al.

(10) Patent No.: US 10,442,851 B2
(45) Date of Patent: Oct. 15, 2019

(54) SERUM ALBUMIN-BINDING FIBRONECTIN TYPE III DOMAINS

(71) Applicant: BRISTOL-MYERS SQUIBB COMPANY, Princeton, NJ (US)

(72) Inventors: Tracy S. Mitchell, Andover, MA (US); Michael L. Gosselin, Boston, MA (US); Dasa Lipovsek, Cambridge, MA (US); Rex Parker, Titusville, NJ (US); Ray Camphausen, Wayland, MA (US); Jonathan Davis, Auburndale, MA (US); David Fabrizio, South Hamilton, MA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 59 days.

(21) Appl. No.: 15/127,166

(22) PCT Filed: Mar. 19, 2015

(86) PCT No.: PCT/US2015/021535

§ 371 (c)(1),
(2) Date: Sep. 19, 2016

(87) PCT Pub. No.: WO2015/143199

PCT Pub. Date: Sep. 24, 2015

(65) Prior Publication Data

US 2017/0174748 A1 Jun. 22, 2017

Related U.S. Application Data

(60) Provisional application No. 61/968,181, filed on Mar. 20, 2014.

(51) Int. Cl.

| | |
|---|---|
| ***C07K 14/78*** | (2006.01) |
| ***A61K 47/64*** | (2017.01) |
| *A61K 38/00* | (2006.01) |

(52) U.S. Cl.

CPC .............. *C07K 14/78* (2013.01); *A61K 47/64* (2017.08); *A61K 38/00* (2013.01); *C07K 2319/00* (2013.01); *C07K 2319/70* (2013.01)

(58) Field of Classification Search

None

See application file for complete search history.

(56) References Cited

U.S. PATENT DOCUMENTS

| | | | |
|---|---|---|---|
| 5,235,041 | A | 8/1993 | Cappello et al. |
| 5,514,581 | A | 5/1996 | Ferrari et al. |
| 5,545,620 | A | 8/1996 | Wahl et al. |
| 5,641,648 | A | 6/1997 | Ferrari et al. |
| 5,770,697 | A | 6/1998 | Ferrari et al. |
| 5,792,742 | A | 8/1998 | Gold et al. |
| 6,018,030 | A | 1/2000 | Ferrari et al. |
| 6,207,446 | B1 | 3/2001 | Szostak et al. |
| 6,214,553 | B1 | 4/2001 | Szostak et al. |
| 6,258,558 | B1 | 7/2001 | Szostak et al. |
| 6,261,804 | B1 | 7/2001 | Szostak et al. |
| 6,281,344 | B1 | 8/2001 | Szostak et al. |
| 6,316,412 | B1 | 11/2001 | Ginsberg et al. |
| 6,342,219 | B1 | 1/2002 | Thorpe et al. |
| 6,383,775 | B1 | 5/2002 | Duff et al. |
| 6,462,189 | B1 | 10/2002 | Koide |
| 6,518,018 | B1 | 2/2003 | Szostak et al. |
| 6,559,126 | B2 | 5/2003 | Tournaire et al. |
| 6,660,492 | B1 | 12/2003 | Bode et al. |
| 6,818,418 | B1 | 11/2004 | Lipovsek et al. |
| 7,115,396 | B2 | 10/2006 | Lipovsek et al. |
| 7,556,925 | B2 | 7/2009 | Koide et al. |
| 7,598,352 | B2 | 10/2009 | Koide |
| 7,847,062 | B2 | 12/2010 | Chen et al. |
| 7,858,739 | B2 | 12/2010 | Chen et al. |
| 8,067,201 | B2 | 11/2011 | Morin et al. |
| 8,221,765 | B2 | 7/2012 | Camphausen et al. |
| 8,258,265 | B2 | 9/2012 | Koide |
| 8,263,741 | B2 | 9/2012 | Koide |
| 8,278,419 | B2 | 10/2012 | Jacobs et al. |
| 8,293,482 | B2 | 10/2012 | Jacobs et al. |
| 8,324,362 | B2 | 12/2012 | Chen et al. |

(Continued)

FOREIGN PATENT DOCUMENTS

| | | | |
|---|---|---|---|
| CA | 2293632 | A1 | 12/1998 |
| DE | 19646372 | C1 | 6/1997 |

(Continued)

OTHER PUBLICATIONS

Hackel et al. Picomolar affinity fibronectin domains engineered utilizing loop length diversity, recursive mutagenesis, and loop shuffling. Journal of Molecular Biology [Jun. 24, 2008, 381(5):1238-1252]. (Year: 2008).*

Ackermann, Maximilian et al., "Anti-VEGFR2 and anti-IGF-1R-Adnectins inhibit Ewing's sarcoma A673-xenograft growth and normalize tumor vascular architecture," Angiogenesis, vol. 15:685-695 (2012).

Apte, Aaron N. et al., "Anchor-Ligated cDNA Libraries: A Technique for Generating a cDNA Library for the Immediate Cloning of the 5' Ends of mRNAs," BioTechniques, vol. 15(5):890-893 (1993).

Baggio, Rick et al., "Identification of epitope-like consensus motifs using mRNA display," Journal of Molecular Recognition, vol. 15:126-134 (2002).

(Continued)

*Primary Examiner* — Maher M Haddad

(74) *Attorney, Agent, or Firm* — Nelson Mullins Riley & Scarborough LLP; Jane E. Remillard, Esq.; Cynthia L. Kanik

(57) ABSTRACT

The present invention relates to polypeptides which include tenth fibronectin type III domains ($^{10}$Fn3) that binds to serum albumin, with south pole loop substitutions. The invention further relates to fusion molecules comprising a serum albumin-binding $^{10}$Fn3 joined to a heterologous protein for use in diagnostic and therapeutic applications.

12 Claims, 20 Drawing Sheets

Specification includes a Sequence Listing.

(56) References Cited

U.S. PATENT DOCUMENTS

| | | | |
|---|---|---|---|
| 8,343,501 | B2 | 1/2013 | Emanuel et al. |
| 8,420,098 | B2 | 4/2013 | Camphausen et al. |
| 8,470,332 | B2 | 6/2013 | Camphausen et al. |
| 8,524,244 | B2 | 9/2013 | Camphausen et al. |
| 8,609,613 | B2 | 12/2013 | Chen et al. |
| 8,728,483 | B2 | 5/2014 | Camphausen et al. |
| 8,969,289 | B2 * | 3/2015 | Gosselin .......... A61K 47/48238 514/13.6 |
| 9,017,655 | B2 | 4/2015 | Emanuel et al. |
| 9,416,170 | B2 * | 8/2016 | Davis .................. C07K 16/241 |
| 9,522,951 | B2 | 12/2016 | Davis et al. |
| 9,540,424 | B2 | 1/2017 | Gosselin et al. |
| 9,605,039 | B2 | 3/2017 | Lipovsek et al. |
| 9,765,132 | B2 * | 9/2017 | Davis ..................... C07K 14/78 |
| 9,902,762 | B2 | 2/2018 | Camphausen et al. |
| 2002/0019517 | A1 | 2/2002 | Koide |
| 2002/0061307 | A1 | 5/2002 | Whitlow et al. |
| 2003/0104520 | A1 | 6/2003 | Ellington et al. |
| 2003/0170753 | A1 | 9/2003 | Koide |
| 2003/0186385 | A1 | 10/2003 | Koide |
| 2005/0255548 | A1 | 11/2005 | Lipovsek et al. |
| 2006/0246059 | A1 | 11/2006 | Lipovsek et al. |
| 2007/0071675 | A1 | 3/2007 | Wu et al. |
| 2007/0082365 | A1 | 4/2007 | Lipovsek et al. |
| 2007/0160533 | A1 | 7/2007 | Chen et al. |
| 2008/0108798 | A1 | 5/2008 | Lipovsek et al. |
| 2008/0193445 | A1 | 8/2008 | Goetsch et al. |
| 2008/0220049 | A1 | 9/2008 | Chen et al. |
| 2009/0176654 | A1 | 7/2009 | Cappuccilli et al. |
| 2010/0144601 | A1 | 6/2010 | Jacobs et al. |
| 2010/0152063 | A1 | 6/2010 | Cappuccilli et al. |
| 2010/0273216 | A1 | 10/2010 | Morin et al. |
| 2010/0298541 | A1 | 11/2010 | Wu et al. |
| 2011/0021746 | A1 | 1/2011 | Cappuccilli et al. |
| 2011/0038866 | A1 | 2/2011 | Hastewell et al. |
| 2011/0123545 | A1 | 5/2011 | Marsh et al. |
| 2011/0124527 | A1 | 5/2011 | Cappuccilli et al. |
| 2011/0275535 | A1 | 11/2011 | Loew |
| 2012/0094909 | A1 | 4/2012 | Camphausen et al. |
| 2012/0208704 | A1 | 8/2012 | Loew et al. |
| 2012/0270797 | A1 | 10/2012 | Wittrup et al. |
| 2013/0079243 | A1 | 3/2013 | Diem et al. |
| 2013/0210703 | A1 | 8/2013 | Camphausen et al. |
| 2013/0310317 | A1 | 11/2013 | Camphausen et al. |
| 2014/0038893 | A1 | 2/2014 | Camphausen et al. |
| 2014/0094595 | A1 | 4/2014 | Lipovsek et al. |
| 2014/0179896 | A1 | 6/2014 | Chen et al. |
| 2014/0349929 | A1 | 11/2014 | Camphausen et al. |
| 2015/0152147 | A1 | 6/2015 | Gosselin et al. |
| 2016/0159883 | A1 | 6/2016 | Camphausen et al. |
| 2017/0137494 | A1 | 5/2017 | Davis et al. |
| 2017/0145464 | A1 | 5/2017 | Gosselin et al. |
| 2017/0183393 | A1 | 6/2017 | Lipovsek |
| 2017/0275342 | A1 | 9/2017 | Lipovsek et al. |
| 2017/0334958 | A1 | 11/2017 | Lipovsek et al. |

FOREIGN PATENT DOCUMENTS

| | | | | |
|---|---|---|---|---|
| EP | 0962527 | A1 | 12/1999 | |
| EP | 0985039 | B1 | 3/2000 | |
| EP | 1477561 | B1 | 11/2004 | |
| EP | 1266025 | B1 | 11/2006 | |
| EP | 1137941 | B1 | 8/2009 | |
| EP | 2141243 | A2 | 1/2010 | |
| EP | 2385067 | A1 | 11/2011 | |
| EP | 2439212 | A1 | 4/2012 | |
| EP | 2379718 | B1 | 3/2013 | |
| WO | 92/02536 | A1 | 2/1992 | |
| WO | 93/03172 | A1 | 2/1993 | |
| WO | 95/11922 | A1 | 5/1995 | |
| WO | 96/22391 | A1 | 7/1996 | |
| WO | 98/12226 | A1 | 3/1998 | |
| WO | 98/31700 | A1 | 7/1998 | |
| WO | 98/056915 | A2 | 12/1998 | |
| WO | 99/51773 | A1 | 10/1999 | |
| WO | 2000/34784 | A1 | 6/2000 | |
| WO | 2000/34787 | A1 | 6/2000 | |
| WO | 2001/07657 | A1 | 2/2001 | |
| WO | 2001/64942 | A1 | 9/2001 | |
| WO | 2002/04523 | A2 | 1/2002 | |
| WO | 2002/32925 | A2 | 4/2002 | |
| WO | 2002/081497 | A2 | 10/2002 | |
| WO | 2002/088171 | A2 | 11/2002 | |
| WO | 2003/022858 | A2 | 3/2003 | |
| WO | 2003/104418 | A2 | 12/2003 | |
| WO | 2005/056764 | A2 | 6/2005 | |
| WO | 2006/020258 | A2 | 2/2006 | |
| WO | 2007/012614 | A2 | 2/2007 | |
| WO | 2007/044688 | A1 | 4/2007 | |
| WO | 2007/062188 | A2 | 5/2007 | |
| WO | 2007/092537 | A2 | 8/2007 | |
| WO | 2007/096076 | A2 | 8/2007 | |
| WO | 2007/121894 | A2 | 11/2007 | |
| WO | 2008/031098 | A1 | 3/2008 | |
| WO | 2008/048970 | A2 | 4/2008 | |
| WO | 2008/066752 | A2 | 6/2008 | |
| WO | 2008/096158 | A2 | 8/2008 | |
| WO | 2008/097497 | A2 | 8/2008 | |
| WO | 2008/108986 | A2 | 9/2008 | |
| WO | 2009/023184 | A2 | 2/2009 | |
| WO | 2009/025806 | A2 | 2/2009 | |
| WO | 2009/058379 | A2 | 5/2009 | |
| WO | 2009/073115 | A1 | 6/2009 | |
| WO | 2009/083804 | A2 | 7/2009 | |
| WO | 2009/086116 | A2 | 7/2009 | |
| WO | 2009/102421 | A2 | 8/2009 | |
| WO | 2009/133208 | A1 | 11/2009 | |
| WO | 2009/142773 | A2 | 11/2009 | |
| WO | 2010/051274 | A2 | 5/2010 | |
| WO | 2010/051310 | A2 | 5/2010 | |
| WO | 2010/060095 | A1 | 5/2010 | |
| WO | 2010/069913 | A1 | 6/2010 | |
| WO | 2010/093627 | A2 | 8/2010 | |
| WO | 2010/093771 | A1 | 8/2010 | |
| WO | 2011/020033 | A2 | 2/2011 | |
| WO | 2011/035202 | A2 | 3/2011 | |
| WO | 2011/051333 | A1 | 5/2011 | |
| WO | 2011/051466 | A1 | 5/2011 | |
| WO | 2011/092233 | A1 | 8/2011 | |
| WO | 2011/100700 | A2 | 8/2011 | |
| WO | 2011/103105 | A1 | 8/2011 | |
| WO | 2011/130324 | A1 | 10/2011 | |
| WO | 2011/130328 | A1 | 10/2011 | |
| WO | 2011/130354 | A1 | 10/2011 | |
| WO | 2011/137319 | A2 | 11/2011 | |
| WO | 2011/140086 | A2 | 11/2011 | |
| WO | WO-2011140086 | A2 * | 11/2011 | ....... A61K 47/48238 |
| WO | 2011/150133 | A2 | 12/2011 | |
| WO | 2012/016245 | A2 | 2/2012 | |
| WO | 2012/088006 | A1 | 6/2012 | |
| WO | 2012/142515 | A2 | 10/2012 | |
| WO | 2012/158678 | A1 | 11/2012 | |
| WO | 2012/158739 | A1 | 11/2012 | |
| WO | 2013/049275 | A1 | 4/2013 | |
| WO | 2014/165093 | A2 | 10/2014 | |
| WO | 2015/143199 | A1 | 9/2015 | |
| WO | WO-2017053617 | A1 * | 3/2017 | ............. C07K 14/78 |

OTHER PUBLICATIONS

Baron, Martin et al., "H NMR Assignment and Secondary Structure of the Cell Adhesion Type III Module of Fibronectin," Biochemistry, vol. 31:2068-2073 (1992).

Baron, Martin et al., "Protein modules," TIBS, vol. 16:13-17 (1991).

Batori, Vincent et al., "Exploring the potential of the monobody scaffold: effects of loop elongation on the stability of a fibronectin type III domain," Protein Engineering, vol. 15(12):1015-1020 (2002).

Bianchi, Elisabetta et al., "High Level Expression and Rational Mutagenesis of a Designed Protein, the Minibody," J. Mol. Biol., vol. 236:649-659 (1994).

(56) References Cited

OTHER PUBLICATIONS

Boder, Eric T. et al., "Directed evolution of antibody fragments with monovalent femtomolar antigen-binding affinity," PNAS, vol. 97(20):10701-10705 (2000).
Boder, Eric T. et al., "Yeast surface display for screening combinatorial polypeptide libraries," Nature Biotechnology, vol. 15:553-557 (1997).
Bork, P. et al., "The Immunoglobulin Fold, Structural Classification, Sequence Patterns and Common Core," J. Mol. Biol., vol. 242:309-320 (1994).
Bork, Peer et al., "Go hunting in sequence databases but watch out for the traps," TIG, vol. 12(10):425-427 (1996).
Bork, Peer et al., "Proposed acquisition of an animal protein domain by bacteria," Proc. Natl. Acad. Sci. USA, vol. 89:8990-8994 (1992).
Bork, Peer, "Powers and Pitfalls in Sequence Analysis: The 70% Hurdle," Genome Research, vol. 10:398-400 (2000).
Brenner, Steven E., "Errors in genome annotation," TIG, vol. 15(4):132-133 (1999).
Brock, Kenny V. et al., "Nucleotide sequencing of 5' and 3' termini of bovine viral diarrhea virus by RNA ligation and PCR," Journal of Virological Methods, vol. 38:39-46 (1992).
Bruzik, James P. et al., "Spliced leader RNAs from lower eukaryotes are trans-spliced in mammalian cells," Nature, vol. 360(6405):692-695 (1992).
Caliceti, Paolo et al., "Pharmacokinetic and biodistribution properties of poly(ethylene glycol)-protein conjugates," Advanced Drug Delivery Reviews, vol. 55:1261-1277 (2003).
Campbell, Iain D. et al., "Building proteins with fibronectin type III modules, Fibronectin type III modules are versatile components of many proteins. Recent structures of module pairs show how these modules are joined together," Structure, vol. 2:333-337 (1994).
Choy, E.H.S. et al., "Efficacy of a novel PEGylated humanized anti-TNF fragment (CDP870) in patients with rheumatoid arthritis: a phase II double-blinded, randomized, dose-escalating trial," Rheumatology, vol. 41:1133-1137 (2002).
Clackson, Tim et al., "In vitro selection from protein and peptide libraries," TibTech, vol. 12(5):173-184 (1994).
Clackson, Tim et al., "Making antibody fragments using phage display libraries," Nature, vol. 352:624-628 (1991).
Clarke, Jane et al., "Folding and Stability of a Fibronectin Type III Domain of Human Tenascin," J. Mol. Biol., vol. 270:771-778 (1997).
Connelly, Roberta et al., "Mitogenic properties of a bispecific single-chain Fv-Ig fusion generated from CD2-specific mAb to distinct epitopes," International Immunology, vol. 10(12):1863-1872 (1998).
Copie, Valerie et al., "Solution Structure and Dynamics of Linked Cell Attachment Modules of Mouse Fibronectin Containing the RGD and Synergy Regions: Comparison wtih the Human Fibronectin Crystal Structure," J. Mol. Biol., vol. 277:663-682 (1998).
Cota, Ernesto et al., "Two Proteins with the Same Structure Respond very Differently to Mutation: The Role of Plasticity in Protein Stability," J. Mol. Biol., vol. 302:713-725 (2000).
Cujec, Thomas P. et al., "Selection of v-Abl Tyrosine Kinase Substrate Sequences from Randomized Peptide and Cellular Proteomic Libraries Using mRNA Display," Chemistry & Biology, vol. 9:253-264 (2002).
Devlin, James J. et al., "Random Peptide Libraries: A Source of Specific Protein Binding Molecules," Science, vol. 249:404-406 (1990).
DGENE Search Results, 33 pages (2005).
Dickinson, Craig D. et al., "Crystal Structure of the Tenth Type III Cell Adhesion Module of Human Fibronectin," J. Mol. Biol., vol. 236:1079-1092 (1994).
Dickinson, Craig D. et al., "Crystals of the Cell-binding Module of Fibronectin Obtained from a Series of Recombinant Fragments Differing in Length," J. Mol. Biol., vol. 238:123-127 (1994).
Doerks, Tobias et al., "Protein annotation: detective work for function prediction," TIG, vol. 14(6):248-250 (1998).
Duan, Jinzhu et al., "Fibronectin Type III Domain Based Monobody with High Avidity," Biochemistry, vol. 46:12656-12664 (2007).
Ely, Kathryn R. et al., "Common molecular scaffold for two unrelated RGD molecules," Protein Engineering, vol. 8 (8):823-827 (1995).
Emanuel, Stuart L. et al., "A fibronectin scaffold approach to bispecific inhibitors of epidermal growth factor receptor and insulin-like growth factor-I receptor," MAbs, vol. 3(1):38-48 (2011).
Emanuel, Stuart L. et al., "Adnectins as a platform for multi-specific targeted biologics: A novel bispecific inhibitor of EGFR and IGF-IR growth factor receptors," Cancer Research, vol. 70(8 Suppl. 1), Abstract 2586, 1 page, AACR 101st Annual Meeting (2010).
Fenton, Bruce et al., "Pathophysiological effects of antibodies to IGF-1R and VEGFR-2 plus fractionated radiation in DU145 prostate carcinoma xenografts," Radiation Research Society 2005 Annual Meeting, Abstract No. PP109, 1 page (2005).
Ferguson, Kimberly C. et al., "The SL1 trans-spliced leader RNA performs an essential embryonic function in Caenorhabditis elegans that can also be supplied by SL2 RNA," Genes & Development, vol. 10:1543-1556 (1996).
GenBank Accession No. AAC48614, MacLeod, J.N. et al., "Fibronectin mRNA splice variant in articular cartilage lacks bases encoding the V, III-15, and I-10 protein segments," J. Biol. Chem., vol. 271(31):18954-18960 (1996), 2 pages, (1996).
GenBank Accession No. CAA26536, Kornblihtt, A.R. et al., "Primary structure of human fibronectin: differential splicing may generate at least 10 polypeptides froma single gene," EMBO J., vol. 4(7):1755-1759 (1985), 7 pages, (1996).
GenBank Accession No. P07589, Skorstengaard, K. et al., "Complete primary structure of bovine plasma fibronectin," Eur. J. Biochem., vol. 161(2):441-453 (1986), 9 pages, (1997).
GenBank Accession No. X02761, Kornblihtt, A.R. et al., "Primary structure of human fibronectin: differential splicing may generate at least 10 polypeptides from a single gene," EMBO J., vol. 4(7):1755-1759 (1985), 4 pages, (1996).
Ghosh, Gourisankar et al., "Structure of NF-kappaB p50 homodimer bound to a kappaB site," Nature, vol. 373:303-310 (1995).
Goedert, M. et al., "Cloning and sequencing of the cDNA encoding an isoform of microtubule-associated protein tau containing four tandem repeats: differential expression of tau protein mRNAs in human brain," The EMBO Journal, vol. 8(2):393-399 (1989).
Grant, Richard P. et al., "Structural Requirements for Biological Activity of the Ninth and Tenth FIII Domains of Human Fibronectin," The Journal of Biological Chemistry, vol. 272(10):6159-6166 (1997).
Hamers-Casterman, C. et al., "Naturally occurring antibodies devoid of light chains," Nature, vol. 363:446-448 (1993).
Hammond, Philip W. et al., "In Vitro Selection and Characterization of Bcl-XL-binding Proteins from a Mix of Tissue-specific mRNA Display Libraries," The Journal of Biological Chemistry, vol. 276(24):20898-20906 (2001).
Harpaz, Yahouda et al., "Many of the IMmunoglobulin Superfamily Domains in Cell Adhesion Molecules and Surface Receptors Belong to a New Structural Set Which is Close to That Containing Variable Domains," J. Mol. Biol., vol. 238:528-539 (1994).
Hocking, Denise C. et al., "A Novel Role for the Integrin-binding III-10 Module in Fibronectin Matrix Assembly," The Journal of Cell Biology, vol. 133(2):431-444 (1996).
Hocking, Denise C. et al., "Activation of Distinct alpha5beta1-mediated Signaling Pathways by Fibronectin's Cell Adhesion and Matrix Assembly Domains," The Journal of Cell Biology, vol. 141(1):241-253 (1998).
Husimi, Y. et al., "Role of the Virus-type Strategy in Encoded Molecular Evolution," Progress in Biophysics and Molecular Biology, vol. 65(Suppl. 1):64 (1996).
Notice of Opposition to European Patent No. 1137941 (Application No. 99 967 261.1), 29 pages, dated May 11, 2010.
Nygren, Per-Ake et al., "Scaffolds for engineering novel binding sites in proteins," Current Opinion in Structural Biology, vol. 7:463-469 (1997).
Parker, M.H. et al., "Antibody mimics based on human fibronectin type three domain engineered for thermostability and high-affinity binding to vascular endothelial growth factor receptor two," Protein Engineering, Design & Selection, vol. 18(9):435-444 (2005).

(56) References Cited

OTHER PUBLICATIONS

Partial European Search Report for Application No. 01981621.4, 5 pages, dated Feb. 25, 2005.
Plaxco, Kevin W. et al., "A Comparison of the Folding Kinetics and Thermodynamics of Two Homologous Fibronectin Type III Modules," J. Mol. Biol., vol. 270:763-770 (1997).
Plaxco, Kevin W. et al., "Rapid refolding of a proline-rich all-beta-sheet fibronectin type III module," Proc. Natl. Acad. Sci. USA, vol. 93:10703-10706 (1996).
Potts, Jennifer R. et al., "Fibronectin structure and assembly," Current Biology, vol. 6:648-655 (1994).
Potts, Jennifer R. et al., "Structure and Function of Fibronectin Modules," Matrix Biology, vol. 15:313-320 (1996).
Roberts, Richard W. et al., "RNA-peptide fusions for the in vitro selection of peptides and proteins," Proc. Natl. Acad. Sci. USA, vol. 94:12297-12302 (1997).
Roberts, Richard W., "Totally in vitro protein selection using mRNA-protein fusions and ribosome display," Current Opinion in Chemical Biology, vol. 3:268-273 (1999).
Rottgen, Peter et al., "A human pancreatic secretory trypsin inhibitor presenting a hyperveriable highly constrained epitope via monovalent phagemid display," Gene, vol. 164:243-250 (1995).
Scott, Jamie K. et al., "Searching for Peptide Ligands with an Epitope Library," Science, vol. 249:386-390 (1990).
Shibata, K. et al., "An attempt to substitute the cell binding domain of human fibronectin in lambda phage J protein: Computer design and expression," Biochimie, vol. 75:459-465 (1993).
Skolnick, Jeffrey et al., "From genes to protein structure and function: novel applications of computational approaches in the genomic era," TibTech, vol. 18:34-39 (2000).
Sleep D. et al., "Albumin as a versatile platform for drug half-life extension",; Biochimica et Biophysica Acta (BBA) General Subjects, vol. 1830(12):5526-5534 (2013).
Smith, George P. et al., "Phage Display," Chem. Rev., vol. 97:391-410 (1997).
Smith, Temple F. et al., "The challenges of genome sequence annotation of 'The devil is in the details,'" Nature Biotechnology, vol. 15:1222-1223 (1997).
Supplementary European Search Report for Application No. 01913159.8, 3 pages, dated Dec. 21, 2004.
Supplementary European Search Report for Application No. 99967261.1, 3 pages, dated Mar. 6, 2002.
Tang, Lisa et al., "Pharmacokinetic Aspects of Biotechnology Products," Journal of Pharmaceutical Sciences, vol. 93 (9):2184-2204 (2004).
Tokuriki, Nobuhiko et al., "Stability effects of mutations and protein evolvability," Current Opinion in Structural Biology, vol. 19:596-604 (2009).
Tramontano, Anna et al., "The Making of the Minibody: an Engineered beta-Protein for the Display of Conformationally Constrained Peptides," Journal of Molecular Recognition, vol. 7:9-24 (1994).
Trinh, Ryan et al., "Optimization of codon pair use within the (GGGGS)3 linker sequence results in enhanced protein expression," Molecular Immunology, vol. 40:717-722 (2004).
Vuento, Matti et al., "Purification of Fibronectin from Human Plasma by Affinity Chromatography under Non-Denaturing Conditions," Biochem. J., vol. 183:331-337 (1979).
Wang, Cheng-I et al., "Isolation of a High Affinity Inhibitor of Urokinase-type Plasminogen Activator by Phage Display of Ecotin," The Journal of Biological Chemistry, vol. 270(20):12250-12256 (1995).
Watanabe, Takeshi et al., "Gene Cloning of Chitinase A1 from Bacillus circulans WL-12 Revealed Its Evolutionary Relationship to Serratia Chitinase and to the Type III Homology Units of Fibronectin," The Journal of Biological Chemistry, vol. 265:15659-15665 (1990).
Wells, James A., "Additivity of Mutational Effects in Proteins," Biochemistry, vol. 29(37):8509-8517 (1990).
Williams, Alan F. et al., "The Immunoglobulin Superfamily—Domains for Cell Surface Recognition," Ann. Rev. Immunol., vol. 6:381-405 (1988).
Williams, Michael J. et al., "Solution Structures of Modular Proteins by Nuclear Magnetic Resonance," Methods in Enzymology, vol. 245:451-469 (1994).
Wilson, David S. et al., "The use of mRNA display to select high-affinity protein-binding peptides," PNAS, vol. 98 (7):3750-3755 (2001).
Written Opinion for Application No. PCT/US01/06414, 5 pages, dated Feb. 7, 2002.
Xu, Lihui et al., "Directed Evolution of High-Affinity Antibody Mimics Using mRNA Display," Chemistry & Biology, vol. 9:933-942 (2002).
Zdanov, Alexander et al., Structure of a single-chain antibody variable domain (Fv) fragment complexed with a carbohydrate antigen at 1.7-A resolution, Proc. Natl. Acad. Sci. USA, vol. 91:6423-6427 (1994).
Hynes, Richard O. et al., "Integrins: Versability, Modulation, and Signaling in Cell Adhesion," Cell, vol. 69:11-25 (1992).
International Preliminary Examination Report for Application No. PCT/US01/06414, 6 pages, dated Aug. 27, 2002.
International Preliminary Examination Report for Application No. PCT/US01/32233, 5 pages, dated Dec. 10, 2003.
International Preliminary Examination Report for Application No. PCT/US99/29317, 4 pages, dated Aug. 14, 2000.
International Preliminary Report on Patentability and Written Opinion for Application No. PCT/US2009/003192, 12 pages, dated Nov. 23, 2010.
International Preliminary Report on Patentability and Written Opinion for Application No. PCT/US2011/034998, 10 pages, dated Nov. 6, 2012.
International Preliminary Report on Patentability, PCT/US2015/21535, dated Sep. 20, 2016, 10 pages.
International Search Report and Written Opinion, PCT/US2015/21535, dated Jul. 2, 2015, 16 pages.
International Search Report for Application No. PCT/US01/06414, 5 pages, dated Aug. 7, 2001.
International Search Report for Application No. PCT/US01/32233, 3 pages, dated Jun. 12, 2003.
International Search Report for Application No. PCT/US2009/003192, 8 pages, dated Jun. 1, 2010.
International Search Report for Application No. PCT/US2011/034998, 5 pages, dated Jul. 17, 2012.
International Search Report for Application No. PCT/US99/29317, 2 pages, dated Apr. 6, 2000.
Jung, Gyoo Yeol et al., "A Functional Protein Chip for Pathway Optimization and in Vitro Metabolic Engineering," Science, vol. 304:428-431 (2004).
Keefe, Anthony D. et al., "Functional proteins from a random-sequence library," Nature, vol. 410:715-718 (2001).
King, Catherine A. et al., "DNA vaccines with single-chain Fv fused to fragment C of tetanus toxin induce protective immunity against lymphoma and myeloma," Nature Medicine, vol. 4(11):1281-1286 (1998).
Klohn P-C et al., "IBC's 23nd Annual Antibody Engineering, 10th Annual Antibody Therapeutics International Conferences and the 2012 Annual Meeting of The Antibody Society: Dec. 3-6, 2012,San Diego, CA", MABS, vol. 5(2): 178-201 (2013).
Kohler, G. et al., "Continuous cultures of fused cells secreting antibody of predefined specificity," Nature, vol. 256:495-497 (1975).
Koide, Akiko et al., "Monobodies. Antibody Mimics Based on the Scaffold of the Fibronectin Type III Domain," Methods in Molecular Biology, vol. 352: Protein Engineering Protocols, K.M. ARndt (Ed.), Humana Press, Totowa, NJ, Chapter 6, pp. 95-109 (2007).
Koide, Akiko et al., "Stabilization of a Fibronectin Type III Domain by the Removal of Unfavorable Electrostatic Interactions on the Protein Surface," Biochemistry, vol. 40:10326-10333 (2001).
Koide, Akiko et al., "The Fibronectin Type III Domain as a Scaffold for Novel Binding Proteins," J. Mol. Biol., vol. 284:1141-1151 (1998).

(56) References Cited

OTHER PUBLICATIONS

Koide, Shohei et al., "Directed Evolution of Fibronectin Type III Domain to Novel Ligand Binding Proteins," FASEB J., vol. 11(9 Suppl.), Poster No. M40, p. A837, (1997).
Koide, Shohei et al., "Directed Evolution of Fibronectin Type III Domain to Novel Ligand Binding Proteins," The Faseb Journal, vol. 11(9):A1155, Poster No. 1739 (1997).
Ku, Jung et al., "Alternate protein frameworks for molecular recognition," Proc. Natl. Acad. Sci. USA, vol. 92:6552-6556 (1995).
Kurz, Markus et al., "Psoralen photo-crosslinked mRNA-puromycin conjugates: a novel template for the rapid and facile preparation of mRNA-protein fusions," Nucleic Acids Research, vol. 28(18):e83, 5 pages (2000).
Leahy, Daniel J. et al., "2.0 A Crystal Structure of a Four-Domain Segment of Human Fibronectin Encompassing the RGD Loop and Synergy Region," Cell, vol. 84:155-164 (1996).
Leahy, Daniel J. et al., "Structure of a Fibronectin Type III Domain from Tenascin Phased by MAD Analysis of the Selenomethionyl Protein," Science, vol. 258:987-991 (1992).
Lee, Grace et al., "Strong Inhibition of Fibrogen Binding to Platelet Receptor Alpha2b beta 3 by RGD Sequences installed into the Presentation Scaffold," Prot. Eng., vol. 6:745-754 (1993).
Lipovsek D: "Adnectins: engineered target-binding protein therapeutics," Protein Engineering, Design and Selection, vol. 24 (1-2):3-9 (2010).
Lipovsek, Dasa et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," J. Mol. Biol., vol. 368:1024-1041 (2007).
Lipovsek, Dasa et al., "In-vitro protein evolution by ribosome display and mRNA display," Journal of Immunological Methods, vol. 290:51-67 (2004).
Litvinovich, Sergei V. et al., "Interactions Between Type III Domains in the 110 kDa Cell-binding Fragments of Fibronectin," J. Mol. Biol., vol. 248:611-626 (1995).
Lombardo, A. et al., "Conformational flexibility and crystallization of tandemly linked type III modules of human fibronectin," Protein Science, vol. 5:1934-1938 (1996).
Lu, Dan et al., "Simultaneous Blockade of Both the Epidermal Growth Factor Receptor and the Insulin-like Growth Factor Receptor Signaling Pathways in Cancer Cells with a Fully Human Recombinant Bispecific Antibody," The Journal of Biological Chemistry, vol. 279(4):2856-2865 (2004).
Main, Alison L. et al., "The Three-Dimensional Structure of the Tenth Type III Module of Fibronectin: An Insight into RGD-Mediated Interactions," Cell, vol. 71:671-678 (1992).
Mao, Yong et al., "Fibronectin fibrillogenesis, a cell-mediated matrix assembly process," Matrix Biology, vol. 24:389-399 (2005).
Markland, William et al., "Iterative Optimization of High-Affinity Protease Inhibitors Using Phage Display. 1. Plasmin," Biochemistry, vol. 35:8045-8057 (1996).
Markland, William et al., "Iterative Optimization of High-Affinity Protease Inhibitors Using Phage Display. 2. Plasma Kallikrein and Thrombin," Biochemistry, vol. 35:8058-8067 (1996).
Maruyama, Kazuo et al., "Oligo-capping: a simple method to replace the cap structure of eukaryotic mRNAs with oligoribonucleotides," Gene, vol. 138:171-174 (1994).
Mattheakis, Larry C. et al., "An in vitro polysome display system for identifying ligands from very large peptide libraries," Proc. Natl. Acad. Sci. USA, vol. 91:9022-9026 (1994).
McConnell, Stephen J. et al., "Tendamistat as a Scaffold for Conformationally Constrained Phage Peptide Libraries," J. Mol. Biol., vol. 250:460-470 (1995).
Meinke, A. et al., "Cellulose-Binding Polypeptides from Cellulomonas fimi: Endoglucanase D (CenD), a Family A beta-1,4-Glucanase," Journal of Bacteriology, vol. 175(7):1910-1918 (1993).
Muller, Christoph W. et al., "Structure of the NF-kappaB p50 homodimer bound to DNA," Nature, vol. 373:311-317 (1995).
Muyldermans, Serge, "Single domain camel antibodies: current status," Reviews in Molecular Biotechnology, vol. 74:277-302 (2001).
Nemoto, Naoto et al., "In vitro virus: Bonding of mRNA bearing puromycin at the 3'-terminal end to the C-terminal end of its encoded protein on the ribosome in vitro," FEBS Letters, vol. 414:405-408 (1997).
Ngo, J. Thomas et al., "Computational Complexity Protein Structure Prediction, and the Levinthal Paradox," The Protein Folding Problem and Tertiary Structure Prediction, Birkhauser, Boston, MA, K. Merz (Ed.), Chapter 14, pp. 491-495 (1994).
Niemeyer, Christof M. et al., "Oligonucleotide-directed self-assembly of proteins: semisynthetic DNA—streptavidin hybrid molecules as connectors for the generation of macroscopic arrays and the construction of supramolecular bioconjugates," Nucleic Acids Research, vol. 22(25):5530-5539 (1994).
Nilsen, Timothy W., "Trans-Splicing in Protozoa and Helminths," Infections Agents and Disease, vol. 1:212-218 (1992).
Nord, Karin et al., "A combinatorial library of an alpha-helical bacterial receptor domain," Prot. Eng., vol. 8:601-608 (1995).
Nord, Karin et al., "Binding proteins selected from combinatorial libraries of an alpha-helical bacterial receptor domain," Nature Biotechnology, vol. 15:772-777 (1997).
U.S. Appl. No. 09/515,260, filed Feb. 29, 2000, Dasa Lipovsek.
U.S. Appl. No. 10/728,078, filed Dec. 3, 2003, Dasa Lipovsek.
U.S. Appl. No. 11/483,918, filed Jul. 7, 2006, Dasa Lipovsek.
U.S. Appl. No. 11/543,316, filed Oct. 3, 2006, Dasa Lipovsek.
U.S. Appl. No. 11/890,627, filed Aug. 6, 2007, Dasa Lipovsek.
U.S. Appl. No. 15/583,561, filed May 1, 2017, Dasa Lipovsek.
U.S. Appl. No. 15/440,730, filed Feb. 23, 2017, Dasa Lipovsek.
U.S. Appl. No. 12/470,989, filed May 22, 2009, Ray Camphausen.
U.S. Appl. No. 13/533,382, filed Jun. 26, 2012, Ray Camphausen.
U.S. Appl. No. 14/229,415, filed Mar. 28, 2014, Ray Camphausen.
U.S. Appl. No. 15/866,919, filed Jan. 10, 2018, Ray Camphausen.
U.S. Appl. No. 13/098,851, filed May 2, 2011, Michael L. Gosselin.
U.S. Appl. No. 14/552,823, filed Nov. 25, 2014, Michael L. Gosselin.
U.S. Appl. No. 15/363,724, filed Nov. 29, 2016, Michael L. Gosselin.
U.S. Appl. No. 14/355,155, filed Apr. 29, 2014, Jonathan Davis.
U.S. Appl. No. 15/341,623, filed Nov. 2, 2016, Jonathan Davis.
U.S. Appl. No. 15/127,183, filed Sep. 9, 2016, Dasa Lipovsek.
U.S. Appl. No. 09/515,260, Dec. 18, 2003.
U.S. Appl. No. 09/515,260, Mar. 11, 2003.
U.S. Appl. No. 09/515,260, Jun. 18, 2002.
U.S. Appl. No. 09/515,260, Sep. 7, 2001.
U.S. Appl. No. 09/515,260, Jun. 1, 2001.
U.S. Appl. No. 10/778,078, Mar. 10, 2006.
U.S. Appl. No. 10/728,078, Jul. 1, 2005.
U.S. Appl. No. 10/728,078, Feb. 9, 2005.
U.S. Appl. No. 11/483,918, Dec. 29, 2009.
U.S. Appl. No. 11/483,918, Jun. 12, 2009.
U.S. Appl. No. 11/483,918, Dec. 15, 2008.
U.S. Appl. No. 11/483,918, Mar. 24, 2008.
U.S. Appl. No. 11/483,918, Sep. 10, 2007.
U.S. Appl. No. 11/483,918, Apr. 11, 2007.
U.S. Appl. No. 11/543,316, Nov. 16, 2016.
U.S. Appl. No. 11/543,316, Feb. 12, 2016.
U.S. Appl. No. 11/543,316, Jul. 10, 2015.
U.S. Appl. No. 11/543,316, Apr. 20, 2011.
U.S. Appl. No. 11/543,316, Aug. 4, 2010.
U.S. Appl. No. 11/543,316, Nov. 12, 2009.
U.S. Appl. No. 11/543,316, Apr. 3, 2009.
U.S. Appl. No. 11/890,627, Nov. 16, 2009.
U.S. Appl. No. 11/890,627, Apr. 2, 2009.
U.S. Appl. No. 15/440,730, Mar. 22, 2018.
U.S. Appl. No. 12/470,989, Mar. 16, 2012.
U.S. Appl. No. 12/470,989, Sep. 1, 2011.
U.S. Appl. No. 12/470,989, Mar. 18, 2011.
U.S. Appl. No. 13/533,382, Jan. 2, 2014.
U.S. Appl. No. 13/533,382, May 24, 2013.
U.S. Appl. No. 13/533,382, Dec. 10, 2012.
U.S. Appl. No. 13/098,851, Aug. 27, 2014.

(56) References Cited

OTHER PUBLICATIONS

U.S. Appl. No. 13/098,851, May 20, 2014.
U.S. Appl. No. 13/098,851, Dec. 4, 2013.
U.S. Appl. No. 13/098,851, Mar. 18, 2013.
U.S. Appl. No. 14/229,415, Oct. 11, 2017.
U.S. Appl. No. 14/229,415, Jun. 16, 2017.
U.S. Appl. No. 14/229,415, Jan. 9, 2017.
U.S. Appl. No. 14/229,415, Aug. 1, 2016.
U.S. Appl. No. 14/229,415, Feb. 9, 2016.
U.S. Appl. No. 14/481,641, Jul. 1, 2016.
U.S. Appl. No. 14/481,641, Nov. 20, 2015.
U.S. Appl. No. 14/552,823, Aug. 31, 2016.
U.S. Appl. No. 14/552,823, Mar. 24, 2016.
U.S. Appl. No. 14/355,155, Aug. 4, 2016.
U.S. Appl. No. 14/355,155, Mar. 29, 2016.
U.S. Appl. No. 14/355,155, Oct. 26, 2015.

* cited by examiner

Figure 5

| Adnectin | | 2987_H07 (myo) | | 2013_E01 (PCSK9) | |
|---|---|---|---|---|---|
| PKE | HSA $EC_{50}$ (nM) | X-PKE | PKE-X | X-PKE | PKE-X |
| 1318_H04 | 5 | 31% (8/26) | 0% (0/26) | 31% (8/26) | X |
| 2629_E06 | 20 | 30% (3/10) | 80% (8/10) | 90% (9/10) | 80% (8/10) |
| 2630_D02 | 9 | 20% (2/10) | 60% (6/10) | 50% (5/10) | 80% (8/10) |

HSA $EC_{50\_tandem}/EC_{50\_mono}$

| |
|---|
| ≤ 2 |
| 2—5 |
| 5—10 |
| 10 |

X = tandems not made

Figure 17

| SEQ ID | Adnectin | Full Protein Sequence |
|---|---|---|
| 23 | 2270_C01 | MASTSGVPRDLEVVAATPTSLLISWDAPAVTVRYYRITYGWQVQMYSDWGPLYIYKEFTVPGSKSTATISGLKPGVDYTITVYAVTGSGESPASSKPISINYRTEGDKPSQHHHHHH* |
| 24 | 2629_A09 | MGVSDVPRDLEVVAATPTSLLISWDAPAVTVRYYRITYGRHVQIYSDLGPLYIYTEFTVPGSKSTATISGLKPGVDYTITVYAVTGSGESPASSKPISINYRTEIDKPSQHHHHHH* |
| 25 | 2629_A11 | MGVSDVPRDLEVVAATPTSLLISWDAPAVTVRYYRITYGRHVHIYSDWGPMYIYTEFTVPGSKSTATISGLKPGVDYTITVYAVTGSGESPASSKPISINYRTEIDKPSQHHHHHH* |
| 26 | 2629_C10 | MGVSDVPRDLEVVAATPTSLLISWDAPAVTVRYYRITYGREVQKYSVLGPLYIYTEFTVPGSKSTATISGLKPGVDYTITVYAVTGSGESPASSKPISINYRTEIDKPSQHHHHHH* |
| 27 | 2629_D09 | MGVSDVPRDLEVVAATPTSLLISWDAPAVTVRYYRITYGREVQMYSDLGPLYVYSEFTVPGSKSTATISGLKPGVDYTITVYAVTGSGESPASSKPISINYRTEIDKPSQHHHHHH* |
| 28 | 2629_E05 | MGVSDVPRDLEVVAATPTSLLISWDAPAVTVRYYRITYGREVQKFSDWGPLYIYTEFTVPGSKSTATISGLKPGVDYTITVYAVTGSGESPASSKPISINYRTEIDKPSQHHHHHH* |
| 29 | 2629_E06 | MGVSDVPRDLEVVAATPTSLLISWDAPAVTVRYYRITYGREVQKYSDLGPLYIYQEFTVPGSKSTATISGLKPGVDYTITVYAVTGSGESPASSKPISINYRTEIDKPSQHHHHHH* |
| 30 | 2629_F04 | MGVSDVPRDLEVVAATPTSLLISWDAPAVTVRYYRITYGREVHQYSDWGPMYIYNEFTVPGSKSTATISGLKPGVDYTITVYAVTGSGESPASSKPISINYRTEIDKPSQHHHHHH* |
| 31 | 2629_H01 | MGVSDVPRDLEVVAATPTSLLISWDAPAVTVXYYRITYGREVHKNSDWGTLYIYTEFTVPGSKSTATISGLKPGVDYTITVXAVTGSGEXPASSKPISINYRTEIDKXSQHHHHHH* |
| 32 | 2629_H06 | MGVSDVPRDLEVVAATPTSLLISWDAPAVTVRYYRITYGREVQKYSDLGPLYIYAEFTVPGSKSTATISGLKPGVDYTITVYAVTGSGESPASSKPISINYRTEIDKPSQHHHHHH* |
| 33 | 2629_H07 | MGVSDVPRDLEVVAATPTSLLISWDAPAVTVRYYRITYGREVHLYSDWGPMYIYTEFTVPGSKSTATISGLKPGVDYTITVYAVTGSGESPASSKPISINYRTEIDKPSQHHHHHH* |
| 34 | 2630_A02 | MGVSDVPRDLEVVATTPTSLLISWDAPAVTVRYYRITYGRHVQMYSDLGPLYIFSEFTVPGSKSTATISGLKPGVDYTITVYAVTGSGESPASSKPISINYRTEIDKPSQHHHHHH* |
| 35 | 2630_A11 | MGVSDVPRDLEVVAATPTSLLISWDAPAVTVRYYRITYGREVHMYSDFGPMYIYTEFTVPGSKSTATISGLKPGVDYTITVYAVTGSGESPASSKPISINYRTEIDKPSQHHHHHH* |
| 36 | 2630_D02 | MGVSDVPRDLEVVAATPTSLLISWDAPAVTVRYYRITYGREVQKYSDWGPLYIYNEFTVPGSKSTATISGLKPGVDYTITVYAVTGSGESPASSKPISINYRTEIDKPSQHHHHHH* |
| 37 | 2630_D10 | MGVSDVPRDLEVVAATPTSLLISWDAPAVTVRYYRITYGREVQMYSDLGPLYIYNEFTVPGSKSTATISGLKPGVDYTITVYAVTGSGESPASSKPISINYRTEIDKPSQHHHHHH* |
| 38 | 2630_F04 | MGVSDVPRDLEVVAATPTSLLISWDAPAVTVRYYRITYGREVQMYSDLGPLYIYTEFTVPGSKSTATISGLKPGVGYTITVYAVTGSGESPASSKPISINYRTEIDKPSQHHHHHH* |
| 39 | 2630_G03 | MGVSDVPRDLEVVAATPTSLLISWDAPAVTVRYYRITYGRHVQIYSDLGPLYIYNEFTVPGSKSTATISGLKPGVDYTITVYAVTGSGESPASSKPISINYRTEIDKPSQHHHHHH* |
| 40 | 2630_G10 | MGVSDVPRDLEVVAATPTSLLISWDAPAVTVRYYRITYGREVQIYSDWGPLYIYNEFTVPGSKSTATISGLKPGVDYTITVYAVTGSGESPASSKPISINYRTEIDKPSQHHHHHH* |
| 41 | 2630_H03 | MGVSDVPRDLEVVAATXTSLLISWDAPAVTVXYYRITYGREVQKYSDWGPLYIYQEFTVPGSXSTATISGLKPGVDYTITVYAVTGSGESPASSKPISINYRTEIDKXSQHHHHHH* |
| 42 | 2631_B04 | MGVSDVPRDLEVVAATPTSLLISWDVPAVTVRYYRITYGRHVHLYSEFGPMYIYNEFTVPGSKSTATISGLKPGVDYTITVYAVTGSGESPASSKPISINYRTEIDKPSQHHHHHH* |
| 43 | 2631_E03 | MGVSDVPRDLEVVAATPTSLLISWDAPAVTVRYYRITYGRDVHMYSDWGPMYIYQEFTVPGSKSTATISGLKPGVDYTITVYAVTGSGESPASSKPISINYRTEIDKPSQHHHHHH* |
| 44 | 2631_G01 | MGVSDVPRDLEVVAATPTSLLISWDAPAVTVRYYRITYGRHVQIYSDWGPLYIYNEFTVPGSKSTATISGLKPGVDYTITVYAVTGSGESPASSKPISINYRTEIDKPSQHHHHHH* |
| 45 | 2631_G03 | MGVSDVPRDLEVVAATPTSLLISWDAPAVTVRYYRITYGRYVQLYSDWGPMYIYTEFTVPGSKSTATISGLKPGVDYTITVYAVTGSGESPASSKPISINYRTEIDKPSQHHHHHH* |
| 46 | 2631_H09 | MGVSDVPRDLEVVAATPTSLLISWDAPAVTVRYYRITYGRQVQVFSDLGPLYIYNEFTVPGSKSTATISGLKPGVDYTITVYAVTGSGESPASSKPISINYRTEIDKPSQHHHHHH* |
| 47 | 2632_G01 | MGVSDVPRDLEVVAATPTSLLISWDAPAVTVRYYRITYGRQVQIYSDWGPLYIYNEFTVPGSKSTATISGLKPGVDYTITVYAVTGSGESPASSKPISINYRTEIDKPSQHHHHHH* |
| 48 | 4079_A04 | MGVSDVPRDLEVVAATPTSLLISWDAPAVTVRYYRITYGRQVQMYSDWGPLYIYAEFTVPGSKSTATISGLKPGVDYTITVYAVTGSGESPASSKPISINYRTEIDKPSQHHHHHH* |

Figure 18A

| SEQ ID | Adnectin | Nucleic Acid Sequence |
|---|---|---|
| 126 | 2270_C01 | ATGGCTAGCACTAGTGGCGTGCCGCGCGACTTGGAAGTGGTTGCCGCGACCCCGACGTCTCTGCTTATTAGCTGGGATGCACCTGCCGTCACAGTGAGATATTATCGCATTACATAT<br>GGTTGGCAGGTTCAGATGTACTCTGACTGGGGTCCGCTGTACATCTACAAAGAGTTCACGGTACCTGGGAGCAAGTCCACAGCTACCATCAGCGGTCTCAAACCTGGAGTTGATTA<br>CACCATTACGGTATACGCAGTCACCGGCTCTGGAGAGAGCCCCGCAAGCAGCAAGCCAATTTCCATTAATTATCGGACCGAAGGCGACAAACCATCCCAGCACCATCACCACCACCA<br>CTGA |
| 127 | 2629_A09 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGG<br>ACGGCATGTTCAGATCTATTCTGACTTAGGCCCGCTGTACATCTACACAGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 128 | 2629_A11 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGT<br>AGACACGTTCATATCTACTCAGACTGGGGTCCGATGTACATCTACACAGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 129 | 2629_C10 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGG<br>GAGAGAGGTTCAGAAATACTCTGTCTTGGGTCCACTGTACATATACACGGAGTTCACTGTGCCTGGGAGCAAGTCCACAGCTACCATCAGCGGCCTTAAACCTGGCGTTGATTATAC<br>CATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTG<br>A |
| 130 | 2629_D09 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGG<br>GAGGGAGGTTCAGATGTACTCTGACTTGGGTCCATTGTACGTATACAGCGAGTTCACTGTGCCTGGGAGCAAGTCCACAGCTACCATCAGCGGCCTTAAACCTGGCGTTGATTATAC<br>CATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTG<br>A |
| 131 | 2629_E05 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGT<br>CGGGAGGTACAGAAGTTCTCGGACTGGGGTCCGCTGTACATCTACACAGAGTTCACTGTGCCTGGGAGCAAGTCCACAGCTACCATCAGCGGCCTTAAACCTGGCGTTGATTATAC<br>CATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTG<br>A |
| 132 | 2629_E06 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGC<br>AGGGAGGTTCAGAAGTACTCGGACTTGGGTCCGTTGTACATCTACCAAGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 133 | 2629_F04 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGT<br>AGGGAGGTTCATCAATACTCTGACTGGGGTCCGATGTACATCTACAACGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 134 | 2629_H01 | ATGGGAGTTTCTGATGTGCCGCGCGACCTGGAAGTGGTTGCTGCCACCCCCACCAGCCTGCTGATCAGCTGGGATGCACCTGCCGTCACAGTGCRATATTACCGCATCACTTACGGT<br>CGGGAGGTTCATAAGAACTCAGACTGGGGTACGCTGTACATCTACACAGAGTTCACTGTGCCTGGGAGCAAGTCCACAGCTACCATCAGCGGCCTTAAACCTGGCGTTGATTATAC<br>CATCACTGTGTRTGCTGTCACTGGCTCTGGAGAGARCCCCGCAAGCAGCAAGCCAATTTCCATTAATTACCGCACAGAAATTGACAAAMCATCCCAGCACCATCACCACCACCACTG<br>A |
| 135 | 2629_H06 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGG<br>ACGGGAGGTTCAGAAGTATTCAGACTTGGGTCCACTGTACATCTACGCAGAGTTCACTGTGCCTGGGAGCAAGTCCACAGCTACCATCAGCGGCCTTAAACCTGGCGTTGATTATAC<br>CATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTG<br>A |

Figure 18B

| SEQ ID | Adnectin | Nucleic Acid Sequence |
|---|---|---|
| 136 | 2629_H07 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGG<br>GCGGGAGGTCCACCTGTACTCCGACTGGGGGCCGATGTACATCTACACAGAGTTCACTGTGCCTGGGAGCAAGTCCACAGCTACCATCAGCGGCCTTAAACCTGGCGTTGATTATA<br>CCATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACT<br>GA |
| 137 | 2630_A02 | ATGGGAGTTTCTGATGTGCCGCGCGACCTGGAAGTGGTTGCTACCACCCCCACCAGCCTGCTGATCAGCTGGGATGCACCTGCCGTCACAGTGCGATATTACCGCATCACTTACGGT<br>AGGCACGTTCAAATGTACTCTGACCTTGGTCCGTTGTACATCTTCAGTGAGTTCACTGTGCCTGGGAGCAAGTCCACAGCTACCATCAGCGGCCTTAAACCTGGCGTTGATTATACCA<br>TCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 138 | 2630_A11 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGA<br>CGGGAGGTTCATATGTACTCTGACTTCGGTCCGATGTACATATACACAGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 139 | 2630_D02 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGT<br>AGAGAAGTTCAGAAATACTCTGACTGGGGCCCGCTCTACATCTACAATGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 140 | 2630_D10 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGT<br>CGGGAGGTTCAGATGTACTCGGACTTGGGTCCGCTCTACATCTACAACGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 141 | 2630_F04 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGT<br>AGAGAGGTCCAGATGTACTCAGACTTGGGGCCGCTGTACATCTATACAGAGTTCACTGTGCCTGGGAGCAAGTCCACAGCTACCATCAGCGGCCTTAAACCTGGCGTTGGTTATAC<br>CATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTG<br>A |
| 142 | 2630_G03 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGA<br>CGGCATGTTCAGATCTACTCCGACTTGGGTCCTCTGTATATCTACAATGAGTTCACTGTGCCTGGGAGCAAGTCCACAGCTACCATCAGCGGCCTTAAACCTGGCGTTGATTATACCA<br>TCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 143 | 2630_G10 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGT<br>CGGGAGGTTCAAATATACTCTGACTGGGGTCCGCTGTATATATACAACGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 144 | 2630_H03 | ATGGGAGTTTCTGATGTGCCGCGCGACCTGGAAGTGGTTGCTGCCACCSCCACCAGCCTGCTGATCAGCTGGGATGCACCTGCCGTCACAGTGCSATATTACCGCATCACTTACGGA<br>CGTGAAGTRCAGAAATACTCTGACTGGGGCCCGCTGTACATCTACCAAGAGTTCACTGTGCCTGGGAGCRAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAAMCATCCCAGCACCATCACCACCACCACTGA |
| 145 | 2631_B04 | ATGGGAGTTTCTGATGTGCCGCGCGACCTGGAAGTGGTTGCTGCCACCCCCACCAGCCTGCTGATCAGCTGGGATGTACCTGCCGTTACAGTGCGATATTACCGCATCACTTACGGC<br>AGGCACGTACATTTGTACTCGGAGTTCGGTCCGATGTATATCTACAACGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |

Figure 18C

| SEQ ID | Adnectin | Nucleic Acid Sequence |
|---|---|---|
| 146 | 2631_E03 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGT<br>AGGGATGTCCACATGTACTCTGACTGGGGTCCGATGTACATATACCAAGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 147 | 2631_G01 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGT<br>AGGCATGTTCAGATATACTCGGACTGGGGTCCGCTGTACATCTACAATGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 148 | 2631_G03 | ATGGGAGTTTCTGATGTGCCGCGCGACCTGGAAGTGGTTGCTGCCACCCCCACCAGCCTACTGATCAGCTGGGATGCACCTGCCGTCACAGTGCGATATTACCGCATCACTTACGGA<br>AGGTATGTTCAGCTATACTCTGACTGGGGTCCGATGTACATCTACACGGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 149 | 2631_H09 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGG<br>ACGGCAAGTGCAAGTGTTCTCAGACTTGGGTCCGCTGTACATATACAACGAGTTCACTGTGCCTGGGAGCAAGTCCACAGCTACCATCAGCGGCCTTAAACCTGGCGTTGATTATAC<br>CATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTG<br>A |
| 150 | 2632_G01 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGT<br>AGACAGGTGCAGATCTACTCTGACTGGGGACCGCTGTACATCTACAATGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 171 | 3852_F10 | ATGGGAGTTTCTGATGTGCCGCGCGACCTGGAAGTGGTTGCTGCCACCCCCACCAGCCTGCTGATCAGCTGGGACGCTCCGGCTGTTGACGGTCGATATTACCGCATCACTTACGG<br>CGAAACAGGAGGCAATAGCCCTGTCCAGGAGTTCACTGTGCCTGGTTCTAAATCTACAGCTACCATCAGCGGCCTTAAACCTGGCGTTGATTATACCATCACTGTGTATGCTGTCACT<br>CCGTACGAATTCCATTTCCCGTACACTCATTACTCTTCTAAACCAATTTCCATTAATTACCGCACAGAAATTGACAAACCATCCCAGCACCATCACCACCACCACTGA |
| 151 | 4079_A04 | ATGGGAGTTTCTGATGTGCCGCGCGACCTGGAAGTGGTTGCTGCCACCCCCACCAGCCTGCTGATCAGCTGGGATGCACCTGCCGTCACAGTGCGATATTACCGCATCACTTACGGT<br>AGGCAGGTACAGATGTACTCTGACTGGGGTCCACTTTACATCTACGCCGAGTTCACTGTGCCTGGGAGCAAGTCCACAGCTACCATCAGCGGCCTTAAACCTGGCGTTGATTATACC<br>ATCACTGTGTATGCTGTCACTGGCTCTGGAGAGAGCCCCGCAAGCAGCAAGCCAATTTCCATTAATTACCGCACAGAAATTGACAAACCATCCCAGCACCATCACCACCACCACTGA |
| 172 | 5190_E01 | ATGGGAGTTTCTGATGTGCCGCGCGACCTGGAAGTGGTTGCTGCCACCCCCACCAGCCTGCTGATCAGCTGGGACGCTCCGGCTGAAGGGTACGGTTATTACCGCATCACTTACGG<br>CGAAACAGGAGGCAATAGCCCTGTCCAGGAGTTCACTGTGCCTGTTTCTAAAGGTACAGCTACCATCAGCGGCCTTAAACCTGGCGTTGATTATACCATCACTGTGTATGCTGTCGA<br>ATTCGACTTCCCCGGCGCCGGTTACTACCATCGTCCAATTTCCATTAATTACCGGACCGAACCGAGCACACCTCCGACCCCGAGTCCGTCAACACCACCGACACCGTCACCGAGCGG<br>AGTTTCTGACGTCCCGCGCGACCTGGAAGTGGTTGCTGCCACCCCCACCAGCCTGCTGATCAGCTGGGATGCACCTGCCGTCACAGTGCGATATTACCGCATCACTTACGGCAGGG<br>AGGTTCAGAAGTACTCGGACTTGGGTCCGTTGTACATCTACCAAGAGTTCACTGTGCCTGGGAGCAAGTCCACAGCTACCATCAGCGGCCTTAAACCTGGCGTTGATTATACCATCA<br>CTGTGTATGCTGTCACTGGCTCTGGAGAGAGCCCCGCAAGCAGCAAGCCAATTTCCATTAATTACCGCACACCGTGA |

SEQUENCE LISTING

```
<160> NUMBER OF SEQ ID NOS: 266

<210> SEQ ID NO 1
<211> LENGTH: 94
<212> TYPE: PRT
<213> ORGANISM: Homo sapiens
<220> FEATURE:
<221> NAME/KEY: misc_feature
<223> OTHER INFORMATION: Wild-type human 10Fn3 domain

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90


<210> SEQ ID NO 2
<211> LENGTH: 168
<212> TYPE: PRT
<213> ORGANISM: Homo sapiens
<220> FEATURE:
<221> NAME/KEY: misc_feature
<223> OTHER INFORMATION: Wild-type human 10Fn3 domain w/loop sequences
      generically defined
<220> FEATURE:
<221> NAME/KEY: misc_feature
<222> LOCATION: (14)..(33)
<223> OTHER INFORMATION: Xaa, if present, can be any naturally occurring
      amino acid; at least two Xaa must be present
<220> FEATURE:
<221> NAME/KEY: misc_feature
<222> LOCATION: (39)..(58)
<223> OTHER INFORMATION: Xaa, if present, can be any naturally occurring
      amino acid; at least two Xaa must be present
<220> FEATURE:
<221> NAME/KEY: misc_feature
```

```
<222> LOCATION: (65)..(84)
<223> OTHER INFORMATION: Xaa, if present, can be any naturally occurring
      amino acid; at least two Xaa must be present
<220> FEATURE:
<221> NAME/KEY: misc_feature
<222> LOCATION: (88)..(107)
<223> OTHER INFORMATION: Xaa, if present, can be any naturally occurring
      amino acid; at least two Xaa must be present
<220> FEATURE:
<221> NAME/KEY: misc_feature
<222> LOCATION: (114)..(133)
<223> OTHER INFORMATION: Xaa, if present, can be any naturally occurring
      amino acid; at least two Xaa must be present
<220> FEATURE:
<221> NAME/KEY: misc_feature
<222> LOCATION: (142)..(161)
<223> OTHER INFORMATION: Xaa, if present, can be any naturally occurring
      amino acid; at least two Xaa must be present

<400> SEQUENCE: 2

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Tyr Arg Ile Thr Tyr
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Phe Thr Val Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Ala Thr Ile Ser Gly
            100                 105                 110

Leu Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Tyr Thr Ile Thr Val Tyr Ala Val Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Ile Ser Ile Asn Tyr Arg Thr
                165


<210> SEQ ID NO 3
<211> LENGTH: 10
<212> TYPE: PRT
<213> ORGANISM: Artificial Sequence
<220> FEATURE:
<223> OTHER INFORMATION: Synthetic: N-terminal leader

<400> SEQUENCE: 3

Met Gly Val Ser Asp Val Pro Arg Asp Leu
1               5                   10


<210> SEQ ID NO 4
<211> LENGTH: 9
<212> TYPE: PRT
<213> ORGANISM: Artificial Sequence
<220> FEATURE:
<223> OTHER INFORMATION: Synthetic: N-terminal leader

<400> SEQUENCE: 4

Gly Val Ser Asp Val Pro Arg Asp Leu
1               5
```

<210> SEQ ID NO 5
<211> LENGTH: 9
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(2)
<223> OTHER INFORMATION: Xaa can be any naturally occurring amino acid and may or may not be present; If one is present, Xaa is Met or Gly; if both are present, then Xaa Xaa is Met-Gly

<400> SEQUENCE: 5

Xaa Xaa Ser Asp Val Pro Arg Asp Leu
1 5

<210> SEQ ID NO 6
<211> LENGTH: 8
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(2)
<223> OTHER INFORMATION: Xaa can be any naturally occurring amino acid and may or may not be present; If one is present, Xaa is Met or Gly; if both are present, then Xaa Xaa is Met-Gly

<400> SEQUENCE: 6

Xaa Xaa Asp Val Pro Arg Asp Leu
1 5

<210> SEQ ID NO 7
<211> LENGTH: 7
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(2)
<223> OTHER INFORMATION: Xaa can be any naturally occurring amino acid and may or may not be present; If one is present, Xaa is Met or Gly; if both are present, then Xaa Xaa is Met-Gly

<400> SEQUENCE: 7

Xaa Xaa Val Pro Arg Asp Leu
1 5

<210> SEQ ID NO 8
<211> LENGTH: 6
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(2)
<223> OTHER INFORMATION: Xaa can be any naturally occurring amino acid and may or may not be present; If one is present, Xaa is Met or Gly; if both are present, then Xaa Xaa is Met-Gly

<400> SEQUENCE: 8

Xaa Xaa Pro Arg Asp Leu
1 5

<210> SEQ ID NO 9

<211> LENGTH: 5
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(2)
<223> OTHER INFORMATION: Xaa can be any naturally occurring amino acid and may or may not be present; If one is present, Xaa is Met or Gly; if both are present, then Xaa Xaa is Met-Gly

<400> SEQUENCE: 9

Xaa Xaa Arg Asp Leu
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic: N-terminal leader
<220> FEATURE:
<221> NAME/KEY: misc_feature
<222> LOCATION: (1)..(2)
<223> OTHER INFORMATION: Xaa can be any naturally occurring amino acid and may or may not be present; If one is present, Xaa is Met or Gly; if both are present, then Xaa Xaa is Met-Gly

<400> SEQUENCE: 10

Xaa Xaa Asp Leu
1

<210> SEQ ID NO 11
<211> LENGTH: 6
<212> TYPE: PRT
<213> ORGANISM: Artificial Sequence
<220> FEATURE:
<223> OTHER INFORMATION: Synthetic: N-terminal leader

<400> SEQUENCE: 11

Met Ala Ser Thr Ser Gly
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic: C-terminal tail

<400> SEQUENCE: 12

Glu Ile Glu Lys
1

<210> SEQ ID NO 13
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 13

Glu Gly Ser Gly Cys
1               5

<210> SEQ ID NO 14
<211> LENGTH: 7
<212> TYPE: PRT

<213> ORGANISM: Artificial Sequence
<220> FEATURE:
<223> OTHER INFORMATION: Synthetic: C-terminal tail

<400> SEQUENCE: 14

Glu Ile Glu Lys Pro Cys Gln
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 15

Glu Ile Glu Lys Pro Ser Gln
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 16

Glu Ile Glu Lys Pro
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 17

Glu Ile Glu Lys Pro Ser
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 18

Glu Ile Glu Lys Pro Cys
1               5

<210> SEQ ID NO 19
<211> LENGTH: 4
<212> TYPE: PRT
<213> ORGANISM: Artificial Sequence
<220> FEATURE:
<223> OTHER INFORMATION: Synthetic: C-terminal tail

<400> SEQUENCE: 19

Glu Ile Asp Lys
1

<210> SEQ ID NO 20
<211> LENGTH: 7
<212> TYPE: PRT
<213> ORGANISM: Artificial Sequence

```
<220> FEATURE:
<223> OTHER INFORMATION: Synthetic: C-terminal tail

<400> SEQUENCE: 20

Glu Ile Asp Lys Pro Cys Gln
1               5


<210> SEQ ID NO 21
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 21

Glu Ile Asp Lys Pro Ser Gln
1               5


<210> SEQ ID NO 22
<211> LENGTH: 6
<212> TYPE: PRT
<213> ORGANISM: Artificial Sequence
<220> FEATURE:
<223> OTHER INFORMATION: Synthetic: 6X His tail

<400> SEQUENCE: 22

His His His His His His
1               5


<210> SEQ ID NO 23
<211> LENGTH: 117
<212> TYPE: PRT
<213> ORGANISM: Artificial Sequence
<220> FEATURE:
<223> OTHER INFORMATION: Synthetic: PKE2 Adnectin 2270_C01

<400> SEQUENCE: 23

Met Ala Ser Thr Ser Gly Val Pro Arg Asp Leu Glu Val Val Ala Ala
1               5                   10                  15

Thr Pro Thr Ser Leu Leu Ile Ser Trp Asp Ala Pro Ala Val Thr Val
            20                  25                  30

Arg Tyr Tyr Arg Ile Thr Tyr Gly Trp Gln Val Gln Met Tyr Ser Asp
        35                  40                  45

Trp Gly Pro Leu Tyr Ile Tyr Lys Glu Phe Thr Val Pro Gly Ser Lys
    50                  55                  60

Ser Thr Ala Thr Ile Ser Gly Leu Lys Pro Gly Val Asp Tyr Thr Ile
65                  70                  75                  80

Thr Val Tyr Ala Val Thr Gly Ser Gly Glu Ser Pro Ala Ser Ser Lys
                85                  90                  95

Pro Ile Ser Ile Asn Tyr Arg Thr Glu Gly Asp Lys Pro Ser Gln His
            100                 105                 110

His His His His His
        115


<210> SEQ ID NO 24
<211> LENGTH: 116
<212> TYPE: PRT
<213> ORGANISM: Artificial Sequence
<220> FEATURE:
<223> OTHER INFORMATION: Synthetic: PKE2 Adnectin 2629_A09

<400> SEQUENCE: 24

Met Gly Val Ser Asp Val Pro Arg Asp Leu Glu Val Val Ala Ala Thr
```

-continued

```
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg His Val Gln Ile Tyr Ser Asp Leu
        35                  40                  45

Gly Pro Leu Tyr Ile Tyr Thr Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115


<210> SEQ ID NO 25
<211> LENGTH: 116
<212> TYPE: PRT
<213> ORGANISM: Artificial Sequence
<220> FEATURE:
<223> OTHER INFORMATION: Synthetic: PKE2 Adnectin 2629_A11

<400> SEQUENCE: 25

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg His Val His Ile Tyr Ser Asp Trp
        35                  40                  45

Gly Pro Met Tyr Ile Tyr Thr Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115


<210> SEQ ID NO 26
<211> LENGTH: 116
<212> TYPE: PRT
<213> ORGANISM: Artificial Sequence
<220> FEATURE:
<223> OTHER INFORMATION: Synthetic: PKE2 Adnectin 2629_C10

<400> SEQUENCE: 26

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Val Leu
        35                  40                  45

Gly Pro Leu Tyr Ile Tyr Thr Glu Phe Thr Val Pro Gly Ser Lys Ser
    50                  55                  60
```

-continued

```
Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115


<210> SEQ ID NO 27
<211> LENGTH: 116
<212> TYPE: PRT
<213> ORGANISM: Artificial Sequence
<220> FEATURE:
<223> OTHER INFORMATION: Synthetic: PKE2 Adnectin 2629_D09

<400> SEQUENCE: 27

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Met Tyr Ser Asp Leu
        35                  40                  45

Gly Pro Leu Tyr Val Tyr Ser Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115


<210> SEQ ID NO 28
<211> LENGTH: 116
<212> TYPE: PRT
<213> ORGANISM: Artificial Sequence
<220> FEATURE:
<223> OTHER INFORMATION: Synthetic: PKE2 Adnectin 2629_E05

<400> SEQUENCE: 28

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Phe Ser Asp Trp
        35                  40                  45

Gly Pro Leu Tyr Ile Tyr Thr Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115
```

<210> SEQ ID NO 29
<211> LENGTH: 116
<212> TYPE: PRT
<213> ORGANISM: Artificial Sequence
<220> FEATURE:
<223> OTHER INFORMATION: Synthetic: PKE2 Adnectin 2629_E06 (also referred to as ATI-1490)

<400> SEQUENCE: 29

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Asp Leu
        35                  40                  45

Gly Pro Leu Tyr Ile Tyr Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115
```

<210> SEQ ID NO 30
<211> LENGTH: 116
<212> TYPE: PRT
<213> ORGANISM: Artificial Sequence
<220> FEATURE:
<223> OTHER INFORMATION: Synthetic: PKE2 Adnectin 2629_F04

<400> SEQUENCE: 30

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val His Gln Tyr Ser Asp Trp
        35                  40                  45

Gly Pro Met Tyr Ile Tyr Asn Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115
```

<210> SEQ ID NO 31
<211> LENGTH: 116
<212> TYPE: PRT
<213> ORGANISM: Artificial Sequence
<220> FEATURE:
<223> OTHER INFORMATION: Synthetic: PKE2 Adnectin 2629_H01
<220> FEATURE:
<221> NAME/KEY: misc_feature

```
<222> LOCATION: (32)..(32)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid

<400> SEQUENCE: 31

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Xaa
            20                  25                  30

Tyr Tyr Arg Ile Thr Tyr Gly Arg Glu Val His Lys Asn Ser Asp Trp
        35                  40                  45

Gly Thr Leu Tyr Ile Tyr Thr Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Xaa Ala Val Thr Gly Ser Gly Glu Xaa Pro Ala Ser Ser Lys Pro
                85                  90                  95

Ile Ser Ile Asn Tyr Arg Thr Glu Ile Asp Lys Xaa Ser Gln His His
            100                 105                 110

His His His His
        115


<210> SEQ ID NO 32
<211> LENGTH: 116
<212> TYPE: PRT
<213> ORGANISM: Artificial Sequence
<220> FEATURE:
<223> OTHER INFORMATION: Synthetic: PKE2 Adnectin 2629_H06

<400> SEQUENCE: 32

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Asp Leu
        35                  40                  45

Gly Pro Leu Tyr Ile Tyr Ala Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115


<210> SEQ ID NO 33
<211> LENGTH: 116
<212> TYPE: PRT
```

```
<213> ORGANISM: Artificial Sequence
<220> FEATURE:
<223> OTHER INFORMATION: Synthetic: PKE2 Adnectin 2629_H07

<400> SEQUENCE: 33

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val His Leu Tyr Ser Asp Trp
        35                  40                  45

Gly Pro Met Tyr Ile Tyr Thr Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115


<210> SEQ ID NO 34
<211> LENGTH: 116
<212> TYPE: PRT
<213> ORGANISM: Artificial Sequence
<220> FEATURE:
<223> OTHER INFORMATION: Synthetic: PKE2 Adnectin 2630_A02

<400> SEQUENCE: 34

Met Gly Val Ser Asp Val Pro Arg Asp Leu Glu Val Val Ala Thr Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg His Val Gln Met Tyr Ser Asp Leu
        35                  40                  45

Gly Pro Leu Tyr Ile Phe Ser Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115


<210> SEQ ID NO 35
<211> LENGTH: 116
<212> TYPE: PRT
<213> ORGANISM: Artificial Sequence
<220> FEATURE:
<223> OTHER INFORMATION: Synthetic: PKE2 Adnectin 2630_A11

<400> SEQUENCE: 35

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30
```

Tyr Tyr Arg Ile Thr Tyr Gly Arg Glu Val His Met Tyr Ser Asp Phe
35 40 45

Gly Pro Met Tyr Ile Tyr Thr Glu Phe Thr Val Pro Gly Ser Lys Ser
50 55 60

Thr Ala Thr Ile Ser Gly Leu Lys Pro Gly Val Asp Tyr Thr Ile Thr
65 70 75 80

Val Tyr Ala Val Thr Gly Ser Gly Glu Ser Pro Ala Ser Ser Lys Pro
85 90 95

Ile Ser Ile Asn Tyr Arg Thr Glu Ile Asp Lys Pro Ser Gln His His
100 105 110

His His His His
115

<210> SEQ ID NO 36
<211> LENGTH: 116
<212> TYPE: PRT
<213> ORGANISM: Artificial Sequence
<220> FEATURE:
<223> OTHER INFORMATION: Synthetic: PKE2 Adnectin 2630_D02

<400> SEQUENCE: 36

Met Gly Val Ser Asp Val Pro Arg Asp Leu Glu Val Val Ala Ala Thr
1 5 10 15

Pro Thr Ser Leu Leu Ile Ser Trp Asp Ala Pro Ala Val Thr Val Arg
20 25 30

Tyr Tyr Arg Ile Thr Tyr Gly Arg Glu Val Gln Lys Tyr Ser Asp Trp
35 40 45

Gly Pro Leu Tyr Ile Tyr Asn Glu Phe Thr Val Pro Gly Ser Lys Ser
50 55 60

Thr Ala Thr Ile Ser Gly Leu Lys Pro Gly Val Asp Tyr Thr Ile Thr
65 70 75 80

Val Tyr Ala Val Thr Gly Ser Gly Glu Ser Pro Ala Ser Ser Lys Pro
85 90 95

Ile Ser Ile Asn Tyr Arg Thr Glu Ile Asp Lys Pro Ser Gln His His
100 105 110

His His His His
115

<210> SEQ ID NO 37
<211> LENGTH: 116
<212> TYPE: PRT
<213> ORGANISM: Artificial Sequence
<220> FEATURE:
<223> OTHER INFORMATION: Synthetic: PKE2 Adnectin 2630_D10

<400> SEQUENCE: 37

Met Gly Val Ser Asp Val Pro Arg Asp Leu Glu Val Val Ala Ala Thr
1 5 10 15

Pro Thr Ser Leu Leu Ile Ser Trp Asp Ala Pro Ala Val Thr Val Arg
20 25 30

Tyr Tyr Arg Ile Thr Tyr Gly Arg Glu Val Gln Met Tyr Ser Asp Leu
35 40 45

Gly Pro Leu Tyr Ile Tyr Asn Glu Phe Thr Val Pro Gly Ser Lys Ser
50 55 60

Thr Ala Thr Ile Ser Gly Leu Lys Pro Gly Val Asp Tyr Thr Ile Thr
65 70 75 80

Val Tyr Ala Val Thr Gly Ser Gly Glu Ser Pro Ala Ser Ser Lys Pro

```
                85                  90                  95

Ile Ser Ile Asn Tyr Arg Thr Glu Ile Asp Lys Pro Ser Gln His His
            100                 105                 110

His His His His
        115


<210> SEQ ID NO 38
<211> LENGTH: 116
<212> TYPE: PRT
<213> ORGANISM: Artificial Sequence
<220> FEATURE:
<223> OTHER INFORMATION: Synthetic: PKE2 Adnectin 2630_F04

<400> SEQUENCE: 38

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Met Tyr Ser Asp Leu
        35                  40                  45

Gly Pro Leu Tyr Ile Tyr Thr Glu Phe Thr Val Pro Gly Ser Lys Ser
    50                  55                  60

Thr Ala Thr Ile Ser Gly Leu Lys Pro Gly Val Gly Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115


<210> SEQ ID NO 39
<211> LENGTH: 116
<212> TYPE: PRT
<213> ORGANISM: Artificial Sequence
<220> FEATURE:
<223> OTHER INFORMATION: Synthetic: PKE2 Adnectin 2630_G03

<400> SEQUENCE: 39

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg His Val Gln Ile Tyr Ser Asp Leu
        35                  40                  45

Gly Pro Leu Tyr Ile Tyr Asn Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115


<210> SEQ ID NO 40
<211> LENGTH: 116
```

<212> TYPE: PRT
<213> ORGANISM: Artificial Sequence
<220> FEATURE:
<223> OTHER INFORMATION: Synthetic: PKE2 Adnectin 2630_G10

<400> SEQUENCE: 40

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Ile Tyr Ser Asp Trp
        35                  40                  45

Gly Pro Leu Tyr Ile Tyr Asn Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115
```

<210> SEQ ID NO 41
<211> LENGTH: 116
<212> TYPE: PRT
<213> ORGANISM: Artificial Sequence
<220> FEATURE:
<223> OTHER INFORMATION: Synthetic: PKE2 Adnectin 2630_H03
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid

<400> SEQUENCE: 41

```
Met Gly Val Ser Asp Val Pro Arg Asp Leu Glu Val Val Ala Ala Thr
1               5                   10                  15

Xaa Thr Ser Leu Leu Ile Ser Trp Asp Ala Pro Ala Val Thr Val Xaa
            20                  25                  30

Tyr Tyr Arg Ile Thr Tyr Gly Arg Glu Val Gln Lys Tyr Ser Asp Trp
        35                  40                  45

Gly Pro Leu Tyr Ile Tyr Gln Glu Phe Thr Val Pro Gly Ser Xaa Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Xaa Ser Gln His His
            100                 105                 110

His His His His
```

115

<210> SEQ ID NO 42
<211> LENGTH: 116
<212> TYPE: PRT
<213> ORGANISM: Artificial Sequence
<220> FEATURE:
<223> OTHER INFORMATION: Synthetic: PKE2 Adnectin 2631_B04

<400> SEQUENCE: 42

```
Met Gly Val Ser Asp Val Pro Arg Asp Leu Glu Val Val Ala Ala Thr
1               5                   10                  15

Pro Thr Ser Leu Leu Ile Ser Trp Asp Val Pro Ala Val Thr Val Arg
            20                  25                  30

Tyr Tyr Arg Ile Thr Tyr Gly Arg His Val His Leu Tyr Ser Glu Phe
        35                  40                  45

Gly Pro Met Tyr Ile Tyr Asn Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115
```

<210> SEQ ID NO 43
<211> LENGTH: 116
<212> TYPE: PRT
<213> ORGANISM: Artificial Sequence
<220> FEATURE:
<223> OTHER INFORMATION: Synthetic: PKE2 Adnectin 2631_E03

<400> SEQUENCE: 43

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Asp Val His Met Tyr Ser Asp Trp
        35                  40                  45

Gly Pro Met Tyr Ile Tyr Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115
```

<210> SEQ ID NO 44
<211> LENGTH: 116
<212> TYPE: PRT
<213> ORGANISM: Artificial Sequence
<220> FEATURE:
<223> OTHER INFORMATION: Synthetic: PKE2 Adnectin 2631_G01

<400> SEQUENCE: 44

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg His Val Gln Ile Tyr Ser Asp Trp
        35                  40                  45

Gly Pro Leu Tyr Ile Tyr Asn Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115


<210> SEQ ID NO 45
<211> LENGTH: 116
<212> TYPE: PRT
<213> ORGANISM: Artificial Sequence
<220> FEATURE:
<223> OTHER INFORMATION: Synthetic: PKE2 Adnectin 2631_G03

<400> SEQUENCE: 45

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Tyr Val Gln Leu Tyr Ser Asp Trp
        35                  40                  45

Gly Pro Met Tyr Ile Tyr Thr Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115


<210> SEQ ID NO 46
<211> LENGTH: 116
<212> TYPE: PRT
<213> ORGANISM: Artificial Sequence
<220> FEATURE:
<223> OTHER INFORMATION: Synthetic: PKE2 Adnectin 2631_H09

<400> SEQUENCE: 46

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Gln Val Gln Val Phe Ser Asp Leu
        35                  40                  45

Gly Pro Leu Tyr Ile Tyr Asn Glu Phe Thr Val Pro Gly Ser Lys Ser
```

```
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115


<210> SEQ ID NO 47
<211> LENGTH: 116
<212> TYPE: PRT
<213> ORGANISM: Artificial Sequence
<220> FEATURE:
<223> OTHER INFORMATION: Synthetic: PKE2 Adnectin 2632_G01

<400> SEQUENCE: 47

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Gln Val Gln Ile Tyr Ser Asp Trp
        35                  40                  45

Gly Pro Leu Tyr Ile Tyr Asn Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110

His His His His
        115


<210> SEQ ID NO 48
<211> LENGTH: 116
<212> TYPE: PRT
<213> ORGANISM: Artificial Sequence
<220> FEATURE:
<223> OTHER INFORMATION: Synthetic: PKE2 Adnectin 4079_A04

<400> SEQUENCE: 48

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Gln Val Gln Met Tyr Ser Asp Trp
        35                  40                  45

Gly Pro Leu Tyr Ile Tyr Ala Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln His His
            100                 105                 110
```

His His His His
        115

<210> SEQ ID NO 49
<211> LENGTH: 111
<212> TYPE: PRT
<213> ORGANISM: Artificial Sequence
<220> FEATURE:
<223> OTHER INFORMATION: Synthetic: 2270_C01 w/o his tag

<400> SEQUENCE: 49

```
Met Ala Ser Thr Ser Gly Val Pro Arg Asp Leu Glu Val Val Ala Ala
1               5                   10                  15

Thr Pro Thr Ser Leu Leu Ile Ser Trp Asp Ala Pro Ala Val Thr Val
            20                  25                  30

Arg Tyr Tyr Arg Ile Thr Tyr Gly Trp Gln Val Gln Met Tyr Ser Asp
        35                  40                  45

Trp Gly Pro Leu Tyr Ile Tyr Lys Glu Phe Thr Val Pro Gly Ser Lys
    50                  55                  60

Ser Thr Ala Thr Ile Ser Gly Leu Lys Pro Gly Val Asp Tyr Thr Ile
65                  70                  75                  80

Thr Val Tyr Ala Val Thr Gly Ser Gly Glu Ser Pro Ala Ser Ser Lys
                85                  90                  95

Pro Ile Ser Ile Asn Tyr Arg Thr Glu Gly Asp Lys Pro Ser Gln
            100                 105                 110
```

<210> SEQ ID NO 50
<211> LENGTH: 110
<212> TYPE: PRT
<213> ORGANISM: Artificial Sequence
<220> FEATURE:
<223> OTHER INFORMATION: Synthetic: 2629_A09 w/o his tag

<400> SEQUENCE: 50

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg His Val Gln Ile Tyr Ser Asp Leu
        35                  40                  45

Gly Pro Leu Tyr Ile Tyr Thr Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110
```

<210> SEQ ID NO 51
<211> LENGTH: 110
<212> TYPE: PRT
<213> ORGANISM: Artificial Sequence
<220> FEATURE:
<223> OTHER INFORMATION: Synthetic: 2629_A11 w/o his tag

<400> SEQUENCE: 51

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
```

```
            20                  25                  30

Tyr Tyr Arg Ile Thr Tyr Gly Arg His Val His Ile Tyr Ser Asp Trp
        35                  40                  45

Gly Pro Met Tyr Ile Tyr Thr Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110


<210> SEQ ID NO 52
<211> LENGTH: 110
<212> TYPE: PRT
<213> ORGANISM: Artificial Sequence
<220> FEATURE:
<223> OTHER INFORMATION: Synthetic: 2629_C10 w/o his tag

<400> SEQUENCE: 52

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Val Leu
        35                  40                  45

Gly Pro Leu Tyr Ile Tyr Thr Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110


<210> SEQ ID NO 53
<211> LENGTH: 110
<212> TYPE: PRT
<213> ORGANISM: Artificial Sequence
<220> FEATURE:
<223> OTHER INFORMATION: Synthetic: 2629_D09 w/o his tag

<400> SEQUENCE: 53

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Met Tyr Ser Asp Leu
        35                  40                  45

Gly Pro Leu Tyr Val Tyr Ser Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110
```

<210> SEQ ID NO 54
<211> LENGTH: 110
<212> TYPE: PRT
<213> ORGANISM: Artificial Sequence
<220> FEATURE:
<223> OTHER INFORMATION: Synthetic: 2629_E05 w/o his tag

<400> SEQUENCE: 54

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Phe Ser Asp Trp
        35                  40                  45

Gly Pro Leu Tyr Ile Tyr Thr Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110
```

<210> SEQ ID NO 55
<211> LENGTH: 110
<212> TYPE: PRT
<213> ORGANISM: Artificial Sequence
<220> FEATURE:
<223> OTHER INFORMATION: Synthetic: 2629_E06 w/o his tag

<400> SEQUENCE: 55

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Asp Leu
        35                  40                  45

Gly Pro Leu Tyr Ile Tyr Gln Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110
```

<210> SEQ ID NO 56
<211> LENGTH: 110
<212> TYPE: PRT
<213> ORGANISM: Artificial Sequence
<220> FEATURE:
<223> OTHER INFORMATION: Synthetic: 2629_F04 w/o his tag

<400> SEQUENCE: 56

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val His Gln Tyr Ser Asp Trp
```

```
        35                  40                  45

Gly Pro Met Tyr Ile Tyr Asn Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110


<210> SEQ ID NO 57
<211> LENGTH: 110
<212> TYPE: PRT
<213> ORGANISM: Artificial Sequence
<220> FEATURE:
<223> OTHER INFORMATION: Synthetic: 2629_H01 w/o his tag
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid

<400> SEQUENCE: 57

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Xaa
            20                  25                  30

Tyr Tyr Arg Ile Thr Tyr Gly Arg Glu Val His Lys Asn Ser Asp Trp
        35                  40                  45

Gly Thr Leu Tyr Ile Tyr Thr Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Xaa Ala Val Thr Gly Ser Gly Glu Xaa Pro Ala Ser Ser Lys Pro
                85                  90                  95

Ile Ser Ile Asn Tyr Arg Thr Glu Ile Asp Lys Xaa Ser Gln
            100                 105                 110


<210> SEQ ID NO 58
<211> LENGTH: 110
<212> TYPE: PRT
<213> ORGANISM: Artificial Sequence
<220> FEATURE:
<223> OTHER INFORMATION: Synthetic: 2629_H06 w/o his tag

<400> SEQUENCE: 58

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Asp Leu
        35                  40                  45
```

Gly Pro Leu Tyr Ile Tyr Ala Glu Phe Thr Val Pro Gly Ser Lys Ser
50 55 60

Thr Ala Thr Ile Ser Gly Leu Lys Pro Gly Val Asp Tyr Thr Ile Thr
65 70 75 80

Val Tyr Ala Val Thr Gly Ser Gly Glu Ser Pro Ala Ser Ser Lys Pro
85 90 95

Ile Ser Ile Asn Tyr Arg Thr Glu Ile Asp Lys Pro Ser Gln
100 105 110

<210> SEQ ID NO 59
<211> LENGTH: 110
<212> TYPE: PRT
<213> ORGANISM: Artificial Sequence
<220> FEATURE:
<223> OTHER INFORMATION: Synthetic: 2629_H07 w/o his tag

<400> SEQUENCE: 59

Met Gly Val Ser Asp Val Pro Arg Asp Leu Glu Val Val Ala Ala Thr
1 5 10 15

Pro Thr Ser Leu Leu Ile Ser Trp Asp Ala Pro Ala Val Thr Val Arg
20 25 30

Tyr Tyr Arg Ile Thr Tyr Gly Arg Glu Val His Leu Tyr Ser Asp Trp
35 40 45

Gly Pro Met Tyr Ile Tyr Thr Glu Phe Thr Val Pro Gly Ser Lys Ser
50 55 60

Thr Ala Thr Ile Ser Gly Leu Lys Pro Gly Val Asp Tyr Thr Ile Thr
65 70 75 80

Val Tyr Ala Val Thr Gly Ser Gly Glu Ser Pro Ala Ser Ser Lys Pro
85 90 95

Ile Ser Ile Asn Tyr Arg Thr Glu Ile Asp Lys Pro Ser Gln
100 105 110

<210> SEQ ID NO 60
<211> LENGTH: 110
<212> TYPE: PRT
<213> ORGANISM: Artificial Sequence
<220> FEATURE:
<223> OTHER INFORMATION: Synthetic: 2630_A02 w/o his tag

<400> SEQUENCE: 60

Met Gly Val Ser Asp Val Pro Arg Asp Leu Glu Val Val Ala Thr Thr
1 5 10 15

Pro Thr Ser Leu Leu Ile Ser Trp Asp Ala Pro Ala Val Thr Val Arg
20 25 30

Tyr Tyr Arg Ile Thr Tyr Gly Arg His Val Gln Met Tyr Ser Asp Leu
35 40 45

Gly Pro Leu Tyr Ile Phe Ser Glu Phe Thr Val Pro Gly Ser Lys Ser
50 55 60

Thr Ala Thr Ile Ser Gly Leu Lys Pro Gly Val Asp Tyr Thr Ile Thr
65 70 75 80

Val Tyr Ala Val Thr Gly Ser Gly Glu Ser Pro Ala Ser Ser Lys Pro
85 90 95

Ile Ser Ile Asn Tyr Arg Thr Glu Ile Asp Lys Pro Ser Gln
100 105 110

<210> SEQ ID NO 61
<211> LENGTH: 110
<212> TYPE: PRT

<213> ORGANISM: Artificial Sequence
<220> FEATURE:
<223> OTHER INFORMATION: Synthetic: 2630_A11 w/o his tag

<400> SEQUENCE: 61

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val His Met Tyr Ser Asp Phe
        35                  40                  45

Gly Pro Met Tyr Ile Tyr Thr Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110
```

<210> SEQ ID NO 62
<211> LENGTH: 110
<212> TYPE: PRT
<213> ORGANISM: Artificial Sequence
<220> FEATURE:
<223> OTHER INFORMATION: Synthetic: 2630_D02 w/o his tag

<400> SEQUENCE: 62

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Lys Tyr Ser Asp Trp
        35                  40                  45

Gly Pro Leu Tyr Ile Tyr Asn Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110
```

<210> SEQ ID NO 63
<211> LENGTH: 110
<212> TYPE: PRT
<213> ORGANISM: Artificial Sequence
<220> FEATURE:
<223> OTHER INFORMATION: Synthetic: 2630_D10 w/o his tag

<400> SEQUENCE: 63

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Glu Val Gln Met Tyr Ser Asp Leu
        35                  40                  45

Gly Pro Leu Tyr Ile Tyr Asn Glu Phe Thr Val Pro Gly Ser Lys Ser
    50                  55                  60
```

Thr Ala Thr Ile Ser Gly Leu Lys Pro Gly Val Asp Tyr Thr Ile Thr
65 70 75 80

Val Tyr Ala Val Thr Gly Ser Gly Glu Ser Pro Ala Ser Ser Lys Pro
85 90 95

Ile Ser Ile Asn Tyr Arg Thr Glu Ile Asp Lys Pro Ser Gln
100 105 110

<210> SEQ ID NO 64
<211> LENGTH: 110
<212> TYPE: PRT
<213> ORGANISM: Artificial Sequence
<220> FEATURE:
<223> OTHER INFORMATION: Synthetic: 2630_F04 w/o his tag

<400> SEQUENCE: 64

Met Gly Val Ser Asp Val Pro Arg Asp Leu Glu Val Val Ala Ala Thr
1 5 10 15

Pro Thr Ser Leu Leu Ile Ser Trp Asp Ala Pro Ala Val Thr Val Arg
20 25 30

Tyr Tyr Arg Ile Thr Tyr Gly Arg Glu Val Gln Met Tyr Ser Asp Leu
35 40 45

Gly Pro Leu Tyr Ile Tyr Thr Glu Phe Thr Val Pro Gly Ser Lys Ser
50 55 60

Thr Ala Thr Ile Ser Gly Leu Lys Pro Gly Val Gly Tyr Thr Ile Thr
65 70 75 80

Val Tyr Ala Val Thr Gly Ser Gly Glu Ser Pro Ala Ser Ser Lys Pro
85 90 95

Ile Ser Ile Asn Tyr Arg Thr Glu Ile Asp Lys Pro Ser Gln
100 105 110

<210> SEQ ID NO 65
<211> LENGTH: 110
<212> TYPE: PRT
<213> ORGANISM: Artificial Sequence
<220> FEATURE:
<223> OTHER INFORMATION: Synthetic: 2630_G03 w/o his tag

<400> SEQUENCE: 65

Met Gly Val Ser Asp Val Pro Arg Asp Leu Glu Val Val Ala Ala Thr
1 5 10 15

Pro Thr Ser Leu Leu Ile Ser Trp Asp Ala Pro Ala Val Thr Val Arg
20 25 30

Tyr Tyr Arg Ile Thr Tyr Gly Arg His Val Gln Ile Tyr Ser Asp Leu
35 40 45

Gly Pro Leu Tyr Ile Tyr Asn Glu Phe Thr Val Pro Gly Ser Lys Ser
50 55 60

Thr Ala Thr Ile Ser Gly Leu Lys Pro Gly Val Asp Tyr Thr Ile Thr
65 70 75 80

Val Tyr Ala Val Thr Gly Ser Gly Glu Ser Pro Ala Ser Ser Lys Pro
85 90 95

Ile Ser Ile Asn Tyr Arg Thr Glu Ile Asp Lys Pro Ser Gln
100 105 110

<210> SEQ ID NO 66
<211> LENGTH: 110
<212> TYPE: PRT
<213> ORGANISM: Artificial Sequence
<220> FEATURE:
<223> OTHER INFORMATION: Synthetic: 2630_G10 w/o his tag

<400> SEQUENCE: 66

Met Gly Val Ser Asp Val Pro Arg Asp Leu Glu Val Val Ala Ala Thr
1 5 10 15

Pro Thr Ser Leu Leu Ile Ser Trp Asp Ala Pro Ala Val Thr Val Arg
20 25 30

Tyr Tyr Arg Ile Thr Tyr Gly Arg Glu Val Gln Ile Tyr Ser Asp Trp
35 40 45

Gly Pro Leu Tyr Ile Tyr Asn Glu Phe Thr Val Pro Gly Ser Lys Ser
50 55 60

Thr Ala Thr Ile Ser Gly Leu Lys Pro Gly Val Asp Tyr Thr Ile Thr
65 70 75 80

Val Tyr Ala Val Thr Gly Ser Gly Glu Ser Pro Ala Ser Ser Lys Pro
85 90 95

Ile Ser Ile Asn Tyr Arg Thr Glu Ile Asp Lys Pro Ser Gln
100 105 110

<210> SEQ ID NO 67
<211> LENGTH: 110
<212> TYPE: PRT
<213> ORGANISM: Artificial Sequence
<220> FEATURE:
<223> OTHER INFORMATION: Synthetic: 2630_H03 w/o his tag
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid

<400> SEQUENCE: 67

Met Gly Val Ser Asp Val Pro Arg Asp Leu Glu Val Val Ala Ala Thr
1 5 10 15

Xaa Thr Ser Leu Leu Ile Ser Trp Asp Ala Pro Ala Val Thr Val Xaa
20 25 30

Tyr Tyr Arg Ile Thr Tyr Gly Arg Glu Val Gln Lys Tyr Ser Asp Trp
35 40 45

Gly Pro Leu Tyr Ile Tyr Gln Glu Phe Thr Val Pro Gly Ser Xaa Ser
50 55 60

Thr Ala Thr Ile Ser Gly Leu Lys Pro Gly Val Asp Tyr Thr Ile Thr
65 70 75 80

Val Tyr Ala Val Thr Gly Ser Gly Glu Ser Pro Ala Ser Ser Lys Pro
85 90 95

Ile Ser Ile Asn Tyr Arg Thr Glu Ile Asp Lys Xaa Ser Gln
100 105 110

<210> SEQ ID NO 68
<211> LENGTH: 110
<212> TYPE: PRT
<213> ORGANISM: Artificial Sequence
<220> FEATURE:
<223> OTHER INFORMATION: Synthetic: 2631_B04 w/o his tag

<400> SEQUENCE: 68

Met Gly Val Ser Asp Val Pro Arg Asp Leu Glu Val Val Ala Ala Thr
1 5 10 15

Pro Thr Ser Leu Leu Ile Ser Trp Asp Val Pro Ala Val Thr Val Arg
20 25 30

Tyr Tyr Arg Ile Thr Tyr Gly Arg His Val His Leu Tyr Ser Glu Phe
35 40 45

Gly Pro Met Tyr Ile Tyr Asn Glu Phe Thr Val Pro Gly Ser Lys Ser
50 55 60

Thr Ala Thr Ile Ser Gly Leu Lys Pro Gly Val Asp Tyr Thr Ile Thr
65 70 75 80

Val Tyr Ala Val Thr Gly Ser Gly Glu Ser Pro Ala Ser Ser Lys Pro
85 90 95

Ile Ser Ile Asn Tyr Arg Thr Glu Ile Asp Lys Pro Ser Gln
100 105 110

<210> SEQ ID NO 69
<211> LENGTH: 110
<212> TYPE: PRT
<213> ORGANISM: Artificial Sequence
<220> FEATURE:
<223> OTHER INFORMATION: Synthetic: 2631_E03 w/o his tag

<400> SEQUENCE: 69

Met Gly Val Ser Asp Val Pro Arg Asp Leu Glu Val Val Ala Ala Thr
1 5 10 15

Pro Thr Ser Leu Leu Ile Ser Trp Asp Ala Pro Ala Val Thr Val Arg
20 25 30

Tyr Tyr Arg Ile Thr Tyr Gly Arg Asp Val His Met Tyr Ser Asp Trp
35 40 45

Gly Pro Met Tyr Ile Tyr Gln Glu Phe Thr Val Pro Gly Ser Lys Ser
50 55 60

Thr Ala Thr Ile Ser Gly Leu Lys Pro Gly Val Asp Tyr Thr Ile Thr
65 70 75 80

Val Tyr Ala Val Thr Gly Ser Gly Glu Ser Pro Ala Ser Ser Lys Pro
85 90 95

Ile Ser Ile Asn Tyr Arg Thr Glu Ile Asp Lys Pro Ser Gln
100 105 110

<210> SEQ ID NO 70
<211> LENGTH: 110
<212> TYPE: PRT
<213> ORGANISM: Artificial Sequence
<220> FEATURE:
<223> OTHER INFORMATION: Synthetic: 2631_G01 w/o his tag

<400> SEQUENCE: 70

Met Gly Val Ser Asp Val Pro Arg Asp Leu Glu Val Val Ala Ala Thr
1 5 10 15

Pro Thr Ser Leu Leu Ile Ser Trp Asp Ala Pro Ala Val Thr Val Arg
20 25 30

Tyr Tyr Arg Ile Thr Tyr Gly Arg His Val Gln Ile Tyr Ser Asp Trp
35 40 45

Gly Pro Leu Tyr Ile Tyr Asn Glu Phe Thr Val Pro Gly Ser Lys Ser
50 55 60

Thr Ala Thr Ile Ser Gly Leu Lys Pro Gly Val Asp Tyr Thr Ile Thr
65 70 75 80

-continued

```
Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110


<210> SEQ ID NO 71
<211> LENGTH: 110
<212> TYPE: PRT
<213> ORGANISM: Artificial Sequence
<220> FEATURE:
<223> OTHER INFORMATION: Synthetic: 2631_G03 w/o his tag

<400> SEQUENCE: 71

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Tyr Val Gln Leu Tyr Ser Asp Trp
        35                  40                  45

Gly Pro Met Tyr Ile Tyr Thr Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110


<210> SEQ ID NO 72
<211> LENGTH: 110
<212> TYPE: PRT
<213> ORGANISM: Artificial Sequence
<220> FEATURE:
<223> OTHER INFORMATION: Synthetic: 2631_H09 w/o his tag

<400> SEQUENCE: 72

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Gln Val Gln Val Phe Ser Asp Leu
        35                  40                  45

Gly Pro Leu Tyr Ile Tyr Asn Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110


<210> SEQ ID NO 73
<211> LENGTH: 110
<212> TYPE: PRT
<213> ORGANISM: Artificial Sequence
<220> FEATURE:
<223> OTHER INFORMATION: Synthetic: 2632_G01 w/o his tag

<400> SEQUENCE: 73

Met Gly Val Ser Asp Val Pro Arg Asp Leu Glu Val Val Ala Ala Thr
```

```
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Gln Val Gln Ile Tyr Ser Asp Trp
        35                  40                  45

Gly Pro Leu Tyr Ile Tyr Asn Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110


<210> SEQ ID NO 74
<211> LENGTH: 110
<212> TYPE: PRT
<213> ORGANISM: Artificial Sequence
<220> FEATURE:
<223> OTHER INFORMATION: Synthetic: 4079_A04 w/o his tag

<400> SEQUENCE: 74

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Arg Gln Val Gln Met Tyr Ser Asp Trp
        35                  40                  45

Gly Pro Leu Tyr Ile Tyr Ala Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Ile Asp Lys Pro Ser Gln
            100                 105                 110


<210> SEQ ID NO 75
<211> LENGTH: 93
<212> TYPE: PRT
<213> ORGANISM: Artificial Sequence
<220> FEATURE:
<223> OTHER INFORMATION: Synthetic: 2270_C01 core

<400> SEQUENCE: 75

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Trp Gln Val
            20                  25                  30

Gln Met Tyr Ser Asp Trp Gly Pro Leu Tyr Ile Tyr Lys Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90
```

<210> SEQ ID NO 76
<211> LENGTH: 93
<212> TYPE: PRT
<213> ORGANISM: Artificial Sequence
<220> FEATURE:
<223> OTHER INFORMATION: Synthetic: 2629_A09 core

<400> SEQUENCE: 76

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg His Val
            20                  25                  30

Gln Ile Tyr Ser Asp Leu Gly Pro Leu Tyr Ile Tyr Thr Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90
```

<210> SEQ ID NO 77
<211> LENGTH: 93
<212> TYPE: PRT
<213> ORGANISM: Artificial Sequence
<220> FEATURE:
<223> OTHER INFORMATION: Synthetic: 2629_A11 core

<400> SEQUENCE: 77

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg His Val
            20                  25                  30

His Ile Tyr Ser Asp Trp Gly Pro Met Tyr Ile Tyr Thr Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90
```

<210> SEQ ID NO 78
<211> LENGTH: 93
<212> TYPE: PRT
<213> ORGANISM: Artificial Sequence
<220> FEATURE:
<223> OTHER INFORMATION: Synthetic: 2629_C10 core

<400> SEQUENCE: 78

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Val Leu Gly Pro Leu Tyr Ile Tyr Thr Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
```

```
65                  70                  75                  80

Pro Ala Ser Ser Lys Pro Ile Ser Ile Asn Tyr Arg Thr
                85                  90


<210> SEQ ID NO 79
<211> LENGTH: 93
<212> TYPE: PRT
<213> ORGANISM: Artificial Sequence
<220> FEATURE:
<223> OTHER INFORMATION: Synthetic: 2629_D09 core

<400> SEQUENCE: 79

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Met Tyr Ser Asp Leu Gly Pro Leu Tyr Val Tyr Ser Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90


<210> SEQ ID NO 80
<211> LENGTH: 93
<212> TYPE: PRT
<213> ORGANISM: Artificial Sequence
<220> FEATURE:
<223> OTHER INFORMATION: Synthetic: 2629_E05 core

<400> SEQUENCE: 80

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Phe Ser Asp Trp Gly Pro Leu Tyr Ile Tyr Thr Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90


<210> SEQ ID NO 81
<211> LENGTH: 93
<212> TYPE: PRT
<213> ORGANISM: Artificial Sequence
<220> FEATURE:
<223> OTHER INFORMATION: Synthetic: 2629_E06 core

<400> SEQUENCE: 81

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Leu Gly Pro Leu Tyr Ile Tyr Gln Glu Phe Thr
        35                  40                  45
```

```
Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90


<210> SEQ ID NO 82
<211> LENGTH: 93
<212> TYPE: PRT
<213> ORGANISM: Artificial Sequence
<220> FEATURE:
<223> OTHER INFORMATION: Synthetic: 2629_F04 core

<400> SEQUENCE: 82

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

His Gln Tyr Ser Asp Trp Gly Pro Met Tyr Ile Tyr Asn Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90


<210> SEQ ID NO 83
<211> LENGTH: 93
<212> TYPE: PRT
<213> ORGANISM: Artificial Sequence
<220> FEATURE:
<223> OTHER INFORMATION: Synthetic: 2629_H01 core
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid

<400> SEQUENCE: 83

Glu Val Val Ala Ala Thr Pro Thr Ser Leu Leu Ile Ser Trp Asp Ala
1               5                   10                  15

Pro Ala Val Thr Val Xaa Tyr Tyr Arg Ile Thr Tyr Gly Arg Glu Val
            20                  25                  30

His Lys Asn Ser Asp Trp Gly Thr Leu Tyr Ile Tyr Thr Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Xaa Ala Val Thr Gly Ser Gly Glu Xaa
65                  70                  75                  80

Pro Ala Ser Ser Lys Pro Ile Ser Ile Asn Tyr Arg Thr
                85                  90
```

<210> SEQ ID NO 84
<211> LENGTH: 93
<212> TYPE: PRT
<213> ORGANISM: Artificial Sequence
<220> FEATURE:
<223> OTHER INFORMATION: Synthetic: 2629_H06 core

<400> SEQUENCE: 84

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Leu Gly Pro Leu Tyr Ile Tyr Ala Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90
```

<210> SEQ ID NO 85
<211> LENGTH: 93
<212> TYPE: PRT
<213> ORGANISM: Artificial Sequence
<220> FEATURE:
<223> OTHER INFORMATION: Synthetic: 2629_H07 core

<400> SEQUENCE: 85

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

His Leu Tyr Ser Asp Trp Gly Pro Met Tyr Ile Tyr Thr Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90
```

<210> SEQ ID NO 86
<211> LENGTH: 93
<212> TYPE: PRT
<213> ORGANISM: Artificial Sequence
<220> FEATURE:
<223> OTHER INFORMATION: Synthetic: 2630_A02 core

<400> SEQUENCE: 86

```
Glu Val Val Ala Thr Thr Pro Thr Ser Leu Leu Ile Ser Trp Asp Ala
1               5                   10                  15

Pro Ala Val Thr Val Arg Tyr Tyr Arg Ile Thr Tyr Gly Arg His Val
            20                  25                  30

Gln Met Tyr Ser Asp Leu Gly Pro Leu Tyr Ile Phe Ser Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80
```

```
Pro Ala Ser Ser Lys Pro Ile Ser Ile Asn Tyr Arg Thr
                85                  90


<210> SEQ ID NO 87
<211> LENGTH: 93
<212> TYPE: PRT
<213> ORGANISM: Artificial Sequence
<220> FEATURE:
<223> OTHER INFORMATION: Synthetic: 2630_A11 core

<400> SEQUENCE: 87

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

His Met Tyr Ser Asp Phe Gly Pro Met Tyr Ile Tyr Thr Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90


<210> SEQ ID NO 88
<211> LENGTH: 93
<212> TYPE: PRT
<213> ORGANISM: Artificial Sequence
<220> FEATURE:
<223> OTHER INFORMATION: Synthetic: 2630_D02 core

<400> SEQUENCE: 88

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Trp Gly Pro Leu Tyr Ile Tyr Asn Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90


<210> SEQ ID NO 89
<211> LENGTH: 93
<212> TYPE: PRT
<213> ORGANISM: Artificial Sequence
<220> FEATURE:
<223> OTHER INFORMATION: Synthetic: 2630_D10 core

<400> SEQUENCE: 89

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Met Tyr Ser Asp Leu Gly Pro Leu Tyr Ile Tyr Asn Glu Phe Thr
        35                  40                  45
```

-continued

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90

<210> SEQ ID NO 90
<211> LENGTH: 93
<212> TYPE: PRT
<213> ORGANISM: Artificial Sequence
<220> FEATURE:
<223> OTHER INFORMATION: Synthetic: 2630_F04 core

<400> SEQUENCE: 90

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Met Tyr Ser Asp Leu Gly Pro Leu Tyr Ile Tyr Thr Glu Phe Thr
        35                  40                  45

Val Pro Gly Ser Lys Ser Thr Ala Thr Ile Ser Gly Leu Lys Pro Gly
    50                  55                  60

Val Gly Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90

<210> SEQ ID NO 91
<211> LENGTH: 93
<212> TYPE: PRT
<213> ORGANISM: Artificial Sequence
<220> FEATURE:
<223> OTHER INFORMATION: Synthetic: 2630_G03 core

<400> SEQUENCE: 91

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg His Val
            20                  25                  30

Gln Ile Tyr Ser Asp Leu Gly Pro Leu Tyr Ile Tyr Asn Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90

<210> SEQ ID NO 92
<211> LENGTH: 93
<212> TYPE: PRT
<213> ORGANISM: Artificial Sequence
<220> FEATURE:
<223> OTHER INFORMATION: Synthetic: 2630_G10 core

<400> SEQUENCE: 92

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val

```
            20                  25                  30

Gln Ile Tyr Ser Asp Trp Gly Pro Leu Tyr Ile Tyr Asn Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90


<210> SEQ ID NO 93
<211> LENGTH: 93
<212> TYPE: PRT
<213> ORGANISM: Artificial Sequence
<220> FEATURE:
<223> OTHER INFORMATION: Synthetic: 2630_H03 core
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid

<400> SEQUENCE: 93

Glu Val Val Ala Ala Thr Xaa Thr Ser Leu Leu Ile Ser Trp Asp Ala
1               5                   10                  15

Pro Ala Val Thr Val Xaa Tyr Tyr Arg Ile Thr Tyr Gly Arg Glu Val
            20                  25                  30

Gln Lys Tyr Ser Asp Trp Gly Pro Leu Tyr Ile Tyr Gln Glu Phe Thr
        35                  40                  45

Val Pro Gly Ser Xaa Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90


<210> SEQ ID NO 94
<211> LENGTH: 93
<212> TYPE: PRT
<213> ORGANISM: Artificial Sequence
<220> FEATURE:
<223> OTHER INFORMATION: Synthetic: 2631_B04 core

<400> SEQUENCE: 94

Glu Val Val Ala Ala Thr Pro Thr Ser Leu Leu Ile Ser Trp Asp Val
1               5                   10                  15

Pro Ala Val Thr Val Arg Tyr Tyr Arg Ile Thr Tyr Gly Arg His Val
            20                  25                  30

His Leu Tyr Ser Glu Phe Gly Pro Met Tyr Ile Tyr Asn Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80
```

Pro Ala Ser Ser Lys Pro Ile Ser Ile Asn Tyr Arg Thr
85 90

<210> SEQ ID NO 95
<211> LENGTH: 93
<212> TYPE: PRT
<213> ORGANISM: Artificial Sequence
<220> FEATURE:
<223> OTHER INFORMATION: Synthetic: 2631_E03 core

<400> SEQUENCE: 95

Glu Val Val Ala Ala Thr Pro Thr Ser Leu Leu Ile Ser Trp Asp Ala
1 5 10 15

Pro Ala Val Thr Val Arg Tyr Tyr Arg Ile Thr Tyr Gly Arg Asp Val
20 25 30

His Met Tyr Ser Asp Trp Gly Pro Met Tyr Ile Tyr Gln Glu Phe Thr
35 40 45

Val Pro Gly Ser Lys Ser Thr Ala Thr Ile Ser Gly Leu Lys Pro Gly
50 55 60

Val Asp Tyr Thr Ile Thr Val Tyr Ala Val Thr Gly Ser Gly Glu Ser
65 70 75 80

Pro Ala Ser Ser Lys Pro Ile Ser Ile Asn Tyr Arg Thr
85 90

<210> SEQ ID NO 96
<211> LENGTH: 93
<212> TYPE: PRT
<213> ORGANISM: Artificial Sequence
<220> FEATURE:
<223> OTHER INFORMATION: Synthetic: 2631_G01 core

<400> SEQUENCE: 96

Glu Val Val Ala Ala Thr Pro Thr Ser Leu Leu Ile Ser Trp Asp Ala
1 5 10 15

Pro Ala Val Thr Val Arg Tyr Tyr Arg Ile Thr Tyr Gly Arg His Val
20 25 30

Gln Ile Tyr Ser Asp Trp Gly Pro Leu Tyr Ile Tyr Asn Glu Phe Thr
35 40 45

Val Pro Gly Ser Lys Ser Thr Ala Thr Ile Ser Gly Leu Lys Pro Gly
50 55 60

Val Asp Tyr Thr Ile Thr Val Tyr Ala Val Thr Gly Ser Gly Glu Ser
65 70 75 80

Pro Ala Ser Ser Lys Pro Ile Ser Ile Asn Tyr Arg Thr
85 90

<210> SEQ ID NO 97
<211> LENGTH: 93
<212> TYPE: PRT
<213> ORGANISM: Artificial Sequence
<220> FEATURE:
<223> OTHER INFORMATION: Synthetic: 2631_G03 core

<400> SEQUENCE: 97

Glu Val Val Ala Ala Thr Pro Thr Ser Leu Leu Ile Ser Trp Asp Ala
1 5 10 15

Pro Ala Val Thr Val Arg Tyr Tyr Arg Ile Thr Tyr Gly Arg Tyr Val
20 25 30

Gln Leu Tyr Ser Asp Trp Gly Pro Met Tyr Ile Tyr Thr Glu Phe Thr
35 40 45

Val Pro Gly Ser Lys Ser Thr Ala Thr Ile Ser Gly Leu Lys Pro Gly

```
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90


<210> SEQ ID NO 98
<211> LENGTH: 93
<212> TYPE: PRT
<213> ORGANISM: Artificial Sequence
<220> FEATURE:
<223> OTHER INFORMATION: Synthetic: 2631_H09 core

<400> SEQUENCE: 98

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Gln Val
            20                  25                  30

Gln Val Phe Ser Asp Leu Gly Pro Leu Tyr Ile Tyr Asn Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90


<210> SEQ ID NO 99
<211> LENGTH: 93
<212> TYPE: PRT
<213> ORGANISM: Artificial Sequence
<220> FEATURE:
<223> OTHER INFORMATION: Synthetic: 2632_G01 core

<400> SEQUENCE: 99

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Gln Val
            20                  25                  30

Gln Ile Tyr Ser Asp Trp Gly Pro Leu Tyr Ile Tyr Asn Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90


<210> SEQ ID NO 100
<211> LENGTH: 93
<212> TYPE: PRT
<213> ORGANISM: Artificial Sequence
<220> FEATURE:
<223> OTHER INFORMATION: Synthetic: 4079_A04 core

<400> SEQUENCE: 100

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Gln Val
            20                  25                  30
```

```
Gln Met Tyr Ser Asp Trp Gly Pro Leu Tyr Ile Tyr Ala Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr
                85                  90


<210> SEQ ID NO 101
<211> LENGTH: 18
<212> TYPE: PRT
<213> ORGANISM: Artificial Sequence
<220> FEATURE:
<223> OTHER INFORMATION: Synthetic: 2629_A09 CD loop

<400> SEQUENCE: 101

Gly Arg His Val Gln Ile Tyr Ser Asp Leu Gly Pro Leu Tyr Ile Tyr
1               5                   10                  15

Thr Glu


<210> SEQ ID NO 102
<211> LENGTH: 18
<212> TYPE: PRT
<213> ORGANISM: Artificial Sequence
<220> FEATURE:
<223> OTHER INFORMATION: Synthetic: 2629_A11 CD loop

<400> SEQUENCE: 102

Gly Arg His Val His Ile Tyr Ser Asp Trp Gly Pro Met Tyr Ile Tyr
1               5                   10                  15

Thr Glu


<210> SEQ ID NO 103
<211> LENGTH: 18
<212> TYPE: PRT
<213> ORGANISM: Artificial Sequence
<220> FEATURE:
<223> OTHER INFORMATION: Synthetic: 2629_C10 CD loop

<400> SEQUENCE: 103

Gly Arg Glu Val Gln Lys Tyr Ser Val Leu Gly Pro Leu Tyr Ile Tyr
1               5                   10                  15

Thr Glu


<210> SEQ ID NO 104
<211> LENGTH: 18
<212> TYPE: PRT
<213> ORGANISM: Artificial Sequence
<220> FEATURE:
<223> OTHER INFORMATION: Synthetic: 2629_D09 CD loop

<400> SEQUENCE: 104

Gly Arg Glu Val Gln Met Tyr Ser Asp Leu Gly Pro Leu Tyr Val Tyr
1               5                   10                  15

Ser Glu


<210> SEQ ID NO 105
<211> LENGTH: 18
<212> TYPE: PRT
<213> ORGANISM: Artificial Sequence
<220> FEATURE:
```

<223> OTHER INFORMATION: Synthetic: 2629_E05 CD loop

<400> SEQUENCE: 105

Gly Arg Glu Val Gln Lys Phe Ser Asp Trp Gly Pro Leu Tyr Ile Tyr
1 5 10 15

Thr Glu

<210> SEQ ID NO 106
<211> LENGTH: 18
<212> TYPE: PRT
<213> ORGANISM: Artificial Sequence
<220> FEATURE:
<223> OTHER INFORMATION: Synthetic: 2629_E06 CD loop

<400> SEQUENCE: 106

Gly Arg Glu Val Gln Lys Tyr Ser Asp Leu Gly Pro Leu Tyr Ile Tyr
1 5 10 15

Gln Glu

<210> SEQ ID NO 107
<211> LENGTH: 18
<212> TYPE: PRT
<213> ORGANISM: Artificial Sequence
<220> FEATURE:
<223> OTHER INFORMATION: Synthetic: 2629_F04 CD loop

<400> SEQUENCE: 107

Gly Arg Glu Val His Gln Tyr Ser Asp Trp Gly Pro Met Tyr Ile Tyr
1 5 10 15

Asn Glu

<210> SEQ ID NO 108
<211> LENGTH: 18
<212> TYPE: PRT
<213> ORGANISM: Artificial Sequence
<220> FEATURE:
<223> OTHER INFORMATION: Synthetic: 2629_H01 CD loop

<400> SEQUENCE: 108

Gly Arg Glu Val His Lys Asn Ser Asp Trp Gly Thr Leu Tyr Ile Tyr
1 5 10 15

Thr Glu

<210> SEQ ID NO 109
<211> LENGTH: 18
<212> TYPE: PRT
<213> ORGANISM: Artificial Sequence
<220> FEATURE:
<223> OTHER INFORMATION: Synthetic: 2629_H06 CD loop

<400> SEQUENCE: 109

Gly Arg Glu Val Gln Lys Tyr Ser Asp Leu Gly Pro Leu Tyr Ile Tyr
1 5 10 15

Ala Glu

<210> SEQ ID NO 110
<211> LENGTH: 18
<212> TYPE: PRT
<213> ORGANISM: Artificial Sequence
<220> FEATURE:
<223> OTHER INFORMATION: Synthetic: 2629_H07 CD loop

<400> SEQUENCE: 110

```
Gly Arg Glu Val His Leu Tyr Ser Asp Trp Gly Pro Met Tyr Ile Tyr
1               5                   10                  15

Thr Glu


<210> SEQ ID NO 111
<211> LENGTH: 18
<212> TYPE: PRT
<213> ORGANISM: Artificial Sequence
<220> FEATURE:
<223> OTHER INFORMATION: Synthetic: 2630_A02 CD loop

<400> SEQUENCE: 111

Gly Arg His Val Gln Met Tyr Ser Asp Leu Gly Pro Leu Tyr Ile Phe
1               5                   10                  15

Ser Glu


<210> SEQ ID NO 112
<211> LENGTH: 18
<212> TYPE: PRT
<213> ORGANISM: Artificial Sequence
<220> FEATURE:
<223> OTHER INFORMATION: Synthetic: 2630_A11 CD loop

<400> SEQUENCE: 112

Gly Arg Glu Val His Met Tyr Ser Asp Phe Gly Pro Met Tyr Ile Tyr
1               5                   10                  15

Thr Glu


<210> SEQ ID NO 113
<211> LENGTH: 18
<212> TYPE: PRT
<213> ORGANISM: Artificial Sequence
<220> FEATURE:
<223> OTHER INFORMATION: Synthetic: 2630_D02 CD loop

<400> SEQUENCE: 113

Gly Arg Glu Val Gln Lys Tyr Ser Asp Trp Gly Pro Leu Tyr Ile Tyr
1               5                   10                  15

Asn Glu


<210> SEQ ID NO 114
<211> LENGTH: 18
<212> TYPE: PRT
<213> ORGANISM: Artificial Sequence
<220> FEATURE:
<223> OTHER INFORMATION: Synthetic: 2630_D10 CD loop

<400> SEQUENCE: 114

Gly Arg Glu Val Gln Met Tyr Ser Asp Leu Gly Pro Leu Tyr Ile Tyr
1               5                   10                  15

Asn Glu


<210> SEQ ID NO 115
<211> LENGTH: 18
<212> TYPE: PRT
<213> ORGANISM: Artificial Sequence
<220> FEATURE:
<223> OTHER INFORMATION: Synthetic: 2630_F04 CD loop

<400> SEQUENCE: 115

Gly Arg Glu Val Gln Met Tyr Ser Asp Leu Gly Pro Leu Tyr Ile Tyr
1               5                   10                  15

Thr Glu
```

<210> SEQ ID NO 116
<211> LENGTH: 18
<212> TYPE: PRT
<213> ORGANISM: Artificial Sequence
<220> FEATURE:
<223> OTHER INFORMATION: Synthetic: 2630_G03 CD loop

<400> SEQUENCE: 116

Gly Arg His Val Gln Ile Tyr Ser Asp Leu Gly Pro Leu Tyr Ile Tyr
1 5 10 15

Asn Glu

<210> SEQ ID NO 117
<211> LENGTH: 18
<212> TYPE: PRT
<213> ORGANISM: Artificial Sequence
<220> FEATURE:
<223> OTHER INFORMATION: Synthetic: 2630_G10 CD loop

<400> SEQUENCE: 117

Gly Arg Glu Val Gln Ile Tyr Ser Asp Trp Gly Pro Leu Tyr Ile Tyr
1 5 10 15

Asn Glu

<210> SEQ ID NO 118
<211> LENGTH: 18
<212> TYPE: PRT
<213> ORGANISM: Artificial Sequence
<220> FEATURE:
<223> OTHER INFORMATION: Synthetic: 2630_H03 CD loop

<400> SEQUENCE: 118

Gly Arg Glu Val Gln Lys Tyr Ser Asp Trp Gly Pro Leu Tyr Ile Tyr
1 5 10 15

Gln Glu

<210> SEQ ID NO 119
<211> LENGTH: 18
<212> TYPE: PRT
<213> ORGANISM: Artificial Sequence
<220> FEATURE:
<223> OTHER INFORMATION: Synthetic: 2631_B04 CD loop

<400> SEQUENCE: 119

Gly Arg His Val His Leu Tyr Ser Glu Phe Gly Pro Met Tyr Ile Tyr
1 5 10 15

Asn Glu

<210> SEQ ID NO 120
<211> LENGTH: 18
<212> TYPE: PRT
<213> ORGANISM: Artificial Sequence
<220> FEATURE:
<223> OTHER INFORMATION: Synthetic: 2631_E03 CD loop

<400> SEQUENCE: 120

Gly Arg Asp Val His Met Tyr Ser Asp Trp Gly Pro Met Tyr Ile Tyr
1 5 10 15

Gln Glu

<210> SEQ ID NO 121
<211> LENGTH: 18

<212> TYPE: PRT
<213> ORGANISM: Artificial Sequence
<220> FEATURE:
<223> OTHER INFORMATION: Synthetic: 2631_G01 CD loop

<400> SEQUENCE: 121

Gly Arg His Val Gln Ile Tyr Ser Asp Trp Gly Pro Leu Tyr Ile Tyr
1 5 10 15

Asn Glu

<210> SEQ ID NO 122
<211> LENGTH: 18
<212> TYPE: PRT
<213> ORGANISM: Artificial Sequence
<220> FEATURE:
<223> OTHER INFORMATION: Synthetic: 2631_G03 CD loop

<400> SEQUENCE: 122

Gly Arg Tyr Val Gln Leu Tyr Ser Asp Trp Gly Pro Met Tyr Ile Tyr
1 5 10 15

Thr Glu

<210> SEQ ID NO 123
<211> LENGTH: 18
<212> TYPE: PRT
<213> ORGANISM: Artificial Sequence
<220> FEATURE:
<223> OTHER INFORMATION: Synthetic: 2631_H09 CD loop

<400> SEQUENCE: 123

Gly Arg Gln Val Gln Val Phe Ser Asp Leu Gly Pro Leu Tyr Ile Tyr
1 5 10 15

Asn Glu

<210> SEQ ID NO 124
<211> LENGTH: 18
<212> TYPE: PRT
<213> ORGANISM: Artificial Sequence
<220> FEATURE:
<223> OTHER INFORMATION: Synthetic: 2632_G01 CD loop

<400> SEQUENCE: 124

Gly Arg Gln Val Gln Ile Tyr Ser Asp Trp Gly Pro Leu Tyr Ile Tyr
1 5 10 15

Asn Glu

<210> SEQ ID NO 125
<211> LENGTH: 18
<212> TYPE: PRT
<213> ORGANISM: Artificial Sequence
<220> FEATURE:
<223> OTHER INFORMATION: Synthetic: 4079_A04 CD loop

<400> SEQUENCE: 125

Gly Arg Gln Val Gln Met Tyr Ser Asp Trp Gly Pro Leu Tyr Ile Tyr
1 5 10 15

Ala Glu

<210> SEQ ID NO 126
<211> LENGTH: 354
<212> TYPE: DNA
<213> ORGANISM: Artificial Sequence
<220> FEATURE:
<223> OTHER INFORMATION: Synthetic: 2270_C01

<400> SEQUENCE: 126
atggctagca ctagtggcgt gccgcgcgac ttggaagtgg ttgccgcgac cccgacgtct 60
ctgcttatta gctgggatgc acctgccgtc acagtgagat attatcgcat tacatatggt 120
tggcaggttc agatgtactc tgactggggt ccgctgtaca tctacaaaga gttcacggta 180
cctgggagca agtccacagc taccatcagc ggtctcaaac ctggagttga ttacaccatt 240
acggtatacg cagtcaccgg ctctggagag agccccgcaa gcagcaagcc aatttccatt 300
aattatcgga ccgaaggcga caaaccatcc cagcaccatc accaccacca ctga 354

<210> SEQ ID NO 127
<211> LENGTH: 351
<212> TYPE: DNA
<213> ORGANISM: Artificial Sequence
<220> FEATURE:
<223> OTHER INFORMATION: Synthetic: 2629_A09

<400> SEQUENCE: 127
atgggagttt ctgatgtgcc gcgcgacctg gaagtggttg ctgccacccc caccagcctg 60
ctgatcagct gggatgcacc tgccgtcaca gtgcgatatt accgcatcac ttacggacgg 120
catgttcaga tctattctga cttaggcccg ctgtacatct acacagagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 128
<211> LENGTH: 351
<212> TYPE: DNA
<213> ORGANISM: Artificial Sequence
<220> FEATURE:
<223> OTHER INFORMATION: Synthetic: 2629_A11

<400> SEQUENCE: 128
atgggagttt ctgatgtgcc gcgcgacctg gaagtggttg ctgccacccc caccagcctg 60
ctgatcagct gggatgcacc tgccgtcaca gtgcgatatt accgcatcac ttacggtaga 120
cacgttcata tctactcaga ctggggtccg atgtacatct acacagagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 129
<211> LENGTH: 351
<212> TYPE: DNA
<213> ORGANISM: Artificial Sequence
<220> FEATURE:
<223> OTHER INFORMATION: Synthetic: 2629_C10

<400> SEQUENCE: 129
atgggagttt ctgatgtgcc gcgcgacctg gaagtggttg ctgccacccc caccagcctg 60
ctgatcagct gggatgcacc tgccgtcaca gtgcgatatt accgcatcac ttacgggaga 120
gaggttcaga aatactctgt cttgggtcca ctgtacatat acacggagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 130
<211> LENGTH: 351
<212> TYPE: DNA
<213> ORGANISM: Artificial Sequence
<220> FEATURE:
<223> OTHER INFORMATION: Synthetic: 2629_D09

<400> SEQUENCE: 130
atgggagttt ctgatgtgcc gcgcgacctg gaagtggttg ctgccacccc caccagcctg 60
ctgatcagct gggatgcacc tgccgtcaca gtgcgatatt accgcatcac ttacgggagg 120
gaggttcaga tgtactctga cttgggtcca ttgtacgtat acagcgagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 131
<211> LENGTH: 351
<212> TYPE: DNA
<213> ORGANISM: Artificial Sequence
<220> FEATURE:
<223> OTHER INFORMATION: Synthetic: 2629_E05

<400> SEQUENCE: 131
atgggagttt ctgatgtgcc gcgcgacctg gaagtggttg ctgccacccc caccagcctg 60
ctgatcagct gggatgcacc tgccgtcaca gtgcgatatt accgcatcac ttacggtcgg 120
gaggtacaga agttctcgga ctggggtccg ctgtacatct acacagagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 132
<211> LENGTH: 351
<212> TYPE: DNA
<213> ORGANISM: Artificial Sequence
<220> FEATURE:
<223> OTHER INFORMATION: Synthetic: 2629_E06

<400> SEQUENCE: 132
atgggagttt ctgatgtgcc gcgcgacctg gaagtggttg ctgccacccc caccagcctg 60
ctgatcagct gggatgcacc tgccgtcaca gtgcgatatt accgcatcac ttacggcagg 120
gaggttcaga agtactcgga cttgggtccg ttgtacatct accaagagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 133
<211> LENGTH: 351
<212> TYPE: DNA
<213> ORGANISM: Artificial Sequence
<220> FEATURE:
<223> OTHER INFORMATION: Synthetic: 2629_F04

<400> SEQUENCE: 133
atgggagttt ctgatgtgcc gcgcgacctg gaagtggttg ctgccacccc caccagcctg 60
ctgatcagct gggatgcacc tgccgtcaca gtgcgatatt accgcatcac ttacggtagg 120
gaggttcatc aatactctga ctggggtccg atgtacatct acaacgagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 134
<211> LENGTH: 351
<212> TYPE: DNA
<213> ORGANISM: Artificial Sequence
<220> FEATURE:
<223> OTHER INFORMATION: Synthetic: 2629_H01

<400> SEQUENCE: 134
atgggagttt ctgatgtgcc gcgcgacctg gaagtggttg ctgccacccc caccagcctg 60
ctgatcagct gggatgcacc tgccgtcaca gtgcratatt accgcatcac ttacggtcgg 120
gaggttcata agaactcaga ctggggtacg ctgtacatct acacagagtt cactgtgcct 180
gggagcaagt ccacagctac catcagcggc cttaaacctg gcgttgatta taccatcact 240
gtgtrtgctg tcactggctc tggagagarc cccgcaagca gcaagccaat ttccattaat 300
taccgcacag aaattgacaa amcatcccag caccatcacc accaccactg a 351

<210> SEQ ID NO 135
<211> LENGTH: 351
<212> TYPE: DNA
<213> ORGANISM: Artificial Sequence
<220> FEATURE:
<223> OTHER INFORMATION: Synthetic: 2629_H06

<400> SEQUENCE: 135
atgggagttt ctgatgtgcc gcgcgacctg gaagtggttg ctgccacccc caccagcctg 60
ctgatcagct gggatgcacc tgccgtcaca gtgcgatatt accgcatcac ttacggacgg 120
gaggttcaga agtattcaga cttgggtcca ctgtacatct acgcagagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 136
<211> LENGTH: 351
<212> TYPE: DNA
<213> ORGANISM: Artificial Sequence
<220> FEATURE:
<223> OTHER INFORMATION: Synthetic: 2629_H07

<400> SEQUENCE: 136
atgggagttt ctgatgtgcc gcgcgacctg gaagtggttg ctgccacccc caccagcctg 60
ctgatcagct gggatgcacc tgccgtcaca gtgcgatatt accgcatcac ttacgggcgg 120
gaggtccacc tgtactccga ctgggggccg atgtacatct acacagagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 137

<211> LENGTH: 351
<212> TYPE: DNA
<213> ORGANISM: Artificial Sequence
<220> FEATURE:
<223> OTHER INFORMATION: Synthetic: 2630_A02

<400> SEQUENCE: 137
atgggagttt ctgatgtgcc gcgcgacctg gaagtggttg ctaccacccc caccagcctg 60
ctgatcagct gggatgcacc tgccgtcaca gtgcgatatt accgcatcac ttacggtagg 120
cacgttcaaa tgtactctga ccttggtccg ttgtacatct tcagtgagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 138
<211> LENGTH: 351
<212> TYPE: DNA
<213> ORGANISM: Artificial Sequence
<220> FEATURE:
<223> OTHER INFORMATION: Synthetic: 2630_A11

<400> SEQUENCE: 138
atgggagttt ctgatgtgcc gcgcgacctg gaagtggttg ctgccacccc caccagcctg 60
ctgatcagct gggatgcacc tgccgtcaca gtgcgatatt accgcatcac ttacggacgg 120
gaggttcata tgtactctga cttcggtccg atgtacatat acacagagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 139
<211> LENGTH: 351
<212> TYPE: DNA
<213> ORGANISM: Artificial Sequence
<220> FEATURE:
<223> OTHER INFORMATION: Synthetic: 2630_D02

<400> SEQUENCE: 139
atgggagttt ctgatgtgcc gcgcgacctg gaagtggttg ctgccacccc caccagcctg 60
ctgatcagct gggatgcacc tgccgtcaca gtgcgatatt accgcatcac ttacggtaga 120
gaagttcaga aatactctga ctggggcccg ctctacatct acaatgagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 140
<211> LENGTH: 351
<212> TYPE: DNA
<213> ORGANISM: Artificial Sequence
<220> FEATURE:
<223> OTHER INFORMATION: Synthetic: 2630_D10

<400> SEQUENCE: 140
atgggagttt ctgatgtgcc gcgcgacctg gaagtggttg ctgccacccc caccagcctg 60
ctgatcagct gggatgcacc tgccgtcaca gtgcgatatt accgcatcac ttacggtcgg 120
gaggttcaga tgtactcgga cttgggtccg ctctacatct acaacgagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 141
<211> LENGTH: 351
<212> TYPE: DNA
<213> ORGANISM: Artificial Sequence
<220> FEATURE:
<223> OTHER INFORMATION: Synthetic: 2630_F04

<400> SEQUENCE: 141
atgggagttt ctgatgtgcc gcgcgacctg gaagtggttg ctgccacccc caccagcctg 60
ctgatcagct gggatgcacc tgccgtcaca gtgcgatatt accgcatcac ttacggtaga 120
gaggtccaga tgtactcaga cttggggccg ctgtacatct atacagagtt cactgtgcct 180
gggagcaagt ccacagctac catcagcggc cttaaacctg gcgttggtta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 142
<211> LENGTH: 351
<212> TYPE: DNA
<213> ORGANISM: Artificial Sequence
<220> FEATURE:
<223> OTHER INFORMATION: Synthetic: 2630_G03

<400> SEQUENCE: 142
atgggagttt ctgatgtgcc gcgcgacctg gaagtggttg ctgccacccc caccagcctg 60
ctgatcagct gggatgcacc tgccgtcaca gtgcgatatt accgcatcac ttacggacgg 120
catgttcaga tctactccga cttgggtcct ctgtatatct acaatgagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 143
<211> LENGTH: 351
<212> TYPE: DNA
<213> ORGANISM: Artificial Sequence
<220> FEATURE:
<223> OTHER INFORMATION: Synthetic: 2630_G10

<400> SEQUENCE: 143
atgggagttt ctgatgtgcc gcgcgacctg gaagtggttg ctgccacccc caccagcctg 60
ctgatcagct gggatgcacc tgccgtcaca gtgcgatatt accgcatcac ttacggtcgg 120
gaggttcaaa tatactctga ctggggtccg ctgtatatat acaacgagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 144
<211> LENGTH: 351
<212> TYPE: DNA
<213> ORGANISM: Artificial Sequence
<220> FEATURE:

<223> OTHER INFORMATION: Synthetic: 2630_H03

<400> SEQUENCE: 144
atgggagttt ctgatgtgcc gcgcgacctg gaagtggttg ctgccaccsc caccagcctg 60
ctgatcagct gggatgcacc tgccgtcaca gtgcsatatt accgcatcac ttacggacgt 120
gaagtrcaga aatactctga ctggggcccg ctgtacatct accaagagtt cactgtgcct 180
gggagcragt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa amcatcccag caccatcacc accaccactg a 351

<210> SEQ ID NO 145
<211> LENGTH: 351
<212> TYPE: DNA
<213> ORGANISM: Artificial Sequence
<220> FEATURE:
<223> OTHER INFORMATION: Synthetic: 2631_B04

<400> SEQUENCE: 145
atgggagttt ctgatgtgcc gcgcgacctg gaagtggttg ctgccacccc caccagcctg 60
ctgatcagct gggatgtacc tgccgttaca gtgcgatatt accgcatcac ttacggcagg 120
cacgtacatt tgtactcgga gttcggtccg atgtatatct acaacgagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 146
<211> LENGTH: 351
<212> TYPE: DNA
<213> ORGANISM: Artificial Sequence
<220> FEATURE:
<223> OTHER INFORMATION: Synthetic: 2631_E03

<400> SEQUENCE: 146
atgggagttt ctgatgtgcc gcgcgacctg gaagtggttg ctgccacccc caccagcctg 60
ctgatcagct gggatgcacc tgccgtcaca gtgcgatatt accgcatcac ttacggtagg 120
gatgtccaca tgtactctga ctggggtccg atgtacatat accaagagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 147
<211> LENGTH: 351
<212> TYPE: DNA
<213> ORGANISM: Artificial Sequence
<220> FEATURE:
<223> OTHER INFORMATION: Synthetic: 2631_G01

<400> SEQUENCE: 147
atgggagttt ctgatgtgcc gcgcgacctg gaagtggttg ctgccacccc caccagcctg 60
ctgatcagct gggatgcacc tgccgtcaca gtgcgatatt accgcatcac ttacggtagg 120
catgttcaga tatactcgga ctggggtccg ctgtacatct acaatgagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 148
<211> LENGTH: 351
<212> TYPE: DNA
<213> ORGANISM: Artificial Sequence
<220> FEATURE:
<223> OTHER INFORMATION: Synthetic: 2631_G03

<400> SEQUENCE: 148
atgggagttt ctgatgtgcc gcgcgacctg gaagtggttg ctgccacccc caccagccta 60
ctgatcagct gggatgcacc tgccgtcaca gtgcgatatt accgcatcac ttacggaagg 120
tatgttcagc tatactctga ctggggtccg atgtacatct acacggagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 149
<211> LENGTH: 351
<212> TYPE: DNA
<213> ORGANISM: Artificial Sequence
<220> FEATURE:
<223> OTHER INFORMATION: Synthetic: 2631_H09

<400> SEQUENCE: 149
atgggagttt ctgatgtgcc gcgcgacctg gaagtggttg ctgccacccc caccagcctg 60
ctgatcagct gggatgcacc tgccgtcaca gtgcgatatt accgcatcac ttacggacgg 120
caagtgcaag tgttctcaga cttgggtccg ctgtacatat acaacgagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 150
<211> LENGTH: 351
<212> TYPE: DNA
<213> ORGANISM: Artificial Sequence
<220> FEATURE:
<223> OTHER INFORMATION: Synthetic: 2632_G01

<400> SEQUENCE: 150
atgggagttt ctgatgtgcc gcgcgacctg gaagtggttg ctgccacccc caccagcctg 60
ctgatcagct gggatgcacc tgccgtcaca gtgcgatatt accgcatcac ttacggtaga 120
caggtgcaga tctactctga ctggggaccg ctgtacatct acaatgagtt cactgtgcct 180
gggagcaagt ccacagctac catcagcggc cttaaacctg gcgttgatta taccatcact 240
gtgtatgctg tcactggctc tggagagagc cccgcaagca gcaagccaat ttccattaat 300
taccgcacag aaattgacaa accatcccag caccatcacc accaccactg a 351

<210> SEQ ID NO 151
<211> LENGTH: 351
<212> TYPE: DNA
<213> ORGANISM: Artificial Sequence
<220> FEATURE:
<223> OTHER INFORMATION: Synthetic: 4079_A04

<400> SEQUENCE: 151

```
atgggagttt ctgatgtgcc gcgcgacctg gaagtggttg ctgccacccc caccagcctg     60

ctgatcagct gggatgcacc tgccgtcaca gtgcgatatt accgcatcac ttacggtagg    120

caggtacaga tgtactctga ctggggtcca ctttacatct acgccgagtt cactgtgcct    180

gggagcaagt ccacagctac catcagcggc cttaaacctg gcgttgatta taccatcact    240

gtgtatgctg tcactggctc tggagagagc cccgcaagca gcaagccaat ttccattaat    300

taccgcacag aaattgacaa accatcccag caccatcacc accaccactg a             351


<210> SEQ ID NO 152
<211> LENGTH: 18
<212> TYPE: PRT
<213> ORGANISM: Artificial Sequence
<220> FEATURE:
<223> OTHER INFORMATION: Synthetic: Linker

<400> SEQUENCE: 152

Pro Ser Thr Pro Pro Thr Pro Ser Pro Ser Thr Pro Pro Thr Pro Ser
1               5                   10                  15

Pro Ser


<210> SEQ ID NO 153
<211> LENGTH: 14
<212> TYPE: PRT
<213> ORGANISM: Artificial Sequence
<220> FEATURE:
<223> OTHER INFORMATION: Synthetic: Linker

<400> SEQUENCE: 153

Gly Ser Gly Ser Gly Ser Gly Ser Gly Ser Gly Ser Gly Ser
1               5                   10


<210> SEQ ID NO 154
<211> LENGTH: 13
<212> TYPE: PRT
<213> ORGANISM: Artificial Sequence
<220> FEATURE:
<223> OTHER INFORMATION: Synthetic: Linker

<400> SEQUENCE: 154

Gly Gly Ser Gly Ser Gly Ser Gly Ser Gly Ser Gly Ser
1               5                   10


<210> SEQ ID NO 155
<211> LENGTH: 16
<212> TYPE: PRT
<213> ORGANISM: Artificial Sequence
<220> FEATURE:
<223> OTHER INFORMATION: Synthetic: Linker

<400> SEQUENCE: 155

Gly Gly Ser Gly Ser Gly Ser Gly Ser Gly Ser Gly Ser Gly Ser Gly
1               5                   10                  15


<210> SEQ ID NO 156
<211> LENGTH: 15
<212> TYPE: PRT
<213> ORGANISM: Artificial Sequence
<220> FEATURE:
<223> OTHER INFORMATION: Synthetic: Linker

<400> SEQUENCE: 156

Gly Ser Glu Gly Ser Glu Gly Ser Glu Gly Ser Glu Gly Ser Glu
1               5                   10                  15
```

<210> SEQ ID NO 157
<211> LENGTH: 8
<212> TYPE: PRT
<213> ORGANISM: Artificial Sequence
<220> FEATURE:
<223> OTHER INFORMATION: Synthetic: Linker

<400> SEQUENCE: 157

```
Gly Gly Ser Glu Gly Gly Ser Glu
1               5
```

<210> SEQ ID NO 158
<211> LENGTH: 8
<212> TYPE: PRT
<213> ORGANISM: Artificial Sequence
<220> FEATURE:
<223> OTHER INFORMATION: Synthetic: Linker

<400> SEQUENCE: 158

```
Gly Ser Gly Ser Gly Ser Gly Ser
1               5
```

<210> SEQ ID NO 159
<211> LENGTH: 35
<212> TYPE: PRT
<213> ORGANISM: Artificial Sequence
<220> FEATURE:
<223> OTHER INFORMATION: Synthetic: Linker

<400> SEQUENCE: 159

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35
```

<210> SEQ ID NO 160
<211> LENGTH: 25
<212> TYPE: PRT
<213> ORGANISM: Artificial Sequence
<220> FEATURE:
<223> OTHER INFORMATION: Synthetic: Linker

<400> SEQUENCE: 160

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 161
<211> LENGTH: 16
<212> TYPE: PRT
<213> ORGANISM: Artificial Sequence
<220> FEATURE:
<223> OTHER INFORMATION: Synthetic: Linker

<400> SEQUENCE: 161

```
Gly Gly Gly Gly Ser Gly Gly Gly Gly Ser Gly Gly Gly Gly Ser Gly
1               5                   10                  15
```

<210> SEQ ID NO 162
<211> LENGTH: 7
<212> TYPE: PRT
<213> ORGANISM: Artificial Sequence
<220> FEATURE:
<223> OTHER INFORMATION: Synthetic: Linker

<400> SEQUENCE: 162

Gly Pro Gly Pro Gly Pro Gly
1 5

<210> SEQ ID NO 163
<211> LENGTH: 11
<212> TYPE: PRT
<213> ORGANISM: Artificial Sequence
<220> FEATURE:
<223> OTHER INFORMATION: Synthetic: Linker

<400> SEQUENCE: 163

Gly Pro Gly Pro Gly Pro Gly Pro Gly Pro Gly
1 5 10

<210> SEQ ID NO 164
<211> LENGTH: 6
<212> TYPE: PRT
<213> ORGANISM: Artificial Sequence
<220> FEATURE:
<223> OTHER INFORMATION: Synthetic: Linker

<400> SEQUENCE: 164

Pro Ala Pro Ala Pro Ala
1 5

<210> SEQ ID NO 165
<211> LENGTH: 12
<212> TYPE: PRT
<213> ORGANISM: Artificial Sequence
<220> FEATURE:
<223> OTHER INFORMATION: Synthetic: Linker

<400> SEQUENCE: 165

Pro Ala Pro Ala Pro Ala Pro Ala Pro Ala Pro Ala
1 5 10

<210> SEQ ID NO 166
<211> LENGTH: 18
<212> TYPE: PRT
<213> ORGANISM: Artificial Sequence
<220> FEATURE:
<223> OTHER INFORMATION: Synthetic: Linker

<400> SEQUENCE: 166

Pro Ala Pro Ala Pro Ala Pro Ala Pro Ala Pro Ala Pro Ala Pro Ala
1 5 10 15

Pro Ala

<210> SEQ ID NO 167
<211> LENGTH: 97
<212> TYPE: PRT
<213> ORGANISM: Artificial Sequence
<220> FEATURE:
<223> OTHER INFORMATION: Synthetic: PCSK9 10Fn3 domain

<400> SEQUENCE: 167

Met Gly Val Ser Asp Val Pro Arg Asp Leu Glu Val Val Ala Ala Thr
1 5 10 15

Pro Thr Ser Leu Leu Ile Ser Trp Asp Ala Pro Ala Glu Gly Tyr Gly
20 25 30

Tyr Tyr Arg Ile Thr Tyr Gly Glu Thr Gly Gly Asn Ser Pro Val Gln

```
        35                  40                  45

Glu Phe Thr Val Pro Val Ser Lys Gly Thr Ala Thr Ile Ser Gly Leu
    50                  55                  60

Lys Pro Gly Val Asp Tyr Thr Ile Thr Val Tyr Ala Val Glu Phe Asp
65                  70                  75                  80

Phe Pro Gly Ala Gly Tyr Tyr His Arg Pro Ile Ser Ile Asn Tyr Arg
                85                  90                  95

Thr


<210> SEQ ID NO 168
<211> LENGTH: 219
<212> TYPE: PRT
<213> ORGANISM: Artificial Sequence
<220> FEATURE:
<223> OTHER INFORMATION: Synthetic: PCSK9-PKE2 tandem Adnectin w/o his
      tag 5190_E01 (ATI-1676)

<400> SEQUENCE: 168

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Glu Gly Tyr Gly
            20                  25                  30

Tyr Tyr Arg Ile Thr Tyr Gly Glu Thr Gly Gly Asn Ser Pro Val Gln
        35                  40                  45

Glu Phe Thr Val Pro Val Ser Lys Gly Thr Ala Thr Ile Ser Gly Leu
    50                  55                  60

Lys Pro Gly Val Asp Tyr Thr Ile Thr Val Tyr Ala Val Glu Phe Asp
65                  70                  75                  80

Phe Pro Gly Ala Gly Tyr Tyr His Arg Pro Ile Ser Ile Asn Tyr Arg
                85                  90                  95

Thr Glu Pro Ser Thr Pro Pro Thr Pro Ser Pro Ser Thr Pro Pro Thr
            100                 105                 110

Pro Ser Pro Ser Gly Val Ser Asp Val Pro Arg Asp Leu Glu Val Val
        115                 120                 125

Ala Ala Thr Pro Thr Ser Leu Leu Ile Ser Trp Asp Ala Pro Ala Val
    130                 135                 140

Thr Val Arg Tyr Tyr Arg Ile Thr Tyr Gly Arg Glu Val Gln Lys Tyr
145                 150                 155                 160

Ser Asp Leu Gly Pro Leu Tyr Ile Tyr Gln Glu Phe Thr Val Pro Gly
                165                 170                 175

Ser Lys Ser Thr Ala Thr Ile Ser Gly Leu Lys Pro Gly Val Asp Tyr
            180                 185                 190

Thr Ile Thr Val Tyr Ala Val Thr Gly Ser Gly Glu Ser Pro Ala Ser
        195                 200                 205

Ser Lys Pro Ile Ser Ile Asn Tyr Arg Thr Pro
    210                 215


<210> SEQ ID NO 169
<211> LENGTH: 225
<212> TYPE: PRT
<213> ORGANISM: Artificial Sequence
<220> FEATURE:
<223> OTHER INFORMATION: Synthetic: PCSK9-PKE2 tandem Adnectin w/ his
      tag 4472_C06 (ATI-1574)

<400> SEQUENCE: 169

Met Gly Val Ser Asp Val Pro Arg Asp Leu Glu Val Val Ala Ala Thr
1               5                   10                  15
```

```
Pro Thr Ser Leu Leu Ile Ser Trp Asp Ala Pro Ala Glu Gly Tyr Gly
            20                  25                  30

Tyr Tyr Arg Ile Thr Tyr Gly Glu Thr Gly Gly Asn Ser Pro Val Gln
        35                  40                  45

Glu Phe Thr Val Pro Val Ser Lys Gly Thr Ala Thr Ile Ser Gly Leu
    50                  55                  60

Lys Pro Gly Val Asp Tyr Thr Ile Thr Val Tyr Ala Val Glu Phe Asp
65                  70                  75                  80

Phe Pro Gly Ala Gly Tyr Tyr His Arg Pro Ile Ser Ile Asn Tyr Arg
                85                  90                  95

Thr Glu Pro Ser Thr Pro Pro Thr Pro Ser Pro Ser Thr Pro Pro Thr
            100                 105                 110

Pro Ser Pro Ser Gly Val Ser Asp Val Pro Arg Asp Leu Glu Val Val
        115                 120                 125

Ala Ala Thr Pro Thr Ser Leu Leu Ile Ser Trp Asp Ala Pro Ala Val
    130                 135                 140

Thr Val Arg Tyr Tyr Arg Ile Thr Tyr Gly Arg Glu Val Gln Lys Tyr
145                 150                 155                 160

Ser Asp Leu Gly Pro Leu Tyr Ile Tyr Gln Glu Phe Thr Val Pro Gly
                165                 170                 175

Ser Lys Ser Thr Ala Thr Ile Ser Gly Leu Lys Pro Gly Val Asp Tyr
            180                 185                 190

Thr Ile Thr Val Tyr Ala Val Thr Gly Ser Gly Glu Ser Pro Ala Ser
        195                 200                 205

Ser Lys Pro Ile Ser Ile Asn Tyr Arg Thr Glu His His His His His
    210                 215                 220

His
225


<210> SEQ ID NO 170
<211> LENGTH: 18
<212> TYPE: PRT
<213> ORGANISM: Artificial Sequence
<220> FEATURE:
<223> OTHER INFORMATION: Synthetic: CD loop consensus
<220> FEATURE:
<221> NAME/KEY: misc_feature
<222> LOCATION: (2)..(2)
<223> OTHER INFORMATION: Xaa is R or W
<220> FEATURE:
<221> NAME/KEY: misc_feature
<222> LOCATION: (3)..(3)
<223> OTHER INFORMATION: Xaa is H, E, D, Y, or Q
<220> FEATURE:
<221> NAME/KEY: misc_feature
<222> LOCATION: (5)..(5)
<223> OTHER INFORMATION: Xaa is Q or H
<220> FEATURE:
<221> NAME/KEY: misc_feature
<222> LOCATION: (6)..(6)
<223> OTHER INFORMATION: Xaa is I, K, M, Q, L, or V
<220> FEATURE:
<221> NAME/KEY: misc_feature
<222> LOCATION: (7)..(7)
<223> OTHER INFORMATION: Xaa is Y, F, or N
<220> FEATURE:
<221> NAME/KEY: misc_feature
<222> LOCATION: (9)..(9)
<223> OTHER INFORMATION: Xaa is D, V, or E
<220> FEATURE:
<221> NAME/KEY: misc_feature
<222> LOCATION: (10)..(10)
<223> OTHER INFORMATION: Xaa is L, W, or F
<220> FEATURE:
```

<221> NAME/KEY: misc_feature
<222> LOCATION: (12)..(12)
<223> OTHER INFORMATION: Xaa is P or T
<220> FEATURE:
<221> NAME/KEY: misc_feature
<222> LOCATION: (13)..(13)
<223> OTHER INFORMATION: Xaa is L or M
<220> FEATURE:
<221> NAME/KEY: misc_feature
<222> LOCATION: (15)..(15)
<223> OTHER INFORMATION: Xaa is I or V
<220> FEATURE:
<221> NAME/KEY: misc_feature
<222> LOCATION: (16)..(16)
<223> OTHER INFORMATION: Xaa is Y or F
<220> FEATURE:
<221> NAME/KEY: misc_feature
<222> LOCATION: (17)..(17)
<223> OTHER INFORMATION: Xaa is T, S, Q, N, or A

<400> SEQUENCE: 170

```
Gly Xaa Xaa Val Xaa Xaa Xaa Ser Xaa Xaa Gly Xaa Xaa Tyr Xaa Xaa
1               5                   10                  15

Xaa Glu
```

<210> SEQ ID NO 171
<211> LENGTH: 342
<212> TYPE: PRT
<213> ORGANISM: Artificial Sequence
<220> FEATURE:
<223> OTHER INFORMATION: Synthetic: 3852_F10

<400> SEQUENCE: 171

```
Ala Thr Gly Gly Gly Ala Gly Thr Thr Thr Cys Thr Gly Ala Thr Gly
1               5                   10                  15

Thr Gly Cys Cys Gly Cys Gly Cys Gly Ala Cys Cys Thr Gly Gly Ala
            20                  25                  30

Ala Gly Thr Gly Gly Thr Thr Gly Cys Thr Gly Cys Cys Ala Cys Cys
        35                  40                  45

Cys Cys Cys Ala Cys Cys Ala Gly Cys Cys Thr Gly Cys Thr Gly Ala
    50                  55                  60

Thr Cys Ala Gly Cys Thr Gly Gly Gly Ala Cys Gly Cys Thr Cys Cys
65                  70                  75                  80

Gly Gly Cys Thr Gly Thr Thr Gly Ala Cys Gly Gly Thr Cys Gly Ala
                85                  90                  95

Thr Ala Thr Thr Ala Cys Cys Gly Cys Ala Thr Cys Ala Cys Thr Thr
            100                 105                 110

Ala Cys Gly Gly Cys Gly Ala Ala Ala Cys Ala Gly Gly Ala Gly Gly
        115                 120                 125

Cys Ala Ala Thr Ala Gly Cys Cys Cys Thr Gly Thr Cys Cys Ala Gly
    130                 135                 140

Gly Ala Gly Thr Thr Cys Ala Cys Thr Gly Thr Gly Cys Cys Thr Gly
145                 150                 155                 160

Gly Thr Thr Cys Thr Ala Ala Ala Thr Cys Thr Ala Cys Ala Gly Cys
                165                 170                 175

Thr Ala Cys Cys Ala Thr Cys Ala Gly Cys Gly Gly Cys Cys Thr Thr
            180                 185                 190

Ala Ala Ala Cys Cys Thr Gly Gly Cys Gly Thr Thr Gly Ala Thr Thr
        195                 200                 205

Ala Thr Ala Cys Cys Ala Thr Cys Ala Cys Thr Gly Thr Gly Thr Ala
    210                 215                 220
```

```
Thr Gly Cys Thr Gly Thr Cys Ala Cys Thr Cys Cys Gly Thr Ala Cys
225                 230                 235                 240

Gly Ala Ala Thr Thr Cys Cys Ala Thr Thr Thr Cys Cys Cys Gly Thr
                245                 250                 255

Ala Cys Ala Cys Thr Cys Ala Thr Thr Ala Cys Thr Cys Thr Thr Cys
            260                 265                 270

Thr Ala Ala Ala Cys Cys Ala Ala Thr Thr Thr Cys Cys Ala Thr Thr
        275                 280                 285

Ala Ala Thr Thr Ala Cys Cys Gly Cys Ala Cys Ala Gly Ala Ala Ala
    290                 295                 300

Thr Thr Gly Ala Cys Ala Ala Ala Cys Cys Ala Thr Cys Cys Cys Ala
305                 310                 315                 320

Gly Cys Ala Cys Cys Ala Thr Cys Ala Cys Cys Ala Cys Cys Ala Cys
                325                 330                 335

Cys Ala Cys Thr Gly Ala
            340


<210> SEQ ID NO 172
<211> LENGTH: 660
<212> TYPE: PRT
<213> ORGANISM: Artificial Sequence
<220> FEATURE:
<223> OTHER INFORMATION: Synthetic: PCSK9-PKE2 tandem Adnectin nucleic
      acid sequence 5190_E01 (ATI-1676)

<400> SEQUENCE: 172

Ala Thr Gly Gly Gly Ala Gly Thr Thr Thr Cys Thr Gly Ala Thr Gly
1               5                   10                  15

Thr Gly Cys Cys Gly Cys Gly Cys Gly Ala Cys Cys Thr Gly Gly Ala
            20                  25                  30

Ala Gly Thr Gly Gly Thr Thr Gly Cys Thr Gly Cys Cys Ala Cys Cys
        35                  40                  45

Cys Cys Cys Ala Cys Cys Ala Gly Cys Cys Thr Gly Cys Thr Gly Ala
    50                  55                  60

Thr Cys Ala Gly Cys Thr Gly Gly Gly Ala Cys Gly Cys Thr Cys Cys
65                  70                  75                  80

Gly Gly Cys Thr Gly Ala Ala Gly Gly Gly Thr Ala Cys Gly Gly Thr
                85                  90                  95

Thr Ala Thr Thr Ala Cys Cys Gly Cys Ala Thr Cys Ala Cys Thr Thr
            100                 105                 110

Ala Cys Gly Gly Cys Gly Ala Ala Ala Cys Ala Gly Gly Ala Gly Gly
        115                 120                 125

Cys Ala Ala Thr Ala Gly Cys Cys Cys Thr Gly Thr Cys Cys Ala Gly
    130                 135                 140

Gly Ala Gly Thr Thr Cys Ala Cys Thr Gly Thr Gly Cys Cys Thr Gly
145                 150                 155                 160

Thr Thr Thr Cys Thr Ala Ala Ala Gly Gly Thr Ala Cys Ala Gly Cys
                165                 170                 175

Thr Ala Cys Cys Ala Thr Cys Ala Gly Cys Gly Gly Cys Cys Thr Thr
            180                 185                 190

Ala Ala Ala Cys Cys Thr Gly Gly Cys Gly Thr Thr Gly Ala Thr Thr
        195                 200                 205

Ala Thr Ala Cys Cys Ala Thr Cys Ala Cys Thr Gly Thr Gly Thr Ala
    210                 215                 220

Thr Gly Cys Thr Gly Thr Cys Gly Ala Ala Thr Thr Cys Gly Ala Cys
225                 230                 235                 240
```

```
Thr Thr Cys Cys Cys Cys Gly Gly Cys Gly Cys Cys Gly Gly Thr Thr
                245                 250                 255

Ala Cys Thr Ala Cys Cys Ala Thr Cys Gly Thr Cys Cys Ala Ala Thr
            260                 265                 270

Thr Thr Cys Cys Ala Thr Thr Ala Ala Thr Thr Ala Cys Cys Gly Gly
        275                 280                 285

Ala Cys Cys Gly Ala Ala Cys Cys Gly Ala Gly Cys Ala Cys Ala Cys
    290                 295                 300

Cys Thr Cys Cys Gly Ala Cys Cys Cys Cys Gly Ala Gly Thr Cys Cys
305                 310                 315                 320

Gly Thr Cys Ala Ala Cys Ala Cys Cys Ala Cys Cys Gly Ala Cys Ala
                325                 330                 335

Cys Cys Gly Thr Cys Ala Cys Cys Gly Ala Gly Cys Gly Gly Ala Gly
            340                 345                 350

Thr Thr Thr Cys Thr Gly Ala Cys Gly Thr Cys Cys Cys Gly Cys Gly
        355                 360                 365

Cys Gly Ala Cys Cys Thr Gly Gly Ala Ala Gly Thr Gly Gly Thr Thr
    370                 375                 380

Gly Cys Thr Gly Cys Cys Ala Cys Cys Cys Cys Cys Ala Cys Cys Ala
385                 390                 395                 400

Gly Cys Cys Thr Gly Cys Thr Gly Ala Thr Cys Ala Gly Cys Thr Gly
                405                 410                 415

Gly Gly Ala Thr Gly Cys Ala Cys Cys Thr Gly Cys Cys Gly Thr Cys
            420                 425                 430

Ala Cys Ala Gly Thr Gly Cys Gly Ala Thr Ala Thr Thr Ala Cys Cys
        435                 440                 445

Gly Cys Ala Thr Cys Ala Cys Thr Thr Ala Cys Gly Gly Cys Ala Gly
    450                 455                 460

Gly Gly Ala Gly Gly Thr Thr Cys Ala Gly Ala Ala Gly Thr Ala Cys
465                 470                 475                 480

Thr Cys Gly Gly Ala Cys Thr Thr Gly Gly Gly Thr Cys Cys Gly Thr
                485                 490                 495

Thr Gly Thr Ala Cys Ala Thr Cys Thr Ala Cys Cys Ala Ala Gly Ala
            500                 505                 510

Gly Thr Thr Cys Ala Cys Thr Gly Thr Gly Cys Cys Thr Gly Gly Gly
        515                 520                 525

Ala Gly Cys Ala Ala Gly Thr Cys Cys Ala Cys Ala Gly Cys Thr Ala
    530                 535                 540

Cys Cys Ala Thr Cys Ala Gly Cys Gly Gly Cys Cys Thr Thr Ala Ala
545                 550                 555                 560

Ala Cys Cys Thr Gly Gly Cys Gly Thr Thr Gly Ala Thr Thr Ala Thr
                565                 570                 575

Ala Cys Cys Ala Thr Cys Ala Cys Thr Gly Thr Gly Thr Ala Thr Gly
            580                 585                 590

Cys Thr Gly Thr Cys Ala Cys Thr Gly Gly Cys Thr Cys Thr Gly Gly
        595                 600                 605

Ala Gly Ala Gly Ala Gly Cys Cys Cys Cys Gly Cys Ala Ala Gly Cys
    610                 615                 620

Ala Gly Cys Ala Ala Gly Cys Cys Ala Ala Thr Thr Thr Cys Cys Ala
625                 630                 635                 640

Thr Thr Ala Ala Thr Thr Ala Cys Cys Gly Cys Ala Cys Ala Cys Cys
                645                 650                 655
```

```
Gly Thr Gly Ala
            660


<210> SEQ ID NO 173
<211> LENGTH: 10
<212> TYPE: PRT
<213> ORGANISM: Artificial Sequence
<220> FEATURE:
<223> OTHER INFORMATION: Synthetic: Linker

<400> SEQUENCE: 173

Pro Ser Pro Glu Pro Pro Thr Pro Glu Pro
1               5                   10


<210> SEQ ID NO 174
<211> LENGTH: 20
<212> TYPE: PRT
<213> ORGANISM: Artificial Sequence
<220> FEATURE:
<223> OTHER INFORMATION: Synthetic: Linker

<400> SEQUENCE: 174

Pro Ser Pro Glu Pro Pro Thr Pro Glu Pro Pro Ser Pro Glu Pro Pro
1               5                   10                  15

Thr Pro Glu Pro
            20


<210> SEQ ID NO 175
<211> LENGTH: 30
<212> TYPE: PRT
<213> ORGANISM: Artificial Sequence
<220> FEATURE:
<223> OTHER INFORMATION: Synthetic: Linker

<400> SEQUENCE: 175

Pro Ser Pro Glu Pro Pro Thr Pro Glu Pro Pro Ser Pro Glu Pro Pro
1               5                   10                  15

Thr Pro Glu Pro Pro Ser Pro Glu Pro Pro Thr Pro Glu Pro
            20                  25                  30


<210> SEQ ID NO 176
<211> LENGTH: 40
<212> TYPE: PRT
<213> ORGANISM: Artificial Sequence
<220> FEATURE:
<223> OTHER INFORMATION: Synthetic: Linker

<400> SEQUENCE: 176

Pro Ser Pro Glu Pro Pro Thr Pro Glu Pro Pro Ser Pro Glu Pro Pro
1               5                   10                  15

Thr Pro Glu Pro Pro Ser Pro Glu Pro Pro Thr Pro Glu Pro Pro Ser
            20                  25                  30

Pro Glu Pro Pro Thr Pro Glu Pro
        35                  40


<210> SEQ ID NO 177
<211> LENGTH: 6
<212> TYPE: PRT
<213> ORGANISM: Artificial Sequence
<220> FEATURE:
<223> OTHER INFORMATION: Synthetic: Linker

<400> SEQUENCE: 177

Glu Glu Glu Glu Asp Glu
1               5
```

<210> SEQ ID NO 178
<211> LENGTH: 11
<212> TYPE: PRT
<213> ORGANISM: Artificial Sequence
<220> FEATURE:
<223> OTHER INFORMATION: Synthetic: Linker

<400> SEQUENCE: 178

Glu Glu Glu Glu Asp Glu Glu Glu Glu Asp Glu
1 5 10

<210> SEQ ID NO 179
<211> LENGTH: 21
<212> TYPE: PRT
<213> ORGANISM: Artificial Sequence
<220> FEATURE:
<223> OTHER INFORMATION: Synthetic: Linker

<400> SEQUENCE: 179

Glu Glu Glu Glu Asp Glu Glu Glu Glu Asp Glu Glu Glu Glu Asp Glu
1 5 10 15

Glu Glu Glu Asp Glu
20

<210> SEQ ID NO 180
<211> LENGTH: 31
<212> TYPE: PRT
<213> ORGANISM: Artificial Sequence
<220> FEATURE:
<223> OTHER INFORMATION: Synthetic: Linker

<400> SEQUENCE: 180

Glu Glu Glu Glu Asp Glu Glu Glu Glu Asp Glu Glu Glu Glu Asp Glu
1 5 10 15

Glu Glu Glu Asp Glu Glu Glu Glu Asp Glu Glu Glu Glu Asp Glu
20 25 30

<210> SEQ ID NO 181
<211> LENGTH: 23
<212> TYPE: PRT
<213> ORGANISM: Artificial Sequence
<220> FEATURE:
<223> OTHER INFORMATION: Synthetic: Linker

<400> SEQUENCE: 181

Arg Gly Gly Glu Glu Lys Lys Lys Glu Lys Glu Lys Glu Glu Gln Glu
1 5 10 15

Glu Arg Glu Thr Lys Thr Pro
20

<210> SEQ ID NO 182
<211> LENGTH: 16
<212> TYPE: PRT
<213> ORGANISM: Artificial Sequence
<220> FEATURE:
<223> OTHER INFORMATION: Synthetic: Exemplary use of linker

<400> SEQUENCE: 182

Asn Tyr Arg Thr Pro Gly Pro Ser Pro Glu Pro Pro Thr Pro Glu Pro
1 5 10 15

<210> SEQ ID NO 183
<211> LENGTH: 15
<212> TYPE: PRT

<213> ORGANISM: Artificial Sequence
<220> FEATURE:
<223> OTHER INFORMATION: Synthetic: Exemplary use of linker

<400> SEQUENCE: 183

Pro Ser Pro Glu Pro Pro Thr Pro Glu Pro Gly Val Ser Asp Val
1 5 10 15

<210> SEQ ID NO 184
<211> LENGTH: 94
<212> TYPE: PRT
<213> ORGANISM: Artificial Sequence
<220> FEATURE:
<223> OTHER INFORMATION: Synthetic: 2270_C01 core with C-terminal proline

<400> SEQUENCE: 184

Glu Val Val Ala Ala Thr Pro Thr Ser Leu Leu Ile Ser Trp Asp Ala
1 5 10 15

Pro Ala Val Thr Val Arg Tyr Tyr Arg Ile Thr Tyr Gly Trp Gln Val
20 25 30

Gln Met Tyr Ser Asp Trp Gly Pro Leu Tyr Ile Tyr Lys Glu Phe Thr
35 40 45

Val Pro Gly Ser Lys Ser Thr Ala Thr Ile Ser Gly Leu Lys Pro Gly
50 55 60

Val Asp Tyr Thr Ile Thr Val Tyr Ala Val Thr Gly Ser Gly Glu Ser
65 70 75 80

Pro Ala Ser Ser Lys Pro Ile Ser Ile Asn Tyr Arg Thr Pro
85 90

<210> SEQ ID NO 185
<211> LENGTH: 94
<212> TYPE: PRT
<213> ORGANISM: Artificial Sequence
<220> FEATURE:
<223> OTHER INFORMATION: Synthetic: 2629_A09 core with C-terminal proline

<400> SEQUENCE: 185

Glu Val Val Ala Ala Thr Pro Thr Ser Leu Leu Ile Ser Trp Asp Ala
1 5 10 15

Pro Ala Val Thr Val Arg Tyr Tyr Arg Ile Thr Tyr Gly Arg His Val
20 25 30

Gln Ile Tyr Ser Asp Leu Gly Pro Leu Tyr Ile Tyr Thr Glu Phe Thr
35 40 45

Val Pro Gly Ser Lys Ser Thr Ala Thr Ile Ser Gly Leu Lys Pro Gly
50 55 60

Val Asp Tyr Thr Ile Thr Val Tyr Ala Val Thr Gly Ser Gly Glu Ser
65 70 75 80

Pro Ala Ser Ser Lys Pro Ile Ser Ile Asn Tyr Arg Thr Pro
85 90

<210> SEQ ID NO 186
<211> LENGTH: 94
<212> TYPE: PRT
<213> ORGANISM: Artificial Sequence
<220> FEATURE:
<223> OTHER INFORMATION: Synthetic: 2629_A11 core with C-terminal proline

<400> SEQUENCE: 186

Glu Val Val Ala Ala Thr Pro Thr Ser Leu Leu Ile Ser Trp Asp Ala

```
1               5                   10                  15

Pro Ala Val Thr Val Arg Tyr Tyr Arg Ile Thr Tyr Gly Arg His Val
            20                  25                  30

His Ile Tyr Ser Asp Trp Gly Pro Met Tyr Ile Tyr Thr Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90


<210> SEQ ID NO 187
<211> LENGTH: 94
<212> TYPE: PRT
<213> ORGANISM: Artificial Sequence
<220> FEATURE:
<223> OTHER INFORMATION: Synthetic: 2629_C10 core with C-terminal
      proline

<400> SEQUENCE: 187

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Val Leu Gly Pro Leu Tyr Ile Tyr Thr Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90


<210> SEQ ID NO 188
<211> LENGTH: 94
<212> TYPE: PRT
<213> ORGANISM: Artificial Sequence
<220> FEATURE:
<223> OTHER INFORMATION: Synthetic: 2629_D09 core with C-terminal
      proline

<400> SEQUENCE: 188

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Met Tyr Ser Asp Leu Gly Pro Leu Tyr Val Tyr Ser Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90


<210> SEQ ID NO 189
<211> LENGTH: 94
<212> TYPE: PRT
```

<213> ORGANISM: Artificial Sequence
<220> FEATURE:
<223> OTHER INFORMATION: Synthetic: 2629_E05 core with C-terminal proline

<400> SEQUENCE: 189

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Phe Ser Asp Trp Gly Pro Leu Tyr Ile Tyr Thr Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90
```

<210> SEQ ID NO 190
<211> LENGTH: 94
<212> TYPE: PRT
<213> ORGANISM: Artificial Sequence
<220> FEATURE:
<223> OTHER INFORMATION: Synthetic: 2629_E06 core with C-terminal proline

<400> SEQUENCE: 190

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Leu Gly Pro Leu Tyr Ile Tyr Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90
```

<210> SEQ ID NO 191
<211> LENGTH: 94
<212> TYPE: PRT
<213> ORGANISM: Artificial Sequence
<220> FEATURE:
<223> OTHER INFORMATION: Synthetic: 2629_F04 core with C-terminal proline

<400> SEQUENCE: 191

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

His Gln Tyr Ser Asp Trp Gly Pro Met Tyr Ile Tyr Asn Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80
```

Pro Ala Ser Ser Lys Pro Ile Ser Ile Asn Tyr Arg Thr Pro
85 90

<210> SEQ ID NO 192
<211> LENGTH: 94
<212> TYPE: PRT
<213> ORGANISM: Artificial Sequence
<220> FEATURE:
<223> OTHER INFORMATION: Synthetic: 2629_H01 core with C-terminal proline
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid

<400> SEQUENCE: 192

Glu Val Val Ala Ala Thr Pro Thr Ser Leu Leu Ile Ser Trp Asp Ala
1 5 10 15

Pro Ala Val Thr Val Xaa Tyr Tyr Arg Ile Thr Tyr Gly Arg Glu Val
20 25 30

His Lys Asn Ser Asp Trp Gly Thr Leu Tyr Ile Tyr Thr Glu Phe Thr
35 40 45

Val Pro Gly Ser Lys Ser Thr Ala Thr Ile Ser Gly Leu Lys Pro Gly
50 55 60

Val Asp Tyr Thr Ile Thr Val Xaa Ala Val Thr Gly Ser Gly Glu Xaa
65 70 75 80

Pro Ala Ser Ser Lys Pro Ile Ser Ile Asn Tyr Arg Thr Pro
85 90

<210> SEQ ID NO 193
<211> LENGTH: 94
<212> TYPE: PRT
<213> ORGANISM: Artificial Sequence
<220> FEATURE:
<223> OTHER INFORMATION: Synthetic: 2629_H06 core with C-terminal proline

<400> SEQUENCE: 193

Glu Val Val Ala Ala Thr Pro Thr Ser Leu Leu Ile Ser Trp Asp Ala
1 5 10 15

Pro Ala Val Thr Val Arg Tyr Tyr Arg Ile Thr Tyr Gly Arg Glu Val
20 25 30

Gln Lys Tyr Ser Asp Leu Gly Pro Leu Tyr Ile Tyr Ala Glu Phe Thr
35 40 45

Val Pro Gly Ser Lys Ser Thr Ala Thr Ile Ser Gly Leu Lys Pro Gly
50 55 60

Val Asp Tyr Thr Ile Thr Val Tyr Ala Val Thr Gly Ser Gly Glu Ser
65 70 75 80

Pro Ala Ser Ser Lys Pro Ile Ser Ile Asn Tyr Arg Thr Pro
85 90

<210> SEQ ID NO 194
<211> LENGTH: 94
<212> TYPE: PRT
<213> ORGANISM: Artificial Sequence
<220> FEATURE:
<223> OTHER INFORMATION: Synthetic: 2629_H07 core with C-terminal proline

<400> SEQUENCE: 194

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

His Leu Tyr Ser Asp Trp Gly Pro Met Tyr Ile Tyr Thr Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90
```

<210> SEQ ID NO 195
<211> LENGTH: 94
<212> TYPE: PRT
<213> ORGANISM: Artificial Sequence
<220> FEATURE:
<223> OTHER INFORMATION: Synthetic: 2630_A02 core with C-terminal proline

<400> SEQUENCE: 195

```
Glu Val Val Ala Thr Thr Pro Thr Ser Leu Leu Ile Ser Trp Asp Ala
1               5                   10                  15

Pro Ala Val Thr Val Arg Tyr Tyr Arg Ile Thr Tyr Gly Arg His Val
            20                  25                  30

Gln Met Tyr Ser Asp Leu Gly Pro Leu Tyr Ile Phe Ser Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90
```

<210> SEQ ID NO 196
<211> LENGTH: 94
<212> TYPE: PRT
<213> ORGANISM: Artificial Sequence
<220> FEATURE:
<223> OTHER INFORMATION: Synthetic: 2630_A11 core with C-terminal proline

<400> SEQUENCE: 196

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

His Met Tyr Ser Asp Phe Gly Pro Met Tyr Ile Tyr Thr Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80
```

```
Pro Ala Ser Ser Lys Pro Ile Ser Ile Asn Tyr Arg Thr Pro
                85                  90


<210> SEQ ID NO 197
<211> LENGTH: 94
<212> TYPE: PRT
<213> ORGANISM: Artificial Sequence
<220> FEATURE:
<223> OTHER INFORMATION: Synthetic: 2630_D02 core with C-terminal
      proline

<400> SEQUENCE: 197

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Lys Tyr Ser Asp Trp Gly Pro Leu Tyr Ile Tyr Asn Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90


<210> SEQ ID NO 198
<211> LENGTH: 94
<212> TYPE: PRT
<213> ORGANISM: Artificial Sequence
<220> FEATURE:
<223> OTHER INFORMATION: Synthetic: 2630_D10 core with C-terminal
      proline

<400> SEQUENCE: 198

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Met Tyr Ser Asp Leu Gly Pro Leu Tyr Ile Tyr Asn Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90


<210> SEQ ID NO 199
<211> LENGTH: 94
<212> TYPE: PRT
<213> ORGANISM: Artificial Sequence
<220> FEATURE:
<223> OTHER INFORMATION: Synthetic: 2630_F04 core with C-terminal
      proline

<400> SEQUENCE: 199

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Met Tyr Ser Asp Leu Gly Pro Leu Tyr Ile Tyr Thr Glu Phe Thr
```

```
        35                  40                  45

Val Pro Gly Ser Lys Ser Thr Ala Thr Ile Ser Gly Leu Lys Pro Gly
    50                  55                  60

Val Gly Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90


<210> SEQ ID NO 200
<211> LENGTH: 94
<212> TYPE: PRT
<213> ORGANISM: Artificial Sequence
<220> FEATURE:
<223> OTHER INFORMATION: Synthetic: 2630_G03 core with C-terminal
      proline

<400> SEQUENCE: 200

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg His Val
            20                  25                  30

Gln Ile Tyr Ser Asp Leu Gly Pro Leu Tyr Ile Tyr Asn Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90


<210> SEQ ID NO 201
<211> LENGTH: 94
<212> TYPE: PRT
<213> ORGANISM: Artificial Sequence
<220> FEATURE:
<223> OTHER INFORMATION: Synthetic: 2630_G10 core with C-terminal
      proline

<400> SEQUENCE: 201

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Glu Val
            20                  25                  30

Gln Ile Tyr Ser Asp Trp Gly Pro Leu Tyr Ile Tyr Asn Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90


<210> SEQ ID NO 202
<211> LENGTH: 94
<212> TYPE: PRT
<213> ORGANISM: Artificial Sequence
<220> FEATURE:
<223> OTHER INFORMATION: Synthetic: 2630_H03 core with C-terminal
      proline
<220> FEATURE:
<221> NAME/KEY: misc_feature
```

<222> LOCATION: (7)..(7)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid

<400> SEQUENCE: 202

```
Glu Val Val Ala Ala Thr Xaa Thr Ser Leu Leu Ile Ser Trp Asp Ala
1               5                   10                  15

Pro Ala Val Thr Val Xaa Tyr Tyr Arg Ile Thr Tyr Gly Arg Glu Val
            20                  25                  30

Gln Lys Tyr Ser Asp Trp Gly Pro Leu Tyr Ile Tyr Gln Glu Phe Thr
        35                  40                  45

Val Pro Gly Ser Xaa Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90
```

<210> SEQ ID NO 203
<211> LENGTH: 94
<212> TYPE: PRT
<213> ORGANISM: Artificial Sequence
<220> FEATURE:
<223> OTHER INFORMATION: Synthetic: 2631_B04 core with C-terminal proline

<400> SEQUENCE: 203

```
Glu Val Val Ala Ala Thr Pro Thr Ser Leu Leu Ile Ser Trp Asp Val
1               5                   10                  15

Pro Ala Val Thr Val Arg Tyr Tyr Arg Ile Thr Tyr Gly Arg His Val
            20                  25                  30

His Leu Tyr Ser Glu Phe Gly Pro Met Tyr Ile Tyr Asn Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Ser Gly Glu Ser
65                  70                  75                  80

Pro Ala Ser Ser Lys Pro Ile Ser Ile Asn Tyr Arg Thr Pro
                85                  90
```

<210> SEQ ID NO 204
<211> LENGTH: 94
<212> TYPE: PRT
<213> ORGANISM: Artificial Sequence
<220> FEATURE:
<223> OTHER INFORMATION: Synthetic: 2631_E03 core with C-terminal proline

<400> SEQUENCE: 204

```
Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Arg Asp Val
            20                  25                  30

His Met Tyr Ser Asp Trp Gly Pro Met Tyr Ile Tyr Gln Glu Phe Thr
        35                  40                  45
```

Val Pro Gly Ser Lys Ser Thr Ala Thr Ile Ser Gly Leu Lys Pro Gly
50 55 60

Val Asp Tyr Thr Ile Thr Val Tyr Ala Val Thr Gly Ser Gly Glu Ser
65 70 75 80

Pro Ala Ser Ser Lys Pro Ile Ser Ile Asn Tyr Arg Thr Pro
85 90

<210> SEQ ID NO 205
<211> LENGTH: 94
<212> TYPE: PRT
<213> ORGANISM: Artificial Sequence
<220> FEATURE:
<223> OTHER INFORMATION: Synthetic: 2631_G01 core with C-terminal proline

<400> SEQUENCE: 205

Glu Val Val Ala Ala Thr Pro Thr Ser Leu Leu Ile Ser Trp Asp Ala
1 5 10 15

Pro Ala Val Thr Val Arg Tyr Tyr Arg Ile Thr Tyr Gly Arg His Val
20 25 30

Gln Ile Tyr Ser Asp Trp Gly Pro Leu Tyr Ile Tyr Asn Glu Phe Thr
35 40 45

Val Pro Gly Ser Lys Ser Thr Ala Thr Ile Ser Gly Leu Lys Pro Gly
50 55 60

Val Asp Tyr Thr Ile Thr Val Tyr Ala Val Thr Gly Ser Gly Glu Ser
65 70 75 80

Pro Ala Ser Ser Lys Pro Ile Ser Ile Asn Tyr Arg Thr Pro
85 90

<210> SEQ ID NO 206
<211> LENGTH: 94
<212> TYPE: PRT
<213> ORGANISM: Artificial Sequence
<220> FEATURE:
<223> OTHER INFORMATION: Synthetic: 2631_G03 core with C-terminal proline

<400> SEQUENCE: 206

Glu Val Val Ala Ala Thr Pro Thr Ser Leu Leu Ile Ser Trp Asp Ala
1 5 10 15

Pro Ala Val Thr Val Arg Tyr Tyr Arg Ile Thr Tyr Gly Arg Tyr Val
20 25 30

Gln Leu Tyr Ser Asp Trp Gly Pro Met Tyr Ile Tyr Thr Glu Phe Thr
35 40 45

Val Pro Gly Ser Lys Ser Thr Ala Thr Ile Ser Gly Leu Lys Pro Gly
50 55 60

Val Asp Tyr Thr Ile Thr Val Tyr Ala Val Thr Gly Ser Gly Glu Ser
65 70 75 80

Pro Ala Ser Ser Lys Pro Ile Ser Ile Asn Tyr Arg Thr Pro
85 90

<210> SEQ ID NO 207
<211> LENGTH: 94
<212> TYPE: PRT
<213> ORGANISM: Artificial Sequence
<220> FEATURE:
<223> OTHER INFORMATION: Synthetic: 2631_H09 core with C-terminal proline

<400> SEQUENCE: 207

Glu Val Val Ala Ala Thr Pro Thr Ser Leu Leu Ile Ser Trp Asp Ala
1 5 10 15

Pro Ala Val Thr Val Arg Tyr Tyr Arg Ile Thr Tyr Gly Arg Gln Val
20 25 30

Gln Val Phe Ser Asp Leu Gly Pro Leu Tyr Ile Tyr Asn Glu Phe Thr
35 40 45

Val Pro Gly Ser Lys Ser Thr Ala Thr Ile Ser Gly Leu Lys Pro Gly
50 55 60

Val Asp Tyr Thr Ile Thr Val Tyr Ala Val Thr Gly Ser Gly Glu Ser
65 70 75 80

Pro Ala Ser Ser Lys Pro Ile Ser Ile Asn Tyr Arg Thr Pro
85 90

<210> SEQ ID NO 208
<211> LENGTH: 94
<212> TYPE: PRT
<213> ORGANISM: Artificial Sequence
<220> FEATURE:
<223> OTHER INFORMATION: Synthetic: 2632_G01 core with C-terminal proline

<400> SEQUENCE: 208

Glu Val Val Ala Ala Thr Pro Thr Ser Leu Leu Ile Ser Trp Asp Ala
1 5 10 15

Pro Ala Val Thr Val Arg Tyr Tyr Arg Ile Thr Tyr Gly Arg Gln Val
20 25 30

Gln Ile Tyr Ser Asp Trp Gly Pro Leu Tyr Ile Tyr Asn Glu Phe Thr
35 40 45

Val Pro Gly Ser Lys Ser Thr Ala Thr Ile Ser Gly Leu Lys Pro Gly
50 55 60

Val Asp Tyr Thr Ile Thr Val Tyr Ala Val Thr Gly Ser Gly Glu Ser
65 70 75 80

Pro Ala Ser Ser Lys Pro Ile Ser Ile Asn Tyr Arg Thr Pro
85 90

<210> SEQ ID NO 209
<211> LENGTH: 94
<212> TYPE: PRT
<213> ORGANISM: Artificial Sequence
<220> FEATURE:
<223> OTHER INFORMATION: Synthetic: 4079_A04 core with C-terminal proline

<400> SEQUENCE: 209

Glu Val Val Ala Ala Thr Pro Thr Ser Leu Leu Ile Ser Trp Asp Ala
1 5 10 15

Pro Ala Val Thr Val Arg Tyr Tyr Arg Ile Thr Tyr Gly Arg Gln Val
20 25 30

Gln Met Tyr Ser Asp Trp Gly Pro Leu Tyr Ile Tyr Ala Glu Phe Thr
35 40 45

Val Pro Gly Ser Lys Ser Thr Ala Thr Ile Ser Gly Leu Lys Pro Gly
50 55 60

Val Asp Tyr Thr Ile Thr Val Tyr Ala Val Thr Gly Ser Gly Glu Ser
65 70 75 80

Pro Ala Ser Ser Lys Pro Ile Ser Ile Asn Tyr Arg Thr Pro
85 90

<210> SEQ ID NO 210
<211> LENGTH: 7

```
<212> TYPE: PRT
<213> ORGANISM: Artificial Sequence
<220> FEATURE:
<223> OTHER INFORMATION: Synthetic: C-terminal tail

<400> SEQUENCE: 210

Glu Ile Glu Pro Lys Ser Ser
1               5


<210> SEQ ID NO 211
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 211

Glu Ile Asp Lys Pro Cys
1               5


<210> SEQ ID NO 212
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 212

Glu Ile Asp Lys Pro
1               5


<210> SEQ ID NO 213
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 213

Glu Ile Asp Lys Pro Ser
1               5


<210> SEQ ID NO 214
<211> LENGTH: 9
<212> TYPE: PRT
<213> ORGANISM: Artificial Sequence
<220> FEATURE:
<223> OTHER INFORMATION: Synthetic: C-terminal tail

<400> SEQUENCE: 214

Glu Ile Asp Lys Pro Ser Gln Leu Glu
1               5


<210> SEQ ID NO 215
<211> LENGTH: 12
<212> TYPE: PRT
<213> ORGANISM: Artificial Sequence
<220> FEATURE:
<223> OTHER INFORMATION: Synthetic: C-terminal tail

<400> SEQUENCE: 215

Glu Ile Glu Asp Glu Asp Glu Asp Glu Asp Glu Asp
1               5                   10


<210> SEQ ID NO 216
<211> LENGTH: 5
<212> TYPE: PRT
```

```
<213> ORGANISM: Artificial Sequence
<220> FEATURE:
<223> OTHER INFORMATION: Synthetic: C-terminal tail

<400> SEQUENCE: 216

Glu Gly Ser Gly Ser
1               5


<210> SEQ ID NO 217
<211> LENGTH: 9
<212> TYPE: PRT
<213> ORGANISM: Artificial Sequence
<220> FEATURE:
<223> OTHER INFORMATION: Synthetic: C-terminal tail

<400> SEQUENCE: 217

Glu Ile Asp Lys Pro Cys Gln Leu Glu
1               5


<210> SEQ ID NO 218
<211> LENGTH: 13
<212> TYPE: PRT
<213> ORGANISM: Artificial Sequence
<220> FEATURE:
<223> OTHER INFORMATION: Synthetic: C-terminal tail

<400> SEQUENCE: 218

Glu Ile Asp Lys Pro Ser Gln His His His His His His
1               5                   10


<210> SEQ ID NO 219
<211> LENGTH: 10
<212> TYPE: PRT
<213> ORGANISM: Artificial Sequence
<220> FEATURE:
<223> OTHER INFORMATION: Synthetic: C-terminal tail

<400> SEQUENCE: 219

Gly Ser Gly Cys His His His His His His
1               5                   10


<210> SEQ ID NO 220
<211> LENGTH: 11
<212> TYPE: PRT
<213> ORGANISM: Artificial Sequence
<220> FEATURE:
<223> OTHER INFORMATION: Synthetic: C-terminal tail

<400> SEQUENCE: 220

Glu Gly Ser Gly Cys His His His His His His
1               5                   10


<210> SEQ ID NO 221
<211> LENGTH: 4
<212> TYPE: PRT
<213> ORGANISM: Artificial Sequence
<220> FEATURE:
<223> OTHER INFORMATION: Synthetic: C-terminal tail

<400> SEQUENCE: 221

Pro Ile Asp Lys
1


<210> SEQ ID NO 222
<211> LENGTH: 4
<212> TYPE: PRT
<213> ORGANISM: Artificial Sequence
```

<220> FEATURE:
<223> OTHER INFORMATION: Synthetic: C-terminal tail

<400> SEQUENCE: 222

Pro Ile Glu Lys
1

<210> SEQ ID NO 223
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 223

Pro Ile Asp Lys Pro
1 5

<210> SEQ ID NO 224
<211> LENGTH: 5
<212> TYPE: PRT
<213> ORGANISM: Artificial Sequence
<220> FEATURE:
<223> OTHER INFORMATION: Synthetic: C-terminal tail

<400> SEQUENCE: 224

Pro Ile Glu Lys Pro
1 5

<210> SEQ ID NO 225
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 225

Pro Ile Asp Lys Pro Ser
1 5

<210> SEQ ID NO 226
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 226

Pro Ile Glu Lys Pro Ser
1 5

<210> SEQ ID NO 227
<211> LENGTH: 6
<212> TYPE: PRT
<213> ORGANISM: Artificial Sequence
<220> FEATURE:
<223> OTHER INFORMATION: Synthetic: C-terminal tail

<400> SEQUENCE: 227

Pro Ile Asp Lys Pro Cys
1 5

<210> SEQ ID NO 228
<211> LENGTH: 6
<212> TYPE: PRT
<213> ORGANISM: Artificial Sequence
<220> FEATURE:

<223> OTHER INFORMATION: Synthetic: C-terminal tail

<400> SEQUENCE: 228

Pro Ile Glu Lys Pro Cys
1 5

<210> SEQ ID NO 229
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 229

Pro Ile Asp Lys Pro Ser Gln
1 5

<210> SEQ ID NO 230
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 230

Pro Ile Glu Lys Pro Ser Gln
1 5

<210> SEQ ID NO 231
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 231

Pro Ile Asp Lys Pro Cys Gln
1 5

<210> SEQ ID NO 232
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 232

Pro Ile Glu Lys Pro Cys Gln
1 5

<210> SEQ ID NO 233
<211> LENGTH: 7
<212> TYPE: PRT
<213> ORGANISM: Artificial Sequence
<220> FEATURE:
<223> OTHER INFORMATION: Synthetic: C-terminal tail

<400> SEQUENCE: 233

Pro His His His His His His
1 5

<210> SEQ ID NO 234
<211> LENGTH: 8
<212> TYPE: PRT
<213> ORGANISM: Artificial Sequence
<220> FEATURE:
<223> OTHER INFORMATION: Synthetic: C-terminal tail

<400> SEQUENCE: 234

Pro Cys His His His His His His
1               5

<210> SEQ ID NO 235
<211> LENGTH: 111
<212> TYPE: PRT
<213> ORGANISM: Artificial Sequence
<220> FEATURE:
<223> OTHER INFORMATION: Synthetic: 2270_C01 w/o his tag and N-terminal methionine and w/ C-terminal proline

<400> SEQUENCE: 235

Ala Ser Thr Ser Gly Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Trp Gln Val Gln Met Tyr Ser Asp Trp
        35                  40                  45

Gly Pro Leu Tyr Ile Tyr Lys Glu Phe Thr Val Pro Gly Ser Lys Ser
    50                  55                  60

Thr Ala Thr Ile Ser Gly Leu Lys Pro Gly Val Asp Tyr Thr Ile Thr
65                  70                  75                  80

Val Tyr Ala Val Thr Gly Ser Gly Glu Ser Pro Ala Ser Ser Lys Pro
                85                  90                  95

Ile Ser Ile Asn Tyr Arg Thr Glu Gly Asp Lys Pro Ser Gln Pro
            100                 105                 110

<210> SEQ ID NO 236
<211> LENGTH: 110
<212> TYPE: PRT
<213> ORGANISM: Artificial Sequence
<220> FEATURE:
<223> OTHER INFORMATION: Synthetic: 2629_A09 w/o his tag and N-terminal methionine and w/ C-terminal proline

<400> SEQUENCE: 236

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg His Val Gln Ile Tyr Ser Asp Leu Gly
        35                  40                  45

Pro Leu Tyr Ile Tyr Thr Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110

<210> SEQ ID NO 237
<211> LENGTH: 110
<212> TYPE: PRT
<213> ORGANISM: Artificial Sequence
<220> FEATURE:
<223> OTHER INFORMATION: Synthetic: 2629_A11 w/o his tag and N-terminal methionine and w/ C-terminal proline

<400> SEQUENCE: 237

Gly Val Ser Asp Val Pro Arg Asp Leu Glu Val Val Ala Ala Thr Pro
1 5 10 15

Thr Ser Leu Leu Ile Ser Trp Asp Ala Pro Ala Val Thr Val Arg Tyr
20 25 30

Tyr Arg Ile Thr Tyr Gly Arg His Val His Ile Tyr Ser Asp Trp Gly
35 40 45

Pro Met Tyr Ile Tyr Thr Glu Phe Thr Val Pro Gly Ser Lys Ser Thr
50 55 60

Ala Thr Ile Ser Gly Leu Lys Pro Gly Val Asp Tyr Thr Ile Thr Val
65 70 75 80

Tyr Ala Val Thr Gly Ser Gly Glu Ser Pro Ala Ser Ser Lys Pro Ile
85 90 95

Ser Ile Asn Tyr Arg Thr Glu Ile Asp Lys Pro Ser Gln Pro
100 105 110

<210> SEQ ID NO 238
<211> LENGTH: 110
<212> TYPE: PRT
<213> ORGANISM: Artificial Sequence
<220> FEATURE:
<223> OTHER INFORMATION: Synthetic: 2629_C10 w/o his tag and N-terminal methionine and w/ C-terminal proline

<400> SEQUENCE: 238

Gly Val Ser Asp Val Pro Arg Asp Leu Glu Val Val Ala Ala Thr Pro
1 5 10 15

Thr Ser Leu Leu Ile Ser Trp Asp Ala Pro Ala Val Thr Val Arg Tyr
20 25 30

Tyr Arg Ile Thr Tyr Gly Arg Glu Val Gln Lys Tyr Ser Val Leu Gly
35 40 45

Pro Leu Tyr Ile Tyr Thr Glu Phe Thr Val Pro Gly Ser Lys Ser Thr
50 55 60

Ala Thr Ile Ser Gly Leu Lys Pro Gly Val Asp Tyr Thr Ile Thr Val
65 70 75 80

Tyr Ala Val Thr Gly Ser Gly Glu Ser Pro Ala Ser Ser Lys Pro Ile
85 90 95

Ser Ile Asn Tyr Arg Thr Glu Ile Asp Lys Pro Ser Gln Pro
100 105 110

<210> SEQ ID NO 239
<211> LENGTH: 110
<212> TYPE: PRT
<213> ORGANISM: Artificial Sequence
<220> FEATURE:
<223> OTHER INFORMATION: Synthetic: 2629_D09 w/o his tag and N-terminal methionine and w/ C-terminal proline

<400> SEQUENCE: 239

Gly Val Ser Asp Val Pro Arg Asp Leu Glu Val Val Ala Ala Thr Pro
1 5 10 15

Thr Ser Leu Leu Ile Ser Trp Asp Ala Pro Ala Val Thr Val Arg Tyr
20 25 30

Tyr Arg Ile Thr Tyr Gly Arg Glu Val Gln Met Tyr Ser Asp Leu Gly
35 40 45

Pro Leu Tyr Val Tyr Ser Glu Phe Thr Val Pro Gly Ser Lys Ser Thr
50 55 60

Ala Thr Ile Ser Gly Leu Lys Pro Gly Val Asp Tyr Thr Ile Thr Val

```
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110


<210> SEQ ID NO 240
<211> LENGTH: 110
<212> TYPE: PRT
<213> ORGANISM: Artificial Sequence
<220> FEATURE:
<223> OTHER INFORMATION: Synthetic: 2629_E05 w/o his tag and N-terminal
      methionine and w/ C-terminal proline

<400> SEQUENCE: 240

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Glu Val Gln Lys Phe Ser Asp Trp Gly
        35                  40                  45

Pro Leu Tyr Ile Tyr Thr Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110


<210> SEQ ID NO 241
<211> LENGTH: 110
<212> TYPE: PRT
<213> ORGANISM: Artificial Sequence
<220> FEATURE:
<223> OTHER INFORMATION: Synthetic: 2629_E06 w/o his tag and N-terminal
      methionine and w/ C-terminal proline

<400> SEQUENCE: 241

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Glu Val Gln Lys Tyr Ser Asp Leu Gly
        35                  40                  45

Pro Leu Tyr Ile Tyr Gln Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110


<210> SEQ ID NO 242
<211> LENGTH: 110
<212> TYPE: PRT
<213> ORGANISM: Artificial Sequence
<220> FEATURE:
<223> OTHER INFORMATION: Synthetic: 2629_F04 w/o his tag and N-terminal
```

methionine and w/ C-terminal proline

<400> SEQUENCE: 242

```
Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Glu Val His Gln Tyr Ser Asp Trp Gly
        35                  40                  45

Pro Met Tyr Ile Tyr Asn Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110
```

<210> SEQ ID NO 243
<211> LENGTH: 110
<212> TYPE: PRT
<213> ORGANISM: Artificial Sequence
<220> FEATURE:
<223> OTHER INFORMATION: Synthetic: 2629_H01 w/o his tag and N-terminal methionine and w/ C-terminal proline
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid

<400> SEQUENCE: 243

```
Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Xaa Tyr
            20                  25                  30

Tyr Arg Ile Thr Tyr Gly Arg Glu Val His Lys Asn Ser Asp Trp Gly
        35                  40                  45

Thr Leu Tyr Ile Tyr Thr Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Xaa Ala Val Thr Gly Ser Gly Glu Xaa Pro Ala Ser Ser Lys Pro Ile
                85                  90                  95

Ser Ile Asn Tyr Arg Thr Glu Ile Asp Lys Xaa Ser Gln Pro
            100                 105                 110
```

<210> SEQ ID NO 244
<211> LENGTH: 110
<212> TYPE: PRT
<213> ORGANISM: Artificial Sequence
<220> FEATURE:

<223> OTHER INFORMATION: Synthetic: 2629_H06 w/o his tag and N-terminal methionine and w/ C-terminal proline

<400> SEQUENCE: 244

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Glu Val Gln Lys Tyr Ser Asp Leu Gly
        35                  40                  45

Pro Leu Tyr Ile Tyr Ala Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110

<210> SEQ ID NO 245
<211> LENGTH: 110
<212> TYPE: PRT
<213> ORGANISM: Artificial Sequence
<220> FEATURE:
<223> OTHER INFORMATION: Synthetic: 2629_H07 w/o his tag and N-terminal methionine and w/ C-terminal proline

<400> SEQUENCE: 245

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Glu Val His Leu Tyr Ser Asp Trp Gly
        35                  40                  45

Pro Met Tyr Ile Tyr Thr Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110

<210> SEQ ID NO 246
<211> LENGTH: 110
<212> TYPE: PRT
<213> ORGANISM: Artificial Sequence
<220> FEATURE:
<223> OTHER INFORMATION: Synthetic: 2630_A02 w/o his tag and N-terminal methionine and w/ C-terminal proline

<400> SEQUENCE: 246

Gly Val Ser Asp Val Pro Arg Asp Leu Glu Val Val Ala Thr Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg His Val Gln Met Tyr Ser Asp Leu Gly
        35                  40                  45

Pro Leu Tyr Ile Phe Ser Glu Phe Thr Val Pro Gly Ser Lys Ser Thr

```
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110


<210> SEQ ID NO 247
<211> LENGTH: 110
<212> TYPE: PRT
<213> ORGANISM: Artificial Sequence
<220> FEATURE:
<223> OTHER INFORMATION: Synthetic: 2630_A11 w/o his tag and N-terminal
      methionine and w/ C-terminal proline

<400> SEQUENCE: 247

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Glu Val His Met Tyr Ser Asp Phe Gly
        35                  40                  45

Pro Met Tyr Ile Tyr Thr Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110


<210> SEQ ID NO 248
<211> LENGTH: 110
<212> TYPE: PRT
<213> ORGANISM: Artificial Sequence
<220> FEATURE:
<223> OTHER INFORMATION: Synthetic: 2630_D02 w/o his tag and N-terminal
      methionine and w/ C-terminal proline

<400> SEQUENCE: 248

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Glu Val Gln Lys Tyr Ser Asp Trp Gly
        35                  40                  45

Pro Leu Tyr Ile Tyr Asn Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110


<210> SEQ ID NO 249
<211> LENGTH: 110
<212> TYPE: PRT
```

<213> ORGANISM: Artificial Sequence
<220> FEATURE:
<223> OTHER INFORMATION: Synthetic: 2630_D10 w/o his tag and N-terminal
      methionine and w/ C-terminal proline

<400> SEQUENCE: 249

```
Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Glu Val Gln Met Tyr Ser Asp Leu Gly
        35                  40                  45

Pro Leu Tyr Ile Tyr Asn Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110
```

<210> SEQ ID NO 250
<211> LENGTH: 110
<212> TYPE: PRT
<213> ORGANISM: Artificial Sequence
<220> FEATURE:
<223> OTHER INFORMATION: Synthetic: 2630_F04 w/o his tag and N-terminal
      methionine and w/ C-terminal proline

<400> SEQUENCE: 250

```
Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Glu Val Gln Met Tyr Ser Asp Leu Gly
        35                  40                  45

Pro Leu Tyr Ile Tyr Thr Glu Phe Thr Val Pro Gly Ser Lys Ser Thr
    50                  55                  60

Ala Thr Ile Ser Gly Leu Lys Pro Gly Val Gly Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110
```

<210> SEQ ID NO 251
<211> LENGTH: 110
<212> TYPE: PRT
<213> ORGANISM: Artificial Sequence
<220> FEATURE:
<223> OTHER INFORMATION: Synthetic: 2630_G03 w/o his tag and N-terminal
      methionine and w/ C-terminal proline

<400> SEQUENCE: 251

```
Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg His Val Gln Ile Tyr Ser Asp Leu Gly
        35                  40                  45
```

```
Pro Leu Tyr Ile Tyr Asn Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110


<210> SEQ ID NO 252
<211> LENGTH: 110
<212> TYPE: PRT
<213> ORGANISM: Artificial Sequence
<220> FEATURE:
<223> OTHER INFORMATION: Synthetic: 2630_G10 w/o his tag and N-terminal
      methionine and w/ C-terminal proline

<400> SEQUENCE: 252

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Glu Val Gln Ile Tyr Ser Asp Trp Gly
        35                  40                  45

Pro Leu Tyr Ile Tyr Asn Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110


<210> SEQ ID NO 253
<211> LENGTH: 110
<212> TYPE: PRT
<213> ORGANISM: Artificial Sequence
<220> FEATURE:
<223> OTHER INFORMATION: Synthetic: 2630_H03 w/o his tag and N-terminal
      methionine and w/ C-terminal proline
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid

<400> SEQUENCE: 253

Gly Val Ser Asp Val Pro Arg Asp Leu Glu Val Val Ala Ala Thr Xaa
1               5                   10                  15

Thr Ser Leu Leu Ile Ser Trp Asp Ala Pro Ala Val Thr Val Xaa Tyr
            20                  25                  30

Tyr Arg Ile Thr Tyr Gly Arg Glu Val Gln Lys Tyr Ser Asp Trp Gly
```

```
        35                  40                  45

Pro Leu Tyr Ile Tyr Gln Glu Phe Thr Val Pro Gly Ser Xaa Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Xaa Ser Gln Pro
            100                 105                 110


<210> SEQ ID NO 254
<211> LENGTH: 110
<212> TYPE: PRT
<213> ORGANISM: Artificial Sequence
<220> FEATURE:
<223> OTHER INFORMATION: Synthetic: 2631_B04 w/o his tag and N-terminal
      methionine and w/ C-terminal proline

<400> SEQUENCE: 254

Gly Val Ser Asp Val Pro Arg Asp Leu Glu Val Val Ala Ala Thr Pro
1               5                   10                  15

Thr Ser Leu Leu Ile Ser Trp Asp Val Pro Ala Val Thr Val Arg Tyr
            20                  25                  30

Tyr Arg Ile Thr Tyr Gly Arg His Val His Leu Tyr Ser Glu Phe Gly
        35                  40                  45

Pro Met Tyr Ile Tyr Asn Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110


<210> SEQ ID NO 255
<211> LENGTH: 110
<212> TYPE: PRT
<213> ORGANISM: Artificial Sequence
<220> FEATURE:
<223> OTHER INFORMATION: Synthetic: 2631_E03 w/o his tag and N-terminal
      methionine and w/ C-terminal proline

<400> SEQUENCE: 255

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Asp Val His Met Tyr Ser Asp Trp Gly
        35                  40                  45

Pro Met Tyr Ile Tyr Gln Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110
```

<210> SEQ ID NO 256
<211> LENGTH: 110
<212> TYPE: PRT
<213> ORGANISM: Artificial Sequence
<220> FEATURE:
<223> OTHER INFORMATION: Synthetic: 2631_G01 w/o his tag and N-terminal methionine and w/ C-terminal proline

<400> SEQUENCE: 256

```
Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg His Val Gln Ile Tyr Ser Asp Trp Gly
        35                  40                  45

Pro Leu Tyr Ile Tyr Asn Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110
```

<210> SEQ ID NO 257
<211> LENGTH: 110
<212> TYPE: PRT
<213> ORGANISM: Artificial Sequence
<220> FEATURE:
<223> OTHER INFORMATION: Synthetic: 2631_G03 w/o his tag and N-terminal methionine and w/ C-terminal proline

<400> SEQUENCE: 257

```
Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Tyr Val Gln Leu Tyr Ser Asp Trp Gly
        35                  40                  45

Pro Met Tyr Ile Tyr Thr Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110
```

<210> SEQ ID NO 258
<211> LENGTH: 110
<212> TYPE: PRT
<213> ORGANISM: Artificial Sequence
<220> FEATURE:
<223> OTHER INFORMATION: Synthetic: 2631_H09 w/o his tag and N-terminal methionine and w/ C-terminal proline

<400> SEQUENCE: 258

```
Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30
```

```
Tyr Arg Ile Thr Tyr Gly Arg Gln Val Gln Val Phe Ser Asp Leu Gly
        35                  40                  45

Pro Leu Tyr Ile Tyr Asn Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110


<210> SEQ ID NO 259
<211> LENGTH: 110
<212> TYPE: PRT
<213> ORGANISM: Artificial Sequence
<220> FEATURE:
<223> OTHER INFORMATION: Synthetic: 2632_G01 w/o his tag and N-terminal
      methionine and w/ C-terminal proline

<400> SEQUENCE: 259

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Gln Val Gln Ile Tyr Ser Asp Trp Gly
        35                  40                  45

Pro Leu Tyr Ile Tyr Asn Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110


<210> SEQ ID NO 260
<211> LENGTH: 110
<212> TYPE: PRT
<213> ORGANISM: Artificial Sequence
<220> FEATURE:
<223> OTHER INFORMATION: Synthetic: 4079_A04 w/o his tag and N-terminal
      methionine and w/ C-terminal proline

<400> SEQUENCE: 260

Gly Val Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Arg Gln Val Gln Met Tyr Ser Asp Trp Gly
        35                  40                  45

Pro Leu Tyr Ile Tyr Ala Glu Phe Thr Val Pro Gly Ser Lys Ser Thr
    50                  55                  60

Ala Thr Ile Ser Gly Leu Lys Pro Gly Val Asp Tyr Thr Ile Thr Val
65                  70                  75                  80

Tyr Ala Val Thr Gly Ser Gly Glu Ser Pro Ala Ser Ser Lys Pro Ile
                85                  90                  95

Ser Ile Asn Tyr Arg Thr Glu Ile Asp Lys Pro Ser Gln Pro
            100                 105                 110
```

<210> SEQ ID NO 261
<211> LENGTH: 218
<212> TYPE: PRT
<213> ORGANISM: Artificial Sequence
<220> FEATURE:
<223> OTHER INFORMATION: Synthetic: PCSK9-PKE2 tandem Adnectin w/o his tag and N-terminal methionine 5190_E01 (ATI-1676)

<400> SEQUENCE: 261

```
Gly Val Ser Asp Val Pro Arg Asp Leu Glu Val Val Ala Ala Thr Pro
1               5                   10                  15

Thr Ser Leu Leu Ile Ser Trp Asp Ala Pro Ala Glu Gly Tyr Gly Tyr
            20                  25                  30

Tyr Arg Ile Thr Tyr Gly Glu Thr Gly Gly Asn Ser Pro Val Gln Glu
        35                  40                  45

Phe Thr Val Pro Val Ser Lys Gly Thr Ala Thr Ile Ser Gly Leu Lys
    50                  55                  60

Pro Gly Val Asp Tyr Thr Ile Thr Val Tyr Ala Val Glu Phe Asp Phe
65                  70                  75                  80

Pro Gly Ala Gly Tyr Tyr His Arg Pro Ile Ser Ile Asn Tyr Arg Thr
                85                  90                  95

Glu Pro Ser Thr Pro Pro Thr Pro Ser Pro Ser Thr Pro Pro Thr Pro
            100                 105                 110

Ser Pro Ser Gly Val Ser Asp Val Pro Arg Asp Leu Glu Val Val Ala
        115                 120                 125

Ala Thr Pro Thr Ser Leu Leu Ile Ser Trp Asp Ala Pro Ala Val Thr
    130                 135                 140

Val Arg Tyr Tyr Arg Ile Thr Tyr Gly Arg Glu Val Gln Lys Tyr Ser
145                 150                 155                 160

Asp Leu Gly Pro Leu Tyr Ile Tyr Gln Glu Phe Thr Val Pro Gly Ser
                165                 170                 175

Lys Ser Thr Ala Thr Ile Ser Gly Leu Lys Pro Gly Val Asp Tyr Thr
            180                 185                 190

Ile Thr Val Tyr Ala Val Thr Gly Ser Gly Glu Ser Pro Ala Ser Ser
        195                 200                 205

Lys Pro Ile Ser Ile Asn Tyr Arg Thr Pro
    210                 215
```

<210> SEQ ID NO 262
<211> LENGTH: 100
<212> TYPE: PRT
<213> ORGANISM: Artificial Sequence
<220> FEATURE:
<223> OTHER INFORMATION: Synthetic: Exemplary linker
<220> FEATURE:
<221> NAME/KEY: misc_feature
<222> LOCATION: (11)..(100)
<223> OTHER INFORMATION: any Pro Ser Pro Glu Pro Pro Thr Pro Glu Pro may or may not be present

<400> SEQUENCE: 262

```
Pro Ser Pro Glu Pro Pro Thr Pro Glu Pro Pro Ser Pro Glu Pro Pro
1               5                   10                  15

Thr Pro Glu Pro Pro Ser Pro Glu Pro Pro Thr Pro Glu Pro Pro Ser
            20                  25                  30

Pro Glu Pro Pro Thr Pro Glu Pro Pro Ser Pro Glu Pro Pro Thr Pro
        35                  40                  45

Glu Pro Pro Ser Pro Glu Pro Pro Thr Pro Glu Pro Pro Ser Pro Glu
```

```
    50                  55                  60

Pro Pro Thr Pro Glu Pro Pro Ser Pro Glu Pro Pro Thr Pro Glu Pro
65                  70                  75                  80

Pro Ser Pro Glu Pro Pro Thr Pro Glu Pro Pro Ser Pro Glu Pro Pro
                85                  90                  95

Thr Pro Glu Pro
            100


<210> SEQ ID NO 263
<211> LENGTH: 61
<212> TYPE: PRT
<213> ORGANISM: Artificial Sequence
<220> FEATURE:
<223> OTHER INFORMATION: Synthetic: Exemplary linker
<220> FEATURE:
<221> NAME/KEY: misc_feature
<222> LOCATION: (7)..(60)
<223> OTHER INFORMATION: any Glu Glu Glu Glu Asp Glu may or may not be
      present

<400> SEQUENCE: 263

Glu Glu Glu Glu Asp Glu Glu Glu Glu Glu Asp Glu Glu Glu Glu Glu
1               5                   10                  15

Asp Glu Glu Glu Glu Glu Asp Glu Glu Glu Glu Glu Asp Glu Glu Glu
            20                  25                  30

Glu Glu Asp Glu Glu Glu Glu Glu Asp Glu Glu Glu Glu Glu Asp Glu
        35                  40                  45

Glu Glu Glu Glu Asp Glu Glu Glu Glu Glu Asp Glu Glu
    50                  55                  60


<210> SEQ ID NO 264
<211> LENGTH: 16
<212> TYPE: PRT
<213> ORGANISM: Artificial Sequence
<220> FEATURE:
<223> OTHER INFORMATION: Synthetic

<400> SEQUENCE: 264

Trp Gln Val Gln Met Tyr Ser Asp Trp Gly Pro Leu Tyr Ile Tyr Lys
1               5                   10                  15


<210> SEQ ID NO 265
<211> LENGTH: 16
<212> TYPE: PRT
<213> ORGANISM: Artificial Sequence
<220> FEATURE:
<223> OTHER INFORMATION: Synthetic

<400> SEQUENCE: 265

Arg Glu Val Gln Lys Tyr Ser Asp Leu Gly Pro Leu Tyr Ile Tyr Gln
1               5                   10                  15


<210> SEQ ID NO 266
<211> LENGTH: 16
<212> TYPE: PRT
<213> ORGANISM: Artificial Sequence
<220> FEATURE:
<223> OTHER INFORMATION: Synthetic

<400> SEQUENCE: 266

Arg Glu Val Gln Lys Tyr Ser Asp Trp Gly Pro Leu Tyr Ile Tyr Asn
1               5                   10                  15
```

SERUM ALBUMIN-BINDING FIBRONECTIN TYPE III DOMAINS

REFERENCE TO RELATED APPLICATIONS

This application is a 35 U.S.C. 371 national stage filing of International Application No. PCT/US2015/021535, filed Mar. 19, 2015, which claims priority to U.S. Provisional Application No. 61/968,181 entitled "Novel Serum Albumin-Binding Fibronectin Type III Domains" filed Mar. 20, 2014. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Sep. 19, 2016, is named MXI_536US_Sequence_Listing.txt and is 200,598 bytes in size.

BACKGROUND

Inadequate half-lives of therapeutics often necessitate their administration at high frequencies and/or higher doses, or the use of sustained release formulations, in order to maintain serum levels necessary for therapeutic effects. Yet, this is often associated with negative side effects. For example, frequent systemic injections present considerable discomfort to the subject, and pose a high risk of administration-related infections, and may require hospitalization or frequent visits to the hospital, in particular when the therapeutic is to be administered intravenously. Moreover, in long term treatments, daily intravenous injections can also lead to considerable side effects of tissue scarring and vascular pathologies caused by the repeated puncturing of vessels. Similar problems are known for all frequent systemic administrations of therapeutics, such as, for example, the administration of insulin to diabetics, or interferon drugs to patients suffering from multiple sclerosis. All these factors lead to a decrease in patient compliance and increased costs for the health system.

This application provides compounds that increase the serum half-life of various therapeutics, compounds having increased serum half-life, and methods for increasing the serum half-life of therapeutics. Such compounds and methods for increasing the serum half-life of therapeutics can be manufactured in a cost effective manner, possess desirable biophysical properties (e.g., Tm, substantially monomeric, or well-folded), and are of a size small enough to permit tissue penetration.

SUMMARY

The invention is based, at least in part, on the discovery of novel south pole-based serum albumin binding fibronectin type III tenth domain ($^{10}$Fn3) containing Adnectins (PKE2 Adnectins), which provide enhanced properties over prior north pole-based serum albumin binding $^{10}$Fn3 domain containing Adnectins.

In one aspect, the invention provides a polypeptide comprising a $^{10}$Fn3 domain, wherein the $^{10}$Fn3 domain comprises a) AB, BC, CD, DE, EF, and FG loops, b) a CD loop with an altered amino acid sequence relative to the sequence of the corresponding CD loop of the human $^{10}$Fn3 domain, and c) wherein the polypeptide binds to human serum albumin with a $K_D$ of less than 500 nM.

In certain embodiments, the $^{10}$Fn3 domain further binds to one or more of rhesus serum albumin, cynomolgus serum albumin, mouse serum albumin, and rat serum albumin. For example, the $^{10}$Fn3 domain may bind to HSA, rhesus serum albumin, and cynomolgus serum albumin, or the $^{10}$Fn3 domain may bind to HSA, rhesus serum albumin, cynomolgus serum albumin, mouse serum albumin, and rat serum albumin. In some embodiments, the $^{10}$Fn3 domain binds to the corresponding serum albumin with a $K_D$ of less than 500 nM, for example, a $K_D$ of less than 100 nM, or even a $K_D$ less than 10 nM. In some embodiments, the $^{10}$Fn3 domain binds to serum albumin at a pH range of 5.5 to 7.4.

In certain embodiments, the $^{10}$Fn3 domain binds to domain I-II of HSA.

In certain embodiments, the serum half-life of the polypeptide comprising the $^{10}$Fn3 domain in the presence of human serum albumin is at least 10 hours, such as at least 20 hours, or at least 30 hours.

In certain embodiments, the CD loop comprises an amino acid sequence according to the formula G-$X_1$-$X_2$-V-$X_3$-$X_4$-$X_5$-S-$X_6$-$X_7$-G-$X_8$-$X_9$-Y-$X_{10}$-$X_{11}$-$X_{12}$-E (SEQ ID NO: 170), wherein, (a) $X_1$ is selected from the group consisting of R or W;
(b) $X_2$ is selected from the group consisting of H, E, D, Y, or Q;
(c) $X_3$ is selected from the group consisting of Q or H;
(d) $X_4$ is selected from the group consisting of I, K, M, Q, L, or V;
(e) $X_5$ is selected from the group consisting of Y, F, or N;
(f) $X_6$ is selected from the group consisting of D, V, or E;
(g) $X_7$ is selected from the group consisting of L, W, or F;
(h) $X_8$ is selected from the group consisting of P or T;
(i) $X_9$ is selected from the group consisting of L or M;
(j) $X_{10}$ is selected from the group consisting of I or V;
(k) $X_{11}$ is selected from the group consisting of Y or F; and
(l) $X_{12}$ is selected from the group consisting of T, S, Q, N, or A.

In a preferred embodiment, (a) $X_1$ is R; (b) $X_2$ is E; (c) $X_3$ is Q; (d) $X_4$ is K; (e) $X_5$ is Y; (f) $X_6$ is D; (g) $X_7$ is L or W; (h) $X_8$ is P; (i) $X_9$ is L; (j) $X_{10}$ is I; (k) $X_{11}$ is Y; and (l) $X_{12}$ is Q or N.

In yet a further preferred embodiment, (a) $X_1$ is R; (b) $X_2$ is E; (c) $X_3$ is Q; (d) $X_4$ is K; (e) $X_5$ is Y; (f) $X_6$ is D; (g) $X_7$ is L; (h) $X_8$ is P; (i) $X_9$ is L; (j) $X_{10}$ is I; (k) $X_{11}$ is Y; and (l) $X_{12}$ is Q.

In yet a further preferred embodiment, (a) $X_1$ is R; (b) $X_2$ is E; (c) $X_3$ is Q; (d) $X_4$ is K; (e) $X_5$ is Y; (f) $X_6$ is D; (g) $X_7$ is W; (h) $X_8$ is P; (i) $X_9$ is L; (j) $X_{10}$ is I; (k) $X_{11}$ is Y; and (l) $X_{12}$ is N.

In certain embodiments, the CD loop comprises an amino acid sequence selected from the group consisting of SEQ ID NOs: 101-125. In a preferred embodiment, the CD loop comprises the amino acid sequence set forth in SEQ ID NO: 106 or 113.

In certain embodiments, the invention provides a polypeptide comprising a $^{10}$Fn3 domain comprising (i) a CD loop comprising an amino acid sequence having the consensus sequence of SEQ ID NO: 170 or the amino acid sequence of any one of SEQ ID NOs: 101-125 and (ii) an amino acid sequence at least 80%, 85%, 90%, 95%, 98%, 99% or 100% identical to the non-CD loop regions of SEQ ID NOs: 23-100, 184-209 and 235-260 or that differs from one of SEQ ID NOs: 23-100, 184-209 and 235-260 in at most 1, 1-2, 1-5, 1-10 or 1-20 amino acids. In certain embodiments, the polypeptide comprises an amino acid sequence that is at least 80%, 85%, 90%, 95%, 98%, 99% or 100% identical to any one of SEQ ID NOs: 23-100, 184-209 and 235-260 or that differs from one of SEQ ID NOs: 23-100, 184-209 and 235-260 in at most 1, 1-2, 1-5, 1-10 or 1-20 amino acids. Amino acid differences may be substitutions, additions or deletions.

In certain aspects, the invention provides a fusion polypeptide comprising a fibronectin type III tenth ($^{10}$Fn3) domain and a heterologous protein, wherein the $^{10}$Fn3 domain comprises a) AB, BC, CD, DE, EF, and FG loops, b) a CD loop with an altered amino acid sequence relative to the sequence of the corresponding loop of the human $^{10}$Fn3 domain, and c) wherein the polypeptide binds to human serum albumin with a $K_D$ of less than 500 nM.

In certain embodiments, the fusion polypeptide comprises an albumin binding Adnectin comprising an amino acid sequence at least 70%, 75%, 80%, 85%, 90%, 95%, 96%, 97%, 98%, 99% or 100% identical to any one of SEQ ID NOs: 23-100, 184-209 and 235-260 or that differs from one of SEQ ID NOs: 23-100, 184-209 and 235-260 in at most 1, 1-2, 1-5, 1-10 or 1-20 amino acids. In a preferred embodiment, the fusion polypeptide comprises an albumin binding Adnectin comprising the amino acid sequence of SEQ ID NO: 55, 81, 190 or 241. In yet another preferred embodiment, the fusion polypeptide comprises an albumin binding Adnectin comprising the amino acid sequence of SEQ ID NO: 62, 88, 197 or 248.

In certain embodiments, the fusion polypeptide comprises an albumin binding Adnectin and a heterologous moiety, wherein the heterologous moiety is a therapeutic moiety.

In certain embodiments, the heterologous protein is a polypeptide comprising a $^{10}$Fn3 domain. In some embodiments, the $^{10}$Fn3 domain binds to a target protein other than serum albumin. In one embodiment, the $^{10}$Fn3 domain binds to PCSK9 (i.e., a PCSK9 Adnectin), and comprises an amino acid sequence at least 70%, 75%, 80%, 85%, 90%, 95%, 96%, 97%, 98%, 99% or 100% identical to SEQ ID NO: 167 or that differs from SEQ ID NO: 167 in at most 1, 1-2, 1-5, 1-10 or 1-20 amino acids.

In certain embodiments, the fusion polypeptide is a PCSK9-PKE2 tandem Adnectin comprising an amino acid sequence at least 70%, 75%, 80%, 85%, 90%, 95%, 96%, 97%, 98%, 99% or 100% identical to SEQ ID NO: 168, 169 or 261 or that differs from one of SEQ ID NOs: 168, 169 or 261 in at most 1, 1-2, 1-5, 1-10 or 1-20 amino acids (and may or may not comprise an N-terminal methionine).

In certain embodiments, the serum half-life of the fusion polypeptide in the presence of mouse serum albumin is at least 10 hours. In some embodiments, the serum half-life of the fusion polypeptide in the presence of cynomolgus serum albumin is at least 50 hours. In certain embodiments, the serum half-life of the fusion polypeptide in the presence of mouse or cynomolgus serum albumin is 10-100 hours, such as 10-90 hours, 10-80 hours, 10-70 hours, 10-60 hours, 10-50 hours, 10-40 hours, 10-30 hours, 10-20 hours, 50-100 hours, 60-100 hours, 70-100 hours, 80-100 hours, 90-100 hours, 20-90 hours, 30-80 hours, 40-70 hours, or 50-60 hours.

In certain aspects, the invention provides a PKE2 Adnectin or PCSK9-PKE2 tandem Adnectin comprising an amino acid sequence selected from the group consisting of SEQ ID NOs: 23-100, 168, 169, 184-209, 235-260, and 261.

In certain aspects, the invention provides a composition comprising any one of the albumin binding Adnectins or fusion proteins comprising such, as described herein, and a carrier.

In certain aspects, the invention provides an isolated nucleic acid molecule encoding any one of the ablumin binding Adnectins or fusion proteins comprising such, as described herein, for example, those set forth in SEQ ID NOs: 126-151 and 172, expression vectors encoding the nucleic acid molecules, and cells comprising the nucleic acid molecules. Also provided are nucleic acids comprising a nucleotide sequence that is at least 70%, 75%, 80%, 85%, 90%, 95%, 96%, 97%, 98%, 99% identical to any of these nucleotide sequences described herein, or which differ therefrom in at most 1-5, 1-10, 1-50 or 1-100 nucleotides.

In certain aspects, the invention provides a method of producing the albumin binding Adnectins or fusion proteins comprising such described herein, comprising culturing the cell comprising the nucleic acid molecules encoding the same under conditions suitable for expressing the Adnectins or fusion proteins, and purifying the same.

BRIEF DESCRIPTION OF THE FIGURES

FIG. 5 depicts a comparison of the modularity of tandem Adnectins. The Adnectin 1318_H04 corresponds to a north pole-based serum albumin binding Adnectin. The "X" refers to the configuration of non-PKE target specific Adnectin (i.e., myostatin; "myo", or PCSK9). The lower panel depicts a legend for the shades of grey in each box which correspond to HSA binding $EC_{50}$ tandem:monoAdnectin ratios as determined by direct binding ELISA (i.e., the darker the shade of grey, the stronger the binding to HSA).

FIG. 17 shows the amino acid sequences of the PKE2 Adnectins described herein.

FIGS. 18A-18C show the nucleic acid sequences of the PKE2 Adnectins and PCSK9-PKE2 tandem Adnectins described herein.

DETAILED DESCRIPTION

Definitions

Figure 1:
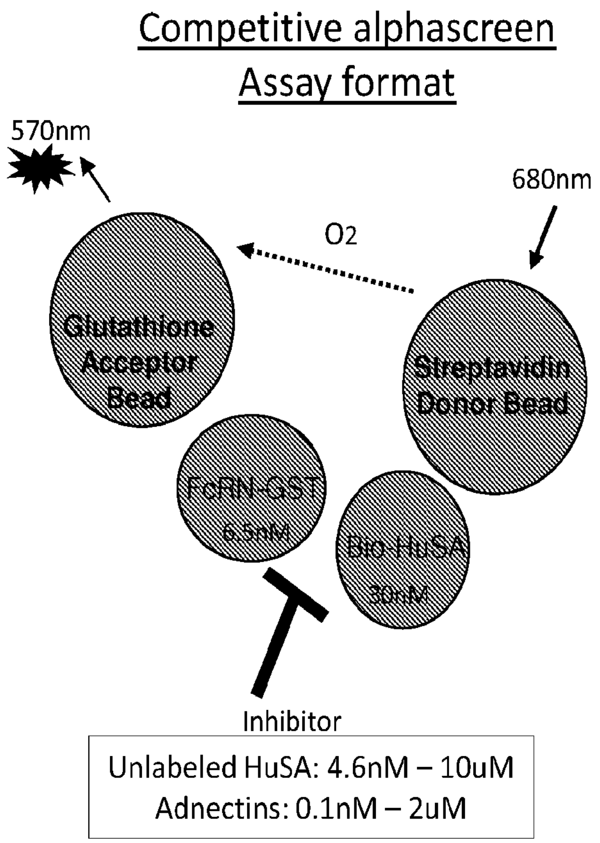
FIG. 1 shows a schematic diagram of the competitive alpha-screen assay described in Example 6.

Unless defined otherwise, all technical and scientific terms used herein have the same meaning as commonly understood by the skilled artisan. Although any methods and compositions similar or equivalent to those described herein can be used in practice or testing of the present invention, the preferred methods and compositions are described herein.

A "polypeptide," as used herein, refers to any sequence of two or more amino acids, regardless of length, post-translation modification, or function. "Polypeptide," "peptide," and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

A "polypeptide chain", as used herein, refers to a polypeptide wherein each of the domains thereof is joined to other domain(s) by peptide bond(s), as opposed to non-covalent interactions or disulfide bonds.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least residues of N-terminal or internal amino acid sequence by use of a spinning cup sequenator, or (3) to homogeneity by SDS-PAGE under reducing or nonreducing condition using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "region" of a $^{10}$Fn3 domain as used herein refers to either a loop (AB, BC, CD, DE, EF and FG), a β-strand (A, B, C, D, E, F and G), the N-terminus (corresponding to amino acid residues 1-7 of SEQ ID NO: 1), or the C-terminus (corresponding to amino acid residues 93-94 of SEQ ID NO: 1) of the human $^{10}$Fn3 domain.

A "north pole loop" refers to any one of the BC, DE and FG loops of a fibronectin human fibronectin type 3 tenth ($^{10}$Fn3) domain.

A "south pole loop" refers to any one of the AB, CD and EF loops of a fibronectin human fibronectin type 3 tenth ($^{10}$Fn3) domain.

A "scaffold region" refers to any non-loop region of a human $^{10}$Fn3 domain. The scaffold region includes the A, B, C, D, E, F and G β-strands as well as the N-terminal region (amino acids corresponding to residues 1-8 of SEQ ID NO: 1) and the C-terminal region (amino acids corresponding to residues 93-94 of SEQ ID NO: 1 and optionally comprising the 7 amino acids constituting the natural linker between the $10^{th}$ and the $11^{th}$ repeat of the Fn3 domain in human fibronectin).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The terms "specifically binds," "specific binding," "selective binding," and "selectively binds," as used interchangeably herein refers to an Adnectin that exhibits affinity for a serum albumin, but does not significantly bind (e.g., less than about 10% binding) to a different polypeptide as measured by a technique available in the art such as, but not limited to, Scatchard analysis and/or competitive binding assays (e.g., competition ELISA, BIACORE assay). The term is also applicable where e.g., a binding domain of an Adnectin of the invention is specific for serum albumin.

The "half-life" of a polypeptide can generally be defined as the time taken for the serum concentration of the polypeptide to be reduced by 50%, in vivo, for example due to degradation of the polypeptide and/or clearance or sequestration of the polypeptide by natural mechanisms. The half-life can be determined in any manner known per se, such as by pharmacokinetic analysis. Suitable techniques will be clear to the person skilled in the art, and may, for example, generally involve the steps of administering a suitable dose of a polypeptide to a primate; collecting blood samples or other samples from said primate at regular intervals; determining the level or concentration of the polypeptide in said blood sample; and calculating, from (a plot of) the data thus obtained, the time until the level or concentration of the polypeptide has been reduced by 50% compared to the initial level upon dosing. Methods for determining half-life may be found, for example, in Kenneth et al., Chemical Stability of Pharmaceuticals: A Handbook for Pharmacists (1986); Peters et al, Pharmacokinetic analysis: A Practical Approach (1996); and "Pharmacokinetics", M Gibaldi & D Perron, published by Marcel Dekker, 2nd Rev. edition (1982).

Half-life can be expressed using parameters such as the $t_{1/2}$-alpha, $t_{1/2}$-beta and the area under the curve (AUC). In the present specification, an "increase in half-life" refers to an increase in any one of these parameters, any two of these parameters, or in all three these parameters. In certain embodiments, an increase in half-life refers to an increase in the t½-beta, either with or without an increase in the $t_{1/2}$-alpha and/or the AUC or both.

The term "$K_D$," as used herein, is intended to refer to the dissociation equilibrium constant of a particular Adnectin-protein interaction or the affinity of an Adnectin for a protein (e.g., serum albumin), as measured using a surface plasmon resonance assay or a cell binding assay. A "desired $K_D$," as used herein, refers to a $K_D$ of an Adnectin that is sufficient for the purposes contemplated. For example, a desired $K_D$ may refer to the $K_D$ of an Adnectin required to elicit a functional effect in an in vitro assay, e.g., a cell-based luciferase assay.

The term "$k_{ass}$", as used herein, is intended to refer to the association rate constant for the association of an Adnectin into the Adnectin/protein complex.

The term "$k_{diss}$", as used herein, is intended to refer to the dissociation rate constant for the dissociation of an Adnectin from the Adnectin/protein complex.

The term "$IC_{50}$", as used herein, refers to the concentration of an Adnectin that inhibits a response, either in an in vitro or an in vivo assay, to a level that is 50% of the maximal inhibitory response, i.e., halfway between the maximal inhibitory response and the untreated response.

The term "therapeutically effective amount" refers to an amount of a drug effective to treat a disease or disorder in a mammal and/or relieve to some extent one or more of the symptoms associated with the disorder.

As used herein, "preventing" a disease or disorder refers to reducing the probability of occurrence of a disease-state in a statistical sample relative to an untreated control sample, or delaying the onset or reducing the severity of one or more symptoms of the disease or disorder relative to the untreated control sample. Patients may be selected for preventative therapy based on factors that are known to increase risk of suffering a clinical disease state compared to the general population. The term "treating" as used herein includes (a) inhibiting the disease-state, i.e., arresting its development; and/or (b) relieving the disease-state, i.e., causing regression of the disease state once it has been established.

Overview

The novel fibronectin based scaffold polypeptides described herein bind to serum albumin of various species and can be coupled to additional molecule(s), such as other $^{10}$Fn3 domains that bind to different targets, or polypeptides for which increased half-life is beneficial.

A. General Structure of Fibronectin Based Scaffolds

Fn3 refers to a type III domain from fibronectin. An Fn3 domain is small, monomeric, soluble, and stable. It lacks disulfide bonds and, therefore, is stable under reducing conditions. The overall structure of Fn3 resembles the immunoglobulin fold. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face ("the south pole") and loops BC, DE, and FG are located on the opposing face ("the north pole"). Any or all of loops AB, BC, CD, DE, EF and FG may participate in ligand binding. There are at least 15 different Fn3 modules in human Fibronectin, and while the sequence homology between the modules is low, they all share a high similarity in tertiary structure.

In some embodiments, the Fn3 domain is an Fn3 domain derived from the wild-type tenth module of the human fibronectin type III domain ($^{10}$Fn3):

(SEQ ID NO: 1)

VSDVPRDLEVVAATPTSLLISWDAPAVTVRYYRITYGETGGNSPVQE
FTVPGSKSTATISGLKPGVDYTITVYAVTGRGDSPASSKPISINYRT
(AB, CD, and EF loops are underlined).

In some embodiments, the non-ligand binding sequences of $^{10}$Fn3, i.e., the "$^{10}$Fn3 scaffold", may be altered provided that the $^{10}$Fn3 retains ligand binding function and/or structural stability. A variety of mutant $^{10}$Fn3 scaffolds have been reported. In one aspect, one or more of Asp 7, Glu 9, and Asp 23 is replaced by another amino acid, such as, for example, a non-negatively charged amino acid residue (e.g., Asn, Lys, etc.). These mutations have been reported to have the effect of promoting greater stability of the mutant $^{10}$Fn3 at neutral pH as compared to the wild-type form (see, e.g., PCT Publication No. WO 02/04523). A variety of additional alterations in the $^{10}$Fn3 scaffold that are either beneficial or neutral have been disclosed. See, for example, Batori et al., Protein Eng., 15(12):1015-1020 (December 2002); Koide et al., Biochemistry, 40(34):10326-10333 (Aug. 28, 2001).

Both variant and wild-type $^{10}$Fn3 proteins are characterized by the same structure, namely seven beta-strand domain sequences designated A through G and six loop regions (AB loop, BC loop, CD loop, DE loop, EF loop, and FG loop) which connect the seven beta-strand domain sequences. The beta strands positioned closest to the N- and C-termini may adopt a beta-like conformation in solution. In SEQ ID NO: 1, the AB loop corresponds to residues 14-17, the BC loop corresponds to residues 23-31, the CD loop corresponds to residues 37-47, the DE loop corresponds to residues 51-56, the EF loop corresponds to residues 63-67, and the FG loop corresponds to residues 76-87.

Accordingly, in some embodiments, the serum albumin binding Adnectin of the invention is an $^{10}$Fn3 polypeptide that is at least 40%, 50%, 60%, 65%, 70%, 75%, 80%, 85%, or 90% identical to the human $^{10}$Fn3 domain, shown in SEQ ID NO: 1. Much of the variability will generally occur in one or more of the loops. Each of the beta or beta-like strands of a $^{10}$Fn3 polypeptide may consist essentially of an amino acid sequence that is at least 80%, 85%, 90%, 95% or 100% identical to the sequence of a corresponding beta or beta-like strand of SEQ ID NO: 1, provided that such variation does not disrupt the stability of the polypeptide in physiological conditions.

Additionally, insertions and deletions in the loop regions may also be made while still producing high affinity serum-binding $^{10}$Fn3 binding domains. Accordingly, in some embodiments, one or more loops selected from AB, BC, CD, DE, EF and FG may be extended or shortened in length relative to the corresponding loop in wild-type human $^{10}$Fn3. In any given polypeptide, one or more loops may be extended in length, one or more loops may be reduced in length, or combinations thereof. In some embodiments, the length of a given loop may be extended by 2-25, 2-20, 2-15, 2-10, 2-5, 5-25, 5-20, 5-15, 5-10, 10-25, 10-20, or 10-15 amino acids. In some embodiments, the length of a given loop may be reduced by 1-15, 1-11, 1-10, 1-5, 1-3, 1-2, 2-10, or 2-5 amino acids.

As described above, amino acid residues corresponding to residues 14-17, 23-30, 37-47, 51-56, 63-67 and 76-87 of SEQ ID NO: 1 define the AB, BC, CD, DE, EF and FG loops, respectively. However, it should be understood that not every residue within a loop region needs to be modified in order to achieve a $^{10}$Fn3 binding domain having strong affinity for a desired target. In some embodiments, only residues in a loop, e.g., the CD loop are modified to produce high affinity target binding $^{10}$Fn3 domains.

In some embodiments, the invention provides polypeptides comprising a $^{10}$Fn3 domain, wherein the $^{10}$Fn3 domain comprises AB, BC, CD, DE, and FG loops, and has at least one loop selected from AB, CD, and EF loops with an altered amino acid sequence relative to the sequence of the corresponding loop of the human $^{10}$Fn3 domain of SEQ ID NO: 1. In some embodiments, the AB, CD, and EF loops are altered. In certain embodiments, only the AB loop is altered. In certain embodiments, only the CD loop is altered. In certain embodiments, only the EF loop is altered. In certain embodiments, the AB and CD loops are both altered. In certain embodiments, the AB and EF loops are both altered. In certain embodiments, the CD and EF loops are both altered. In some embodiments, one or more specific scaffold alterations are combined with one or more loop alterations. By "altered" is meant one or more amino acid sequence alterations relative to a template sequence (i.e., the corresponding wild-type human fibronectin domain) and includes amino acid additions, deletions, and substitutions.

In some embodiments, the fibronectin based scaffold protein comprises a $^{10}$Fn3 domain having a combination of north and south pole loop alterations. For example, one or more of loops AB, CD, and EF, in combination with one or more of loops BC, DE, and FG, can be altered relative to the corresponding loops of the human $^{10}$Fn3 domain of SEQ ID NO: 1.

In some embodiments, the polypeptide comprises a $^{10}$Fn3 domain that comprises an amino acid sequence at least 80, 85, 90, 95, 98, 99, or 100% identical to the non-loop regions and/or non-modified loop regions of SEQ ID NO: 1, wherein at least one loop selected from AB, CD, and EF is altered. For example, in certain embodiments, the AB loop may have up to 4 amino acid substitutions, up to 10 amino acid insertions, up to 3 amino acid deletions, or a combination thereof; the CD loop may have up to 6 amino acid substitutions, up to 10 amino acid insertions, up to 4 amino acid deletions, or a combination thereof; and the EF loop may have up to 5 amino acid substations, up to 10 amino acid insertions, up to 3 amino acid deletions, or a combination thereof; and/or the FG loop may have up to 12 amino acid substitutions, up to 11 amino acid deletions, up to 25 amino acid insertions, or a combination thereof.

In some embodiments, one or more residues of the integrin-binding motif "arginine-glycine-aspartic acid" (RGD) (amino acids 78-80 of SEQ ID NO: 1) may be substituted so as to disrupt integrin binding. In some embodiments, the FG loop of the polypeptides provided herein does not contain an RGD integrin binding site. In one embodiment, the RGD sequence is replaced by a polar amino acid-neutral amino acid-acidic amino acid sequence (in the N-terminal to C-terminal direction). In certain embodiments, the RGD sequence is replaced with SGE. In yet certain embodiments, the RGD sequence is replaced with RGE.

In certain embodiments, the fibronectin based scaffold protein comprises a $^{10}$Fn3 domain that is defined generally by following the sequence:

(SEQ ID NO: 2)

VSDVPRDLEVVAA$(X)_u$LLISW$(X)_v$YRITY$(X)_w$FTV$(X)_x$ATISGL $(X)_y$YTITVYA$(X)_z$ISINYRT

In SEQ ID NO: 2, the AB loop is represented by $(X)_u$, the BC loop is represented by $(X)_v$, the CD loop is represented by $(X)_w$, the DE loop is represented by $(X)_x$, the EF loop is represented by $(X)_y$ and the FG loop is represented by $X_z$. X represents any amino acid and the subscript following the X represents an integer of the number of amino acids. In particular, u, v, w, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. The sequences of the beta strands (underlined) may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 2. In some embodiments, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 2. In certain embodiments, the hydrophobic core amino acid residues (bolded residues in SEQ ID NO: 2 above) are fixed, and any substitutions, conservative substitutions, deletions or additions occur at residues other than the hydrophobic core amino acid residues. In some embodiments, the hydrophobic core residues of the polypeptides provided herein have not been modified relative to the wild-type human $^{10}$Fn3 domain (SEQ ID NO: 1).

In some embodiments, the amino acid sequences of the N-terminal and/or C-terminal regions of the polypeptides provided herein may be modified by deletion, substitution or insertion relative to the amino acid sequences of the corresponding regions of the wild-type human $^{10}$Fn3 domain (SEQ ID NO: 1). The $^{10}$Fn3 domains generally begin with amino acid number 1 of SEQ ID NO: 1. However, domains with amino acid deletions are also encompassed by the invention. Additional sequences may also be added to the N- or C-terminus of a $^{10}$Fn3 domain having the amino acid sequence of SEQ ID NO: 1. For example, in some embodiments, the N-terminal extension consists of an amino acid sequence selected from the group consisting of: M, MG, and G.

In exemplary embodiments, an alternative N-terminal region having from 1-20, 1-15, 1-10, 1-8, 1-5, 1-4, 1-3, 1-2, or 1 amino acids in length can be added to the N-terminal region of SEQ ID NO: 1. Exemplary alternative N-terminal regions include (represented by the single letter amino acid code) M, MG, G, MGVSDVPRDL (SEQ ID NO: 3) and GVSDVPRDL (SEQ ID NO: 4). Other suitable alternative N-terminal regions include, for example, $X_n$SDVPRDL (SEQ ID NO: 5), $X_n$DVPRDL (SEQ ID NO: 6), $X_n$VPRDL (SEQ ID NO: 7), $X_n$PRDL (SEQ ID NO: 8) $X_n$RDL (SEQ ID NO: 9), $X_n$DL (SEQ ID NO: 10), or $X_n$L, wherein n=0, 1 or 2 amino acids, wherein when n=1, X is Met or Gly, and when n=2, X is Met-Gly. When a Met-Gly sequence is added to the N-terminus of a $^{10}$Fn3 domain, the M will usually be cleaved off, leaving a G at the N-terminus. In certain embodiments, the alternative N-terminal region comprises the amino acid sequence MASTSG (SEQ ID NO: 11).

In exemplary embodiments, an alternative C-terminal region having from 1-20, 1-15, 1-10, 1-8, 1-5, 1-4, 1-3, 1-2, or 1 amino acids in length can be added to the C-terminal region of SEQ ID NO: 1. Specific examples of alternative C-terminal region sequences include, for example, polypeptides comprising, consisting essentially of, or consisting of, EIEK (SEQ ID NO: 12), EGSGC (SEQ ID NO: 13), EIEKPCQ (SEQ ID NO: 14), EIEKPSQ (SEQ ID NO: 15), EIEKP (SEQ ID NO: 16), EIEKPS (SEQ ID NO: 17), or EIEKPC (SEQ ID NO: 18). In some embodiments, the alternative C-terminal region comprises EIDK (SEQ ID NO: 19), and in particular embodiments, the alternative C-terminal region is either EIDKPCQ (SEQ ID NO: 20) or EIDKPSQ (SEQ ID NO: 21). Additional suitable alternative C-terminal regions include those set forth in Table 20 and SEQ ID NOs: 210-220.

In certain embodiments, the C-terminal extension sequences comprise E and D residues, and may be between 8 and 50, 10 and 30, 10 and 20, 5 and 10, and 2 and 4 amino acids in length. In some embodiments, tail sequences include ED-based linkers in which the sequence comprises tandem repeats of ED. In exemplary embodiments, the tail sequence comprises 2-10, 2-7, 2-5, 3-10, 3-7, 3-5, 3, 4 or 5 ED repeats. In certain embodiments, the ED-based tail sequences may also include additional amino acid residues, such as, for example: EI, EID, ES, EC, EGS, and EGC. Such sequences are based, in part, on known Adnectin tail sequences, such as EIDKPSQ (SEQ ID NO: 21), in which residues D and K have been removed. In exemplary embodiments, the ED-based tail comprises an E, I or EI residues before the ED repeats.

In certain embodiments, an alternative C-terminal moiety, which can be linked to the C-terminal amino acids RT (i.e., amino acid 93-94 of SEQ ID NO: 1) of any of the Adnectins provided herein comprises the amino acids $P_mX_n$, wherein P is proline, X is any amino acid, m is an integer that is at least 1 and n is 0 or an interger that is at least 1. In certain embodiments, the alternative C-terminal moiety comprises the amino acids PC. In certain embodiments, the alternative C-terminal moiety comprises the amino acids PI, PC, PID, PIE, PIDK (SEQ ID NO: 221), PIEK (SEQ ID NO: 222), PIDKP (SEQ ID NO: 223), PIEKP (SEQ ID NO: 224), PIDKPS (SEQ ID NO: 225), PIEKPS (SEQ ID NO: 226), PIDKPC (SEQ ID NO: 227), PIEKPC (SEQ ID NO: 228), PIDKPSQ (SEQ ID NO: 229), PIEKPSQ (SEQ ID NO: 230), PIDKPCQ (SEQ ID NO: 231), PIEKPCQ (SEQ ID NO: 232), PHHHHHH (SEQ ID NO: 233), and PCHHHHHH (SEQ ID NO: 234).

In certain embodiments, the fibronectin based scaffold proteins comprise a $^{10}$Fn3 domain having both an alternative N-terminal region sequence and an alternative C-terminal region sequence.

B. Serum Albumin Binders Having Modified South Pole Loop(s)

$^{10}$Fn3 domains are cleared rapidly from circulation via renal filtration and degradation due to their small size of about 10 kDa ($t_{1/2}$=15-45 minutes in mice; 3 hours in monkeys). In certain aspects, the application provides $^{10}$Fn3 domains with south pole modifications that bind specifically to serum albumin, e.g., human serum albumin (HSA) to prolong the $t_{1/2}$ of the $^{10}$Fn3 domain.

HSA has a serum concentration of 600 μM and a $t_{1/2}$ of 19 days in humans. The extended $t_{1/2}$ of HSA has been attributed, in part, to its recycling via the neonatal Fc receptor (FcRn). HSA binds FcRn in a pH-dependent manner after endosomal uptake into endothelial cells; this interaction recycles HSA back into the bloodstream, thereby shunting it away from lysosomal degradation. FcRn is widely expressed and the recycling pathway is thought to be constitutive. In the majority of cell types, most FcRn resides in the intracellular sorting endosome. HSA is readily internalized by a nonspecific mechanism of fluid-phase pinocytosis and rescued from degradation in the lysosome by FcRn. At the acidic pH found in the endosome, HSA's affinity for FcRn increases (5 μM at pH 6.0). Once bound to FcRn, HSA is shunted away from the lysosomal degradation pathway, transcytosed to and released at the cell surface.

North pole-based serum albumin binding Adnectins, herein referred to as "first generation" serum albumin binding Adnectins, have been described in, e.g., WO2011140086. In order to improve upon first generation north pole-based serum albumin binding Adnectins (SABAs), of which some did not bind to mouse or rat serum albumin, did not have high affinity for serum albumins across species, and were not always compatible in a multivalent $^{10}$Fn3-based platform, second generation south pole-based serum albumin binding Adnectins (PKE2 Adnectins) with modified south pole loops were developed as described in the Examples.

Accordingly, in one aspect, the invention provides a $^{10}$Fn3 domain having (i) a modification in the amino acid sequence of at least one south pole loop selected from the AB, CD, and EF loops relative to the corresponding loop of the wild-type human $^{10}$Fn3 domain (SEQ ID NO: 1), wherein the $^{10}$Fn3 domain binds to serum albumin (e.g., human serum albumin). The modified south pole loop(s) contribute to binding to the same target. Various combinations of modified south pole loops are contemplated. For example, a $^{10}$Fn3 may comprise one modified south pole loops, two modified south pole loops, or even all three south pole loops modified. In certain embodiments, one or more modified south pole loops can be made in conjunction with one or more modified north pole loops (i.e., one or more of BC, DE, and FG loops). The modified loops may have sequence modifications across an entire loop or only in a portion of the loop. Additionally, one or more of the modified loops may have insertions or deletions such that the length of the loop is varied relative to the length of the corresponding loop of the wild-type sequence (i.e., SEQ ID NO: 1). In certain embodiments, additional regions in the $^{10}$Fn3 domain (i.e., in addition to the south pole loops), such as 3-strand, N-terminal and/or C-terminal regions, may also be modified in sequence relative to the wild-type $^{10}$Fn3 domain, and such additional modifications may also contribute to binding to the target. In certain embodiments, a South Pole loop is the only domain that is modified. In specific embodiments, the CD loop is the only domain that is modified. In certain embodiments, the serum binding $^{10}$Fn3 domain may be modified to comprise an N-terminal extension sequence and/or a C-terminal extension sequence, as described supra.

In one embodiment, the invention provides Adnectins that bind to serum albumin having an altered CD loop relative to the corresponding loop of the wild-type human $^{10}$Fn3 domain, for example, $^{10}$Fn3 domains set forth in SEQ ID NOs: 23-100, 184-209 and 235-260. In some embodiments, the albumin binding Adnectins comprise, or alternatively lack a 6× his tail. In some embodiments, the albumin binding Adnectins correspond to core Adnectins which lack the N-terminal leader and C-terminal tail, as set forth in SEQ ID NOs: 75-100.

In exemplary embodiments, the serum albumin binding $^{10}$Fn3 proteins described herein bind to human serum albumin with a $K_D$ of less than 3 μM, 2.5 μM, 2 μM, 1.5 μM, 1 μM, 500 nM, 100 nM, 50 nM, 10 nM, 1 nM, 500 μM, 100 μM, 100 μM, 50 μM, or 10 μM. The Kd may be, e.g., in the range of 0.1 nM to 50 nM, 0.1 nM to 100 nM, 0.1 nM to 1 μM, 0.5 nM to 50 nM, 0.5 nM to 100 nM, 0.5 nM to 1 μM, 1 nM to 50 nM, 1 nM to 100 nM or 1 nM to 1 μM.

In certain embodiments, the albumin binding Adnectins (or $^{10}$Fn3 proteins) described herein may also bind serum albumin from one or more of cynomolgus monkey, rhesus monkey, rat, or mouse.

In certain embodiments, the serum albumin binding $^{10}$Fn3 proteins described herein bind to rhesus serum albumin (RhSA) or cynomolgous monkey serum albumin (CySA) with a $K_D$ of less than 3 μM, 2.5 μM, 2 μM, 1.5 μM, 1 μM, 500 nM, 100 nM, 50 nM, 10 nM, 1 nM, 500 μM or 100 μM. The $K_D$ may be, e.g., in the range of 0.1 nM to 50 nM, 0.1 nM to 100 nM, 0.1 nM to 1 μM, 0.5 nM to 50 nM, 0.5 nM to 100 nM, 0.5 nM to 1 μM, 1 nM to 50 nM, 1 nM to 100 nM or 1 nM to 1 μM.

In certain embodiments, the serum albumin binding $^{10}$Fn3 proteins described herein bind to rhesus serum albumin (RhSA), cynomolgous monkey serum albumin (CySA), and mouse serum albumin (MSA) with a $K_D$ of less than 3 μM, 2.5 μM, 2 μM, 1.5 μM, 1 μM, 500 nM, 100 nM, 50 nM, 10 nM, 1 nM, 500 μM or 100 μM. The $K_D$ may be, e.g., in the range of 0.1 nM to 50 nM, 0.1 nM to 100 nM, 0.1 nM to 1 μM, 0.5 nM to 50 nM, 0.5 nM to 100 nM, 0.5 nM to 1 μM, 1 nM to 50 nM, 1 nM to 100 nM or 1 nM to 1 μM.

In certain embodiments, the serum albumin binding $^{10}$Fn3 proteins described herein bind to rhesus serum albumin (RhSA), cynomolgous monkey serum albumin (CySA), mouse serum albumin (MSA), and rat serum albumin (RSA) with a $K_D$ of less than 3 μM, 2.5 μM, 2 M, 1.5 μM, 1 μM, 500 nM, 100 nM, 50 nM, 10 nM, 1 nM, 500 μM or 100 μM. The $K_D$ may be, e.g., in the range of 0.1 nM to 50 nM, 0.1 nM to 100 nM, 0.1 nM to 1 μM, 0.5 nM to 50 nM, 0.5 nM to 100 nM, 0.5 nM to 1 μM, 1 nM to 50 nM, 1 nM to 100 nM or 1 nM to 1 μM.

In certain embodiments, the albumin binding Adnectins described herein bind to serum albumin at a pH range of 5.5 to 7.4.

In certain embodiments, the albumin binding Adnectins described herein bind to domain I-II of human serum albumin.

In certain embodiments, the serum half-life of the albumin binding Adnectins of the invention or the serum half-life of the albumin binding Adnectins linked to a heterologous moiety, e.g., a second Adnectin, is at least 2 hours, 2.5 hours, 3 hours, 4 hours, 5 hours, 6 hours, 7 hours, 8 hours, 9 hours, 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours. In certain embodiments, the serum half-life of the albumin binding Adnectins or the serum half-life of the albumin binding Adnectins linked to a heterologous moiety, e.g., a second Adnectin, is 2-200 hours, 5-200 hours, 10-200 hours, 25-200 hours, 50-200 hours, 100-200 hours, 150-200 hours, 2-150 hours, 2-100 hours, 2-50 hours, 2-25 hours, 2-10 hours, 2-5 hours, 5-150 hours, 10-100 hours, or 25-50 hours.

In certain embodiments, the albumin binding Adnectins comprises a sequence having at least 40%, 50%, 60%, 70%, 75%, 80% or 85% identity to the wild-type $^{10}$Fn3 domain (SEQ ID NO: 1). In one embodiment, at least one of the AB, CD, or EF loops is modified relative to the wild-type $^{10}$Fn3 domain. In certain embodiments, at least two of the AB, CD, or EF loops are modified relative to the wild-type $^{10}$Fn3 domain. In certain embodiments, all three of the AB, CD, or EF loops are modified relative to the wild-type $^{10}$Fn3 domain. In certain embodiments, a serum albumin binding $^{10}$Fn3 domain comprises a sequence having at least 40%, 50%, 60%, 70%, 75%, 80%, 85%, 90%, 95%, 96%, 97%, 98%, 99% or 100% identity to any one of SEQ ID NOs: 23-100, 184-209 and 235-260.

In certain embodiments, a serum albumin binding $^{10}$Fn3 domain (or Adnectin) may comprise the sequence as set forth in SEQ ID NO: 2, wherein the CD loop is represented by $(X)_w$ and is replaced with a CD loop from any of the 26 core PKE2 Adnectin sequences (i.e., SEQ ID NOs: 75-100). The scaffold regions of such albumin binding Adnectins may have anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the scaffold amino acids residues of SEQ ID NO: 1. Such scaffold modifications may be made, so long as the ablumin binding Adnectin is capable of binding serum albumin, e.g., HSA, with a desired $K_D$.

In some embodiments, the CD loop region of the albumin binding Adnectins of the invention can be described according to a consensus sequence.

Accordingly, in some embodiments, the CD loop is defined by the consensus sequence (SEQ ID NO: 170)

$$G\text{-}X_1\text{-}X_2\text{-}V\text{-}X_3\text{-}X_4\text{-}X_5\text{-}S\text{-}X_6\text{-}X_7\text{-}G\text{-}X_8\text{-}X_9\text{-}Y\text{-}X_{10}\text{-}X_{11}\text{-}X_{12}\text{-}E,$$

wherein, (a) $X_1$ is selected from the group consisting of R or W;

(b) $X_2$ is selected from the group consisting of H, E, D, Y, or Q;

(c) $X_3$ is selected from the group consisting of Q or H;

(d) $X_4$ is selected from the group consisting of I, K, M, Q, L, or V;

(e) $X_5$ is selected from the group consisting of Y, F, or N;

(f) $X_6$ is selected from the group consisting of D, V, or E;

(g) $X_7$ is selected from the group consisting of L, W, or F;

(h) $X_8$ is selected from the group consisting of P or T;

(i) $X_9$ is selected from the group consisting of L or M;

(j) $X_{10}$ is selected from the group consisting of I or V;

(k) $X_{11}$ is selected from the group consisting of Y or F; and (l) $X_{12}$ is selected from the group consisting of T, S, Q, N, or A.

In certain preferred embodiments, (a) $X_1$ is R;

(b) $X_2$ is E;

(c) $X_3$ is Q;

(d) $X_4$ is K;

(e) $X_5$ is Y;

(f) $X_6$ is D;

(g) $X_7$ is L or W;

(h) $X_8$ is P;

(i) $X_9$ is L;

(j) $X_{10}$ is I;

(k) $X_{11}$ is Y; and (l) $X_{12}$ is Q or N.

In a preferred embodiment, $X_7$ is L and $X_{12}$ is Q.

In another preferred embodiment, $X_7$ is W and $X_{12}$ is N.

In some embodiments, the albumin binding Adnectins of the invention comprise a CD loop having sequences at least 75%, 80%, 85%, 90%, 95%, 96%, 97%, 98%, 99% or 100% identical to the CD loop sequences set forth in SEQ ID NOs: 101-125, or comprise at most 1, 1-2 or 1-3 amino acid difference (i.e., substitution, e.g., deletion, addition or conservative substitution). The scaffold regions of such albumin binding Adnectins may comprise anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the scaffold amino acids residues of SEQ ID NO: 1. Such scaffold modifications may be made, so long as the Adnectins are capable of binding to serum albumin with a desired $K_D$.

In a preferred embodiment, the CD loop of the albumin binding Adnectins of the invention comprises an amino acid sequence selected from the group consisting of:

(SEQ ID NO: 101)
GRHVQIYSDLGPLYIYTE, (SEQ ID NO: 102)
GRHVHIYSDWGPMYIYTE, (SEQ ID NO: 103)
GREVQKYSVLGPLYIYTE, (SEQ ID NO: 104)
GREVQMYSDLGPLYVYSE, (SEQ ID NO: 105)
GREVQKFSDWGPLYIYTE, (SEQ ID NO: 106)
GREVQKYSDLGPLYIYQE, (SEQ ID NO: 107)
GREVHQYSDWGPMYIYNE,

-continued (SEQ ID NO: 108)
GREVHKNSDWGTLYIYTE, (SEQ ID NO: 109)
GREVQKYSDLGPLYIYAE, (SEQ ID NO: 110)
GREVHLYSDWGPMYIYTE, (SEQ ID NO: 111)
GRHVQMYSDLGPLYIFSE, (SEQ ID NO: 112)
GREVHMYSDFGPMYIYTE, (SEQ ID NO: 113)
GREVQKYSDWGPLYIYNE, (SEQ ID NO: 114)
GREVQMYSDLGPLYIYNE, (SEQ ID NO: 115)
GREVQMYSDLGPLYIYTE, (SEQ ID NO: 116)
GRHVQIYSDLGPLYIYNE, (SEQ ID NO: 117)
GREVQIYSDWGPLYIYNE, (SEQ ID NO: 118)
GREVQKYSDWGPLYIYQE, (SEQ ID NO: 119)
GRHVHLYSEFGPMYIYNE, (SEQ ID NO: 120)
GRDVHMYSDWGPMYIYQE, (SEQ ID NO: 121)
GRHVQIYSDWGPLYIYNE, (SEQ ID NO: 122)
GRYVQLYSDWGPMYIYTE, (SEQ ID NO: 123)
GRQVQVFSDLGPLYIYNE, (SEQ ID NO: 124)
GRQVQIYSDWGPLYIYNE,
and (SEQ ID NO: 125)
GRQVQMYSDWGPLYIYAE.

In some embodiments, the albumin binding Adnectin comprises an amino acid sequence at least 70%, 75%, 80%, 85%, 90%, 95%, 98%, 99% or 100% identical to any one of SEQ ID NOs: 23-100, 184-209 and 235-260 or differs therefrom in at most 1, 1-2, 1-3, 1-5, 1-10 or 1-20 amino acid differences, e.g., amino acid deletions, additions or substitutions (e.g., conservative substitutions). In certain embodiments, the albumin binding molecules comprise an amino acid sequence at least 80%, 85%, 90%, 95%, 98%, 99% or 100% identical to the non-CD loop region of SEQ ID NOs: 23-100, 184-209 and 235-260.

In a preferred embodiment, the albumin binding Adnectin comprises the amino acid sequence set forth in any one of SEQ ID NOs: 29, 55, 81, 190 and 241. In another preferred embodiment, the albumin binding Adnectin comprises the amino acid sequence set forth in any one of SEQ ID NOs: 36, 62, 88, 197 and 248.

In some embodiments, the invention provides mutant albumin binding Adnectin molecules which have a cysteine residue introduced at a specific position. Exemplary cysteine mutations are A12C, A26C, S55C, T56C and T58C (see Table 7 in the Examples). In a preferred embodiment, the cysteine mutations do not substantially alter the binding of the albumin binding Adnectin to serum albumin.

In certain embodiments, a proline residue is introduced at the C-terminus of the $^{10}$Fn3 domain, for example, as shown, e.g., in SEQ ID NOs: 184-209 and 235-260. In certain embodiments, the proline residue is introduced at the C-terminus of a tandem albumin binding Adnectin, as shown, e.g., in SEQ ID NO: 168 and 261. Addition of the proline residue does not preclude the addition of additional amino acid sequences to the C-termius of an albumin binding Adnectin or tandem albumin binding Adnectin.

C. Cross-Competing Adnectins and/or Adnectins that Bind to the Same Adnectin Binding Site Provided herein are proteins, such as Adnectins, antibodies or antigen binding fragments thereof, small molecules, peptides, and the like that compete (e.g., cross-compete) for binding to serum albumin (e.g., HSA) with the particular PKE2 Adnectins described herein. Such competing proteins, e.g., Adnectins, can be identified based on their ability to competitively inhibit binding to serum albumin (e.g., HSA) of Adnectins described herein in standard serum albumin binding assays. For example, standard ELISA assays can be used in which a recombinant serum albumin protein is immobilized on the plate, one of the proteins is fluorescently labeled and the ability of non-labeled protein to compete off the binding of the labeled protein is evaluated.

The following exemplary competition assays are provided in the context of Adnectins competing for binding to serum albumin with one of the PKE2 proteins described herein. The same assays can be performed where a non-Adnectin protein is tested for competition. In one embodiment, a competitive ELISA format can be performed to determine whether two serum albumin Adnectins bind overlapping Adnectin binding sites (epitopes) on serum albumin (e.g., HSA). In one format, Adnectin #1 is coated on a plate, which is then blocked and washed. To this plate is added either serum albumin alone, or serum albumin pre-incubated with a saturating concentration of Adnectin #2. After a suitable incubation period, the plate is washed and probed with a polyclonal anti-serum albumin antibody, followed by detection with streptavidin-HRP conjugate and standard tetramethylbenzidine development procedures. If the OD signal is the same with or without preincubation with Adnectin #2, then the two Adnectins bind independently of one another, and their Adnectin binding sites do not overlap. If, however, the OD signal for wells that received serum albumin/Adnectin#2 mixtures is lower than for those that received serum albumin alone, then binding of Adnectin #2 is confirmed to block binding of Adnectin #1 to serum albumin.

Alternatively, a similar experiment is conducted by surface plasmon resonance (SPR, e.g., BIAcore). Adnectin #1 is immobilized on an SPR chip surface, followed by injections of either serum albumin alone or serum albumin pre-incubated with a saturating concentration of Adnectin #2. If the binding signal for serum albumin/Adnectin#2 mixtures is the same or higher than that of serum albumin alone, then the two Adnectins bind independently of one another, and their Adnectin binding sites do not overlap. If, however, the binding signal for serum albumin/Adnectin#2 mixtures is lower than the binding signal for serum albumin alone, then binding of Adnectin #2 is confirmed to block binding of Adnectin #1 to serum albumin. A feature of these experiments is the use of saturating concentrations of Adnectin #2. If serum albumin is not saturated with Adnectin #2, then the conclusions above do not hold. Similar experiments can be used to determine if any two serum albumin binding proteins bind to overlapping Adnectin binding sites.

Both assays exemplified above may also be performed in the reverse order where Adnectin#2 is immobilized and serum albumin—Adnectin#1 are added to the plate. Alternatively, Adnectin #1 and/or #2 can be replaced with a monoclonal antibody and/or soluble receptor-Fc fusion protein.

In certain embodiments, competition can be determined using a HTRF sandwich assay.

In certain embodiments, the competing Adnectin is an Adnectin that binds to the same Adnectin binding site on serum albumin as a particular PKE2 Adnectin described herein. Standard mapping techniques, such as protease mapping, mutational analysis, x-ray crystallography and 2-dimensional nuclear magnetic resonance, can be used to determine whether an Adnectin binds to the same Adnectin binding site as a reference Adnectin (see, e.g., *Epitope Mapping Protocols in Methods in Molecular Biology*, Vol. 66, G. E. Morris, Ed. (1996)).

Candidate competing albumin binding proteins, e.g., Adnectins, can inhibit the binding of PKE2 Adnectins of the invention to serum albumin (e.g., HSA) by at least 50%, at least 55%, at least 60%, at least 65%, at least 70%, at least 75%, at least 80%, at least 85%, at least 90%, at least 95%, at least 97%, at least 98%, or at least 99%. The % competition can be determined using the methods described above.

D. Multivalent/Tandem Adnectins

Provided herein are multivalent proteins that comprise two or more $^{10}$Fn3 domains binding specifically to a target (Adnectins). For example, a multivalent protein may comprise 2, 3 or more $^{10}$Fn3 domains that are covalently associated. In exemplary embodiments, multivalent protein is a bispecific or dimeric protein comprising two $^{10}$Fn3 domains. In certain embodiments, a multivalent protein comprises a first $^{10}$Fn3 domain that binds to serum albumin (e.g., human serum albumin) and a second $^{10}$Fn3 domain that binds to a second target molecule (e.g., PCSK9). When both the first and second target molecules are serum albumin, the first and second $^{10}$Fn3 domains may bind to the same or different epitopes. Additionally, when the first and second target molecules are the same, the regions of modification in the $^{10}$Fn3 domain that are associated with target binding may be the same or different. In exemplary embodiments, each $^{10}$Fn3 domain of a multivalent fibronectin based protein scaffold binds to a desired target with a $K_D$ of less than 500 nM, 100 nM, 50 nM, 1 nM, 500 μM, 100 μM or less. In some embodiments, each $^{10}$Fn3 domain of a multivalent fibronectin based protein scaffold binds to a desired target with a $K_D$ between 1 μM and 1 μM, between 100 μM and 500 nM, between 1 nM and 500 nM, or between 1 nM and 100 nM. In exemplary embodiments, each $^{10}$Fn3 domain of a multivalent fibronectin based protein scaffold binds specifically to a target that is not bound by a wild-type $^{10}$Fn3 domain, particularly the wild-type human $^{10}$Fn3 domain.

The $^{10}$Fn3 domains in a multivalent fibronectin based scaffold protein may be connected by a polypeptide linker. Exemplary polypeptide linkers include polypeptides having from 1-20, 1-15, 1-10, 1-8, 1-5, 1-4, 1-3, or 1-2 amino acids. Suitable linkers for joining the $^{10}$Fn3 domains are those which allow the separate domains to fold independently of each other forming a three dimensional structure that permits high affinity binding to a target molecule. Specific examples of suitable linkers include glycine-serine based linkers, glycine-proline based linkers, proline-alanine based linkers as well as linkers having the amino acid sequence PSTPPTPSPSTPPTPSPS (SEQ ID NO: 152). In some embodiments, the linker is a glycine-serine based linker. In some embodiments, the linker is a glycine-serine based linker. These linkers comprise glycine and serine residues and may be between 8 and 50, 10 and 30, and 10 and 20 amino acids in length. Examples include linkers having an amino acid sequence $(GS)_7$ (SEQ ID NO: 153), $G(GS)_6$ (SEQ ID NO: 154), and G(GS)7G (SEQ ID NO: 155). Other linkers contain glutamic acid, and include, for example, $(GSE)_5$ (SEQ ID NO: 156) and GGSEGGSE (SEQ ID NO: 157). Other exemplary glycine-serine linkers include $(GS)_4$ (SEQ ID NO: 158), $(GGGGS)_7$ (SEQ ID NO: 159), $(GGGGS)_5$ (SEQ ID NO: 160), and $(GGGGS)_3G$ (SEQ ID NO: 161). In some embodiments, the linker is a glycine-proline based linker. These linkers comprise glycine and proline residues and may be between 3 and 30, 10 and 30, and 3 and 20 amino acids in length. Examples include linkers having an amino acid sequence $(GP)_3G$ (SEQ ID NO: 162), $(GP)_5G$ (SEQ ID NO: 163), and GPG. In certain embodiments, the linker may be a proline-alanine based linker having between 3 and 30, 10 and 30, and 3 and 20 amino acids in length. Examples of proline alanine based linkers include, for example, $(PA)_3$ (SEQ ID NO: 164), $(PA)_6$ (SEQ ID NO: 165) and $(PA)_9$ (SEQ ID NO: 166). It is contemplated, that the optimal linker length and amino acid composition may be determined by routine experimentation by methods well known in the art. In exemplary embodiments, the linker does not contain any Asp-Lys (DK) pairs.

In certain embodiments, the linker has the amino acid sequence PSPEPPTPEP (SEQ ID NO: 173), PSPEPPTPEPPSPEPPTPEP (SEQ ID NO: 174), PSPEPPTPEPPSPEPPTPEPPSPEPPTPEP (SEQ ID NO: 175), or PSPEPPTPEPPSPEPPTPEPPSPEPPTPEPPSPEPPTPEP (SEQ ID NO: 176). Generally a linker may comprise the amino acid sequence $(PSPEPPTPEP)_n$ (SEQ ID NO: 262), wherein n is 1, 2, 3, 4, 5, 6, 7, 8, 9, 10, 1-5 or 1-10. In certain embodiments, the linker has the amino acid sequence EEEEDE (SEQ ID NO: 177), EEEEDEEEEDE (SEQ ID NO: 178), EEEEDEEEEDEEEEDEEEEDE (SEQ ID NO: 179), EEEEDEEEEDEEEEDEEEEDEEEEDEEEEDE (SEQ ID NO: 180). Generally, a linker may comprise the sequence $(EEEEDE)_nE$ (SEQ ID NO: 263), wherein n is 1, 2, 3, 4, 5, 6, 7, 8, 9, 10, 1-5 or 1-10. In certain embodiments, the linker has the amino acid sequence RGGEEKKKEKEKEEQEERETKTP (SEQ ID NO: 181). Such linkers may be used to connect the albumin binding Adnectin to another polypeptide (e.g., another Adnectin). Exemplary uses of the PSPEPPTPEP (SEQ ID NO: 173) linker is shown below.

N-Terminal Adnectin Connected to C-Terminal Polypeptide:

```
                                    (SEQ ID NO: 182)
    . . . NYRTPGPSPEPPTPEP-polypeptide
```

N-Terminal Polypeptide Connected to C-Terminal Adnectin:

```
                                    (SEQ ID NO: 183)
    polypeptide-PSPEPPTPEPGVSDV . . .
```

In some embodiments, the multivalent Adnectin is a tandem Adnectin comprising a first $^{10}$Fn3 domain which binds to a serum albumin (e.g., a PKE2 Adnectin), and a second $^{10}$Fn3 domain that binds to a specific target. Tandem Adnectins may have the configuration albumin binding Adnectin-X and X-albumin binding Adnectin, wherein X is a target specific $^{10}$Fn3 domain. The skilled artisan would be familiar with methods for testing the functional activity and assessing the biophysical properties of such such tandem Adnectin molecules.

In one aspect, the invention provides a fusion polypeptide comprising a first fibronectin type III tenth ($^{10}$Fn3) domain and a second $^{10}$Fn3 domain, wherein the first $^{10}$Fn3 domain comprises a) AB, BC, CD, DE, EF, and FG loops, b) a CD loop with an altered amino acid sequence relative to the sequence of the corresponding loop of the human $^{10}$Fn3 domain, and c) wherein the polypeptide binds to human serum albumin with a $K_D$ of less than 500 nM. A "first" domain and a second "domain" may be in the N- to C-terminal or C- to N-terminal orientation.

In some embodiments, e.g., of multivalent Adnectins, the first $^{10}$Fn3 domain comprises an amino acid sequence at least 70%, 75%, 80%, 85%, 90%, 95%, 96%, 97%, 98%, 99% or 100% identical to any one of SEQ ID NOs: 23-100, 184-209 and 235-260 or differs therefrom in at most 1, 1-2, 1-5, 1-10 or 1-20 amino acids, e.g., amino acid deletions, additions or substitutions (e.g., conservative amino acid substitutions).

In some embodiments, the first $^{10}$Fn3 domain comprises the amino acid sequence of any one of SEQ ID NOs: 23-100, 184-209 and 235-260.

In a preferred embodiment, the first $^{10}$Fn3 domain comprises the amino acid sequence of SEQ ID NO: 29, 55, 81, 190 or 241. In another preferred embodiment, the first $^{10}$Fn3 domain comprises the amino acid sequence of SEQ ID NO: 36, 62, 88, 197 or 248.

In some embodiments, the multivalent Adnectin comprises a second $^{10}$Fn3 domain that is a $^{10}$Fn3 domain that specifically binds to a target protein other than serum albumin.

In a preferred embodiment, the second $^{10}$Fn3 domain specifically binds to PCSK9.

Accordingly, in one embodiment, the second $^{10}$Fn3 domain comprises an amino acid sequence at least 70%, 75%, 80%, 85%, 90%, 95%, 96%, 97%, 98%, 99% or 100% identical to SEQ ID NO: 168 or 261 or differs therefrom in at most 1, 1-2, 1-5, 1-10 or 1-20 amino acids, e.g., amino acid deletions, additions or substitutions (e.g., conservative amino acid substitutions).

Additional suitable $^{10}$Fn3 domains that bind to PCSK9 are disclosed in, e.g., WO2011/130354, the contents of which are herein incorporated by reference.

In one embodiment, the second $^{10}$Fn3 domain has the amino acid sequence set forth in SEQ ID NO: 168 or 261.

In certain embodiments, the invention provides a PCSK9-serum albumin binding tandem Adnectin comprising the amino acid sequence set forth in SEQ ID NO: 168 or 261, as well as PCSK9-serum albumin tandem Adnectins with amino acid sequences at least 70%, 75%, 80%, 85%, 90%, 95%, 96%, 97%, 98%, 99% or 100% identical thereto or differs therefrom in at most 1, 1-2, 1-5, 1-10 or 1-20 amino acids, e.g., amino acid deletions, additions or substitutions (e.g., conservative amino acid substitutions), wherein the tandem Adnectin retains binding to PCSK9 and serum albumin.

In one embodiment, the invention provides nucleic acids encoding a PCSK9-serum albumin binding tandem Adnectin comprising the nucleic acid sequence set forth in SEQ ID NO: 172, as well as nucleic acid sequences at least 70%, 75%, 80%, 85%, 90%, 95%, 96%, 97%, 98%, 99% or 100% identical thereto, wherein the encoded PCSK9-serum albumin binding tandem Adnectin retains binding to PCSK9 and serum albumin. In some embodiments, the nucleotide substitutions do not alter the resulting translated amino acid sequence (i.e., silent mutations).

In one aspect, the serum albumin binding-based tandem Adnectins (e.g., PCSK9-PKE2 tandem Adnectin) described herein bind to human serum albumin with a $K_D$ of less than 3 μM, 2.5 μM, 2 μM, 1.5 μM, 1 μM, 500 nM, 100 nM, 50 nM, 10 nM, 1 nM, 500 μM, 100 μM, 100 μM, 50 μM, or 10 μM. The $K_D$ may be, e.g., in the range of 0.1 nM to 50 nM, 0.1 nM to 100 nM, 0.1 nM to 1 μM, 0.5 nM to 50 nM, 0.5 nM to 100 nM, 0.5 nM to 1 μM, 1 nM to 50 nM, 1 nM to 100 nM or 1 nM to 1 μM.

In certain embodiments, the serum albumin binding-based tandem Adnectins (e.g., PCSK9-PKE2 tandem Adnectin) described herein may also bind serum albumin from one or more of cynomolgus monkey, rhesus monkey, rat, or mouse.

In certain embodiments, the serum albumin binding-based tandem Adnectins (e.g., PCSK9-PKE2 tandem Adnectin) described herein bind to rhesus serum albumin (RhSA) or cynomolgous monkey serum albumin (CySA) with a $K_D$ of less than 3 μM, 2.5 μM, 2 μM, 1.5 μM, 1 μM, 500 nM, 100 nM, 50 nM, 10 nM, 1 nM, 500 μM or 100 μM. The $K_D$ may be, e.g., in the range of 0.1 nM to 50 nM, 0.1 nM to 100 nM, 0.1 nM to 1 μM, 0.5 nM to 50 nM, 0.5 nM to 100 nM, 0.5 nM to 1 μM, 1 nM to 50 nM, 1 nM to 100 nM or 1 nM to 1 μM.

In certain embodiments, the serum albumin binding-based tandem Adnectins (e.g., PCSK9-PKE2 tandem Adnectin) described herein bind to rhesus serum albumin (RhSA), cynomolgous monkey serum albumin (CySA), and mouse serum albumin (MSA) with a $K_D$ of less than 3 μM, 2.5 μM, 2 μM, 1.5 μM, 1 μM, 500 nM, 100 nM, 50 nM, 10 nM, 1 nM, 500 μM or 100 μM. The $K_D$ may be, e.g., in the range of 0.1 nM to 50 nM, 0.1 nM to 100 nM, 0.1 nM to 1 μM, 0.5 nM to 50 nM, 0.5 nM to 100 nM, 0.5 nM to 1 μM, 1 nM to 50 nM, 1 nM to 100 nM or 1 nM to 1 μM.

In certain embodiments, the serum albumin binding-based tandem Adnectins (e.g., PCSK9-PKE2 tandem Adnectin) described herein bind to rhesus serum albumin (RhSA), cynomolgous monkey serum albumin (CySA), mouse serum albumin (MSA), and rat serum albumin (RSA) with a $K_D$ of less than 3 μM, 2.5 μM, 2 μM, 1.5 μM, 1 μM, 500 nM, 100 nM, 50 nM, 10 nM, 1 nM, 500 μM or 100 μM. The $K_D$ may be, e.g., in the range of 0.1 nM to 50 nM, 0.1 nM to 100 nM, 0.1 nM to 1 μM, 0.5 nM to 50 nM, 0.5 nM to 100 nM, 0.5 nM to 1 μM, 1 nM to 50 nM, 1 nM to 100 nM or 1 nM to 1 μM.

In certain embodiments, the serum albumin binding-based tandem Adnectins (e.g., PCSK9-PKE2 tandem Adnectin) described herein bind to serum albumin at a pH range of 5.5 to 7.4.

In certain embodiments, the tandem serum albumin binding-based Adnectins (e.g., PCSK9-PKE2 tandem Adnectin) described herein bind to domain I-II of human serum albumin.

In certain embodiments, the tandem serum albumin binding-based Adnectins (e.g., PCSK9-PKE2 tandem Adnectin) described herein has a serum half-life in the presence of human serum albumin, cynomolgus monkey serum albumin, rhesus monkey serum albumin, mouse serum albumin, and/or rat serum albumin of at least 1 hour, 2 hours, 5 hours, 10 hours, 20 hours, 30 hours, 40 hours, 50 hours, 60 hours, 70 hours, 80 hours, 90 hours, 100 hours, 150 hours, 200 hours, or at least about 300 hours. In certain embodiments, the tandem serum albumin binding-based Adnectins (e.g., PCSK9-PKE2 tandem Adnectin) described herein has a serum half-life in the presence of human serum albumin, cynomolgus monkey serum albumin, rhesus monkey serum albumin, mouse serum albumin, and/or rat serum albumin of 1-300 hours, such as 1-250 hours, 1-200 hours, 1-150 hours, 1-100 hours, 1-90 hours, 1-80 hours, 1-70 hours, 1-60 hours, 1-50 hours, 1-40 hours, 1-30 hours, 1-20 hours, 1-10 hours, 1-5 hours, 5-300 hours, 10-300 hours, 20-300 hours, 30-300 hours, 40-300 hours, 50-300 hours, 60-300 hours, 70-300 hours, 80-300 hours, 90-300 hours, 100-300 hours, 150-300 hours, 200-300 hours, 250-300 hours, 5-250 hours, 10-200 hours, 50-150 hours, or 80-120 hours.

In certain embodiments, the serum half-life of the partner Adnectin in the serum albumin-based tandem Adnectin (e.g., PCSK9 Adnectin in the case of a PCSK9-PKE2 tandem Adnectin) is increased relative to the serum half-life of the partner Adnectin when not conjugated to the serum albumin binding Adnectin. In certain embodiments, the serum half-life of the serum albumin-based tandem Adnectin is at least 20, 40, 60, 80, 100, 120, 150, 180, 200, 400, 600, 800, 1000, 1200, 1500, 1800, 1900, 2000, 2500, or 3000% longer relative to the serum half-life of the partner Adnectin when not fused to the serum albumin binding Adnectin. In certain embodiments, the serum half-life of the serum albumin-based tandem Adnectin is 20-3000%, such as 40-3000%, 60-3000%, 80-3000%, 100-3000%, 120-3000%, 150-3000%, 180-3000%, 200-3000%, 400-3000%, 600-3000%, 800-3000%, 1000-3000%, 1200-3000%, 1500-3000%, 1800-3000%, 1900-3000%, 2000-3000%, 2500-3000%, 20-2500%, 20-2000%, 20-1900%, 20-1800%, 20-1500%, 20-1200%, 20-1000%, 20-800%, 20-600%, 20-400%, 20-200%, 20-180%, 20-150%, 20-120%, 20-100%, 20-80%, 20-60%, 20-40%, 50-2500%, 100-2000%, 150-1500%, 200-1000%, 400-800%, or 500-700% longer relative to the serum half-life of the partner Adnectin when not fused to the serum albumin binding Adnectin. In certain embodiments, the serum half-life of the serum albumin binding-based tandem Adnectin is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the partner Adnectin when not fused to the serum albumin binding Adnectin. In certain embodiments, the serum half-life of the serum albumin binding-based tandem Adnectin is 1.5-50 fold, such as 1.5-40 fold, 1.5-35 fold, 1.5-30 fold, 1.5-27 fold, 1.5-25 fold, 1.5-22 fold, 1.5-20 fold, 1.5-17 fold, 1.5-15 fold, 1.5-13 fold, 1.5-12 fold, 1.5-10 fold, 1.5-9 fold, 1.5-8 fold, 1.5-7 fold, 1.5-6 fold, 1.5-5 fold, 1.5-4.5 fold, 1.5-4 fold, 1.5-3.5 fold, 1.5-3 fold, 1.5-2.5 fold, 1.5-2 fold, 2-50 fold, 2.5-50 fold, 3-50 fold, 3.5-50 fold, 4-50 fold, 4.5-50 fold, 5-50 fold, 6-50 fold, 7-50 fold, 8-50 fold, 10-50 fold, 12-50 fold, 13-50 fold, 15-50 fold, 17-50 fold, 20-50 fold, 22-50 fold, 25-50 fold, 27-50 fold, 30-50 fold, 40-50 fold, 2-40 fold, 5-35 fold, 10-20 fold, or 10-15 fold greater than the serum half-life of the partner Adnectin when not fused to the serum albumin binding Adnectin. In certain embodiments, the serum half-life of the serum albumin binding-based tandem Adnectin is at least 2 hours, 2.5 hours, 3 hours, 4 hours, 5 hours, 6 hours, 7 hours, 8 hours, 9 hours, 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours. In certain embodiments, the serum half-life of the serum albumin binding-based tandem Adnectin is 2-200 hours, 2.5-200 hours, 3-200 hours, 4-200 hours, 5-200 hours, 6-200 hours, 7-200 hours, 8-200 hours, 9-200 hours, 10-200 hours, 15-200 hours, 20-200 hours, 25-200 hours, 30-200 hours, 35-200 hours, 40-200 hours, 50-200 hours, 60-200 hours, 70-200 hours, 80-200 hours, 90-200 hours, 100-200 hours, 125-200 hours, 150-200 hours, 175-200 hours, 190-200 hours, 2-190 hours, 2-175 hours, 2-150 hours, 2-125 hours, 2-100 hours, 2-90 hours, 2-80 hours, 2-70 hours, 2-60 hours, 2-50 hours, 2-40 hours, 2-35 hours, 2-30 hours, 2-25 hours, 2-20 hours, 2-15 hours, 2-10 hours, 2-9 hours, 2-8 hours, 2-7 hours, 2-6 hours, 2-5 hours, 2-4 hours, 2-3 hours, 5-175 hours, 10-150 hours, 15-125 hours, 20-100 hours, 25-75 hours, or 30-60 hours.

E. Conjugates of Serum Albumin Binding Adnectins

Certain aspects of the present invention provide for conjugates comprising a serum albumin binding Adnectin and at least one additional moiety (e.g., a therapeutic moiety). The additional moiety may be useful for any diagnostic, imaging, or therapeutic purpose.

In some embodiments, the serum albumin binding Adnectin is fused to a second moiety that is a small organic molecule, a nucleic acid, a peptide, or a protein. In some embodiments, the serum albumin binding Adnectin is fused to a therapeutic moiety that targets receptors, receptor ligands, viral coat proteins, immune system proteins, hormones, enzymes, antigens, or cell signaling proteins. The fusion may be formed by attaching the second moiety to either end of the serum albumin binding Adnectin, i.e., serum albumin binding Adnectin-therapeutic molecule or therapeutic molecule-serum albumin binding Adnectin arrangements.

In certain embodiments, the serum half-life of the moiety fused to the serum albumin binding Adnectin is increased relative to the serum half-life of the moiety when not conjugated to the serum albumin binding Adnectin. In certain embodiments, the serum half-life of the serum albumin binding Adnectin fusion is at least 20, 40, 60, 80, 100, 120, 150, 180, 200, 400, 600, 800, 1000, 1200, 1500, 1800, 1900, 2000, 2500, or 3000% longer relative to the serum half-life of the moiety when not fused to the serum albumin binding Adnectin. In certain embodiments, the serum half-life of the serum albumin binding Adnectin fusion is 20-3000%, such as 40-3000%, 60-3000%, 80-3000%, 100-3000%, 120-3000%, 150-3000%, 180-3000%, 200-3000%, 400-3000%, 600-3000%, 800-3000%, 1000-3000%, 1200-3000%, 1500-3000%, 1800-3000%, 1900-3000%, 2000-3000%, 2500-3000%, 20-2500%, 20-2000%, 20-1900%, 20-1800%, 20-1500%, 20-1200%, 20-1000%, 20-800%, 20-600%, 20-400%, 20-200%, 20-180%, 20-150%, 20-120%, 20-100%, 20-80%, 20-60%, 20-40%, 50-2500%, 100-2000%, 150-1500%, 200-1000%, 400-800%, or 500-700% longer relative to the serum half-life of the moiety when not fused to the serum albumin binding Adnectin. In certain embodiments, the serum half-life of the PKE2 Adnectin fusion is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the moiety when not fused to the serum albumin binding Adnectin. In certain embodiments, the serum half-life of the PKE2 Adnectin fusion is 1.5-50 fold, such as 1.5-40 fold, 1.5-35 fold, 1.5-30 fold, 1.5-27 fold, 1.5-25 fold, 1.5-22 fold, 1.5-20 fold, 1.5-17 fold, 1.5-15 fold, 1.5-13 fold, 1.5-12 fold, 1.5-10 fold, 1.5-9 fold, 1.5-8 fold, 1.5-7 fold, 1.5-6 fold, 1.5-5 fold, 1.5-4.5 fold, 1.5-4 fold, 1.5-3.5 fold, 1.5-3 fold, 1.5-2.5 fold, 1.5-2 fold, 2-50 fold, 2.5-50 fold, 3-50 fold, 3.5-50 fold, 4-50 fold, 4.5-50 fold, 5-50 fold, 6-50 fold, 7-50 fold, 8-50 fold, 10-50 fold, 12-50 fold, 13-50 fold, 15-50 fold, 17-50 fold, 20-50 fold, 22-50 fold, 25-50 fold, 27-50 fold, 30-50 fold, 40-50 fold, 2-40 fold, 5-35 fold, 10-20 fold, or 10-15 fold greater than the serum half-life of the moiety when not fused to the serum albumin binding Adnectin. In some embodiments, the serum half-life of the serum albumin binding Adnectin fusion is at least 2 hours, 2.5 hours, 3 hours, 4 hours, 5 hours, 6 hours, 7 hours, 8 hours, 9 hours, 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours. In certain embodiments, the serum half-life of the serum albumin binding Adnectin fusion is 2-200 hours, 2.5-200 hours, 3-200 hours, 4-200 hours, 5-200 hours, 6-200 hours, 7-200 hours, 8-200 hours, 9-200 hours, 10-200 hours, 15-200 hours, 20-200 hours, 25-200 hours, 30-200 hours, 35-200 hours, 40-200 hours, 50-200 hours, 60-200 hours, 70-200 hours, 80-200 hours, 90-200 hours, 100-200 hours, 125-200 hours, 150-200 hours, 175-200 hours, 190-200 hours, 2-190 hours, 2-175 hours, 2-150 hours, 2-125 hours, 2-100 hours, 2-90 hours, 2-80 hours, 2-70 hours, 2-60 hours, 2-50 hours, 2-40 hours, 2-35 hours, 2-30 hours, 2-25 hours, 2-20 hours, 2-15 hours, 2-10 hours, 2-9 hours, 2-8 hours, 2-7 hours, 2-6 hours, 2-5 hours, 2-4 hours, 2-3 hours, 5-175 hours, 10-150 hours, 15-125 hours, 20-100 hours, 25-75 hours, or 30-60 hours.

In certain embodiments, the serum albumin binding Adnectin fusion proteins bind to HSA with a $K_D$ of less than 3 μM, 2.5 μM, 2 μM, 1.5 μM, 1 μM, 500 nM, 100 nM, 50 nM, 10 nM, 1 nM, 500 μM, 100 μM, 100 μM, 50 μM or 10 μM. The $K_D$ may be, e.g., in the range of 0.1 nM to 50 nM, 0.1 nM to 100 nM, 0.1 nM to 1 μM, 0.5 nM to 50 nM, 0.5 nM to 100 nM, 0.5 nM to 1 μM, 1 nM to 50 nM, 1 nM to 100 nM or 1 nM to 1 μM.

In some embodiments, a therapeutic moiety may be directly or indirectly linked to a serum albumin binding Adnectin via a polymeric linker, as described herein. Polymeric linkers can be used to optimally vary the distance between each component of the fusion to create a protein fusion with one or more of the following characteristics: 1) reduced or increased steric hindrance of binding of one or more protein domains when binding to a protein of interest, 2) increased protein stability or solubility, 3) decreased protein aggregation, and 4) increased overall avidity or affinity of the protein.

In some embodiments, the fusions described herein are linked to the serum albumin binding Adnectin via a polypeptide linker having a protease site that is cleavable by a protease in the blood or target tissue. Such embodiments can be used to release a therapeutic protein for better delivery or therapeutic properties or more efficient production.

Additional linkers or spacers may be introduced at the C-terminus of an $^{10}$Fn3 domain between the $^{10}$Fn3 domain and the polypeptide linker.

In some embodiments, a therapeutic moiety is linked to a serum albumin binding Adnectin via a biocompatible polymer such as a polymeric sugar. The polymeric sugar can include an enzymatic cleavage site that is cleavable by an enzyme in the blood or target tissue. Such embodiments can be used to release therapeutic proteins for better delivery or therapeutic properties or more efficient production.

The serum albumin binding Adnectin fusion molecules described herein are useful for increasing the half-life of a therapeutic moiety by creating a fusion between the therapeutic moiety and the serum albumin binding Adnectin. Such fusion molecules may be used to treat conditions which respond to the biological activity of the therapeutic moiety contained in the fusion. The present invention contemplates the use of the serum albumin binding Fn3 fusion molecules in diseases caused by the disregulation of any of the following proteins or molecules.

In exemplary embodiments, the therapeutic moiety that is linked (either C-terminal or N-terminal) to the serum albumin binding Adnectin is VEGF, VEGF-R1, VEGF-R2, VEGF-R3, Her-1, Her-2, Her-3, EGF-I, EGF-2, EGF-3, Alpha3, cMet, ICOS, CD40L, LFA-I, c-Met, ICOS, LFA-I, IL-6, B7.1, W1.2, OX40, IL-1b, TACI, IgE, BAFF or BLys, TPO-R, CD19, CD20, CD22, CD33, CD28, IL-I-R1, TNF-alpha, TRAIL-R1, Complement Receptor 1, FGFa, Osteopontin, Vitronectin, Ephrin A1-A5, Ephrin B1-B3, alpha-2-macroglobulin, CCL, CCL2, CCL3, CCL4, CCL5, CCL6, CCL7, CXCL, CXCL9, CXCL10, CXCL11, CXCL2, CCL13, CCL4, CCL5, CXCL16, CCL16, CCL17, CCL18, CCL19, CCL20, CCL21, CCL22, PDGF, TGFb, GMCSF, SCF, p40 (IL12/IL23), IL1b, IL1a, IL1ra, IL2, IL3, IL4, IL5, IL6, IL, IL, 10, IL12, IL15, IL23, Fas, FasL, Flt3 ligand, 41BB, ACE, ACE-2, KGF, FGF-7, SCF, Netrin1,2, IFNa,b, g, Caspase-2,3,7,8,10, ADAM S1,S5,8,9,15,TS1,TS5; Adiponectin, ALCAM, ALK-I, APRIL, Annexin V, Angiogenin, Amphiregulin, Angiopoietin-1,2,4, B7-1/CD80, B7-2/CD86, B7-H1, B7-H2, B7-H3, Bcl-2, BACE-I, BAK, BCAM, BDNF, bNGF, bECGF, BMP2,3,4,5,6,7,8; CRP, Cadherin 6, 8, 11; Cathepsin A,B,C,D,E,L,S,V,X; CD 1 1a/LFA-1, LFA-3, GP2b3a, GH receptor, RSV F protein, IL-23 (p40, p19), IL-12, CD80, CD86, CD28, CTLA-4, alpha4-beta1, alpha4-beta7, TNF/Lymphotoxin, IgE, CD3, CD20, IL-6, IL-6R, BLYS/BAFF, IL-2R, HER2, EGFR, CD33, CD52, Digoxin, Rho (D), Varicella, Hepatitis, CMV, Tetanus, Vaccinia, Antivenom, Botulinum, Trail-R1, Trail-R2, cMet, TNF-R family, such as LA NGF-R, CD27, CD30, CD40, CD95, Lymphotoxin a/b receptor, WsI-I, TLIAITNFSF15, BAFF, BAFF-R/TNFRSF13C, TRAIL R2ITNFRSF10B, TRAIL R2ITNFRSF10B, FasITNFRSF6 CD27/TNFRSF7, DR3/TNFRSF25, HVEMTNFRSF14, TROY/TNFRSF19, CD40 Ligand/TNFSF5, BCMA/TNFRSF17, CD30/TNFRSF8, LIGHT/TNFSF14, 4-1BB/TNFRSF9, CD40/TNFRSF5, GITR/[Gamma]NFRSF 18, Osteoprotegerin/TNFRSF1 IB, RANKTNFRSF1 IA, TRAIL R3/TNFRSFIOC, TRAIIJTNFSFIO, TRANCE/RANK LITNFSF11, 4-1BB Ligand/TNFSF9, TWEAK/TNFSF12, CD40 LigandITNFSFS, Fas LigandITNFSF6, RELT/TNFRSF19L, APRIUITNFSF13, DcR3/TNFRSF6B, TNF R1/TNFRSFIA, TRAIL R1/TNFRSFIOA, TRAIL R4/TNFRSF10D, CD30 LigandITNFSF8, GITR LigandITNFSF18, TNFSF18, TACI/TNFRSF13B, NGF RTNFRSF16, OX40 Ligand/TNFSF4, TRAIL R2ITNFRSF10B, TRAIL R3/TNFRSF10C, TWEAK RITNFRSF12, BAFF/BLyS/TNFSF13, DR6/TNFRSF21, TNF-alpha/TNFSF1 A, Pro-TNF-alpha/TNFSF1A, Lymphotoxin beta RTNFRSF3, Lymphotoxin beta R (LTbR)/Fc Chimera, TNF RITNFRSFIA, TNF-beta/TNFSF1B, PGRP-S, TNF RI/TNFRSFIA, TNF RII/TNFRSFIB, EDA-A2, TNF-alpha/TNFSFIA, EDAR, XEDAR, TNF RI/TNFRSFIA.

In exemplary embodiments, the therapeutic moiety that is linked (either C-terminal or N-terminal) to the serum albumin binding Adnectin is any of the following proteins or proteins binding thereto: 4EBP1, 14-3-3 zeta, 53BP1, 2B4/SLAMF4, CCL21/6Ckine, 4-1BB/TNFRSF9, 8D6A, 4-1BB LigandITNFSF9, 8-oxo-dG, 4-Amino-1,8-naphthalimide, A2B5, Aminopeptidase LRAP/ERAP2, A33, Aminopeptidase N/ANPEP, Aag, Aminopeptidase P2/XPNPEP2, ABCG2, Aminopeptidase P1/XPNPEP1, ACE, Aminopeptidase PILS/ARTS1, ACE-2, Amnionless, Actin, Amphiregulin, beta-Actin, AMPK alpha 1/2, Activin A, AMPK alpha 1, Activin AB, AMPK alpha 2, Activin B, AMPK beta 1, Activin C, AMPK beta 2, Activin RIA/ALK-2, Androgen R/NR3C4, Activin RIB/ALK-4, Angiogenin, Activin RIA, Angiopoietin-1, Activin RIIB, Angiopoietin-2, ADAMS, Angiopoietin-3, ADAM9, Angiopoietin-4, ADAM 10, Angiopoietin-like 1, ADAM 12, Angiopoietin-like 2, ADAM 15, Angiopoietin-like 3, TACE/ADAM 17, Angiopoietin-like 4, ADAM 19, Angiopoietin-like 7/CDT6, ADAM33, Angiostatin, ADAMTS4, Annexin A1/Annexin I, ADAMTS5, Annexin A7, ADAMTS1, Annexin A10, ADAMTSL-1/Punctin, Annexin V, Adiponectin/Acrp30, ANP, AEBSF, AP Site, Aggrecan, APAF-I, Agrin, APC, AgRP, APE, AGTR-2, APJ, AIF, APLP-I, Akt, APLP-2, Akt1, Apolipoprotein AL, Akt2, Apolipoprotein B, Akt3, APP, Serum Albumin, APRIUITNFSF13, ALCAM, ARC, ALK-I, Artemin, ALK-7, Arylsulfatase AJARSA, Alkaline Phosphatase, ASAH2/N-acylsphingosine Amidohydrolase-2, alpha 2u-Globulin, ASC, alpha-i-Acid Glycoprotein, ASGR1, alpha-Fetoprotein, ASKi, ALS, ATM, Ameloblastic ATRIP, AMICA/JAML, Aurora A, AMIGO, Aurora B, AMIG02, Axin-1, AMIG03, AxI, Aminoacylase/ACY1, Azurocidin/CAP37/HBP, Aminopeptidase A/ENPEP, B4GALT, BIM, B7-1/CD80, 6-Biotin-17-NAD, B7-2/CD86, BLAME/SLAMF8, B7-H1/PD-L1, CXCL13/BLC/BCA-1, B7-H2, BLIMPI, B7-H3, BIk, B7-H4, BMI-I, BACE-I, BMP-1/PCP, BACE-2, BMP-2, Bad, BMP-3, BAFF/TNFSF13B, BMP-3b/GDF-10, BAFF R/TNFRSF 13C, BMP-4, Bag-1, BMP-5, BAK, BMP-6, BAMBI/NMA, BMP-7, BARD 1, BMP-8, Bax, BMP-9, BCAM, BMP-10, Bcl-10, BMP-15/GDF-9B, Bcl-2, BMPR-IA/ALK-3, Bcl-2 related protein A1, BMPR-IB/ALK-6, Bcl-w, BMPR-II, Bcl-x, BNIP3L, Bcl-xL, BOC, BCMA/TNFRSF17, BOK, BDNF, BPDE, Benzamide, Brachyury, Common beta Chain, B-Raf, beta IG-H3, CXCL14/BRAK, Betacellulin, BRCA1, beta-Defensin 2, BRCA2, BID, BTLA, Biglycan, Bub-1, Bik-like Killer Protein, c-jun, CD90Thyl, c-Rel, CD94, CCL6/C10, CD97, CIq R1/CD93, CD151, CIqTNF, CD160, ClqTNF4, CD163, ClqTNF5, CD164, Complement Component CIr, CD200, Complement Component CIs, CD200 R1, Complement Component C2, CD229/SLAMF3, Complement Component C3a, CD23/Fc epsilon R11, Complement Component C3d, CD2F-10/SLAMF9, Complement Component C5a, CD5L, Cadherin-4/R-Cadherin, CD69, Cadherin-6, CDC2, Cadherin-8, CDC25A, Cadherin-11, CDC25B, Cadherin-12, CDCP1, Cadherin-13, CDO, Cadherin-17, CDX4, E-Cadherin, CEACAM-1/CD66a, N-Cadherin, CEACAM-6, P-Cadherin, Cerberus 1, VE-Cadherin, CFTR, Calbindin D, cGMP, Calcineurin A, Chem R23, Calcineurin B, Chemerin, Calreticulin-2, Chemokine Sampler Packs, CaM Kinase II, Chitinase 3-like 1, cAMP, Chitotriosidase/CHIT1, Cannabinoid R1, Chk1, Cannabinoid R2/CB2/CNR2, Chk2, CAR/NR1I3, CHL-1/L1CAM-2, Carbonic Anhydrase I, Choline Acetyltransferase/CbAT, Carbonic Anhydrase II, Chondrolectin, Carbonic Anhydrase III, Chordin, Carbonic Anhydrase IV, Chordin-Like 1, Carbonic Anhydrase VA, Chordin-Like 2, Carbonic Anhydrase VB, CINC-I, Carbonic Anhydrase VI, CINC-2, Carbonic Anhydrase VII, CINC-3, Carbonic Anhydrase VIII, Claspin, Carbonic Anhydrase IX, Claudin-6, Carbonic Anhydrase X, CLC, Carbonic Anhydrase XII, CLEC-I, Carbonic Anhydrase XIII, CLEC-2, Carbonic Anhydrase XIV, CLECSF 13/CLEC4F, Carboxymethyl Lysine, CLECSF8, Carboxypeptidase A1/CPA1, CLF-I, Carboxypeptidase A2, CL-P1/COLEC12, Carboxypeptidase A4, Clusterin, Carboxypeptidase B1, Clusterin-like 1, Carboxypeptidase E/CPE, CMG-2, Carboxypeptidase X1, CMV UL146, Cardiotrophin-1, CMV UL147, Carnosine Dipeptidase 1, CNP, Caronte, CNTF, CART, CNTF R alpha, Caspase, Coagulation Factor IIThrombin, Caspase-1, Coagulation Factor I11/Tissue Factor, Caspase-2, Coagulation Factor VII, Caspase-3, Coagulation Factor X, Caspase- 4, Coagulation Factor XI, Caspase-6, Coagulation Factor XIV/Protein C, Caspase-7, COCO, Caspase-8, Cohesin, Caspase-9, Collagen I, Caspase-10, Collagen II, Caspase-12, Collagen IV, Caspase-13, Common gamma Chain/IL-2 R gamma, Caspase Peptide Inhibitors, COMP/Thrombospondin-5, Catalase, Complement Component CIrLP, beta-Catenin, Complement Component CIqA, Cathepsin 1, Complement Component CIqC, Cathepsin 3, Complement Factor D, Cathepsin 6, Complement Factor I, Cathepsin A, Complement MASP3, Cathepsin B, Connexin 43, Cathepsin C/DPPI, Contactin-1, Cathepsin D, Contactin-2/TAG 1, Cathepsin E, Contactin-4, Cathepsin F, Contactin-5, Cathepsin H, Corin, Cathepsin L, Cornulin, Cathepsin O, CORS26/ClqTNF,3, Cathepsin S, Rat Cortical Stem Cells, Cathepsin V, Cortisol, Cathepsin XITJ?, COUP-TF I/NR2F1, CBP, COUP-TF II/NR2F2, CCI, COX-I, CCK-A R, COX-2, CCL28, CRACC/SLAMF7, CCR1, C-Reactive Protein, CCR2, Creatine Kinase, Muscle/CKMM, CCR3, Creatinine, CCR4, CREB, CCR5, CREG, CCR6, CRELD, CCR7, CRELD2, CCR8, CRHBP, CCR9, CRHR-I, CCR1O, CRIMI, CD155/PVR, Cripto, CD2, CRISP-2, CD3, CRISP-3, CD4, Crossveinless-2, CD4+/45RA−, CRTAM, CD4+/45RO, CRTH-2, CD4+/CD62L−/CD44, CRY1, CD4+/CD62L+/CD44, Cryptic, CD5, CSB/ERCC6, CD6, CCL27/CTACK, CD8, CTGF/CCN2, CD8+/45RA−, CTLA-4, CD8+/45RO−, Cubilin, CD9, CX3CR1, CD14, CXADR, CD27/TNFRSF7, CXCL16, CD27 Ligand/TNFSF7, CXCR3, CD28, CXCR4, CD30/TNFRSF8, CXCR5, CD30 Ligand/TNFSF8, CXCR6, CD31/PECAM-1, Cyclophilin A, CD34, Cyr61/CCN1, CD36/SR-B3, Cystatin A, CD38, Cystatin B, CD40/TNFRSF5, Cystatin C, CD40 Ligand/TNFSF5, Cystatin D, CD43, Cystatin E/M, CD44, Cystatin F, CD45, Cystatin H, CD46, Cystatin H2, CD47, Cystatin S, CD48/SLAMF2, Cystatin SA, CD55/DAF, Cystatin SN, CD58/LFA-3, Cytochrome c, CD59, Apocytochrome c, CD68, Holocytochrome c, CD72, Cytokeratin 8, CD74, Cytokeratin 14, CD83, Cytokeratin 19, CD84/SLAMF5, Cytonin, D6, DISPI, DAN, Dkk-1, DANCE, Dkk-2, DARPP-32, Dkk-3, DAX1/NR0B1, Dkk-4, DCC, DLEC, DCIR/CLEC4A, DLL1, DCAR, DLL4, DcR3/TNFRSF6B, d-Luciferin, DC-SIGN, DNA Ligase IV, DC-SIGNR/CD299, DNA Polymerase beta, DcTRAIL R1ITNFRSF23, DNAM-I, DcTRAIL R2/TNFRSF22, DNA-PKcs, DDR1, DNER, DDR2, Dopa Decarboxylase/DDC, DEC-205, DPCR-I, Decapentaplegic, DPP6, Decorin, DPP A4, Dectin-1/CLEC7A, DPPA5/ESGI, Dectin-2/CLEC6A, DPPII/QPP/DPP7, DEP-1/CD148, DPPIV/CD26, Desert Hedgehog, DR3/TNFRSF25, Desmin, DR6/TNFRSF21, Desmoglein-1, DSCAM, Desmoglein-2, DSCAM-L1, Desmoglein-3, DSPG3, Dishevelled-1, Dtk, Dishevelled-3, Dynamin, EAR2/NR2F6, EphA5, ECE-I, EphA6, ECE-2, EphA7, ECF-UCHI3L3, EphA8, ECM-I, EphB1, Ecotin, EphB2, EDA, EphB3, EDA-A2, EphB4, EDAR, EphB6, EDG-I, Ephrin, EDG-5, Ephrin-A1, EDG-8, Ephrin-A2, eEF-2, Ephrin-A3, EGF, Ephrin-A4, EGF R, Ephrin-A5, EGR1, Ephrin-B, EG-VEGF/PK1, Ephrin-B1, eIF2 alpha, Ephrin-B2, eIF4E, Ephrin-B3, Elk-I, Epigen, EMAP-II, Epimorphin/Syntaxin 2, EMMPRIN/CD147, Epiregulin, CXCL5/ENA, EPR-I/Xa Receptor, Endocan, ErbB2, Endoglin/CD105, ErbB3, Endoglycan, ErbB4, Endonuclease III, ERCC1, Endonuclease IV, ERCC3, Endonuclease V, ERK1/ERK2, Endonuclease VIII, ERK1, Endorepellin/Perlecan, ERK2, Endostatin, ERK3, Endothelin-1, ERK5/BMKI, Engrailed-2, ERR alpha/NR3B1, EN-RAGE, ERR beta/NR3B2, Enteropeptidase/Enterokinase, ERR gamma/NR3B3, CCL1 1/Eotaxin, Erythropoietin, CCL24/Eotaxin-2, Erythropoietin R, CCL26/Eotaxin-3, ESAM, EpCAM/TROP-1, ER alpha/NR3A1, EPCR, ER beta/NR3A2, Eph, Exonuclease III, EphA1, Exostosin-like 2/EXTL2, EphA2, Exostosin-like 3/EXTL3, EphA3, FABP1, FGF-BP, FABP2, FGF R1-4, FABP3, FGF R1, FABP4, FGF R2, FABP5, FGF R3, FABP7, FGF R4, FABP9, FGF R5, Complement Factor B, Fgr, FADD, FHR5, FAM3A, Fibronectin, FAM3B, Ficolin-2, FAM3C, Ficolin-3, FAM3D, FITC, Fibroblast Activation Protein alpha/FAP, FKBP38, Fas/TNFRSF6, Flap, Fas Ligand/TNFSF6, FLIP, FATP1, FLRG, FATP4, FLRT1, FATP5, FLRT2, Fc gamma R1/CD64, FLRT3, Fc gamma RIIB/CD32b, Flt-3, Fc gamma RIIC/CD32c, Fit-3 Ligand, Fc gamma RIIA/CD32a, Follistatin, Fc gamma RIII/CD16, Follistatin-like 1, FcRH1/IRTA5, FosB/GOS3, FcRH2/IRTA4, FoxD3, FcRH4/IRTA1, FoxJ1, FcRH5/IRTA2, FoxP3, Fc Receptor-like 3/CD16-2, Fpg, FEN-I, FPR1, Fetuin A, FPRL1, Fetuin B, FPRL2, FGF acidic, CX3CL1/Fractalkine, FGF basic, Frizzled-1, FGF-3, Frizzled-2, FGF-4, Frizzled-3, FGF-5, Frizzled-4, FGF-6, Frizzled-5, FGF-8, Frizzled-6, FGF-9, Frizzled-7, FGF-IO, Frizzled-8, FGF-11, Frizzled-9, FGF-12, Frk, FGF-13, sFRP-1, FGF-16, sFRP-2, FGF-17, sFRP-3, FGF-19, sFRP-4, FGF-20, Furin, FGF-21, FXR/NR1H4, FGF-22, Fyn, FGF-23, G9a/EHMT2, GFR alpha-3/GDNF R alpha-3, GABA-A-R alpha 1, GFR alpha-4/GDNF R alpha-4, GABA-A-R alpha 2, GITR/TNFRSF18, GABA-A-R alpha 4, GITR Ligand/TNFSF18, GABA-A-R alpha 5, GLI-I, GABA-A-R alpha 6, GLI-2, GABA-A-R beta 1, GLP/EHMT1, GABA-A-R beta 2, GLP-I R, GABA-A-R beta 3, Glucagon, GABA-A-R gamma 2, Glucosamine (N-acetyl)-6-Sulfatase/GNS, GABA-B-R2, GIuR1, GAD1/GAD67, GluR2/3, GAD2/GAD65, GluR2, GADD45 alpha, GluR3, GADD45 beta, Glut1, GADD45 gamma, Glut2, Galectin-1, Glut3, Galectin-2, Glut4, Galectin-3, Glut5, Galectin-3 BP, Glutaredoxin 1, Galectin-4, Glycine R, Galectin-7, Glycophorin A, Galectin-8, Glypican 2, Galectin-9, Glypican 3, GalNAc4S-6ST, Glypican 5, GAP-43, Glypican 6, GAPDH, GM-CSF, Gas1, GM-CSF R alpha, Gas6, GMF-beta, GASP-1/WFIKKNRP, gpl30, GASP-2/WFIKKN, Glycogen Phosphorylase BB/GPBB, GATA-I, GPR15, GATA-2, GPR39, GATA-3, GPVI, GATA-4, GR/NR3C1, GATA-5, Gr-1/Ly-6G, GATA-6, Granulysin, GBL, Granzyme A, GCNF/NR6A1, Granzyme B, CXCL6/GCP-2, Granzyme D, G-CSF, Granzyme G, G-CSF R, Granzyme H, GDF-I, GRASP, GDF-3 GRB2, GDF-5, Gremlin, GDF-6, GRO, GDF-7, CXCL1/GRO alpha, GDF-8, CXCL2/GRO beta, GDF-9, CXCL3/GRO gamma, GDF-11, Growth Hormone, GDF-15, Growth Hormone R, GDNF, GRP75/HSPA9B, GFAP, GSK-3 alpha/beta, GFI-I, GSK-3 alpha, GFR alpha-1/GDNF R alpha-1, GSK-3 beta, GFR alpha-2/GDNF R alpha-2, EZFIT, H2AX, Histidine, H60, HM74A, HAI-I, HMGA2, HAI-2, HMGB1, HAI-2A, TCF-2/HNF-1 beta, HAI-2B, HNF-3 beta/FoxA2, HAND1, HNF-4 alpha/NR2A1, HAPLN1, HNF-4 gamma/NR2A2, Airway Trypsin-like Protease/HAT, HO-1/HMOX1/HSP32, HB-EGF, HO-2/HMOX2, CCL 14a/HCC-1, HPRG, CCL14b/HCC-3, Hrk, CCL16/HCC-4, HRP-I, alpha HCG, HS6ST2, Hck, HSD-I, HCR/CRAM-A/B, HSD-2, HDGF, HSP 10/EPF, Hemoglobin, HSP27, Hepassocin, HSP60, HES-1, HSP70, HES-4, HSP90, HGF, HTRA/Protease Do, HGF Activator, HTRA1/PRSS11, HGF R, HTRA2/0 ml, HIF-I alpha, HVEM/TNFRSF14, HIF-2 alpha, Hyaluronan, HIN-1/Secretoglobulin 3A1, 4-Hydroxynonenal, Hip, CCL1/I-309/TCA-3, IL-IO, cIAP (pan), IL-IO R alpha, cIAP-1/HIAP-2, IL-10 R beta, cIAP-2/HIAP-1, IL-1, IBSP/Sialoprotein II, EL-11 R alpha, ICAM-1/CD54, IL-12, ICAM-2/CD102, IL-12/IL-23 p40, ICAM-3/CD50, IL-12 R beta 1, ICAM-5, IL-12 R beta 2, ICAT, IL-13, ICOS, IL-13

R alpha 1, Iduronate 2-Sulfatase/EOS, IL-13 R alpha 2, EFN, IL-15, IFN-alpha, IL-15 R alpha, IFN-alpha 1, IL-16, IFN-alpha 2, IL-17, IFN-alpha 4b, IL-17 R, IFN-alpha A, IL-17 RC, IFN-alpha B2, IL-17 RD, IFN-alpha C, IL-17B, IFN-alpha D, IL-17B R, IFN-alpha F, IL-17C, IFN-alpha G, IL-17D, IFN-alpha H2, IL-17E, IFN-alpha I, IL-17F, IFN-alpha J 1, IL-18/IL-1F4, IFN-alpha K, IL-18 BPa, IFN-alpha WA, IL-18 BPc, IFN-alpha/beta R1, IL-18 BPd, IFN-alpha/beta R2, IL-18 R alpha/IL-1 R5, IFN-beta, IL-18 R beta/IL-1 R7, IFN-gamma, IL-19, IFN-gamma R1, IL-20, IFN-gamma R2, IL-20 R alpha, IFN-omega, IL-20 R beta, IgE, IL-21, IGFBP-I, IL-21 R, IGFBP-2, IL-22, IGFBP-3, IL-22 R, IGFBP-4, IL-22BP, IGFBP-5, IL-23, IGFBP-6, IL-23 R, IGFBP-L1, IL-24, IGFBP-rp1/IGFBP-7, IL-26/AK155, IGFBP-rPIO, IL-27, IGF-I, EL-28A, IGF-I R, IL-28B, IGF-II, IL-29/EFN-lambda 1, IGF-II R, IL-3 1, IgG, EL-31 RA, IgM, IL-32 alpha, IGSF2, IL-33, IGSF4A/SynCAM, ILT2/CD85J, IGSF4B, ILT3/CD85k, IGSF8, ILT4/CD85d, IgY, ILT5/CD85a, IkB-beta, ILT6/CD85e, IKK alpha, Indian Hedgehog, IKK epsilon, INSRR, EKK gamma, Insulin, IL-1 alpha/IL-IF1, Insulin R/CD220, IL-1 beta/IL-1F2, Proinsulin, IL-ira/IL-1F3, Insulysin/EDE, IL-F5/FIL1 delta, Integrin alpha 2/CD49b, IL-F6/FIL1 epsilon, Integrin alpha 3/CD49c, IL-1F7/FIL1 zeta, Integrin alpha 3 beta 1/VNLA-3, IL-1F8/FIL1 eta, Integrin alpha 4/CD49d, IL-1F9/IL-1 H1, Integrin alpha 5/CD49e, IL-1F10/IL-1HY2, Integrin alpha 5 beta 1, IL-I RI, Integrin alpha 6/CD49f, IL-I RII, Integrin alpha 7, IL-I R3/IL-1 R AcP, Integrin alpha 9, IL-I R4/ST2, Integrin alpha E/CD103, IL-I R6/IL-1 R rp2, Integrin alpha L/CD1 Ia, IL-I R8, Integrin alpha L beta 2, IL-I R9, Integrin alpha M/CD1 Ib, IL-2, Integrin alpha M beta 2, IL-2 R alpha, Integrin alpha V/CD5 1, IL-2 R beta, Integrin alpha V beta 5, IL-3, Integrin alpha V beta 3, IL-3 R alpha, Integrin alpha V beta 6, IL-3 R beta, Integrin alpha XJCD1 Ic, IL-4, Integrin beta 1/CD29, IL-4 R, Integrin beta 2/CD18, IL-5, Integrin beta 3/CD61, IL-5 R alpha, Integrin beta 5, IL-6, Integrin beta 6, IL-6 R, Integrin beta 7, IL-7, CXCL10/EP-10/CRG-2, IL-7 R alpha/CD127, IRAKI, CXCR1/IL-8 RA, IRAK4, CXCR2/IL-8 RB, ERS-I, CXCL8/IL-8, Islet-1, IL-9, CXCL1 1/I-TAC, IL-9 R, Jagged 1, JAM-4/IGSF5, Jagged 2, JNK, JAM-A, JNK1/JNK2, JAM-BNE-JAM, JNK1, JAM-C, JNK2, Kininogen, Kallikrein 3/PSA, Kininostatin, Kallikrein 4, KER/CD158, Kallikrein 5, KER2D1, Kallikrein 6/Neurosin, KIR2DL3, Kallikrein 7, KIR2DL4/CD158d, Kallikrein 8/Neuropsin, KIR2DS4, Kallikrein 9, KIR3DL1, Plasma Kallikrein/KLKB1, KER3DL2, Kallikrein 10, Kirrel2, Kallikrein 11, KLF4, Kallikrein 12, KLF5, Kallikrein 13, KLF6, Kallikrein 14, Klotho, Kallikrein 15, Klotho beta, KC, KOR, Keap1, Kremen-1, Kel1, Kremen-2, KGF/FGF-7, LAG-3, LINGO-2, LAIR, Lipin 2, LAIR2, Lipocalin-1, Laminin alpha 4, Lipocalin-2/NGAL, Laminin gamma 1,5-Lipoxygenase, Laminin I, LXR alpha/NR1H3, Laminin S, LXR beta/NR1H2, Laminin-1, Livin, Laminin-5, LEX, LAMP, LMIR1/CD300A, Langerin, LMIR2/CD300c, LAR, LMIR3/CD300LF, Latexin, LMIR5/CD300LB, Layilin, LMIR6/CD300LE, LBP, LMO2, LDL R, LOX-1/SR-E1, LECT2, LRH-1/NR5A2, LEDGF, LRIG, Lefty, LRIG3, Lefty-1, LRP-I, Lefty-A, LRP-6, Legumain, LSECtin/CLEC4G, Leptin, Lumican, Leptin R, CXCL15/Lungkine, Leukotriene B4, XCL1/Lymphotactin, Leukotriene B4 R1, Lymphotoxin, LEF, Lymphotoxin beta/TNFSF3, LIF R alpha, Lymphotoxin beta R/TNFRSF3, LIGHT/TNFSF4, Lyn, Limitin, Lyp, LIMPII/SR-B2, Lysyl Oxidase Homolog 2, LIN-28, LYVE-I, LINGO-I, alpha 2-Macroglobulin, CXCL9/MIG, MAD2L1, Mimecan, MAdCAM-1, Mindin, MafB, Mineralocorticoid R/NR3C2, MafF, CCL3L1/MIP-1 alpha Isoform LD78 beta, MafG, CCL3/MIP-1 alpha, MafK, CCL4L1/LAG-1, MAG/Siglec-4-a, CCL4/MIP-1 beta, MANF, CCL5/MEP-1 delta, MAP2, CCL9/10/MIP-1 gamma, MAPK, MIP-2, Marapsin/Pancreasin, CCL19/MIP-3 beta, MARCKS, CCL20/MIP-3 alpha, MARCO, MIP-I, Mash1, MIP-II, Matrilin-2, MIP-III, Matrilin-3, MIS/AMH, Matrilin-4, MIS RII, Matriptase/ST14, MIXL1, MBL, MKK3/MKK6, MBL-2, MKK3, Melanocortin 3R/MC3R, MKK4, MCAM/CD146, MKK6, MCK-2, MKK7, McI-I, MKP-3, MCP-6, MLH-I, CCL2/MCP-1, MLK4 alpha, MCP-11, MMP, CCL8/MCP-2, MMP-1, CCL7/MCP-3/MARC, MMP-2, CCL13/MCP-4, MMP-3, CCL2/MCP-5, MMP-7, M-CSF, MMP-8, M-CSF R, MMP-9, MCV-type II, MMP-IO, MD-I, MMP-I 1, MD-2, MMP-12, CCL22/MDC, MMP-13, MDL-1/CLEC5A, MMP-14, MDM2, MMP-15, MEA-I, MMP-16/MT3-MMP, MEK1/MEK2, MMP-24/MT5-MMP, MEK1, MMP-25/MT6-MMP, MEK2, MMP-26, Melusin, MMR, MEPE, MOG, Meprin alpha, CCL23/MPIF-1, Meprin beta, M-Ras/R-Ras3, Mer, Mrel 1, Mesothelin, MRPI Meteorin, MSK1/MSK2, Methionine Aminopeptidase 1, MSK1, Methionine Aminopeptidase, MSK2, Methionine Aminopeptidase 2, MSP, MFG-E8, MSP R/Ron, MFRP, Mug, MgcRacGAP, MULT-I, MGL2, Musashi-1, MGMT, Musashi-2, MIA, MuSK, MICA, MutY DNA Glycosylase, MICB, MyD88, MICUICLEC12A, Myeloperoxidase, beta 2 Microglobulin, Myocardin, Midkine, Myocilin, MIF, Myoglobin, NAIP NGFI-B gamma/NR4A3, Nanog, NgR2/NgRH1, CXCL7/NAP-2, NgR3/NgRH2, Nbsl, Nidogen-1/Entactin, NCAM-1/CD56, Nidogen-2, NCAM-L1, Nitric Oxide, Nectin-1, Nitrotyrosine, Nectin-2/CD1 12, NKG2A, Nectin-3, NKG2C, Nectin-4, NKG2D, Neogenin, NKp30, Neprilysin/CDIO, NKp44, Neprilysin-2/MMEL1/MMEL2, NKp46/NCR, Nestin, NKp80/KLRF, NETO2, NKX2.5, Netrin-1, NMDA R, NR1 Subunit, Netrin-2, NMDA R, NR2A Subunit, Netrin-4, NMDA R, NR2B Subunit, Netrin-Gla, NMDA R, NR2C Subunit, Netrin-G2a, N-Me-6,7-diOH-TIQ, Neuregulin-1/NRG1, Nodal, Neuregulin-3/NRG3, Noggin, Neuritin, Nogo Receptor, NeuroDi, Nogo-A, Neurofascin, NOMO, Neurogenin-1, Nope, Neurogenin-2, Norrin, Neurogenin-3, eNOS, Neurolysin, iNOS, Neurophysin II, nNOS, Neuropilin-1, Notch-1, Neuropilin-2, Notch-2, Neuropoietin, Notch-3, Neurotrimin, Notch-4, Neurturin, NOV/CCN3, NFAMi, NRAGE, NF-H, NrCAM, NFkB1, NRL, NFkB2, NT-3, NF-L, NT-4, NF-M, NTB-A/SLAMF6, NG2/MCSP, NTH1, NGF RITNFRSF6, Nucleostemin, beta-NGF, Nurr-1/NR4A2, NGFI-B alpha/NR4A1, OAS2, Orexin B, OBCAM, OSCAR, OCAM, OSF-2/Periostin, OCIIJCLEC2d, Oncostatin M/OSM, OCILRP2/CLEC21, OSM R beta, Oct-3/4, Osteoactivin/GPNMB, OGG1, Osteoadherin, Olig 1, 2, 3, Osteocalcin, Olig1, Osteocrin, Olig2, Osteopontin, Olig3, OsteoprotegeriniTNFRSFi IB, Oligodendrocyte Marker O1, Otx2, Oligodendrocyte Marker O4, OV-6, OMgp, OX40ITNFRSF4, Opticin, OX40 LigandfTNFSF4, Orexin A, OAS2, Orexin B, OBCAM, OSCAR, OCAM, OSF-2/Periostin, OCIIJCLEC2d, Oncostatin M/OSM, OCILRP2/CLEC2i, OSM R beta, Oct-3/4, Osteoactivin/GPNMB, OGG1, Osteoadherin, Olig 1, 2, 3, Osteocalcin, Olig1, Osteocrin, Olig2, Osteopontin, Olig3, Osteoprotegerin/TNFRSF1 IB, Oligodendrocyte Marker 01, Otx2, Oligodendrocyte Marker O4, OV-6, OMgp, OX40/TNFRSF4, Opticin, OX40 Ligand/TNFSF4, Orexin A, RACK1, Ret, Rad1, REV-ERB alpha/NR1D1, Rad17, REV-ERB beta/NR1D2, Rad51, Rex-1, Rae-1, RGM-A, Rae-1 alpha, RGM-B, Rae-1 beta, RGM-C, Rae-1 delta, Rheb, Rae-1 epsilon, Ribosomal Protein S6, Rae-1 gamma, RIP1, Raf-1, ROBO1, RAGE, ROBO2, Ra1A/Ra1B, R0B03, RaIA, ROBO4, RaIB, R0R/NRIF1-3 (pan), RANK/TNFRSF1 1A, ROR alpha/NR1F1, CCL5/RANTES, ROR gamma/NR1F3, Rap1A/B, RTK-like Orphan Receptor 1/ROR1, RAR alpha/NR1B1, RTK-like Orphan Receptor 2/ROR2, RAR beta/NR1B2, RP105, RAR gamma/NR1B3, RP A2, Ras, RSK (pan), RBP4, RSK1/RSK2, RECK, RSK1, Reg 2/PAP, RSK2, Reg I, RSK3, Reg II, RSK4, Reg III, R-Spondin 1, Reg I1ia, R-Spondin 2, Reg IV, R-Spondin 3, Relaxin-1, RUNX1/CBFA2, Relaxin-2, RUNX2/CBFA1, Relaxin-3, RUNX3/CBFA3, RELM alpha, RXR alpha/NR2B1, RELM beta, RXR beta/NR2B2, RELT/TNFRSF19L, RXR gamma/NR2B3, Resistin, S1OOAlO, SLITRK5, S100A8, SLPI, S100A9, SMAC/Diablo, S1OOB, Smad1, S1OOP, Smad2, SALL1, Smad3, delta-Sarcoglycan, Smad4, Sca-1/Ly6, Smad5, SCD-I, Smad7, SCF, Smad8, SCF R/c-kit, SMC1, SCGF, alpha-Smooth Muscle Actin, SCI/Tall, SMUG1, SCP3/SYCP3, Snail, CXCL12/SDF-1, Sodium Calcium Exchanger 1, SDNSF/MCFD2, Soggy-1, alpha-Secretase, Sonic Hedgehog, gamma-Secretase, S or CS1, beta-Secretase, S or CS3, E-Selectin, Sortilin, L-Selectin, SOST, P-Selectin, SOX1, Semaphorin 3A, SOX2, Semaphorin 3C, SOX3, Semaphorin 3E, SOX7, Semaphorin 3F, SOX9, Semaphorin 6A, SOX10, Semaphorin 6B, SOX 17, Semaphorin 6C, SOX21 Semaphorin 6D, SPARC, Semaphorin 7 A, SPARC-like 1, Separase, SP-D, SerineThreonine Phosphatase Substrate I, Spinesin, Serpin A1, F-Spondin, Serpin A3, SR-AI/MSR, Serpin A4/Kallistatin, Src, Serpin AS/Protein C Inhibitor, SREC-I/SR-F1, Serpin A8/Angiotensinogen, SREC-II, Serpin B5, SSEA-I, Serpin C1/Antithrombin-III, SSEA-3, Serpin D1/Heparin Cofactor II, SSEA-4, Serpin E1/PAI-1, ST7/LRP12, Serpin E2, Stabilin-1, Serpin F1, Stabilin-2, Serpin F2, Stanniocalcin 1, Serpin G1/C1 Inhibitor, Stanniocalcin 2, Serpin 12, STAT1, Serum Amyloid A1, STAT2, SF-1/NR5A1, STAT3, SGK, STAT4, SHBG, STAT5a/b, SHIP, STAT5a, SHP/NROB2, STAT5b, SHP-I, STATE, SHP-2, VE-Statin, SIGIRR, Stella/Dppa3, Siglec-2/CD22, STRO-I, Siglec-3/CD33, Substance P, Siglec-5, Sulfamidase/SGSH, Siglec-6, Sulfatase Modifying Factor 1/SUMF1, Siglec-7, Sulfatase Modifying Factor 2/SUMF2, Siglec-9, SUMO1, Siglec-10, SUMO2/3/4, Siglec-11, SUMO3, Siglec-F, Superoxide Dismutase, SIGNR1/CD209, Superoxide Dismutase-1/Cu[0099]—Zn SOD, SIGNR4, Superoxide Dismutase-2/Mn-SOD, SIRP beta 1, Superoxide Dismutase-3/EC-SOD, SK1, Survivin, SLAM/CD150, Synapsin I, Sleeping Beauty Transposase, Syndecan-I/CD 138, Slit3, Syndecan-2, SLITRK1, Syndecan-3, SLITRK2, Syndecan-4, SLITRK4, TACITNFRSF13B, TMEFF 1lTomoregulin-1, TAO2, TMEFF2, TAPPI, TNF-alpha/TNFSF IA, CCL17/TARC, TNF-betaITNFSF1B, Tau, TNF R1/TNFRSFIA, TC21/R-Ras2, TNF RII/TNFRSF1B, TCAM-I, TOR, TCCR/WSX-1, TP-I, TC-PTP, TP63/TP73L, TDG, TR, CCL25/TECK, TR alpha/NR1A1, Tenascin C, TR beta 1/NR1A2, Tenascin R, TR2/NR2C1, TER-119, TR4/NR2C2, TERT, TRA-1-85, Testican 1/SPOCK1, TRADD, Testican 2/SPOCK2, TRAF-1, Testican 3/SPOCK3, TRAF-2, TFPI, TRAF-3, TFPI-2, TRAF-4, TGF-alpha, TRAF-6, TGF-beta, TRAILITNFSF10, TGF-beta 1, TRAIL R1/TNFRSFIOA, LAP (TGF-beta 1), TRAIL R2ITNFRSF10B, Latent TGF-beta 1, TRAIL R3/TNFRSF10C, TGF-beta 1.2, TRAIL R4/TNFRSF10D, TGF-beta 2, TRANCEITNFSF1 1, TGF-beta 3, TfR (Transferrin R), TGF-beta 5, Apo-Transferrin, Latent TGF-beta by 1, Holo-Transferrin, Latent TGF-beta bp2, Trappin-2/Elafin, Latent TGF-beta bp4, TREM-1, TGF-beta R1/ALK-5, TREM-2, TGF-beta R11, TREM-3, TGF-beta RIIb, TREML1/TLT-1, TGF-beta RIII, TRF-I, Thermolysin, TRF-2, Thioredoxin-1, TRH-degrading Ectoenzyme/TRHDE, Thioredoxin-2, TRIMS, Thioredoxin-80, Tripeptidyl-Peptidase I, Thioredoxin-like 5/TRP14, TrkA, THOP1, TrkB, Thrombomodulin/CD141, TrkC, Thrombopoietin, TROP-2, Thrombopoietin R, Troponin I Peptide 3, Thrombospondin-1, Troponin T, Thrombospondin-2, TROY/TNFRSF 19, Thrombospondin-4, Trypsin 1, Thymopoietin, Trypsin 2/PRSS2, Thymus Chemokine-1, Trypsin 3/PRSS3, Tie-1, Tryptase-5/Prss32, Tie-2, Tryptase alpha/TPS1, TIM-I/KIM-I/HAVCR, Tryptase beta-1/MCPT-7, TIM-2, Tryptase beta-2/TPSB2, TIM-3, Tryptase epsilon/BSSP-4, TIM-4, Tryptase gamma-1/TPSG1, TIM-5, Tryptophan Hydroxylase, TIM-6, TSC22, TIMP-I, TSG, TIMP-2, TSG-6, TIMP-3, TSK, TIMP-4, TSLP, TL1A/TNFSF15, TSLP R, TLR1, TSP50, TLR2, beta-III Tubulin, TLR3, TWEAK/TNFSF12, TLR4, TWEAK R/TNFRSF 12, TLR5, Tyk2, TLR6, Phospho-Tyrosine, TLR9, Tyrosine Hydroxylase, TLX/NR2E1, Tyrosine Phosphatase Substrate I, Ubiquitin, UNC5H3, Ugi, UNC5H4, UGRP1, UNG, ULBP-I, uPA, ULBP-2, uPAR, ULBP-3, URB, UNC5H1, UVDE, UNC5H2, Vanilloid R1, VEGF R, VASA, VEGF R1/Flt-1, Vasohibin, VEGF R2/KDR/Flk-1, Vasorin, VEGF R3/FU-4, Vasostatin, Versican, Vav-1, VG5Q, VCAM-1, VHR, VDR/NR1I1, Vimentin, VEGF, Vitronectin, VEGF-B, VLDLR, VEGF-C, vWF-A2, VEGF-D, Synuclein-alpha, Ku70, WASP, Wnt-7b, WIF-I, Wnt-8a WISP-1/CCN4, Wnt-8b, WNK1, Wnt-9a, Wnt-1, Wnt-9b, Wnt-3a, Wnt-10a, Wnt-4, Wnt-10b, Wnt-5a, Wnt-1, Wnt-5b, wnvNS3, Wnt7a, XCR1, XPE/DDB1, XEDAR, XPE/DDB2, Xg, XPF, XIAP, XPG, XPA, XPV, XPD, XRCC1, Yes, YY1, EphA4.

Numerous human ion channels are targets of particular interest. Non-limiting examples include 5-hydroxytryptamine 3 receptor B subunit, 5-hydroxytryptamine 3 receptor precursor, 5-hydroxytryptamine receptor 3 subunit C, AAD 14 protein, Acetylcholine receptor protein, alpha subunit precursor, Acetylcholine receptor protein, beta subunit precursor, Acetylcholine receptor protein, delta subunit precursor, Acetylcholine receptor protein, epsilon subunit precursor, Acetylcholine receptor protein, gamma subunit precursor, Acid sensing ion channel 3 splice variant b, Acid sensing ion channel 3 splice variant c, Acid sensing ion channel 4, ADP-ribose pyrophosphatase, mitochondrial precursor, Alphal A-voltage-dependent calcium channel, Amiloride-sensitive cation channel 1, neuronal, Amiloride-sensitive cation channel 2, neuronal Amiloride-sensitive cation channel 4, isoform 2, Amiloride-sensitive sodium channel, Amiloride-sensitive sodium channel alpha-subunit, Amiloride-sensitive sodium channel beta-subunit, Amiloride-sensitive sodium channel delta-subunit, Amiloride-sensitive sodium channel gamma-subunit, Annexin A7, Apical-like protein, ATP-sensitive inward rectifier potassium channel 1, ATP-sensitive inward rectifier potassium channel 10, ATP-sensitive inward rectifier potassium channel 11, ATP-sensitive inward rectifier potassium channel 14, ATP-sensitive inward rectifier potassium channel 15, ATP-sensitive inward rectifier potassium channel 8, Calcium channel alpha12.2 subunit, Calcium channel alpha12.2 subunit, Calcium channel alpha1E subunit, delta19 delta40 delta46 splice variant, Calcium-activated potassium channel alpha subunit 1, Calcium-activated potassium channel beta subunit 1, Calcium-activated potassium channel beta subunit 2, Calcium-activated potassium channel beta subunit 3, Calcium-dependent chloride channel-1, Cation channel TRPM4B, CDNA FLJ90453 fis, clone NT2RP3001542, highly similar to Potassium channel tetramerisation domain containing 6, CDNA FL190663 fis, clone PLACE 1005031, highly similar to Chloride intracellular channel protein 5, CGMP-gated cation channel beta subunit, Chloride channel protein, Chloride channel protein 2, Chloride channel protein 3, Chloride channel protein 4, Chloride channel protein 5, Chloride channel protein 6, Chloride channel protein C1C-Ka, Chloride channel protein C C-Kb, Chloride channel protein, skeletal muscle, Chloride intracellular channel 6, Chloride intracellular channel protein 3, Chloride intracellular channel protein 4, Chloride intracellular channel protein 5, CHRNA3 protein, Clcn3e protein, CLCNKB protein, CNGA4 protein, Cullin-5, Cyclic GMP gated potassium channel, Cyclic-nucleotide-gated cation channel 4, Cyclic-nucleotide-gated cation channel alpha 3, Cyclic-nucleotide-gated cation channel beta 3, Cyclic-nucleotide-gated olfactory channel, Cystic fibrosis transmembrane conductance regulator, Cytochrome B-245 heavy chain, Dihydropyridine-sensitive L-type, calcium channel alpha-2/delta subunits precursor, FXYD domain-containing ion transport regulator 3 precursor, FXYD domain-containing ion transport regulator 5 precursor, FXYD domain-containing ion transport regulator 6 precursor, FXYD domain-containing ion transport regulator 7, FXYD domain-containing ion transport regulator 8 precursor, G protein-activated inward rectifier potassium channel 1, G protein-activated inward rectifier potassium channel 2, G protein-activated inward rectifier potassium channel 3, G protein-activated inward rectifier potassium channel 4, Gamma-aminobutyric-acid receptor alpha-1 subunit precursor, Gamma-aminobutyric-acid receptor alpha-2 subunit precursor, Gamma-aminobutyric-acid receptor alpha-3 subunit precursor, Gamma-aminobutyric-acid receptor alpha-4 subunit precursor, Gamma-aminobutyric-acid receptor alpha-5 subunit precursor, Gamma-aminobutyric-acid receptor alpha-6 subunit precursor, Gamma-aminobutyric-acid receptor beta-1 subunit precursor, Gamma-aminobutyric-acid receptor beta-2 subunit precursor, Gamma-aminobutyric-acid receptor beta-3 subunit precursor, Gamma-aminobutyric-acid receptor delta subunit precursor, Gamma-aminobutyric-acid receptor epsilon subunit precursor, Gamma-aminobutyric-acid receptor gamma-1 subunit precursor, Gamma-aminobutyric-acid receptor gamma-3 subunit precursor, Gamma-aminobutyric-acid receptor pi subunit precursor, Gamma-aminobutyric-acid receptor rho-1 subunit precursor, Gamma-aminobutyric-acid receptor rho-2 subunit precursor, Gamma-aminobutyric-acid receptor theta subunit precursor, GluR6 kainate receptor, Glutamate receptor 1 precursor, Glutamate receptor 2 precursor, Glutamate receptor 3 precursor, Glutamate receptor 4 precursor, Glutamate receptor 7, Glutamate receptor B, Glutamate receptor delta-1 subunit precursor, Glutamate receptor, ionotropic kainate 1 precursor, Glutamate receptor, ionotropic kainate 2 precursor, Glutamate receptor, ionotropic kainate 3 precursor, Glutamate receptor, ionotropic kainate 4 precursor, Glutamate receptor, ionotropic kainate 5 precursor, Glutamate [NMDA] receptor subunit 3A precursor, Glutamate [NMDA] receptor subunit 3B precursor, Glutamate [NMDA] receptor subunit epsilon 1 precursor, Glutamate [NMDA] receptor subunit epsilon 2 precursor, Glutamate [NMDA] receptor subunit epsilon 4 precursor, Glutamate [NMDA] receptor subunit zeta 1 precursor, Glycine receptor alpha-1 chain precursor, Glycine receptor alpha-2 chain precursor, Glycine receptor alpha-3 chain precursor, Glycine receptor beta chain precursor, H/ACA ribonucleoprotein complex subunit 1, High affinity immunoglobulin epsilon receptor beta-subunit, Hypothetical protein DKFZp31310334, Hypothetical protein DKFZp761M1724, Hypothetical protein FLJ12242, Hypothetical protein FLJ14389, Hypothetical protein FLJ14798, Hypothetical protein FLJ14995, Hypothetical protein FLJ16180, Hypothetical protein FLJ16802, Hypothetical protein FLJ32069, Hypothetical protein FLJ37401, Hypothetical protein FLJ38750, Hypothetical protein FLJ40162, Hypothetical protein FLJ41415, Hypothetical protein FLJ90576, Hypothetical protein FLJ90590, Hypothetical protein FLJ90622, Hypothetical protein KCTD15, Hypothetical protein MGC15619, Inositol 1,4,5-trisphosphate receptor type 1, Inositol 1,4,5-trisphosphate receptor type 2, Inositol 1,4,5-trisphosphate receptor type 3, Intermediate conductance calcium-activated potassium channel protein 4, Inward rectifier potassium channel 13, Inward rectifier potassium channel 16, Inward rectifier potassium channel 4, Inward rectifying K(+) channel negative regulator Kir2.2v, Kainate receptor subunit KA2a, KCNH5 protein, KCTD 17 protein, KCTD2 protein, Keratinocytes associated transmembrane protein 1, Kv channel-interacting protein 4, Melastatin 1, Membrane protein MLC1, MGC 15619 protein, Mucolipin-1, Mucolipin-2, Mucolipin-3, Multidrug resistance-associated protein 4, N-methyl-D-aspartate receptor 2C subunit precursor, NADPH oxidase homolog 1, Nay 1.5, Neuronal acetylcholine receptor protein, alpha-10 subunit precursor, Neuronal acetylcholine receptor protein, alpha-2 subunit precursor, Neuronal acetylcholine receptor protein, alpha-3 subunit precursor, Neuronal acetylcholine receptor protein, alpha-4 subunit precursor, Neuronal acetylcholine receptor protein, alpha-5 subunit precursor, Neuronal acetylcholine receptor protein, alpha-6 subunit precursor, Neuronal acetylcholine receptor protein, alpha-7 subunit precursor, Neuronal acetylcholine receptor protein, alpha-9 subunit precursor, Neuronal acetylcholine receptor protein, beta-2 subunit precursor, Neuronal acetylcholine receptor protein, beta-3 subunit precursor, Neuronal acetylcholine receptor protein, beta-4 subunit precursor, Neuronal voltage-dependent calcium channel alpha 2D subunit, P2X purinoceptor 1, P2X purinoceptor 2, P2X purinoceptor 3, P2X purinoceptor 4, P2X purinoceptor 5, P2X purinoceptor 6, P2X purinoceptor 7, Pancreatic potassium channel TALK-Ib, Pancreatic potassium channel TALK-Ic, Pancreatic potassium channel TALK-Id, Phospholemman precursor, Plasmolipin, Polycystic kidney disease 2 related protein, Polycystic kidney disease 2-like 1 protein, Polycystic kidney disease 2-like 2 protein, Polycystic kidney disease and receptor for egg jelly related protein precursor, Polycystin-2, Potassium channel regulator, Potassium channel subfamily K member 1, Potassium channel subfamily K member 10, Potassium channel subfamily K member 12, Potassium channel subfamily K member 13, Potassium channel subfamily K member 15, Potassium channel subfamily K member 16, Potassium channel subfamily K member 17, Potassium channel subfamily K member 2, Potassium channel subfamily K member 3, Potassium channel subfamily K member 4, Potassium channel subfamily K member 5, Potassium channel subfamily K member 6, Potassium channel subfamily K member 7, Potassium channel subfamily K member 9, Potassium channel tetramerisation domain containing 3, Potassium channel tetramerisation domain containing protein 12, Potassium channel tetramerisation domain containing protein 14, Potassium channel tetramerisation domain containing protein 2, Potassium channel tetramerisation domain containing protein 4, Potassium channel tetramerisation domain containing protein 5, Potassium channel tetramerization domain containing 10, Potassium channel tetramerization domain containing protein 13, Potassium channel tetramerization domain-containing 1, Potassium voltage-gated channel subfamily A member 1, Potassium voltage-gated channel subfamily A member 2, Potassium voltage-gated channel subfamily A member 4, Potassium voltage-gated channel subfamily A member 5, Potassium voltage-gated channel subfamily A member 6, Potassium voltage-gated channel subfamily B member 1, Potassium voltage-gated channel subfamily B member 2, Potassium voltage-gated channel subfamily C member 1, Potassium voltage-gated channel subfamily C member 3, Potassium voltage-gated channel subfamily C member 4, Potassium voltage-gated channel subfamily D member 1, Potassium voltage-gated channel subfamily D member 2, Potassium voltage-gated channel subfamily D member 3, Potassium voltage-gated channel subfamily E member 1, Potassium voltage-gated channel subfamily E member 2, Potassium voltage-gated channel subfamily E member 3, Potassium voltage-gated channel subfamily E member 4, Potassium voltage-gated channel subfamily F member 1, Potassium voltage-gated channel subfamily G member 1, Potassium voltage-gated channel subfamily G member 2, Potassium voltage-gated channel subfamily G member 3, Potassium voltage-gated channel subfamily G member 4, Potassium voltage-gated channel subfamily H member 1, Potassium voltage-gated channel subfamily H member 2, Potassium voltage-gated channel subfamily H member 3, Potassium voltage-gated channel subfamily H member 4, Potassium voltage-gated channel subfamily H member 5, Potassium voltage-gated channel subfamily H member 6, Potassium voltage-gated channel subfamily H member 7, Potassium voltage-gated channel subfamily H member 8, Potassium voltage-gated channel subfamily KQT member 1, Potassium voltage-gated channel subfamily KQT member 2, Potassium voltage-gated channel subfamily KQT member 3, Potassium voltage-gated channel subfamily KQT member 4, Potassium voltage-gated channel subfamily KQT member 5, Potassium voltage-gated channel subfamily S member 1, Potassium voltage-gated channel subfamily S member 2, Potassium voltage-gated channel subfamily S member 3, Potassium voltage-gated channel subfamily V member 2, Potassium voltage-gated channel, subfamily H, member 7, isoform 2, Potassium/sodium hyperpolarization-activated cyclic nucleotide-gated channel 1, Potassium/sodium hyperpolarization-activated cyclic nucleotide-gated channel 2, Potassium/sodium hyperpolarization-activated cyclic nucleotide-gated channel 3, Potassium/sodium hyperpolarization-activated cyclic nucleotide-gated channel 4, Probable mitochondrial import receptor subunit TOM40 homolog, Purinergic receptor P2X5, isoform A, Putative 4 repeat voltage-gated ion channel, Putative chloride channel protein 7, Putative GluR6 kainate receptor, Putative ion channel protein CATSPER2 variant 1, Putative ion channel protein CATSPER2 variant 2, Putative ion channel protein CATSPER2 variant 3, Putative regulator of potassium channels protein variant 1, Putative tyrosine-protein phosphatase TPTE, Ryanodine receptor 1, Ryanodine receptor 2, Ryanodine receptor 3, SH3 KBP1 binding protein 1, Short transient receptor potential channel 1, Short transient receptor potential channel 4, Short transient receptor potential channel 5, Short transient receptor potential channel 6, Short transient receptor potential channel 7, Small conductance calcium-activated potassium channel protein 1, Small conductance calcium-activated potassium channel protein 2, isoform b, Small conductance calcium-activated potassium channel protein 3, isoform b, Small-conductance calcium-activated potassium channel SK2, Small-conductance calcium-activated potassium channel SK3, Sodium channel, Sodium channel beta-1 subunit precursor, Sodium channel protein type II alpha subunit, Sodium channel protein type III alpha subunit, Sodium channel protein type IV alpha subunit, Sodium channel protein type IX alpha subunit, Sodium channel protein type V alpha subunit, Sodium channel protein type VII alpha subunit, Sodium channel protein type VIII alpha subunit, Sodium channel protein type X alpha subunit, Sodium channel protein type XI alpha subunit, Sodium- and chloride-activated ATP-sensitive potassium channel, Sodium/potassium-transporting ATPase gamma chain, Sperm-associated cation channel 1, Sperm-associated cation channel 2, isoform 4, Syntaxin-1B1, Transient receptor potential cation channel subfamily A member 1, Transient receptor potential cation channel subfamily M member 2, Transient receptor potential cation channel subfamily M member 3, Transient receptor potential cation channel subfamily M member 6, Transient receptor potential cation channel subfamily M member 7, Transient receptor potential cation channel subfamily V member 1, Transient receptor potential cation channel subfamily V member 2, Transient receptor potential cation channel subfamily V member 3, Transient receptor potential cation channel subfamily V member 4, Transient receptor potential cation channel subfamily V member 5, Transient receptor potential cation channel subfamily V member 6, Transient receptor potential channel 4 epsilon splice variant, Transient receptor potential channel 4 zeta splice variant, Transient receptor potential channel 7 gamma splice variant, Tumor necrosis factor, alpha-induced protein 1, endothelial, Two-pore calcium channel protein 2, VDAC4 protein, Voltage gated potassium channel Kv3.2b, Voltage gated sodium channel beta1B subunit, Voltage-dependent anion channel, Voltage-dependent anion channel 2, Voltage-dependent anion-selective channel protein 1, Voltage-dependent anion-selective channel protein 2, Voltage-dependent anion-selective channel protein 3, Voltage-dependent calcium channel gamma-1 subunit, Voltage-dependent calcium channel gamma-2 subunit, Voltage-dependent calcium channel gamma-3 subunit, Voltage-dependent calcium channel gamma-4 subunit, Voltage-dependent calcium channel gamma-5 subunit, Voltage-dependent calcium channel gamma-6 subunit, Voltage-dependent calcium channel gamma-7 subunit, Voltage-dependent calcium channel gamma-8 subunit, Voltage-dependent L-type calcium channel alpha-1C subunit, Voltage-dependent L-type calcium channel alpha-1D subunit, Voltage-dependent L-type calcium channel alpha-IS subunit, Voltage-dependent L-type calcium channel beta-1 subunit, Voltage-dependent L-type calcium channel beta-2 subunit, Voltage-dependent L-type calcium channel beta-3 subunit, Voltage-dependent L-type calcium channel beta-4 subunit, Voltage-dependent N-type calcium channel alpha-1B subunit, Voltage-dependent P/Q-type calcium channel alpha-1A subunit, Voltage-dependent R-type calcium channel alpha-1E subunit, Voltage-dependent T-type calcium channel alpha-1G subunit, Voltage-dependent T-type calcium channel alpha-1H subunit, Voltage-dependent T-type calcium channel alpha-1I subunit, Voltage-gated L-type calcium channel alpha-1 subunit, Voltage-gated potassium channel beta-1 subunit, Voltage-gated potassium channel beta-2 subunit, Voltage-gated potassium channel beta-3 subunit, Voltage-gated potassium channel KCNA7. The Nav1.x family of human voltage-gated sodium channels is also a particularly promising target. This family includes, for example, channels Nav1.6 and Nav1.8.

In certain embodiments, the therapeutic protein may be a G-Protein Coupled Receptor (GPCR). Exemplary GPCRs include, but are not limited to, Class A Rhodopsin like receptors such as Muscatinic (Muse.) acetylcholine Vertebrate type 1, Muse, acetylcholine Vertebrate type 2, Muse, acetylcholine Vertebrate type 3, Muse, acetylcholine Vertebrate type 4; Adrenoceptors (Alpha Adrenoceptors type 1, Alpha Adrenoceptors type 2, Beta Adrenoceptors type 1, Beta Adrenoceptors type 2, Beta Adrenoceptors type 3, Dopamine Vertebrate type 1, Dopamine Vertebrate type 2, Dopamine Vertebrate type 3, Dopamine Vertebrate type 4, Histamine type 1, Histamine type 2, Histamine type 3, Histamine type 4, Serotonin type 1, Serotonin type 2, Serotonin type 3, Serotonin type 4, Serotonin type 5, Serotonin type 6, Serotonin type 7, Serotonin type 8, other Serotonin types, Trace amine, Angiotensin type 1, Angiotensin type 2, Bombesin, Bradykinin, C5a anaphylatoxin, Fmet-leu-phe, APJ like, Interleukin-8 type A, Interleukin-8 type B, Interleukin-8 type others, C-C Chemokine type 1 through type 11 and other types, C-X-C Chemokine (types 2 through 6 and others), C-X3-C Chemokine, Cholecystokinin CCK, CCK type A, CCK type B, CCK others, Endothelin, Melanocortin (Melanocyte stimulating hormone, Adrenocorticotropic hormone, Melanocortin hormone), Duffy antigen, Prolactin-releasing peptide (GPRIO), Neuropeptide Y (type 1 through 7), Neuropeptide Y, Neuropeptide Y other, Neurotensin, Opioid (type D, K, M, X), Somatostatin (type 1 through 5), Tachykinin (Substance P (NK1), Substance K (NK2), Neuromedin K (NK3), Tachykinin like 1, Tachykinin like 2, Vasopressin/vasotocin (type 1 through 2), Vasotocin, Oxytocin/mesotocin, Conopressin, Galanin like, Proteinase-activated like, Orexin & neuropeptides FF.QRFP, Chemokine receptor-like, Neuromedin U like (Neuromedin U, PRXamide), hormone protein (Follicle stimulating hormone, Lutropin-choriogonadotropic hormone, Thyrotropin, Gonadotropin type I, Gonadotropin type II), (Rhod)opsin, Rhodopsin Vertebrate (types 1-5), Rhodopsin Vertebrate type 5, Rhodopsin Arthropod, Rhodopsin Arthropod type 1, Rhodopsin Arthropod type 2, Rhodopsin Arthropod type 3, Rhodopsin Mollusc, Rhodopsin, Olfactory (Olfactory II fam 1 through 13), Prostaglandin (prostaglandin E2 subtype EP1, Prostaglandin E2/D2 subtype EP2, prostaglandin E2 subtype EP3, Prostaglandin E2 subtype EP4, Prostaglandin F2-alpha, Prostacyclin, Thromboxane, Adenosine type 1 through 3, Purinoceptors, Purinoceptor P2RY1-4,6,1 1 GPR91, Purinoceptor P2RY5,8,9,10 GPR35,92,174, Purinoceptor P2RY12-14 GPR87 (UDP-Glucose), Cannabinoid, Platelet activating factor, Gonadotropin-releasing hormone, Gonadotropin-releasing hormone type I, Gonadotropin-releasing hormone type II, Adipokinetic hormone like, Corazonin, Thyrotropin-releasing hormone & Secretagogue, Thyrotropin-releasing hormone, Growth hormone secretagogue, Growth hormone secretagogue like, Ecdysis-triggering hormone (ETHR), Melatonin, Lysosphingolipid & LPA (EDG), Sphingosine 1-phosphate Edg-1, Lysophosphatidic acid Edg-2, Sphingosine 1-phosphate Edg-3, Lysophosphatidic acid Edg-4, Sphingosine 1-phosphate Edg-5, Sphingosine 1-phosphate Edg-6, Lysophosphatidic acid Edg-7, Sphingosine 1-phosphate Edg-8, Edg Other Leukotriene B4 receptor, Leukotriene B4 receptor BLT1, Leukotriene B4 receptor BLT2, Class A Orphan/other, Putative neurotransmitters, SREB, Mas proto-oncogene & Mas-related (MRGs), GPR45 like, Cysteinyl leukotriene, G-protein coupled bile acid receptor, Free fatty acid receptor (GP40, GP41, GP43), Class B Secretin like, Calcitonin, Corticotropin releasing factor, Gastric inhibitory peptide, Glucagon, Growth hormone-releasing hormone, Parathyroid hormone, PACAP, Secretin, Vasoactive intestinal polypeptide, Latrophilin, Latrophilin type 1, Latrophilin type 2, Latrophilin type 3, ETL receptors, Brain-specific angiogenesis inhibitor (BAI), Methuselah-like proteins (MTH), Cadherin EGF LAG (CELSR), Very large G-protein coupled receptor, Class C Metabotropic glutamate/pheromone, Metabotropic glutamate group I through III, Calcium-sensing like, Extracellular calcium-sensing, Pheromone, calcium-sensing like other, Putative pheromone receptors, GABA-B, GABA-B subtype 1, GABA-B subtype 2, GABA-B like, Orphan GPRC5, Orphan GPCR6, Bride of sevenless proteins (BOSS), Taste receptors (T1R), Class D Fungal pheromone, Fungal pheromone A-Factor like (STE2.STE3), Fungal pheromone B like (BAR,BBR,RCB, PRA), Class E cAMP receptors, Ocular albinism proteins, Frizzled/Smoothened family, frizzled Group A (Fz 1&2&4&5&7-9), frizzled Group B (Fz 3 & 6), frizzled Group C (other), Vomeronasal receptors, Nematode chemoreceptors, Insect odorant receptors, and Class Z Archaeal/bacterial/fiingal opsins.

In certain embodiments, the serum albumin binding Fn3 fusions described herein may comprise any of the following active polypeptides: BOTOX, Myobloc, Neurobloc, Dysport (or other serotypes of botulinum neurotoxins), alglucosidase alfa, daptomycin, YH-16, choriogonadotropin alfa, filgrastim, cetrorelix, interleukin-2, aldesleukin, teceleukin, denileukin diftitox, interferon alfa-n3 (injection), interferon alfa-nl, DL-8234, interferon, Suntory (gamma-Ia), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alfa, collagenase, carperitide, recombinant human epidermal growth factor (topical gel, wound healing), DWP-401, darbepoetin alfa, epoetin omega, epoetin beta, epoetin alfa, desirudin, lepirudin, bivalirudin, nonacog alpha, Mononine, eptacog alfa (activated), recombinant Factor VIII+VWF, Recombinate, recombinant Factor VIII, Factor VIII (recombinant), Alphanate, octocog alfa, Factor VIII, palifermin, Indikinase, tenecteplase, alteplase, pamiteplase, reteplase, nateplase.monteplase, follitropin alfa, rFSH, hpFSH, micafungin, pegfilgrastim, lenograstim, nartograstim, sermorelin, glucagon, exenatide, pramlintide, imiglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, somatropin, Eutropin, KP-102 program, somatropin, somatropin, mecasermin (growth failure), enfuvirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasermin, Roferon-A, interferon-alpha 2, Alfaferone, interferon alfacon-1, interferon alpha, Avonex recombinant human luteinizing hormone, dornase alfa, trafermin, ziconotide, taltirelin, diboterminalfa, atosiban, becaplermin, eptifibatide, Zemaira, CTC-lll, Shanvac-B, HPV vaccine (quadrivalent), NOV-002, octreotide, lanreotide, ancestim, agalsidase beta, agalsidase alfa, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-2 IS, vapreotide, idursulfase, omapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-I, interferon (alpha), lucinactant, aviptadil (inhaled, pulmonary disease)), icatibant, ecallantide, omiganan, Aurograb, pexiganan acetate, ADI-PEG-20, LDI-200, degarelix, cintredekin besudotox, FavId, MDX-1379, ISAtx-247, liraglutide, teriparatide (osteoporosis), tifacogin, AA-4500, T4N5 liposome lotion, catumaxomab, DWP-413, ART-123, Chrysalin, desmoteplase, amediplase, corifollitropin alpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alfa-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-5 10, Bowman Birk Inhibitor Concentrate, XMP-629, 99 mTc-Hynic-Annexin V, kahalalide F, CTCE-9908, teverelix (extended release), ozarelix, romidepsin, BAY-50-4798, interleukin-4, PRX-321, Pepscan, iboctadekin, rh lactoferrin, TRU-015, IL-21, ATN-161, cilengitide, Albuferon, Biphasix, IRX-2, omega interferon, PCK-3145, CAP-232, pasireotide, huN901-DM1, ovarian cancer immunotherapeutic vaccine, SB-249553, Oncovax-CL, OncoVax-P, BLP-25, CerVax-16, multi-epitope peptide melanoma vaccine (MART-I, gp 100, tyrosinase), nemifitide, rAAT (inhaled), rAAT (dermatological), CGRP (inhaled, asthma), pegsunercept, thymosin beta-4, plitidepsin, GTP-200, ramoplanin, GRASPA, OBI-I, AC-100, salmon calcitonin (oral, eligen), calcitonin (oral, osteoporosis), examorelin, capromorelin, Cardeva, velafermin, 131I-TM-601, KK-220, TP-10, ularitide, depelestat, hematide, Chrysalin (topical), rNAPc2, recombinant Factor VIII (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, AOD-9604, linaclotide acetate, CETi-I, Hemospan, VAL (injectable), fast-acting insulin (injectable, Viadel), intranasal insulin, insulin (inhaled), insulin (oral, eligen), recombinant methionyl human leptin, pitrakinra subcutaneous injection, eczema), pitrakinra (inhaled dry powder, asthma), Multikine, RG-1068, MM-093, NBI-6024, AT-001, PI-0824, Org-39141, Cpn 10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alfa-n3 (topical), IRX-3, RDP-58, Tauferon, bile salt stimulated lipase, Merispase, alkaline phosphatase, EP-2104R, Melanotan-II, bremelanotide, ATL-104, recombinant human microplasmin, AX-200, SEMAX, ACV-I, Xen-2174, CJC-1008, dynorphin A, SI-6603, LAB GHRH, AER-002, BGC-728, malaria vaccine (virosomes, PeviPRO), ALTU-135, parvovirus B 19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85 A vaccine (tuberculosis), FAR-404, BA-210, recombinant plague F1V vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, P1A, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT388IL-3, TST-10088, PRO-1762, Combotox, cholecystokinin-B/gastrin-receptor binding peptides, 1 1 1ln-hEGF, AE-37, trastuzumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/I540/KLH vaccine (cancer), VX-001, AVE-9633, AC-9301, NY-ESO-I vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A2 (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1001 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV-4710, ALG-889, Org-41259, rhCCIO, F-991, thymopentin (pulmonary diseases), r(m)CRP, hepatoselective insulin, subalin, L 19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S. pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumine, BIM-23190, tuberculosis vaccine, multi-epitope tyrosinase peptide, cancer vaccine, enkastim, APC-8024, G1-5005, ACC-OO1, TTS-CD3, vascular-targeted TNF (solid tumors), desmopressin (buccal controlled-release), onercept, TP-9201.

Additional Modifications

In certain embodiments, the serum albumin binders and their fusions may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified serum albumin binders and their fusions s may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogenicity of the protein. See, e.g., Raju et al. Biochemistry. 2001 Jul. 31; 40(30):8868-76. Effects of such non-amino acid elements on the functionality of the serum albumin binders or their fusions may be tested for their ability to bind a particular serum albumin (e.g., HSA or RhSA) and/or the functional role conferred by a specific non-$^{10}$Fn3 moiety in the context of a fusion.

F. Nucleic Acid-Protein Fusion Technology

In one aspect, the application provides fibronectin based scaffold proteins comprising a fibronectin type III domain that binds to HSA. One way to rapidly make and test Fn3 domains with specific binding properties is the nucleic acid-protein fusion technology of Adnexus, a Bristol-Myers Squibb Company. Such in vitro expression and tagging technology, termed PROfusion, that exploits nucleic acid-protein fusions (RNA- and DNA-protein fusions) may be used to identify novel polypeptides and amino acid motifs that are important for binding to proteins. Nucleic acid-protein fusion technology is a technology that covalently couples a protein to its encoding genetic information. For a detailed description of the RNA-protein fusion technology and fibronectin-based scaffold protein library screening methods see Szostak et al., U.S. Pat. Nos. 6,258,558; 6,261,804; 6,214,553; 6,281,344; 6,207,446; 6,518,018; PCT Publication Nos. WO0/34784; WO01/64942; WO02/032925; and Roberts and Szostak, Proc Natl. Acad. Sci. 94: 12297-12302, 1997, herein incorporated by reference.

G. Vectors & Polynucleotides Embodiments

Also included in the present disclosure are nucleic acid sequences encoding any of the proteins described herein. As appreciated by those skilled in the art, because of third base degeneracy, almost every amino acid can be represented by more than one triplet codon in a coding nucleotide sequence. In addition, minor base pair changes may result in a conservative substitution in the amino acid sequence encoded but are not expected to substantially alter the biological activity of the gene product. Therefore, a nucleic acid sequence encoding a protein described herein may be modified slightly in sequence and yet still encode its respective gene product. Certain exemplary nucleic acids encoding the serum albumin binders and their fusions described herein include nucleic acids having the sequences set forth in SEQ ID NOs: 126-151. Also encompassed by the invention are nucleic acid sequences that are at least 50%, such as at least 55%, at least 60%, at least 65%, at least 70%, at least 75%, at least 80%, at least 85%, at least 90%, at least 95%, at least 96%, at least 97%, at least 98%, or at least 99% identical to SEQ ID NOs: 126-151, and preferably encode a protein that binds to serum albumin, and for nucleic acids encoding a tandem PCSK9-PKE2 Adnectin, that they preferably bind to serum albumin and PCSK9. In some embodiments, nucleotide substitutions are introduced so as not to alter the resulting translated amino acid sequence.

Nucleic acids encoding any of the various proteins or polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc Natl Acad Sci USA. 2003 100(2):438-42; Sinclair et al. Protein Expr Purif. 2002 (1):96-105; Connell N D. Curr Opin Biotechnol. 2001 (5):446-9; Makrides et al. Microbiol. Rev. 1996 60(3):512-38; and Sharp et al. Yeast. 1991 7(7):657-78.

General techniques for nucleic acid manipulation are within the purview of one skilled in the art and are also described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding a protein is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated. Suitable regulatory elements are well-known in the art.

The proteins and fusion proteins described herein may be produced as a fusion protein with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, 1 pp, or heat-stable enterotoxin II leaders. For yeast secretion, the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in PCT Publication No. WO 90/13646. In mammalian cell expression, mammalian signal sequences as well as viral secretory leaders, for example, the herpes simplex gD signal, are available. The DNA for such precursor regions may be ligated in reading frame to DNA encoding the protein.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the multivalent antibody. One useful transcription termination component is the bovine growth hormone polyadenylation region. See PCT Publication No. WO 94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York, 1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). In some instance it will be desired to produce proteins in vertebrate cells, such as for glycosylation, and the propagation of vertebrate cells in culture (tissue culture) has become a routine procedure. Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. For many applications, the small size of the protein multimers described herein would make *E. coli* the preferred method for expression.

H. Protein Production

Host cells are transformed with the herein-described expression or cloning vectors for protein production and cultured in conventional nutrient media modified as appropriate for inducing promoters, selecting transformants, or amplifying the genes encoding the desired sequences. The host cells used to produce the fibronectin based scaffold proteins or fusions thereof may be cultured in a variety of media. Commercially available media such as Ham's F10 (Sigma), Minimal Essential Medium ((MEM), (Sigma)), RPMI-1640 (Sigma), and Dulbecco's Modified Eagle's Medium ((DMEM), (Sigma)) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO90/03430; WO87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Fibronectin based scaffold proteins disclosed herein or fusions thereof can also be produced using cell-free translation systems. For such purposes the nucleic acids encoding the fibronectin based scaffold protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

Fibronectin based scaffold proteins or fusions thereof can also be produced by chemical synthesis (e.g., by the methods described in Solid Phase Peptide Synthesis, 2nd ed., 1984, The Pierce Chemical Co., Rockford, Ill.). Modifications to the fibronectin based scaffold protein can also be produced by chemical synthesis.

The fibronectin based scaffold proteins disclosed herein or fusions thereof can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, fibronectin based scaffold proteins may be exchanged into different buffers and/or concentrated by any of a variety of methods known to the art, including, but not limited to, filtration and dialysis.

The purified fibronectin based scaffold protein or fusions thereof is preferably at least 85% pure, more preferably at least 95% pure, and most preferably at least 98% pure. Regardless of the exact numerical value of the purity, the fibronectin based scaffold protein is sufficiently pure for use as a pharmaceutical product.

I. Imaging, Diagnostic, and Other Applications

The serum albumin binding $^{10}$Fn3 fusions provided herein may be used to treat a variety of diseases and disorders, based on the identity of the heterogenous molecule fused to the serum albumin binding $^{10}$Fn3 domain. The applications for the serum albumin binding $^{10}$Fn3 fusions may be determined by the skilled artisan based on the knowledge in the art and the information provided herein. Uses for various serum albumin binding $^{10}$Fn3 fusion proteins are described in detail herein. Serum albumin binding $^{10}$Fn3fusions may be administered to any mammalian subject or patient, including both human and non-human organisms.

The serum albumin binders and fusion molecules described herein can be detectably labeled and used to contact cells expressing, e.g., a protein bound by the fusion molecule for imaging or diagnostic applications. Any method known in the art for conjugating a protein to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982).

In certain embodiments, the serum albumin binders and fusion molecules described herein are further attached to a label that is able to be detected (e.g., the label can be a radioisotope, fluorescent compound, enzyme or enzyme co-factor). The label may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, 68Ga, $^{123}$I, $^{125}$I $^{131}$I, $^{132}$I, or $^{9}$Tc. In certain embodiments, the label can be a fluorescent or chemiluminescent compound, such as fluorescein isothiocyanate, rhodamine, or luciferin; or an enzyme, such as alkaline phosphatase, beta-galactosidase or horseradish peroxidase. A serum albumin binder or fusion molecule affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety.

Serum albumin binders and fusion molecules also are useful as affinity purification agents. In this process, the proteins are immobilized on a suitable support, such a Sephadex resin or filter paper, using methods well known in the art. The proteins can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)).

J. Biophysical and Biochemical Characterization

Binding of a serum albumin binding Adnectin described herein to serum albumin (e.g., HSA) may be assessed in terms of equilibrium constants (e.g., dissociation, $K_D$) and in terms of kinetic constants (e.g., on-rate constant, $k_{on}$ and off-rate constant, $k_{off}$). A serum albumin binding Adnectin (e.g., a PKE2-mono- or tandem-Adenctin) will generally bind to a target molecule with a $K_D$ of less than 500 nM, 100 nM, 10 nM, 1 nM, 500 μM, 200 μM, or 100 μM, although higher $K_D$ values may be tolerated where the $k_{off}$ is sufficiently low or the $k_{on}$, is sufficiently high.

In Vitro Assays for Binding Affinity

A PKE2-Adnectin that binds to serum albumin (e.g., HSA) can be identified using various in vitro assays. In certain embodiments, the assays are high-throughput assays that allow for screening multiple candidate Adnectins simultaneously.

Exemplary assays for determining the binding affinity of an Adnectin to its target includes, but is not limited to, solution phase methods such as the kinetic exclusion assay (KinExA) (Blake et al., *JBC* 1996; 271:27677-85; Drake et al., *Anal Biochem* 2004; 328:35-43), surface plasmon resonance (SPR) with the Biacore system (Uppsala, Sweden) (Welford et al. *Opt. Quant. Elect* 1991; 23:1; Morton and Myszka, *Methods in Enzymology* 1998; 295:268) and homogeneous time resolved fluorescence (HTRF) assays (Newton et al., *J Biomol Screen* 2008; 13:674-82; Patel et al., *Assay Drug Dev Technol* 2008; 6:55-68).

In certain embodiments, biomolecular interactions can be monitored in real time with the Biacore system, which uses SPR to detect changes in the resonance angle of light at the surface of a thin gold film on a glass support due to changes in the refractive index of the surface up to 300 nm away. Biacore analysis (e.g., as described in Example 2) generates association rate constants, dissociation rate constants, equilibrium dissociation constants, and affinity constants. Binding affinity is obtained by assessing the association and dissociation rate constants using a Biacore surface plasmon resonance system (Biacore, Inc.). A biosensor chip is activated for covalent coupling of the target. The target is then diluted and injected over the chip to obtain a signal in response units of immobilized material. Since the signal in resonance units (RU) is proportional to the mass of immobilized material, this represents a range of immobilized target densities on the matrix. Association and dissociation data are fit simultaneously in a global analysis to solve the net rate expression for a 1:1 bimolecular interaction, yielding best fit values for $k_{on}$, $k_{off}$ and $R_{max}$ (maximal response at saturation). Equilibrium dissociation constants for binding, $K_D$'s are calculated from SPR measurements as $k_{off}/k_{on}$.

It should be understood that the assays described herein above are exemplary, and that any method known in the art for determining the binding affinity between proteins (e.g., fluorescence based-transfer (FRET), enzyme-linked immunosorbent assay, and competitive binding assays (e.g., radioimmunoassays)) can be used to assess the binding affinities of the PKE2-Adnectins described herein.

In certain embodiments, the melting temperature ($T_m$) of serum albumin binding Adnectin described herein, of fusion proteins comprising such, is at least 50° C., such as at least 51° C., at least 52° C. at least 53° C. at least 54° C., at least 55° C., at least 56° C., at least 57° C., at least 58° C., at least 59° C., at least 60° C., at least 61° C., at least 62° C., at least 63° C., at least 64° C., at least 65° C., at least 66° C., at least 67° C. at least 68° C., at least 69° C., at least 70° C., at least 71° C. at least 72° C., at least 73° C., at least 74° C., or at least 75° C., when measured using differential scanning calorimetry (DSC) or thermal scanning fluorescence (TSF), e.g., as described in the Examples. In certain embodiments, the melting temperature ($T_m$) of serum albumin binding Adnectin described herein, or fusion proteins comprising such, is 50-75° C., such as 51-75° C., 52-75° C., 53-75° C., 54-75° C., 55-75° C., 56-75° C., 57-75° C. 58-75° C., 59-75° C., 60-75° C., 61-75° C., 62-75° C., 63-75° C., 64-75° C., 65-75° C., 66-75° C., 67-75° C., 68-75° C., 69-75° C., 70-75° C., 50-74° C., 50-73° C., 50-72° C. 50-71° C., 50-70° C., 50-69° C. 50-68° C., 50-67° C., 50-66° C., 50-65° C., 50-64° C. 50-63° C., 50-62° C., 50-61° C., 50-60° C., 50-59° C., 50-58° C., 50-57° C., 50-56° C., 50-55° C., 51-74° C., 52-73° C., 53-71° C., 54-70° C., or 55-65° C. when measured using differential scanning calorimetry (DSC) or thermal scanning fluorescence (TSF), e.g., as described in the Examples.

K. Therapeutic In Vivo Uses

Provided herein are fibronectin based scaffold proteins that are useful in the treatment of disorders. In the case of fusion proteins comprising a serum albumin binding Adnectin, the diseases or disorders that may be treated will be dictated by the binding specificity of the moiety, e.g., a second Adnectin, that is linked to the Adnectin. As described herein, fibronectin based scaffold proteins may be designed to bind to any target of interest. In one embodiment, the target is PCSK9. Fibronectin based scaffold proteins that bind to PSCK9 and the fusion proteins comprising such can be used to treat atherosclerosis, hypercholesterolemia and other cholesterol related diseases.

The application also provides methods for administering fibronectin based scaffold proteins to a subject. In some embodiments, the subject is a human. In some embodiments, the fibronectin based scaffold proteins are pharmaceutically acceptable to a mammal, in particular a human. A "pharmaceutically acceptable" composition refers to a composition that is administered to an animal without significant adverse medical consequences. Examples of pharmaceutically acceptable compositions include compositions comprising $^{10}$Fn3 domains that lack the integrin-binding domain (RGD) and compositions that are essentially endotoxin or pyrogen free or have very low endotoxin or pyrogen levels.

L. Formulations and Administration

The present application provides methods for administering a therapeutic moiety fused to a serum albumin binding $^{10}$Fn3 domain, wherein the half-life of the therapeutic moiety is extended when fused to the serum albumin binding $^{10}$Fn3 domain. Techniques and dosages for administration of the fusion constructs will vary depending on the type of therapeutic moiety fused to the serum albumin binding $^{10}$Fn3 domain and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA). In certain embodiments, pharmaceutical formulations of serum albumin binding $^{10}$Fn3 domains and their fusion molecules comprise, e.g., 1-20 mM succinic acid, 2-10% sorbitol, and 1-10% glycine at pH 4.0-7.0. In an exemplary embodiment, pharmaceutical formulations of serum albumin binding $^{10}$Fn3 domains and their fusion molecules comprise, e.g., 10 mM succinic acid, 8% sorbitol, and 5% glycine at pH 6.0.

In some embodiments, the serum albumin binding $^{10}$Fn3 domains and fusions thereof are pharmaceutically acceptable to a mammal, in particular a human. A "pharmaceutically acceptable" polypeptide refers to a polypeptide that is administered to an animal without significant adverse medical consequences. Examples of pharmaceutically acceptable serum albumin binding $^{10}$Fn3 domain and fusions thereof include $^{10}$Fn3 domains that lack the integrin-binding domain (RGD) and compositions of serum albumin binding $^{10}$Fn3 domains or serum albumin binding $^{10}$Fn3 domain fusions that are essentially endotoxin free or have very low endotoxin levels.

Therapeutic compositions may be administered with a pharmaceutically acceptable diluent, carrier, or excipient, in unit dosage form. Administration may be parenteral (e.g., intravenous, subcutaneous), oral, or topical, as non-limiting examples. The composition can be in the form of a pill, tablet, capsule, liquid, or sustained release tablet for oral administration; a liquid for intravenous, subcutaneous or parenteral administration; or a gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the serum albumin binding $^{10}$Fn3 domains or serum albumin binding $^{10}$Fn3 domain fusion is administered at about 0.01 μg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or less frequently (e.g., once every other day, once or twice weekly, once every two weeks, or monthly). In addition, as is known in the art, adjustments for age as well as the body weight, general health, sex, diet, time of administration, drug interaction, and the severity of the disease may be necessary, and will be ascertainable with routine experimentation by those skilled in the art.

The contents of all figures and all references, Genbank sequences, patents and published patent applications cited throughout this application are expressly incorporated herein by reference. In particular, the disclosure of U.S. Provisional Patent Application No. 61/968,181 (filed on Mar. 20, 2014) is expressly incorporated herein by reference.

The above disclosure generally describes the present disclosure, which is further exemplified by the following examples. These specific examples are described solely for purposes of illustration, and are not intended to limit the scope of this disclosure. Although specific targets, terms, and values have been employed herein, such targets, terms, and values will likewise be understood as exemplary and non-limiting to the scope of this disclosure.

EXAMPLES

High Throughput Protein Production (HTPP)

Selected binders cloned into the PET9d vector upstream of a $HIS_6$tag and transformed into *E. coli* BL21 DE3 plysS cells were inoculated in 5 ml LB medium containing 50 g±g/mL kanamycin in a 24-well format and grown at 37° C. overnight. Fresh 5 ml LB medium (50 μg/mL kanamycin) cultures were prepared for inducible expression by aspiration of 200 μl from the overnight culture and dispensing it into the appropriate well. The cultures were grown at 37° C. until $A_{600}$ 0.6-0.9. After induction with 1 mM isopropyl-β-thiogalactoside (IPTG), the culture was expressed for 6 hours at 30° C. and harvested by centrifugation for 10 minutes at 2750 g at 4° C.

Cell pellets (in 24-well format) were lysed by resuspension in 450 μl of Lysis buffer (50 mM $NaH_2PO_4$, 0.5 M NaCl, 1× Complete m Protease Inhibitor Cocktail-EDTA free (Roche), 1 mM PMSF, 10 mM CHAPS, 40 mM imidazole, 1 mg/ml lysozyme, 30 g±g/ml DNAse, 2 μg/ml aprotonin, pH 8.0) and shaken at room temperature for 1-3 hours. Lysates were cleared and re-racked into a 96-well format by transfer into a 96-well Whatman GF/D Unifilter fitted with a 96-well, 1.2 ml catch plate and filtered by positive pressure. The cleared lysates were transferred to a 96-well Nickel or Cobalt-Chelating Plate that had been equilibrated with equilibration buffer (50 mM $NaH_2PO_4$, 0.5 M NaCl, 40 mM imidazole, pH 8.0) and were incubated for 5 min. Unbound material was removed by positive pressure. The resin was washed twice with 0.3 ml/well with Wash buffer #1 (50 mM $NaH_2PO_4$, 0.5 M NaCl, 5 mM CHAPS, 40 mM imidazole, pH 8.0). Each wash was removed by positive pressure. Prior to elution, each well was washed with 50 μl Elution buffer (PBS+20 mM EDTA), incubated for 5 min, and this wash was discarded by positive pressure. Protein was eluted by applying an additional 100 μl of Elution buffer to each well. After a 30 minute incubation at room temperature, the plate(s) were centrifuged for 5 minutes at 200 g and eluted protein collected in 96-well catch plates containing 5 μl of 0.5 M $MgCl_2$ added to the bottom of elution catch plate prior to elution. Eluted protein was quantified using a total protein assay with wild-type $^{10}$Fn3 domain as the protein standard.

Midscale Expression and Purification of Insoluble Fibronectin-Based Scaffold Protein Binders For expression of insoluble clones, the clone(s), followed by the $HIS_6$tag, are cloned into a pET9d (EMD Bioscience, San Diego, Calif.) vector and are expressed in *E. coli* HMS174 cells. Twenty ml of an inoculum culture (generated from a single plated colony) is used to inoculate 1 liter of LB medium containing 50 μg/ml carbenicillin and 34 μg/ml chloramphenicol. The culture is grown at 37° C. until $A_{600}$ 0.6-1.0. After induction with 1 mM isopropyl-β-thiogalactoside (IPTG) the culture is grown for 4 hours at 30° C. and is harvested by centrifugation for 30 minutes at >10,000 g at 4° C. Cell pellets are frozen at −80° C. The cell pellet is resuspended in 25 ml of lysis buffer (20 mM $aH2PO_4$, 0.5 M NaCl, lx Complete Protease Inhibitor Cocktail-EDTA free (Roche), ImM PMSF, pH 7.4) using an ULTRA-TURRAX® homogenizer (IKA works) on ice. Cell lysis is achieved by high pressure homongenization (>18,000 psi) using a Model M-1 10S MICROFLUIDIZER® (Microfluidics). The insoluble fraction is separated by centrifugation for 30 minutes at 23,300 g at 4° C. The insoluble pellet recovered from centrifugation of the lysate is washed with 20 mM sodiumphosphate/500 mM NaCl, pH7.4. The pellet is resolubilized in 6.0M guanidine hydrochloride in 20 mM sodium phosphate/500M NaCl pH 7.4 with sonication followed by incubation at 37 degrees for 1-2 hours. The resolubilized pellet is filtered to 0.45 μm and loaded onto a Histrap column equilibrated with the 20 mM sodium phosphate/500 M NaCl/6.0 M guanidine pH 7.4 buffer. After loading, the column is washed for an additional 25 CV with the same buffer. Bound protein is eluted with 50 mM Imidazole in 20 mM sodium phosphate/500 mM NaCl/6.0 M guan-HCl pH7.4. The purified protein is refolded by dialysis against 50 mM sodium acetate/150 mM NaCl pH 4.5.

Midscale Expression and Purification of Soluble Fibronectin-Base Scaffold Protein Binders For expression of soluble clones, the clone(s), followed by the $HIS_6$tag, were cloned into a pET9d (EMD Bioscience, San Diego, Calif.) vector and were expressed in *E. coli* HMS174 cells. Twenty ml of an inoculum culture (generated from a single plated colony) was used to inoculate 1 liter of LB medium containing 50 μg/ml carbenicillin and 34 μg/ml chloramphenicol. The culture was grown at 37° C. until $A_{600}$ 0.6-1.0. After induction with 1 mM isopropyl-3-thiogalactoside (IPTG), the culture was grown for 4 hours at 30° C. and was harvested by centrifugation for 30 minutes at >10,000 g at 4° C. Cell pellets were frozen at −80° C. The cell pellet was resuspended in 25 ml of lysis buffer (20 mM $NaH_2P0_4$, 0.5 M NaCl, lx Complete Protease Inhibitor Cocktail-EDTA free (Roche), ImM PMSF, pH 7.4) using an ULTRA-TURRAX® homogenizer (IKA works) on ice. Cell lysis was achieved by high pressure homongenization (>18,000 psi) using a Model M-1 10S MICROFLUIDIZER® (Microfluidics). The soluble fraction was separated by centrifugation for 30 minutes at 23,300 g at 4° C. The supernatant was clarified via 0.45 μm filter. The clarified lysate was loaded onto a Histrap column (GE) pre-equilibrated with the 20 mM sodium phosphate/500M NaCl pH 7.4. The column was then washed with 25 column volumes of the same buffer, followed by 20 column volumes of 20 mM sodium phosphate/500 M NaCl/25 mM Imidazole, pH 7.4 and then 35 column volumes of 20 mM sodium phosphate/500 M NaCl/40 mM Imidazole, pH 7.4. Protein was eluted with 15 column volumes of 20 mM sodium phosphate/500 M NaCl/500 mM Imidazole, pH 7.4, fractions were pooled based on absorbance at $A_{280}$ and were dialyzed against 1×PBS, 50 mM Tris, 150 mM NaCl; pH 8.5 or 50 mM NaOAc; 150 mM NaCl; pH4.5. Any precipitate was removed by filtering at 0.22 μm.

Example 1: Screening for Serum Albumin Binding Parent South Loop (CD Loop)-Based Binders In order to improve upon first generation north pole-based serum albumin binding Adnectins (SABAs) which did not bind to mouse and rat serum albumin, did not have high affinity for serum albumins across species, and were not always compatible in a multivalent $^{10}$Fn3-based platform, second generation south pole-based serum albumin binding Adnectins (PKE2 Adnectins) with modified CD loop sequences were screened using mRNA display as described below.

Libraries of CD loop-based binder polypeptides comprising a modified $^{10}$Fn3 domain were screened using mRNA display (Xu et al., *Chem Biol* 2002; 9:933-42) for the ability to bind to human serum albumin (HSA). The CD loop binders were designed with varying CD loop lengths up to +7 amino acids and the rest of the $^{10}$Fn3 sequence remained wildtype. Target binding was monitored by qPCR and populations were cloned and expressed in *E. Coli* when a specific binding signal was observed.

Example 2: Identification of CD Loop Binders Capable of Binding HSA and that Cross-React with Rh-SA and MSA A direct binding ELISA format was used to identify CD loop binders that were generated in Example 1 and that bound HSA and cross-reacted with rhesus serum albumin (Rh-SA) and/or with murine serum albumin (MSA). MaxiSorp™ ELISA plates were coated with 10 μg/mL of either HSA, Rh-SA, or MSA and purified CD loop binders were tested at 1 μM. Bound Adnectins were detected via an HRP-conjugated anti-histidine mAb (R&D Systems) and the TMB detection reagents (BD Biosciences). The ELISA results were confirmed using Biacore as described below. CD loop binders identified in the ELISA experiment as cross-reacting with Rh-SA and/or MSA (>2× background) were then analyzed by SEC for aggregation in order to demonstrate that binding was due to a monomeric species, as expected of a stable, well-folded protein. The stability of the protein was confirmed by differential scanning calorimetry (DSC) as described below.

One of the identified clones, herein referred to as 2270_C01, had the following amino acid sequence:

```
(2270_C01; SEQ ID NO: 23)
MASTSGVPRDLEVVAATPTSLLISWDAPAVTVRYYRITYGWQVQMYS

DWGPLYIYKEFTVPGSKSTATISGLKPGVDYTITVYAVTGSGESPAS

SKPISINYRTEGDKPSQHHHHHH
```

The CD loop is underlined. The AB, BC, DE, EF, and FG loops have sequences identical to the wild-type human $^{10}$Fn3 domain (SEQ ID NO: 1). Size exclusion chromatography and DSC analyses were performed on midscaled 2270_C01 to confirm monomericity and determine thermal stability.

Standard size exclusion chromatography (SEC) was performed on 2270_C01 resulting from the midscale process. SEC of midscaled material was performed using a Superdex 200 10/30 or on a Superdex 75 10/30 column (GE Healthcare) on an Agilent 1100 or 1200 HPLC system with UV detection at A214 nm and A280 nm and with fluorescence detection (excitation=280 nm, emission=350 nm). A buffer of 100 mM sodium sulfate, 100 mM sodium phosphate, 150 mM sodium chloride, pH 6.8 at an appropriate flow rate of the SEC column was employed. Gel filtration standards (Bio-Rad Laboratories, Hercules, Calif.) were used for molecular weight calibration. As shown in Table 2, 2270_C01 was primarily monomeric (98% monomer).

Differential Scanning Calorimetry (DSC) analyses of the midscaled Adnectins were performed to determine their respective $T_m$'s. A 0.5 mg/ml solution was scanned in a VP-Capillary Differential Scanning calorimeter (GE Microcal) by ramping the temperature from 15° C. to 110° C. at a rate of 1 degree per minute under 70 p.s.i pressure. The data was analyzed vs. a control run of the appropriate buffer using a best fit using Origin Software (OriginLab Corp). As shown in Table 2, 2270_C01 had a Tm of 64° C.

To determine the kinetics of binding to human, rhesus, and mouse serum albumin, as well as whether binding was retained at both physiological and endosomal pHs, the respective serum albumins were immobilized on a Biacore CM5 chip to a surface density of ~1200RU using standard NHS/EDC coupling. A concentration range (0.25 nM-5 uM) of 2270_C01 was applied in HBS-P+(0.01M HEPES pH 7.4, 0.15M NaCl, 0.05% v/v surfactant P-20) or Acetate (0.02 mM sodium acetate pH 5.5, 0.15M NaCl, 0.05% v/v surfactant P-20) running buffers to the immobilized albumins. Kinetic measurements were carried out using a 3 min association and 6-10 min dissociation phase. Kinetic traces of reference-subtracted sensorgrams were fit to a 1:1 binding model using the Biaevaluation software. As shown in Table 1, 2270_C01 bound with equivalent affinity at neutral and low pH to each species of albumin, however the affinity for mouse albumin was approximately 10-fold weaker than that of binding to human or rhesus albumin.

TABLE 1

2270_C01 binds to MuSA with slightly faster on-rates and significantly faster off-rates, compared to HuSA and RhSA at both pH 7.4 and 5.5

| Buffer | Binding to | ka (1/Ms) | kd (1/s) | KD (nM) | Rmax (RU) |
|---|---|---|---|---|---|
| HBS-P, pH 7.4 | HuSA | 6.59E+04 | 3.68E−04 | 5.58 | 121.6 |
| | RhSA | 8.27E+04 | 5.77E−04 | 6.98 | 103.3 |
| | MuSA | 1.34E+05 | 9.09E−03 | 67.67 | 77.64 |
| Acetate, pH 5.5 | HuSA | 1.02E+05 | 8.98E−04 | 8.82 | 111.9 |
| | RhSA | 5.96E+04 | 1.05E−03 | 17.55 | 85.5 |
| | MuSA | 7.59E+04 | 1.46E−02 | ~192.4 | 57.91 |

To improve on properties of 2270_C01, namely in silico predicted immunogenicity, the 2270_C01 sequence was subjected to optimization by mRNA display. Resulting Adnectins from this optimization are herein referred to as PKE2 Adnectins.

Example 3: Generation of 2270_C01 Progeny Adnectins with Further Modified CD Loop: PKE2 Adnectins The 2270_C01 sequence was subjected to optimization by mRNA display utilizing custom-designed libraries to reduce immunogenicity potential, and screened for binding to both human and mouse serum albumins during the mRNA display process in order to obtain lower immunogenicity progeny molecules that retained cross-species albumin binding. Resulting sequences were evaluated for in silico predicted immunogenicity and only clones that had an in silico immunogenicity score lower than the pre-determined cut-off were progressed into protein production by HTPP. Resulting Adnectins were purified by HTPP and screened by direct binding ELISA and SEC-HPLC as described above.

Of the 308 PKE2 Adnectins obtained in the screening of 2270_C01 progeny and tested, the following 25 were the best performing molecules in terms of in silico predicted immunogenicity, monomericity as determined by SEC and binding to serum albumin from various species as determined by direct binding ELISA. Affinity determinations of the top candidates were analyzed by SPR as described above.

| SEQ ID | PKE2 Adnectins | Sequence (with CD loop underlined) |
|---|---|---|
| 24 | 2629_A09 | MGVSDVPRDLEVVAATPTSLLISWDAPA VTVRYYRITYGRHVQIYSDLGPLYIYTE FTVPGSKSTATISGLKPGVDYTITVYAV TGSGESPASSKPISINYRTEIDKPSQHH HHHH |
| 25 | 2629_A11 | MGVSDVPRDLEVVAATPTSLLISWDAPA VTVRYYRITYGRHVHIYSDWGPMYIYTE FTVPGSKSTATISGLKPGVDYTITVYAV TGSGESPASSKPISINYRTEIDKPSQHH HHHH |
| 26 | 2629_C10 | MGVSDVPRDLEVVAATPTSLLISWDAPA VTVRYYRITYGREVQKYSVLGPLYIYTE FTVPGSKSTATISGLKPGVDYTITVYAV TGSGESPASSKPISINYRTEIDKPSQHH HHHH |
| 27 | 2629_D09 | MGVSDVPRDLEVVAATPTSLLISWDAPA VTVRYYRITYGREVQMYSDLGPLYVYSE FTVPGSKSTATISGLKPGVDYTITVYAV TGSGESPASSKPISINYRTEIDKPSQHH HHHH |

-continued

| SEQ ID | PKE2 Adnectins | Sequence (with CD loop underlined) |
|---|---|---|
| 28 | 2629_E05 | MGVSDVPRDLEVVAATPTSLLISWDAPA<br>VTVRYYRITYGREVQKFSDWGPLYIYTE<br>FTVPGSKSTATISGLKPGVDYTITVYAV<br>TGSGESPASSKPISINYRTEIDKPSQHH<br>HHHH |
| 29 | 2629_E06 | MGVSDVPRDLEVVAATPTSLLISWDAPA<br>VTVRYYRITYGREVQKYSDLGPLYIYQE<br>FTVPGSKSTATISGLKPGVDYTITVYAV<br>TGSGESPASSKPISINYRTEIDKPSQHH<br>HHHH |
| 30 | 2629_F04 | MGVSDVPRDLEVVAATPTSLLISWDAPA<br>VTVRYYRITYGREVHQYSDWGPMYIYNE<br>FTVPGSKSTATISGLKPGVDYTITVYAV<br>TGSGESPASSKPISINYRTEIDKPSQHH<br>HHHH |
| 31 | 2629_H01 | MGVSDVPRDLEVVAATPTSLLISWDAPA<br>VTVXYYRITYGREVHKNSDWGTLYIYTE<br>FTVPGSKSTATISGLKPGVDYTITVXAV<br>TGSGEXPASSKPISINYRTEIDKXSQHH<br>HHHH |
| 32 | 2629_H06 | MGVSDVPRDLEVVAATPTSLLISWDAPA<br>VTVRYYRITYGREVQKYSDLGPLYIYAE<br>FTVPGSKSTATISGLKPGVDYTITVYAV<br>TGSGESPASSKPISINYRTEIDKPSQHH<br>HHHH |
| 33 | 2629_H07 | MGVSDVPRDLEVVAATPTSLLISWDAPA<br>VTVRYYRITYGREVHLYSDWGPMYIYTE<br>FTVPGSKSTATISGLKPGVDYTITVYAV<br>TGSGESPASSKPISINYRTEIDKPSQHH<br>HHHH |
| 34 | 2630_A02 | MGVSDVPRDLEVVATTPTSLLISWDAPA<br>VTVRYYRITYGRHVQMYSDLGPLYIFSE<br>FTVPGSKSTATISGLKPGVDYTITVYAV<br>TGSGESPASSKPISINYRTEIDKPSQHH<br>HHHH |
| 35 | 2630_A11 | MGVSDVPRDLEVVAATPTSLLISWDAPA<br>VTVRYYRITYGREVHMYSDFGPMYIYTE<br>FTVPGSKSTATISGLKPGVDYTITVYAV<br>TGSGESPASSKPISINYRTEIDKPSQHH<br>HHHH |
| 36 | 2630_D02 | MGVSDVPRDLEVVAATPTSLLISWDAPA<br>VTVRYYRITYGREVQKYSDWGPLYIYNE<br>FTVPGSKSTATISGLKPGVDYTITVYAV<br>TGSGESPASSKPISINYRTEIDKPSQHH<br>HHHH |
| 37 | 2630_D10 | MGVSDVPRDLEVVAATPTSLLISWDAPA<br>VTVRYYRITYGREVQMYSDLGPLYIYNE<br>FTVPGSKSTATISGLKPGVDYTITVYAV<br>TGSGESPASSKPISINYRTEIDKPSQHH<br>HHHH |
| 38 | 2630_F04 | MGVSDVPRDLEVVAATPTSLLISWDAPA<br>VTVRYYRITYGREVQMYSDLGPLYIYTE<br>FTVPGSKSTATISGLKPGVGYTITVYAV<br>TGSGESPASSKPISINYRTEIDKPSQHH<br>HHHH |
| 39 | 2630_G03 | MGVSDVPRDLEVVAATPTSLLISWDAPA<br>VTVRYYRITYGRHVQIYSDLGPLYIYNE<br>FTVPGSKSTATISGLKPGVDYTITVYAV<br>TGSGESPASSKPISINYRTEIDKPSQHH<br>HHHH |

-continued

| SEQ ID | PKE2 Adnectins | Sequence (with CD loop underlined) |
|---|---|---|
| 40 | 2630_G10 | MGVSDVPRDLEVVAATPTSLLISWDAPA<br>VTVRYYRITYGREVQIYSDWGPLYIYNE<br>FTVPGSKSTATISGLKPGVDYTITVYAV<br>TGSGESPASSKPISINYRTEIDKPSQHH<br>HHHH |
| 41 | 2630_H03 | MGVSDVPRDLEVVAATXTSLLISWDAPA<br>VTVXYYRITYGREVQKYSDWGPLYIYQE<br>FTVPGSXSTATISGLKPGVDYTITVYAV<br>TGSGESPASSKPISINYRTEIDKXSQHH<br>HHHH |
| 42 | 2631_B04 | MGVSDVPRDLEVVAATPTSLLISWDVPA<br>VTVRYYRITYGRHVHLYSEFGPMYIYNE<br>FTVPGSKSTATISGLKPGVDYTITVYAV<br>TGSGESPASSKPISINYRTEIDKPSQHH<br>HHHH |
| 43 | 2631_E03 | MGVSDVPRDLEVVAATPTSLLISWDAPA<br>VTVRYYRITYGRDVHMYSDWGPMYIYQE<br>FTVPGSKSTATISGLKPGVDYTITVYAV<br>TGSGESPASSKPISINYRTEIDKPSQHH<br>HHHH |
| 44 | 2631_G01 | MGVSDVPRDLEVVAATPTSLLISWDAPA<br>VTVRYYRITYGRHVQIYSDWGPLYIYNE<br>FTVPGSKSTATISGLKPGVDYTITVYAV<br>TGSGESPASSKPISINYRTEIDKPSQHH<br>HHHH |
| 45 | 2631_G03 | MGVSDVPRDLEVVAATPTSLLISWDAPA<br>VTVRYYRITYGRYVQLYSDWGPMYIYTE<br>FTVPGSKSTATISGLKPGVDYTITVYAV<br>TGSGESPASSKPISINYRTEIDKPSQHH<br>HHHH |
| 46 | 2631_H09 | MGVSDVPRDLEVVAATPTSLLISWDAPA<br>VTVRYYRITYGRQVQVFSDLGPLYIYNE<br>FTVPGSKSTATISGLKPGVDYTITVYAV<br>TGSGESPASSKPISINYRTEIDKPSQHH<br>HHHH |
| 47 | 2632_G01 | MGVSDVPRDLEVVAATPTSLLISWDAPA<br>VTVRYYRITYGRQVQIYSDWGPLYIYNE<br>FTVPGSKSTATISGLKPGVDYTITVYAV<br>TGSGESPASSKPISINYRTEIDKPSQHH<br>HHHH |
| 48 | 4079_A04 | MGVSDVPRDLEVVAATPTSLLISWDAPA<br>VTVRYYRITYGRQVQMYSDWGPLYIYAE<br>FTVPGSKSTATISGLKPGVDYTITVYAV<br>TGSGESPASSKPISINYRTEIDKPSQHH<br>HHHH |

Example 4: Biophysical Properties of PKE2 Adnectins

Size exclusion chromatography (SEC) was performed as described above on two of the PKE2 Adnectins, 2629_E06 and 2630_D02, identified in the screen as being well behaved in Example 3. As shown in Table 2, both PKE2 molecules were mostly monomeric.

Differential Scanning Calorimetry (DSC) analyses of the two PKE2 Adnectins were performed to determine their respective Tm's as described above. As shown in Table 2, 2629_E06 and 2630_D02 had $T_M$s of 56 and 57° C., respectively.

TABLE 2

| PKE2 Adnectin | Binding loop | SEC (% monomer) | $T_M$ (° C.) |
|---|---|---|---|
| 2270_C01 | CD | 98% | 64 |
| 2629_E06 | CD | >95% | 56 |
| 2630_D02 | CD | >95% | 57 |

Example 5: Characterization of the Binding of PKE2 Adnectins to Serum Albumin of Various Species The kinetics of binding to serum albumins by 2629_E06 and 2630_D02, as well as that of a first generation north pole-based serum albumin binding Adnectin, 1318_H04, were determined as described above. In addition, binding to albumin was carried out under various pH conditions ranging from pH 5.5 to pH 7.4. Neither 2629_E06 nor 2630_D02 showed pH dependent binding to human, rhesus, or mouse serum albumin, suggesting they would maintain binding in the endosome. As shown in Table 3, 1318_H04 had lower affinity for human, cynomolgus, and rhesus serum albumin relative to 2629_E06 and 2630_D02, and further did not bind to mouse or rat serum albumin. Moreover, 1318_H04 exhibited a 10-fold weaker affinity for rhesus serum albumin relative to human serum albumin, whereas the affinities of the PKE2 Adnectins for different albumin species were relatively equivalent.

Both PKE2 Adnectins, 2629_E06 and 2630_D02, showed substantially higher affinity for all serum albumins tested relative to 1318_H04, as discussed above, with $K_D$S for human, cynomolgus, rhesus, and mouse serum albumin in the low nanomolar range. 2629_E06 also exhibited a $K_D$ for rat serum albumin in the low nanomolar range, and 2630_D02 exhibited a $K_D$ for rat serum albumin of 200 nM.

TABLE 3

| Adnectin | Ligand | ka (1/Ms) | kd (1/s) | KD (nM) | Rmax (RU) |
|---|---|---|---|---|---|
| North pole-based SABA | HSA (n = 4) | 1.10E+04 | 1.58E−03 | 156 ± 72 | 87.0 |
| 1318_H04 | cynoSA (n = 3) | 7.15E+03 | 2.53E−02 | 4170 ± 2530* | 76.2 |
| | RhSA (n = 3) | 7.04E+03 | 2.64E−02 | 4220 ± 2110* | 84.0 |
| | MSA | | | no significant binding | |
| | Rat SA | | | no significant binding | |
| PKE2 Adnectin | HSA (n = 5) | 6.10E+04 | 1.85E−04 | 3.2 ± 1.6 | 112.7 |
| 2629_E06 | cynoSA (n = 3) | 7.37E+04 | 2.29E−04 | 3.2 ± 1.5 | 106.8 |
| | RhSA (n = 3) | 7.39E+04 | 2.40E−04 | 3.4 ± 1.8 | 99.4 |
| | MSA (n = 2) | 2.19E+05 | 5.31E−04 | 2.4 ± 0.4 | 105.4 |
| | Rat SA (n = 2) | 9.97E+04 | 1.26E−03 | 12.8 ± 2.2 | 89.5 |
| PKE2 Adnectin | HSA (n = 4) | 1.67E+05 | 1.62E−04 | 1.0 ± 0.4 | 123.2 |
| 2630_D02 | cynoSA (n = 3) | 2.08E+05 | 3.35E−04 | 1.6 ± 0.7 | 113.1 |
| | RhSA (n = 3) | 2.07E+05 | 3.62E−04 | 1.8 ± 0.8 | 107.4 |
| | MSA | 6.78E+05 | 9.20E−03 | 13.6 | 99.2 |
| | Rat SA | 1.50E+05 | 2.99E−02 | 200 | 89.3 |

Example 6: Competition of PKE2 Adnectins with hFcRn for Binding to HSA

Given that inhibiting the binding of HSA to the hFcRn receptor would prevent HSA recycling via hFcRn and reduce the long half-life of HSA, thus potentially reducing the magnitude of pharmacokinetic enhancement, the level of competition with hFcRn for binding to HSA was tested for the PKE2 Adnectins using a competitive alpha screen, which is depicted in FIG. 1. Adnectins were serially diluted in assay buffer (50 mM Acetate/150 mM NaCl/0.1% Tween-20, pH 5.5+0.005% antifoam-204) to obtain the desired final assay concentration range. A master mix of proteins and alphascreen beads was prepared in assay buffer to obtain final assay concentrations of 6.5 nM hFcRn-GST (BMS), 30 nM biotinylated human serum albumin (Abcam) and 5 ug/ml each of Alphascreen Streptavidin donor beads and AlphaLISA Glutathione acceptor beads (Perkin Elmer). 10 ul/well of serially diluted Adnectin, followed by 10 ul/well of proteins+beads solution were added to a 384-well small-volume assay plate (Greiner Bio-one). The alphascreen beads and all transfers to the assay plate were protected from ambient light. The assay plate was sealed with an adhesive foil seal and incubated for 2-2.5 h with shaking at room temperature. The plate was read in a Synergy 4 reader (Biotek) with excitation at 570 nm and emission at 680 nm. Average signal from control wells without Adnectin was set as 0% inhibition and percent inhibition of the FcRn-HSA interaction was calculated relative to that signal; average background signal from control wells without biotinylated HSA was subtracted from all data points.

Figure 2:
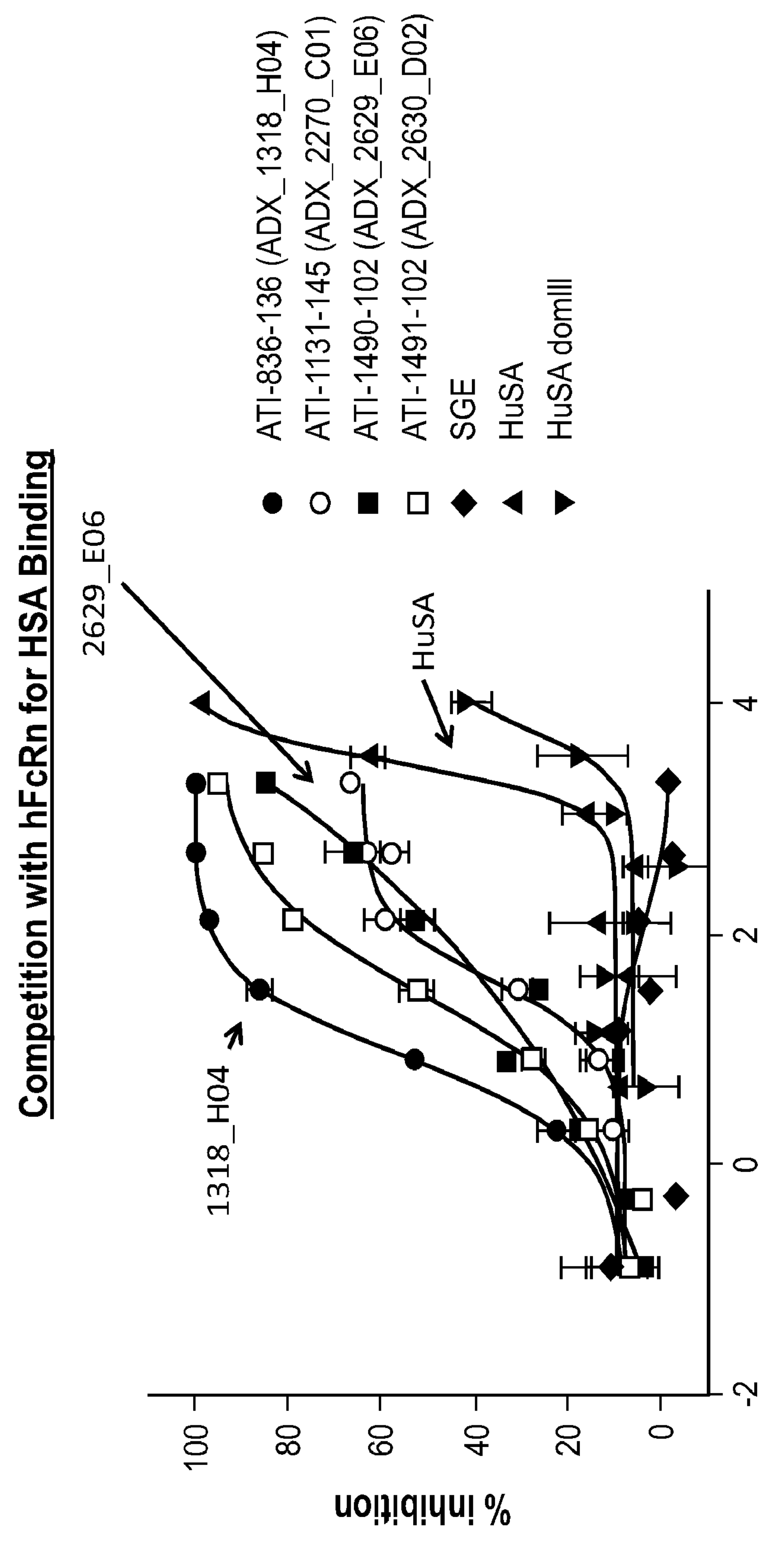
FIG. 2 is a graph depicting the competition of various Adnectins with human FcRn receptor for binding to human serum albumin (HSA).

Table 4 and FIG. 2 show the results of the screen. Notably, 1318_H04 more strongly competed with hFcRn for binding to HSA than the second generation parent 2270_C01 Adnectin and PKE2 2629_E06 and 2630_D02 Adnectins, suggesting that the PKE2 Adnectins may provide improved PK enhancement relative to 1318_H04.

Moreover, the domains on HSA bound by 1318_H04, 2629_E06, and 2630_D02 were determined by SPR. As shown in Table 4, the 1318_H04 Adnectin bound to domain I of HSA, and 2270_C01, 2629_E06, and 2630_D02 bound to domain I-II of HSA but not domain I alone, suggesting that 1318_H04 and the PKE2 Adnectins bind to distinct epitopes on HSA. None of the Adnectins in Table 4 bound to domain III of HSA, which domain is an important interaction site of HSA with FcRn.

TABLE 4

| Adnectin | hFcRn:HSA competition IC50 (nM) | HuSA Binding domain from SPR |
|---|---|---|
| 1318_H04 | 8.0 | I |
| 2270_C01 | 37.0 | I–II |
| 2629_E06 | * | I–II |
| 2630_D02 | 28.7 | I–II |

TABLE 4-continued

| Adnectin | hFcRn:HSA competition IC50 (nM) | HuSA Binding domain from SPR |
|---|---|---|
| HuSA | 2941 | |
| HuSA domainIII | >10 μM | |

*dose response did not saturate up to 2 μM, although the percent inhibition (i.e., inhibiting the binding of hFcRn to HSA) was about 80%

Example 7: In Vivo Half-Life of Candidate PKE2 Adnectins

The PKE2 Adnectins 2629_E06 and 2630_D02 were prepared, purified and endotoxin removed. Wild-type mice (n=3/group) were injected with either 2629_E06 or 2630_D02 at 1 mg/kg into the tail vein, and the concentration in blood samples taken at intervals post-injection was determined using a quantitative ELISA-based assay that was developed to detect the Adnectin in plasma samples. Specifically, Adnectin drug levels were measured in mouse plasma using the Mesoscale technology platform or standard colorimetric ELISAs. 2629_E06 and 2630_D02 were captured via an anti-His mAb (BMS) and detected using a rabbit anti-sera directed against the Adnectin scaffold in combination with a goat anti-rabbit HRP conjugated pAb. Alternatively, they were detected via species-specific albumin bound to the Adnectin and a species specific anti-Albumin sulfo-tagged secondary pAb. The pharmacokinetic parameters of each Adnectin were determined using non-compartmental modeling with Phoenix WinNonlin software.

Figure 3:
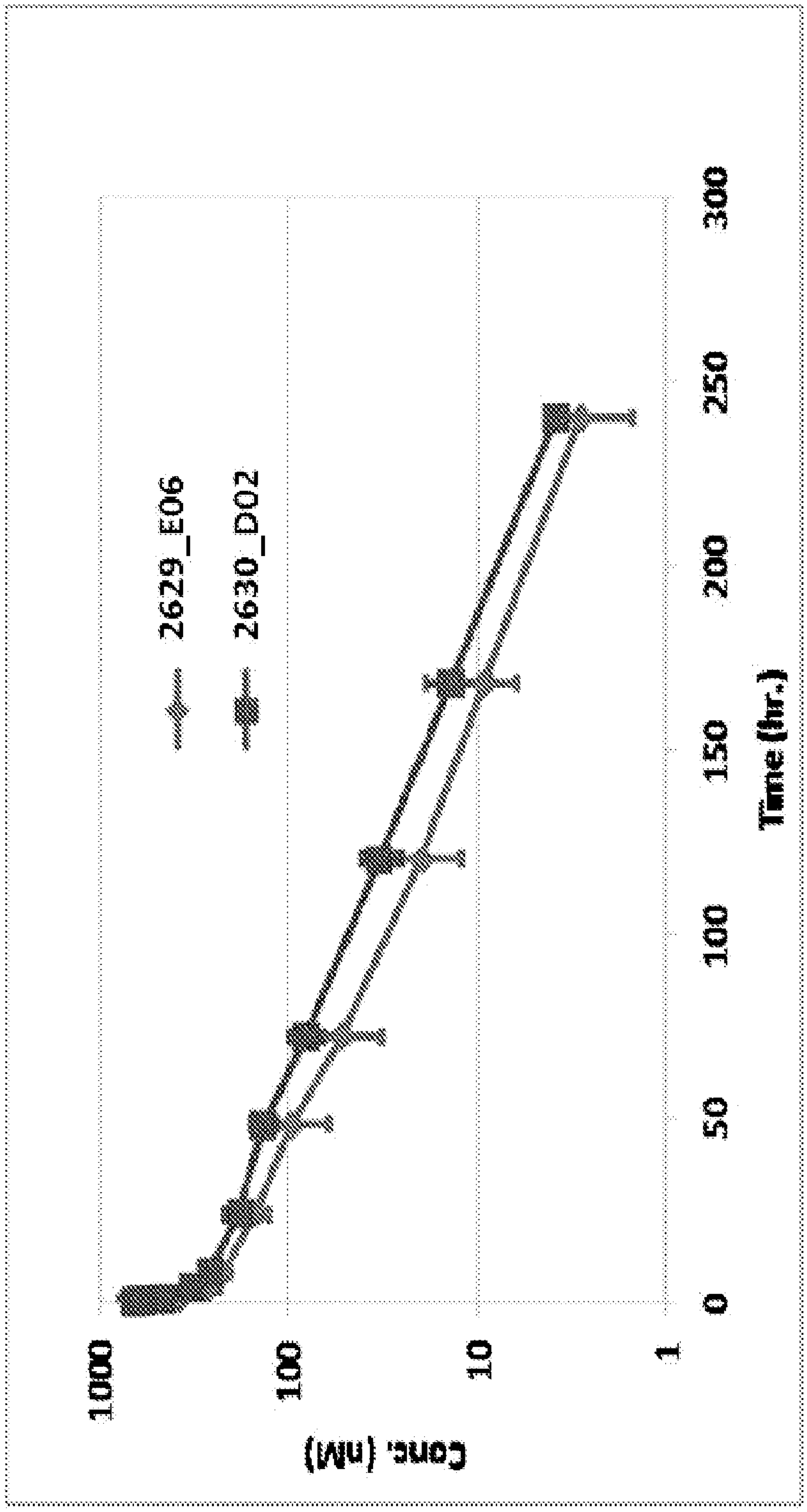
FIG. 3 is a graph depicting the plasma half-lives of 2629_E06 and 2630_D02 PKE2 Adnectins in WT mice.

The pharmacokinetic profiles of 2629_E06 and 2630_D02 were compared as shown in FIG. 3 and Table 5. The half-life of 2629_E06 in mice plasma was 33-41 hours, whereas the half-life of 2630_D02 was 35-39 hours.

TABLE 5

| Adnectin | T1/2 (h) | Cl_obs (mL/h/kg) | Vz_obs (mL/kg) | AUCall (h * nmol/L) | MRTINF_pred (h) |
|---|---|---|---|---|---|
| 2629_E06 | 36.5 ± 3.9 | 6.0 | 318 | 13150 | 45.8 |
| 2630_D02 | 37.6 ± 2.4 | 4.5 | 243 | 17318 | 51.2 |

Example 8: Immunogenicity of PKE2 Adnectins

In silico prediction of HLA binding was evaluated using Epimatrix software (Epivax). A comparison of the scores is shown in Table 6. The PKE2 Adnectins 2629_E06 and 2630_D09 showed reduced in silico scores relative to 2270_C01. Additionally, in vitro proliferation of CD4+ T-cells in response to 1318_H04, 2270_C01 and the PKE2 Adnectins was evaluated as an ex vivo assessment of potential human immunogenicity. The Ficoll density gradient method was used to isolate peripheral blood mononuclear cells (PBMC) from whole blood obtained from 40 independent donors which were MHC Class II matched to the general population. Cells from each donor were stored in liquid N2 following isolation and thawed prior to use. Cells from each donor were labeled with the fluorescent dye carboxyfluorescein succinimidyl ester (CFSE), and incubated with the Adnectins of interest for 7 days at 37° C. T cells were labeled with an anti CD4 antibody and proliferation was evaluated by flow cytometry using the BD FACS Canto and FlowJo analysis software. Antigenicity of a protein was calculated as the percentage of donors that showed a significant increase in CD4+ proliferation.

Figure 4:
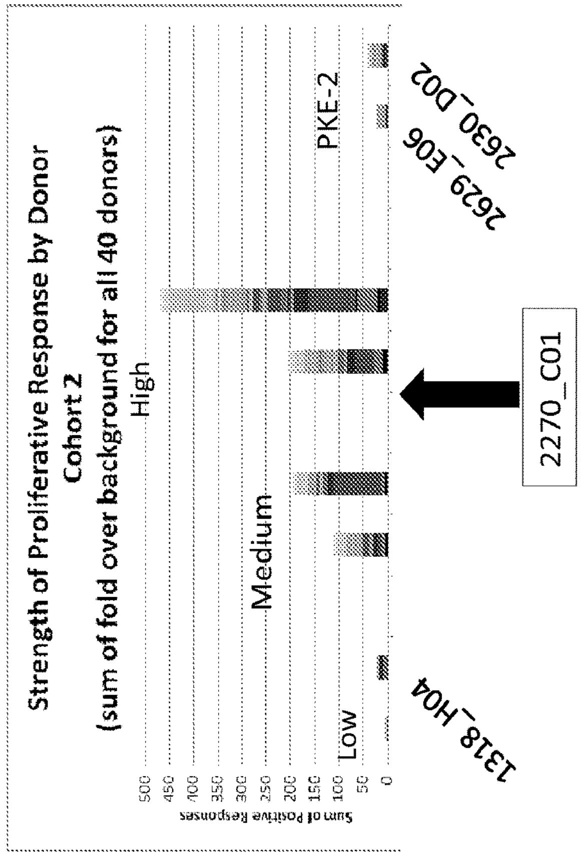
FIG. 4 is a graph depicting T-cell proliferation results for percentage antigenicity and strength of proliferative responses for 2629_E06 and 2630_D02 Adnectins, and the parent 2270_C01 molecule.
Figure 4:
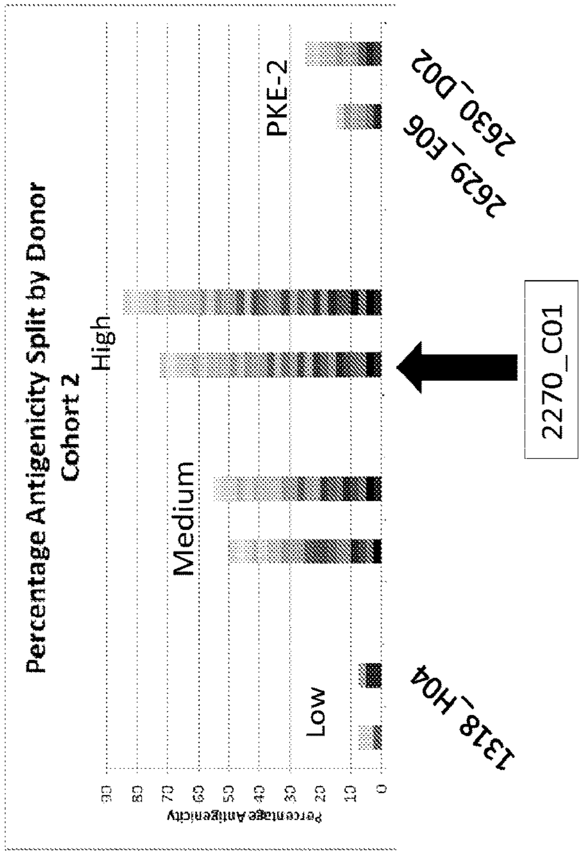

Comparisons of the parent 2270_C01 and its two progeny 2629_E06 or 2630_D02 revealed that the parent molecule had higher antigenicity (FIG. 4 and Table 6), suggesting that the two progeny PKE2 Adnectins show reduced immunogenicity potential relative to the parent molecule.

TABLE 6

| Adnectins | Percentage Antigenicity | Strength of Response (Avg of Pos responders) | Response Index | Epi-matrix Score CD Loop | CD Loop Sequence |
|---|---|---|---|---|---|
| 1381_H04 | 0.08 | 5.23 | 0.39 | | |
| 2270_C01 | 0.73 | 6.82 | 4.95 | 1.71 | WQVQMYSD WGPLYIYK |
| 2629_E06 | 0.16 | 4.04 | 0.64 | -5.63 | REVQKYSD LGPLYIYQ |
| 2630_D02 | 0.26 | 4.16 | 1.10 | -5.98 | REVQKYSD WGPLYIYN |

Example 9: Effects of Single Cysteine Mutants of PKE2 Adnectins on Binding to Albumin Single cysteine residues were incorporated at sites distinct from the HSA binding residues of the PKE-2 Adnectins in order to allow chemical conjugation to therapeutic molecules of interest via standard maleimide chemistry. It was important to retain binding to serum albumin (and thus PK enhancement) in the context of a cysteine mutation, therefore the effects of these mutations on binding to serum albumin of various species were tested, using the 2629_E06 molecule as the basis for mutation. The off-rate ($k_{off}$) of each of the mutants was analyzed via an SPR-based assay, with albumins immobilized and Adnectins used as analytes at 250 nM. As shown in Table 7, introduction of single cysteine mutations in 2629_E06 showed similar off-rates from serum albumins across various species as the parent 2629_E06 molecule, indicating that binding to serum albumin is retained in the context of these specific mutations. Therefore, any one of these cysteine mutants could serve as a chemical conjugation partner for therapeutic molecules of interest and provide PK enhancement.

TABLE 7

| Description | Adnectin | HSA off-rate ($s^{-1}$) | RhSA off-rate ($s^{-1}$) | MSA off-rate ($s^{-1}$) | Rat SA off-rate ($s^{-1}$) |
|---|---|---|---|---|---|
| PKE_2-NYRTEIDKPSQH6 | 2629_E06 * | 1.69E−04 | 2.19E−04 | 4.01E−04 | 7.67E−04 |
| 2629_E06-NYRTPCH6 | 5916_E03.PS5-2 | 2.11E−04 | 2.72E−04 | 4.52E−04 | 7.86E−04 |
| 2629_E06-NYRTPEDEDGCH6 | 5916_A04.PS5-2 | 1.48E−04 | 1.72E−04 | 3.07E−04 | 5.47E−04 |
| MGCSTSGVSD-2629_E06-NYRTPH6 | 5963_A02.PS5-2 | 2.53E−04 | 3.13E−04 | 4.92E−04 | 9.02E−04 |

TABLE 7-continued

| Description | Adnectin | HSA off-rate ($s^{-1}$) | RhSA off-rate ($s^{-1}$) | MSA off-rate ($s^{-1}$) | Rat SA off-rate ($s^{-1}$) |
|---|---|---|---|---|---|
| 2629_E06(S55C)-NYRTPH6 | 5963_C03.PS5-2 | 2.29E−04 | 3.03E−04 | 4.63E−04 | 7.89E−04 |
| 2629_E06(A12C)-NYRTPH6 | 5963_D01.PS5-2 | 2.47E−04 | 3.13E−04 | 4.99E−04 | 8.58E−04 |
| 2629_E06(T58C)-NYRTPH6 | 5963_E01.PS5-2 | 2.50E−04 | 3.13E−04 | 5.07E−04 | 8.48E−04 |
| 2629_E06(T56C)-NYRTPH6 | 5963_E02.PS5-2 | 2.28E−04 | 2.84E−04 | 4.61E−04 | 7.60E−04 |
| 2629_E06(A26C)-NYRTPH6 | 5963_F03.PS5-2 | 2.51E−04 | 3.12E−04 | 5.04E−04 | 8.25E−04 |

Example 10: Biophysical Properties of Single Cysteine Mutants of 2629_E06

The biophysical properties of the single cysteine mutants described in Example 9 were assessed, and are shown in Table 8. Every mutant yielded a thermally stable and monomeric protein.

TABLE 8

| Mutant | Buffer | Conc. (mg/ml) | Protein available (mg) | SEC | ASSA (M) | DSC (° C. @ 0.5 mg/ml) |
|---|---|---|---|---|---|---|
| 2629__E06(A26C)-NYRTPH6 | PBS | 2.3 | 4.1 | >99% monomer | 1.72 | 65.5 |
| 2629__E06-NYRTPCH6 | PBS | 2.6 | 4.7 | >99% monomer | 1.77 | 67.2 |
| 2629__E06(T56C)-NYRTPH6 | PBS | 2.7 | 4.8 | >99% monomer | 1.72 | 68.3 |
| 2629__E06(T58C)-NYRTPH6 | PBS | 2.4 | 4.3 | >99% monomer | 1.72 | 68.7 |
| 2629__E06(A12C)-NYRTPH6 | PBS | 2.8 | 5.1 | >99% monomer | 1.70 | 68.2 |
| 2629__E06(S55C)-NYRTPH6 | PBS | 2.4 | 4.2 | >99% monomer | 1.75 | 69.4 |
| 2629__E06-NYRTPEDEDGCH6 | PBS | 0.7 | 1.3 | >90% monomer | 1.73 | 70.5 |
| MGCSTSGVSD-2629__E06-NYRTPH6 | PBS | 1.6 | 2.8 | >90% monomer | 1.71 | 67.8 |

Example 11: PKE2 Adnectin Tandem Molecule Modularity

One of the limitations of the north pole serum albumin binding Adnectins was the lack of compatibility for use in tandem with other $^{10}$Fn3 proteins. Therefore, the compatibility of the PKE2 Adnectins with other $^{10}$Fn3 proteins was explored. The biophysical behavior of the PKE2 Adnectins was tested when fused in tandem with an Adnectin specific for a different target. The PKE2 Adnectins were tested in both possible configurations: in the N-terminal location (PKE2-X) and the C-terminal location (X-PKE2). Size exclusion chromatography behavior was tested using molecules obtained using the HTPP method. Fusions with the first generation north pole-based 1318_H04 Adnectin was directly compared to fusions with the PKE2 Adnectins 2629_E06 and 2630_D02. Tested fusion partners included a myostatin binding $^{10}$Fn3 domain (2987_H07; see WO2014/043344), two PCSK9 binding $^{10}$Fn3 domains (2013_E01 and 2382_D09), and a EGFR binding $^{10}$Fn3 domain (1312_E01). The sequences of PCSK9 Adnectins 2382_D09 and 2013_E01 can be found in WO2011/130354, herein incorporated by reference. As shown in Table 9, both PKE2 Adnectins molecules consistently retained good biophysical behavior, as reflected in the proportion of molecules with an SEC grading of A (i.e., corresponding to ≥90% monomeric Adnectins), relative to the north pole-based 1318_H04 SABA molecule, in the context of a tandem Adnectin. PKE in the table refers to a serum albumin binding $^{10}$Fn3 domain (i.e., PK-enhancing $^{10}$Fn3 domain). Ratios represent the # of clones with SEC=A/total # of clones tested. Tandems which were not generated are denoted as "-".

TABLE 9

| | % PKE Tandems with SEC = A | | | | | | | |
|---|---|---|---|---|---|---|---|---|
| Adnectin | 2987_H07 (Myo) | | 2013_E01 (PCSK9) | | 1312_E01 (EGFR) | | 2382_D09 (PCSK9) | |
| Orientation | X-PKE | PKE-X | X-PKE | PKE-X | X-PKE | PKE-X | X-PKE | PKE-X |
| PKE 1318_H04 | 31 (8/26) | 0 (0/26) | 31 (8/26) | — | — | — | 8 (8/26) | — |
| 2629_E06 | 30 (3/10) | 80 (8/10) | 90 (9/10) | 80 (8/10) | 70 (7/10) | 70 (7/10) | 58 (51/88) | — |
| 2630_D02 | 20 (2/10) | 60 (6/10) | 50 (5/10) | 80 (8/10) | 70 (7/10) | 70 (7/10) | — | — |

The data in FIG. 5 reproduce the data in Table 9 for the 2987_H07 myostatin binding $^{10}$Fn3 domain and the 2013_E01 PCSK9 binding $^{10}$Fn3 domain, with the exception that the various shades of gray reflect the ability of the tandem molecules to still bind to HSA as determined in the direct binding ELISA assay described above. The different shades of grey in FIG. 5 correspond to different $EC_{50_}$tandem Adnectin/$EC_{50_}$monoAdnectin ratios for binding to HSA, with darker shades representing stronger binding of the tandem molecules to HSA. The data in FIG. 5 show that the PKE2-based tandem molecules had better monomericity (i.e., less prone to dimerization and aggregation) and HSA binding (i.e., lost less HSA and RhSA binding) relative to the 1318_H04 Adnectin. Similar patterns were observed with four additional target-binding Adnectins. These data indicate that the PKE2 Adnectins provide a more stable and active binding partner for other $^{10}$Fn3 proteins than the north pole serum albumin binding Adnectins.

Example 12: PCSK9-PKE2 Tandem Molecules Exhibit Good Potency in PCSK9 Biochemical Assays, Low EpiMatrix Scores, Good Biophysical Properties and Cross-Species Albumin Binding Various PCSK9-PKE2 tandem Adnectins were produced based on the PKE2 Adnectin 2629_E06 and the PCSK9 Adnectin 2382_D09, as shown in Table 10. Each of the tandem molecules differ only by linker, and all were tested for their biophysical and functional properties to ensure retention of activities of both the albumin-binding PKE2 and the PCSK9-binding Adnectin. Cross-species albumin binding was determined using the ELISA method described above. The relative thermal stability was assessed by Thermal Scanning Fluorescence (TSF). HTPP samples were normalized to 0.2 mg/ml in PBS. 1 pd of Sypro orange dye diluted 1:40 with PBS was added to 25 ul of each sample and the plate was sealed with a clear 96 well microplate adhesive seal. Samples were scanned using a BioRad RT-PCR machine by ramping the temperature from 25° C.-95° C., at a rate of 2 degrees per minute. The data was analyzed using BioRad CFX manager 2.0 software. The values obtained by TSF have been shown to correlate well with Tm values obtained by DSC over a melting range of 40° C. to 70° C. This is considered the acceptable working range for this technique. A result of ND ("No data") is obtained when the slope of the transition curve is too small to allow its derivative peak (the rate of change in fluorescence with time) to be distinguished from noise.

The PCSK9:EGFA FRET assay measured the inhibition of PCSK9 binding to the low density lipoprotein receptor (LDLR) epidermal growth factor precursor homology domain (EGFA domain), using recombinant human PCSK9 expressed in baculovirus and a synthetic 40-mer EGFA peptide (biotinylated). EGFA has been shown to represent the key interacting domain of LDLR with PCSK9 (Kwon, H. J. et al., Proc. Natl. Acad. Sci. USA, 105(6): 1820-1825 (2008)). This assay used a PCSK9 C-terminal domain binding mAb (mAb 4H5) labeled with Eu-chelate to provide FRET interaction with biotinylated EGFA through the streptavidin/l allophycocyanin fluorophore complex. The PCSK9-LDLR FRET assay was run in a similar manner using the extracellular domain of LDLR in place of the EGFA peptide.

All tandem molecules had low immunogenicity (negative Epimatrix score), high monomericity (as assessed by SEC), acceptable relative thermal stability (TSF) and favorable cross-species albumin binding by ELISA assay. Moreover, the PCSK9-PKE2 tandem Adnectins retained good potency in PCSK9 biochemical assays with $IC_{50}$s similar to the unformatted 2382_D09 Adnectin.

TABLE 10

| PCSK9-PKE2 tandem | Linker | Epimatrix | Conc (ug/mL) | SEC | TSF | HuSA EC50 (nM) | RhSA EC50 (nM) | MuSA EC50 (nM) | EGFA FRET 1 (IC50, nM) | EGFA FRET 2 (IC50, nM) | PCSK9: LDLR FRET (IC50, nM) |
|---|---|---|---|---|---|---|---|---|---|---|---|
| 4472_E09 | A | −12.3 | 3490 | A | 58.5 | 23.8 | 19.8 | 7.0 | 5.81 | 4.81 | 1.3 |
| 4472_A11 | B | −21.2 | 4530 | A | 61 | 26.9 | 15.7 | 3.9 | 6.13 | 3.76 | 1.4 |
| 4472_H09 | C | −10.2 | 2410 | A | 62.5 | 27.8 | 26.8 | 4.0 | 9.66 | 7.17 | 3 |
| 4472_F04 | D | −18.8 | 3410 | A | 60.5 | 40.3 | 27.8 | 3.8 | 3.99 | 4.18 | 1.2 |
| 4472_C08 | E | −14.4 | 2880 | A | 60 | 40.4 | 25.7 | 4.8 | 9.38 | 5.09 | 1.9 |
| 4472_F08 | F | −13.0 | 5050 | A | 61 | 55.4 | 35.2 | 7.3 | 7.88 | 5.88 | 2.5 |
| 4472_F06 | G | NA | 4450 | A | 61 | 58.9 | 40.8 | 11.3 | 4.50 | 3.42 | 1.1 |
| 4472_G10 | H | −15.7 | 1694 | A | 61 | 61.3 | 48.3 | 10.0 | 7.81 | 6.81 | 2.4 |
| 4472_E06 | I | −15.4 | 4810 | A | 60 | 67.3 | 40.1 | 4.2 | 7.67 | 5.68 | 1.6 |
| 4472_B10 | J | −5.4 | 1299 | A | 59.5 | 67.7 | 38.9 | 10.9 | 9.69 | 6.97 | 2.2 |
| 4472_B09 | K | −3.4 | 2230 | A | 59.5 | 69.2 | 45.1 | 9.8 | 9.36 | 6.95 | 2.4 |
| 4472_B11 | L | −11.5 | 835 | A | 59.0 | 70.1 | 54.0 | 13.5 | 6.54 | 5.03 | 2 |
| 4472_A06 | M | −7.0 | 3720 | A | 58 | 77.8 | 44.4 | 8.6 | 9.06 | 2.72 | 1.6 |
| 4472_D08 | N | −13.1 | 4140 | A | 60 | 80.2 | 54.1 | 9.5 | 6.32 | 5.22 | 1.7 |
| 4472_B05 | O | −6.2 | 639 | A | 57.5 | 85.1 | 59.5 | 9.3 | 6.66 | 5.55 | 1.9 |
| 4472_H11 | P | −1.7 | 1099 | A | nd | 85.3 | 58.1 | 13.2 | 8.76 | 6.24 | 1.3 |
| 4472_E04 | Q | −5.6 | 1244 | A | 60.5 | 100.9 | 64.8 | 8.9 | 9.45 | 7.54 | 2 |
| 4472_E05 | R | −2.5 | 933*** | A | 54.5 | 102.2 | 63.1 | 13.1 | 5.66 | 4.35 | 1.5 |
| 4472_B03 | S | −7.9 | 1239 | A | 59 | 123.5 | 98.2 | 14.8 | 7.45 | 4.83 | 1.4 |
| 4472_D06 | T | −17.7 | 2850 | A | 61.5 | 139.2 | 93.1 | 15.6 | 8.12 | 6.51 | 1.8 |
| 4472_A04 | U | −6.6 | 1142 | A | nd | 143.7 | 84.0 | 16.7 | 5.14 | 4.44 | 1.1 |
| 4472_C06 | PSTPPTPSPSTPPTPSPS | −19.6 | 6760 | A | 61 | 184.3 | 131.1 | 15.6 | 9.18 | 3.09 | 1.4 |
| ADX_2382_D09 | n/a | | | | 83 (DSC) | n/a | n/a | n/a | 19.70 | 10.6 | 2.3 |
| ADX_2629_E06 | n/a | | | | 56 (DSC) | 14.5 | 10.5 | 2.8 | n/a | n/a | n/a |

Example 13: Binding Kinetics of PCSK9-PKE2 Tandem Molecules to Human PCSK9

Figure 6:
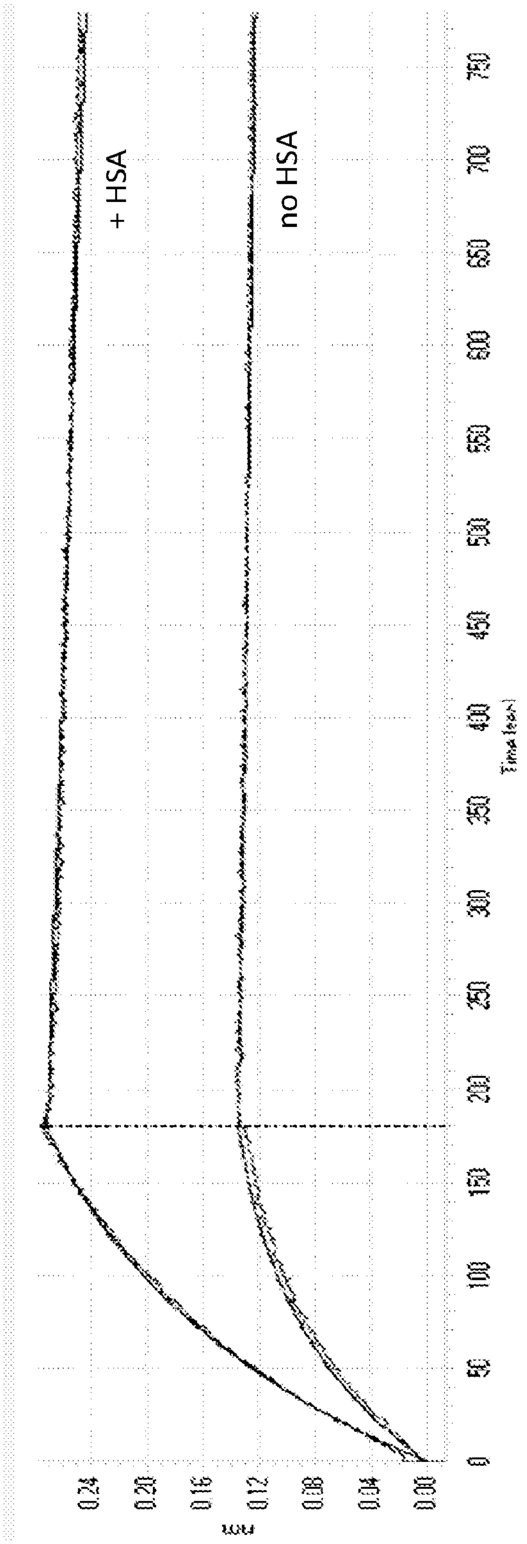
FIG. 6 shows the Bio-Layer Interferometry sensograms of PCSK9-PKE2 tandem Adnectins binding to hPCSK9 in the presence or absence of HSA.

PCSK9-PKE2 tandem Adnectin binding to immobilized human PCSK9 was measured in the presence or absence of HSA by biolayer interferometry (Octet Red 96, using Super-streptavidin sensor tips, ForteBio, Menlo Park Calif.). Association and dissociation events were captured in real time for a series of Adnectin concentrations with biotinylated full-length PCSK9 captured on sensor tips. Binding curves were globally fit to produce values for $K_D$, $k_{on}$, and $k_{off}$. Tandem Adnectin-HSA complexes were pre-formed by incubating the tandem in excess and running the binding analysis in the presence of excess HSA. A complex between the tandem Adnectin-HSA complexes with human PCSK9 was considered to have formed when there was an increased apparent mass for the tandem Adnectins in the presence of HSA at the same concentration (see, e.g., FIG. 6). As shown in Table 11, all tandem PCSK9-PKE2 molecules tested had similar binding kinetics and potencies for PCSK9. A slight reduction was seen for the association and somewhat faster dissociation for the HSA-Adnectin complex binding to huPCSK9.

TABLE 11

PCSK9: PKE2 Adnectin binding data table

| | no HSA | | | +HSA | | |
|---|---|---|---|---|---|---|
| | $K_D$ (nM) | $k_{on}$ (1/Ms) | $k_{off}$ (1/s) | $K_D$ (nM) | $k_{on}$ (1/Ms) | $k_{off}$ (1/s) |
| 4472_F08 | 0.404 | 2.89E+05 | 1.18E−04 | 0.902 | 1.61E+05 | 1.48E−04 |
| 4472_E06 | 0.724 | 2.81E+05 | 2.00E−04 | 1.003 | 2.07E+05 | 2.09E−04 |
| 4472_C06 | 0.515 | 3.36E+05 | 1.68E−04 | 1.547 | 1.97E+05 | 3.05E−04 |

Example 14: Characterization of the Binding of PCSK9-PKE2 Tandem Molecules to Serum Albumin of Various Species Affinities of PCSK9-PKE2 tandem molecules for serum albumin of various species, alongside the affinity of the PKE2 Adnectin 2629_E06, were assessed by Biacore analysis, as described in Example 2.

As shown in Table 12, all three PCSK9-PKE2 tandem molecules showed comparable affinities to serum albumins across species, although the affinities of the tandems were 5-7-fold weaker (with similar off-rates) compared to the 2629_E06 PKE2 Adnectin.

TABLE 12

| Tandem Adnectin | Binding to | ka (1/Ms) | kd (1/s) | KD (nM) | Rmax (RU) |
|---|---|---|---|---|---|
| 2629_E06 | HuSA | 1.74E+04 | 2.13E−04 | 12.3 | 106.8 |
| | RhSA | 1.95E+04 | 2.83E−04 | 14.5 | 86.24 |
| | MuSA | 6.84E+04 | 2.42E−04 | 3.6 | 97.99 |
| 4472_F08 | HuSA | 4.82E+03 | 3.24E−04 | 67.1 | 187.8 |
| | RhSA | 5.34E+03 | 3.67E−04 | 68.7 | 157.9 |
| | MuSA | 1.35E+04 | 3.44E−04 | 25.5 | 166.7 |
| 4472_E06 | HuSA | 5.30E+03 | 3.62E−04 | 68.4 | 215.4 |
| | RhSA | 5.77E+03 | 4.15E−04 | 71.9 | 181.4 |
| | MuSA | 1.50E+04 | 3.00E−04 | 20.0 | 186.2 |

TABLE 12-continued

| Tandem Adnectin | Binding to | ka (1/Ms) | kd (1/s) | KD (nM) | Rmax (RU) |
|---|---|---|---|---|---|
| 4472_C06 | HuSA | 3.92E+03 | 2.89E−04 | 73.7 | 182.5 |
| | RhSA | 4.38E+03 | 3.37E−04 | 77.0 | 155.9 |
| | MuSA | 1.15E+04 | 3.01E−04 | 26.1 | 163.1 |

A similar experiment (under the conditions described in Example 2) was performed with the 4472_C06 tandem Adnectin without a 6× histidine tail (referred to as 5190_E01). As shown in Table 13, 5190_E01 bound to mouse serum albumin with a $K_D$ similar to that of human, cynomolgus, and rhesus serum albumin, and bound to rat serum albumin with a $K_D$ of 200 nM.

TABLE 13

| Tandem Adnectin | Ligand | ka (1/Ms) | kd (1/s) | KD (nM) | Rmax (RU) |
|---|---|---|---|---|---|
| 5190_E01 | HSA (n = 4) | 4.79E+03 | 2.72E−04 | 57.2 ± 8.6 | 173.2 |
| (no 6X His) | cynoSA (n = 3) | 6.44E+03 | 3.26E−04 | 50.5 ± 5.4 | 168.5 |
| | RhSA (n = 3) | 6.52E+03 | 3.51E−04 | 53.8 ± 8.8 | 158.7 |
| | MSA | 1.67E+04 | 7.23E−04 | 43.3 | 148.8 |
| | Rat SA | 7.35E+03 | 1.47E−03 | 200 | 139.7 |

The effects of pH on binding of PKE2 Adnectin 2629_E06 and PCSK9-PKE2 tandem Adnectins 4472_C06, 4427_E06, and 4472_F08 were also tested. As shown in Tables 14 and 15, all Adnectins tested showed pH insensitive binding to serum albumin of various species.

TABLE 14

| Adnectin | Buffer | Binding to | ka (1/Ms) | kd (1/s) | KD (M) | Rmax (RU) | $Chi^2$ ($RU^2$) |
|---|---|---|---|---|---|---|---|
| PKE2 Adnectin 2629_E06 | HBSP, pH 7.4 | HuSA | 2.07E+04 | 2.19E−04 | 10.6 | 101.7 | 1.8 |
| | | RhSA | 2.18E+04 | 2.76E−04 | 12.7 | 91.41 | 1.51 |
| | | MuSA | 7.91E+04 | 2.72E−04 | 3.43 | 101.1 | 1.87 |
| | Acetate, pH 7.4 | HuSA | 2.80E+04 | 2.72E−04 | 9.74 | 112.9 | 4.64 |
| | | RhSA | 2.79E+04 | 3.28E−04 | 11.8 | 100.8 | 3.75 |
| | | MuSA | 7.68E+04 | 2.68E−04 | 3.48 | 105.2 | 2.34 |
| | Acetate, pH 5.5 | HuSA | 7.04E+04 | 3.26E−04 | 4.64 | 88.62 | 3.25 |
| | | RhSA | 4.85E+04 | 5.84E−04 | 12.0 | 68.33 | 1.05 |

TABLE 14-continued

| Adnectin | Buffer | Binding to | ka (1/Ms) | kd (1/s) | KD (M) | Rmax (RU) | $Chi^2$ ($RU^2$) |
|---|---|---|---|---|---|---|---|
| | | MuSA | 8.40E+04 | 1.25E−03 | 14.9 | 87.71 | 4.1 |
| PCSK9-PKE2 tandem | HBSP, pH 7.4 | HuSA | 3.58E+03 | 2.58E−04 | 72.0 | 167.5 | 4.02 |
| ADX_4472_C06 | | RhSA | 3.86E+03 | 3.05E−04 | 78.9 | 154.3 | 3.62 |
| | | MuSA | 1.19E+04 | 3.36E−04 | 28.2 | 157.1 | 2.64 |
| | Acetate, pH 7.4 | HuSA | 4.35E+03 | 3.25E−04 | 74.7 | 170.1 | 7.34 |
| | | RhSA | 4.51E+03 | 3.64E−04 | 80.7 | 161.2 | 5.58 |
| | | MuSA | 1.08E+04 | 3.75E−04 | 34.8 | 160.7 | 2.53 |
| | Acetate, pH 5.5 | HuSA | 1.22E+04 | 4.66E−04 | 38.2 | 143.1 | 6.01 |
| | | RhSA | 8.36E+03 | 8.15E−04 | 97.5 | 105.2 | 1.6 |
| | | MuSA | 1.31E+04 | 1.61E−03 | 123 | 132.3 | 7.08 |
| PCSK9-PKE2 tandem | HBSP, pH 7.4 | HuSA | 4.76E+03 | 2.92E−04 | 61.4 | 181.2 | 8.92 |
| 4472_E06 | | RhSA | 5.11E+03 | 3.32E−04 | 64.9 | 166 | 7.94 |
| | | MuSA | 1.52E+04 | 3.30E−04 | 21.8 | 172.6 | 6.43 |
| | Acetate, pH 7.4 | HuSA | 5.91E+03 | 3.83E−04 | 64.9 | 185.6 | 17.1 |
| | | RhSA | 6.24E+03 | 4.08E−04 | 65.4 | 173.8 | 12.8 |
| | | MuSA | 1.41E+04 | 3.68E−04 | 26.1 | 177.4 | 6.35 |
| | Acetate, pH 5.5 | HuSA | 1.36E+04 | 4.78E−04 | 35.2 | 164.1 | 12.4 |
| | | RhSA | 8.64E+03 | 7.88E−04 | 91.1 | 137.5 | 3.73 |
| | | MuSA | 1.34E+04 | 1.52E−03 | 114 | 164 | 14.5 |

TABLE 15

| Adnectin | Buffer | Binding to | ka (1/Ms) | kd (1/s) | KD (M) | Rmax (RU) | $Chi^2$ ($RU^2$) |
|---|---|---|---|---|---|---|---|
| PKE2 Adnectin | HBSP, pH 7.4 | HuSA | 1.79E+04 | 1.92E−04 | 10.7 | 107.0 | 0.9 |
| 2629_E06 | | RhSA | 2.35E+04 | 2.67E−04 | 11.4 | 108.2 | 1.8 |
| | | MuSA | 7.96E+04 | 2.62E−04 | 3.3 | 100.9 | 1.2 |
| | Acetate, pH 7.4 | HuSA | 2.54E+04 | 2.43E−04 | 9.6 | 114.6 | 2.7 |
| | | RhSA | 2.86E+04 | 2.97E−04 | 10.4 | 116.0 | 3.0 |
| | | MuSA | 4.49E+04 | 5.03E−04 | 11.2 | 81.0 | 1.2 |
| | Acetate, pH 5.5 | HuSA | 7.07E+04 | 2.87E−04 | 4.1 | 95.1 | 3.9 |
| | | RhSA | 4.49E+04 | 5.03E−04 | 11.2 | 81.0 | 1.2 |
| | | MuSA | 7.70E+04 | 1.13E−03 | 14.6 | 85.3 | 3.2 |
| PCSK9-PKE2 tandem | HBSP, pH 7.4 | HuSA | 3.59E+03 | 3.01E−04 | 83.8 | 185.4 | 4.4 |
| 4472_F08 | | RhSA | 4.82E+03 | 3.46E−04 | 71.7 | 191.2 | 9.1 |
| | | MuSA | 1.37E+04 | 3.59E−04 | 26.3 | 164.4 | 4.1 |
| | Acetate, pH 7.4 | HuSA | 4.61E+03 | 3.87E−04 | 83.9 | 176.3 | 8.9 |
| | | RhSA | 5.38E+03 | 4.05E−04 | 75.4 | 194.2 | 10.2 |
| | | MuSA | 1.16E+04 | 4.07E−04 | 35.0 | 165.1 | 2.7 |
| | Acetate, pH 5.5 | HuSA | 1.11E+04 | 4.89E−04 | 43.9 | 187.1 | 10.1 |
| | | RhSA | 7.40E+03 | 8.18E−04 | 110.5 | 161.0 | 2.6 |
| | | MuSA | 1.10E+04 | 1.50E−03 | 136.6 | 156.5 | 7.2 |

Example 15: Dual Binding of Tandem PCSK9-PKE2 Adnectins to Albumins and PCSK9

Figure 7:
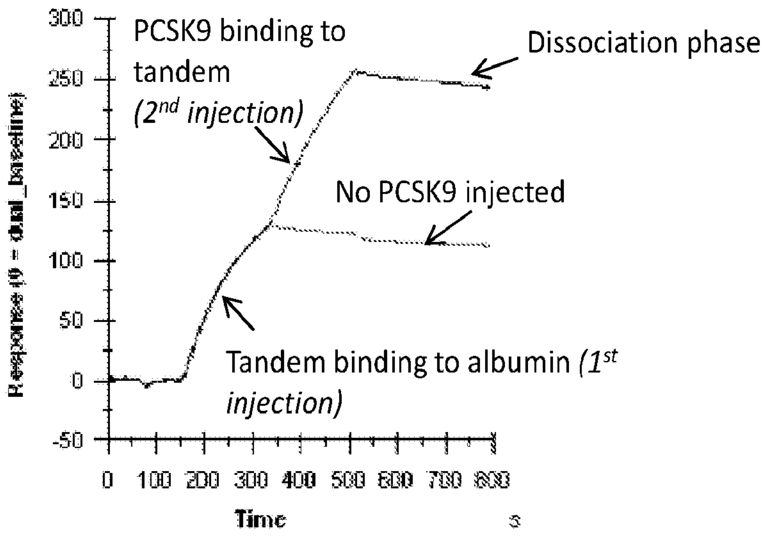
FIG. 7 is a Biacore sensogram showing the binding of the 4472_C06 PCSK9-PKE2 tandem Adnectin first to HSA, then to PCSK9 after injection of the corresponding proteins.

The ability of the tandem PCSK9-PKE2 Adnectins to simultaneously bind to serum albumin and PCSK9 were assessed using SPR. It is likely that the tandem will be bound to albumin most of the time in vivo and therefore it would be essential for activity of the PCSK9 Adnectin to be retained when bound to albumin. Binding of the tandem PCSK9-PKE2 Adnectins simultaneously to both targets was tested in the dual injection mode with a first injection of the tandem on to the immobilized albumin on the chip surface, followed by a second injection of human PCSK9, and recording the binding levels after a 3 min association phase for each injection. The increase in SPR binding signal upon injection of PCSK9 vs buffer, indicates simultaneous binding of the tandem to HSA and PCSK9, as shown in FIG. 7. PCSK9 shows ~40% of the expected binding level to 500 nM or 1 uM tandem Adnectin pre-bound to HSA. As an additional control, PCSK9 shows no binding to PKE-2 alone (data not shown).

Example 16: In Vivo Clearance of PCSK9-PKE2 Adnectins in WT C57 BL/6 Mice

Figure 8:
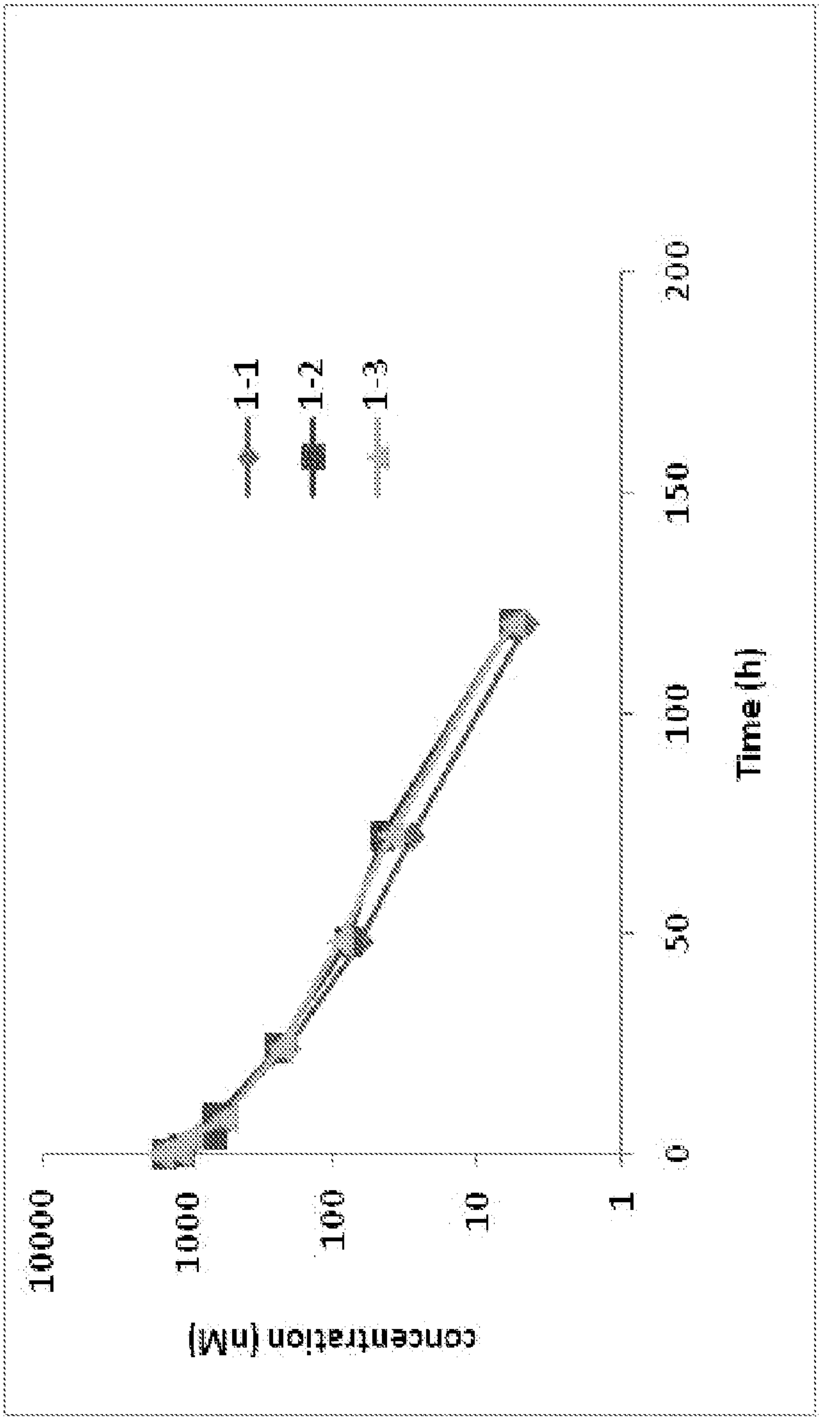
FIG. 8 is a graph depicting the in vivo PK profile of the tandem PCSK9-PKE2 Adnectin 4772_C06 in wild-type C57 Bl/6 mice.

The in vivo half-life of the tandem PCSK9-PKE2 Adnectin 4772_C06 was determined in a 2 week single 2 mg/kg IV dose study in wild-type C57 Bl/6 mice. Tandem Adnectin plasma levels were determined using the MesoScale Discovery platform. Biotinylated human PCSK9 was used to capture the Adnectin and detection was via mouse serum albumin bound to the tandem and an anti-mouse serum albumin sulfo-tagged secondary pAb. Non-compartmental analyses were performed using Phoenix WinNonlin 6.3 (Pharsight Corporation, Mountain View, Calif.) using a plasma model and linear up/log down calculation method. As shown in Table 16 and FIG. 8, the average half-life of the 4772_C06 tandem Adnectin was 16.7 hours.

TABLE 16

| strain | dose | mouse_ID | HL_Lambda_z (h) | Cl_obs (mL/h/kg) | Vss_obs (mL/kg) | AUCall (h*nmol/L) | AUCINF_obs (h*nmol/L) | AUC_%Extrap_obs (%) | MRTINF_obs (h) |
|---|---|---|---|---|---|---|---|---|---|
| C57Bl/6 | 2 mg/kg | N | 3 | 3 | 3 | 3 | 3 | 3 | 3 |
| | | Mean | 16.7 | 4.39 | 92.0 | 18657 | 18787 | 0.69 | 21.0 |
| | | SD | 1.0 | 0.21 | 4.0 | 868 | 893 | 0.10 | 1.5 |
| | | SE | 0.6 | 0.12 | 2.3 | 501 | 515 | 0.06 | 0.9 |
| | | CV % | 6 | 4.8 | 4.4 | 4.7 | 4.8 | 15.1 | 7.4 |

Example 17: PCSK9-PKE2 Tandem Adnectins Exhibit Robust PCSK9 Target Engagement In Vivo The pharmacodynamic activity of the PCSK9-PKE2 tandem Adnectin 4472_C06 was assessed in a human PCSK9 transgenic mouse model that exhibits normal levels of human PCSK9. This model is a genomic hPCSK9 transgenic (BAC-transgenic) which is regulated in liver similarly to mouse PCSK9 and which expresses near human-normal levels of hPCSK9 in plasma. Unbound hPCSK9 was evaluated following a single IP dose of PBS vehicle or 0.5 or 2 mg/kg tandem with 8 animals per group. An enzyme linked immunosorbance assays (ELISA) specific for free (unbound) human PCSK9 that does not detect mouse PCSK9 was developed. The assay employed streptavidin-pretreated 96-well plates coated with 2 μg/mL of biotinylated PCSK9-Adnectin 2013_E01 as capturing reagent. Plasma samples frozen once only were diluted as appropriate in ELISA buffer (25 mM Tris, 150 mM NaCl, pH 7.2 with 0.05% Tween-20 and 0.1% BSA), added to wells and incubated for 1 hr at 20° C. Wells were then washed and incubated with 5 ug/mL of rabbit polyclonal anti-human PCSK9 IgG (BMS custom antibody produced by Lampire Biological Labs, Pipersville Pa.) for 1 hr, followed by processing for HRP-labeled anti-rabbit IgG with TMB by standard ELISA methods. Standard curves were generated using purified recombinant human PCSK9.

Figure 9:
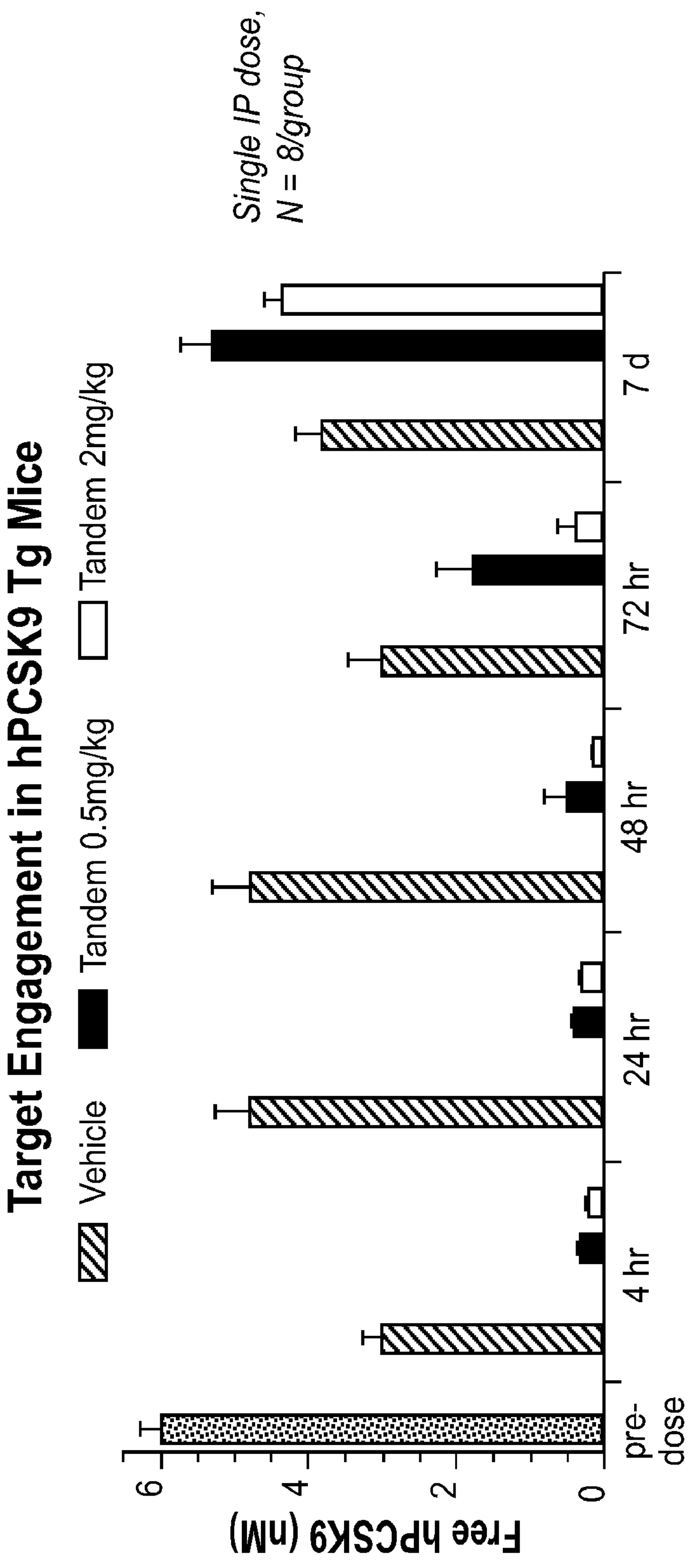
FIG. 9 shows free PCSK9 levels following dosing of vehicle or PCSK9-PKE2 Adnectin 4472_C06 at 0.5 mg/kg or 2 mg/kg in hPCSK9 transgenic mice.

As shown in FIG. 9, analysis of the free hPCSK9 levels indicates potent target engagement by the PCSK9-PKE2 tandem Adnectin at both doses tested. Free hPCSK9 was inhibited in a dose dependent manner as shown by the greater duration of response of the 2 mg/kg dose relative to the 0.5 mg/kg dose. These data demonstrate in vivo activity of the PCSK9-PKE2 tandem Adnectin.

Figure 10:
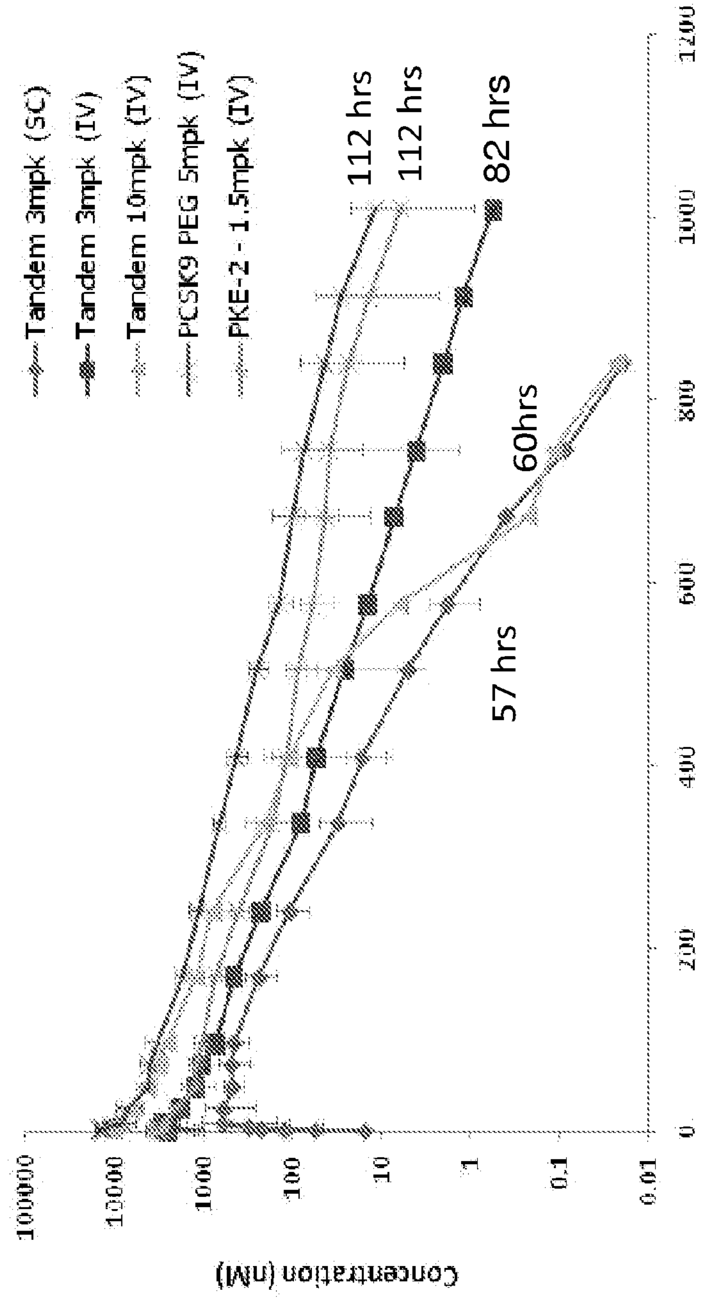
FIG. 10 is a graph showing the plasma PK profiles and half-lives of PKE2 Adnectin 2629_E06, PCSK9-PKE2 tandem 5190_E01 Adnectin, and PEGylated PCSK9 in cynomolgus monkeys.

Example 18: In Vivo Half-Life of PKE2 Mono-Adnectins and Tandem PCSK9-PKE2 Adnectins in Cynomolgus Monkeys Single dose PK/PD studies were conducted in normal lean female cynos with comparisons of the PCSK9-PKE2 tandem between the PKE2 monoAdnectin or a PEGylated PCSK9 Adnectin comparator at molar dose equivalents, as indicated by the shading in Table 17 below. PKE2 Adnectin 2629_E06 or PCSK9-PKE2 tandem 5190_E01 Adnectin, or a PEGylated PCSK9 Adnectin (referred to as ATI-1476) as a comparator, were administered to cynos at the indicated concentrations and routes (see Table 17 and FIG. 10), and blood plasma (K2EDTA) and serum samples were collected at time intervals for pharmacokinetic and pharmacodynamic assessment. Adnectin drug levels were measured in cyno plasma using the Mesoscale technology platform. 2629_E06 was captured via an anti-His mAb (BMS) and detected using cyno serum albumin bound to the Adnectin and an anti-cyno serum albumin sulfo-tagged secondary pAb. For tandem analyses, biotinylated human PCSK9 was used to capture the Adnectin and detection was via cyno albumin as described above. The PEGylated Adnectin ATI-1476 was captured via biotinylated hPCSK9 and detected via an anti-PEG mAb (Epitomics) in conjunction with a goat anti-rabbit sulfo-tagged pAb. Non-compartmental analyses were performed using Phoenix WinNonlin 6.3 (Pharsight Corporation, Mountain View, Calif.) using a plasma model and linear up/log down calculation method.

As shown in Table 17, the plasma half-life of 2629_E06 and ATI-1476 were equivalent at 112 hours. The half-life of 5190-E01 was shorter than that of the PKE2 monoAdnectin and ranged from 60-82 hr following intravenous administration. 5190_E01 exhibited dose proportional exposure between 3 and 10 mg/kg intravenous doses ($AUC_{ALL}$ ratio of 1.02). For all proteins tested, the volume of distribution was less than the plasma volume, suggesting that the distribution of the PCSK9-PKE2 tandem Adnectin and PEGylated Adnectin was primarily limited to the vascular space. Clearance was low in general and comparable across the various doses and formats. Subcutaneous bioavailability of the 5190_E01 tandem Adnectin was 41-49%.

TABLE 17

| Format | Dose | HL_Lambda_z (h) | Cl_obs (mL/h/kg) | Vss_obs (mL/kg) | AUCall (h*umol/L) | AUCINF_obs (h*umol/L) | AUC_%Extrap_obs (%) | MRTINF_obs (h) |
|---|---|---|---|---|---|---|---|---|
| PCSK9-PKE2 | 3 mg/kg SC | — | — | — | 92 ± 17 | 92 ± 17 | 0.54 ± 0.4 | — |
| tandem | 3 mg/kg IV | 82 ± 5.1 | 0.55 ± 0.03 | 57 ± 4.3 | 222 ± 24 | 234 ± 12 | 5.45 ± 5.4 | 104.6 ± 2.5 |
| 5190_E01 | 10 mg/kg IV | 60 ± 6.5 | 0.58 ± 0.09 | 50 ± 6.8 | 754 ± 98 | 769 ± 103 | 1.76 ± 1.4 | 87.3 ± 10.4 |
| PCSK9-PEG ATI-1476 | 5 mg/kg IV | 112 ± 7.6 | 0.46 ± 0.08 | 65 ± 10 | 1000 ± 14 | 1008 ± 14 | 0.70 ± 0.5 | 141.6 ± 7.6 |
| PKE2 2629_E06 | 1.5 mg/kg IV | 112 ± 7.3 | 0.37 ± 0.05 | 56 ± 5.2 | 305 ± 49 | 328 ± 45 | 6.92 ± 6.6 | 152 ± 8.2 |

Figure 11:
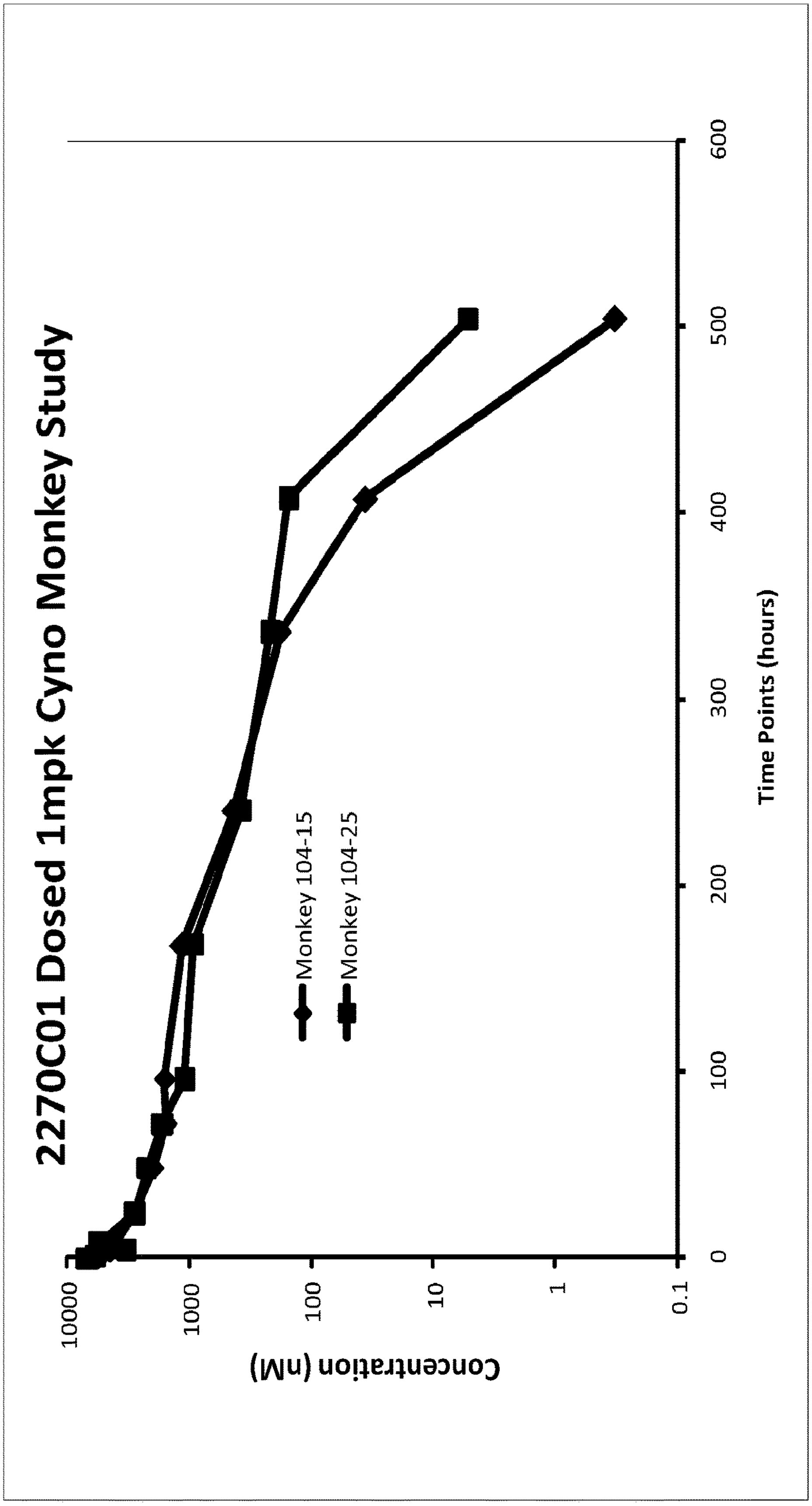
FIG. 11 is a graph showing the plasma half-life of PKE2 Adnectin 2270_C01 in cynomolgus monkeys.

The pharmacokinetics of parent 2270_C01 Adnectin was also tested in cynomolgus monkeys in a separate study. Adnectin drug levels were quantified as described above for the mouse PK studies. As shown in Table 18 and in FIG. 11, the 2270_C01 Adnectin had a half-life of 83.5 hours following a single IV bolus dose of 1 mg/kg.

TABLE 18

| | HL_Lambda_z (hr) | Vz_obs (mL/kg) | Cl_obs (mL/hr/kg) | AUCINF_obs (hr * nmol/L) | MRTINF_obs (hr) |
|---|---|---|---|---|---|
| N | 2 | 2 | 2 | 2 | 2 |
| Mean | 83.5 | 22.319 | 0.185 | 419981.536 | 102.847 |
| SD | 8.632 | 2.819 | 0.004 | 9680.781 | 1.888 |
| SE | 6.104 | 1.993 | 0.003 | 6845.346 | 1.335 |
| Min | 77.4 | 20.33 | 0.18 | 413136.19 | 101.51 |
| Max | 89.6 | 24.31 | 0.19 | 426826.88 | 104.18 |
| CV % | 10.3 | 12.6 | 2.3 | 2.3 | 1.8 |

Example 19: Tandem PCSK9-PKE2 Adnectin Functions as a PCSK9 Inhibitor in Cynomolgus Monkeys The cynomolgous monkey PK/PD study described above was evaluated for the pharmacodynamic effects of inhibiting PCSK9. Enzyme linked immunosorbance assays (ELISA) specific for cynomolgus PCSK9 were developed. The free (unbound) PCSK9 assay employed the MesoScale Discovery platform and incorporated streptavidin-pretreated 96-well MSD plates coated with 2 μg/mL of biotinylated PCSK9-Adnectin 2013_E01 as capturing reagent. Samples were diluted 1:4 with block and sulfo-tagged rabbit polyclonal anti-human PCSK9 IgG (BMS custom antibody produced by Lampire Biological Labs, Pipersville Pa.), added to wells and incubated for 10 minutes at room temperature. Wells were then washed and read using MSD 2× read buffer. The total PCSK9 ELISA assay was conducted similarly as described above except mAb-4H5 (BMS custom antibody produced by Lampire Biological Labs, Pipersville Pa.) was incorporated as the capture antibody and the detection step was performed separate from the capture step. The mAb-4H5 binds the C-terminal domain of PCSK9, and when bound to the 96-well plates efficiently captures total PCSK9 (both Adnectin-PCSK9 complex plus free PCSK9). The capture and detection steps for total PCSK9 were incubated for 1 hour. Standard curves were generated using purified recombinant human or cynomolgus PCSK9. Serum analytes were assayed on a Siemens Advia 1800 Clinical Chemistry System using standardized enzymatic procedures. LDL-cholesterol was assayed by the direct LDL method (Roche Diagnostics). Other analytes tested were: aspartate aminotransferase; alanine aminotransferase; alkaline phosphatase; gamma glutamyltransferase; total bilirubin; blood urea nitrogen; creatinine; total cholesterol; trigylceride; high density lipoprotein; low density lipoprotein; glucose; total protein; albumin; globulins; albumin/globulin ratio; calcium; inorganic phosphorus; sodium; potassium; chloride.

Figure 12:
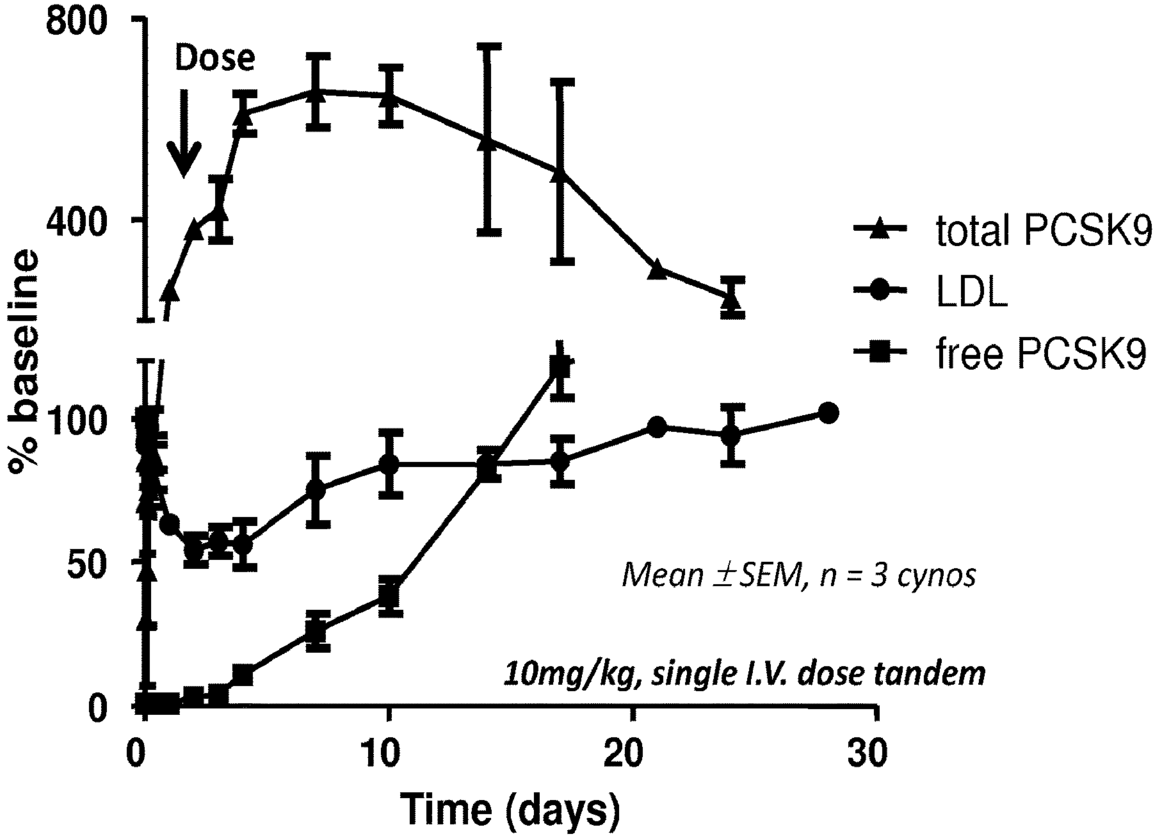
FIG. 12 is a graph showing the pharmacodynamic profile of LDL-c and PCSK9 in cynos following administration of the PCSK9-PKE2 tandem Adnectin 5190_E01 in cynomolgus monkeys. The profile demonstrates robust lowering of LDL-c, inhibition of free PCSK9 and an increase in total PCSK9, all of which return to baseline by the end of the study.
Figure 13:
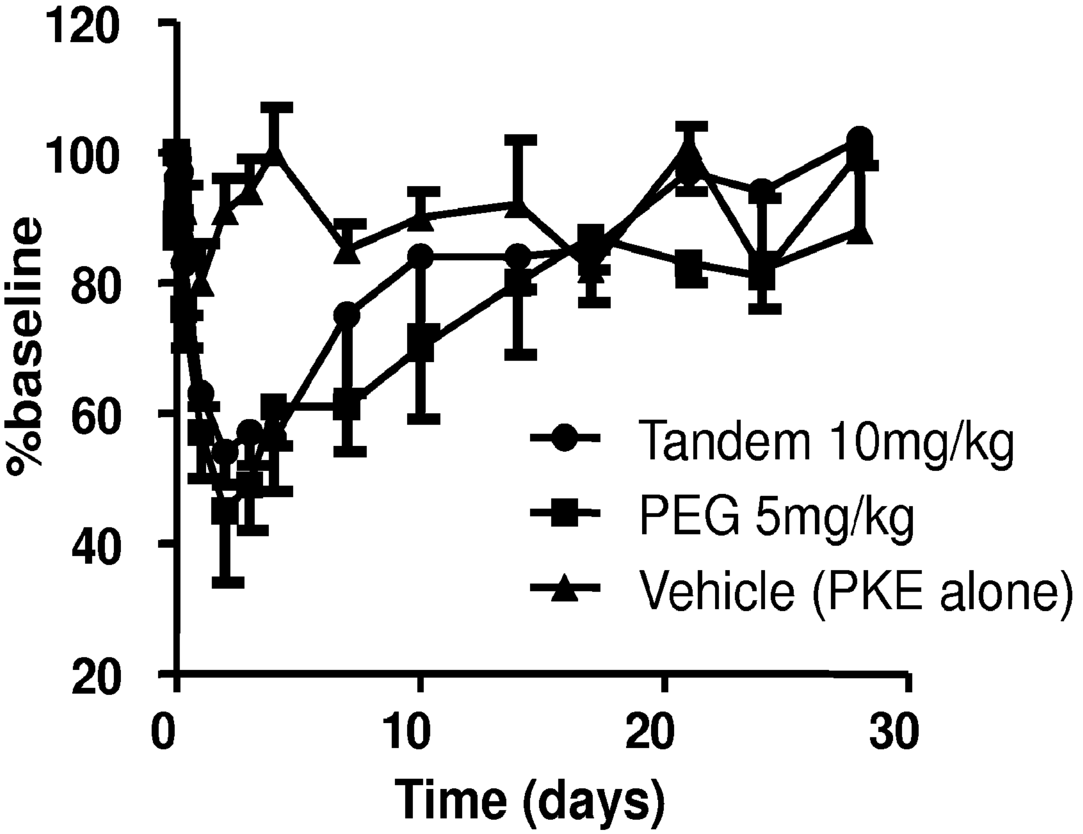
FIG. 13 is a graph showing the LDL-c lowering effects of PCSK9-PKE2 tandem Adnectin 5190_E01 and a PEGylated PCSK9 Adnectin comparator, along with the 2629_E06 PKE2 control in cynomolgus monkeys.

As shown in FIG. 12, 5190_E01 elicited the pharmacodynamic effects on unbound/free PCSK9, total PCSK9 and LDL-c that have been previously observed with other PCSK9 Adnectin inhibitors. Specifically, rapid target engagement was observed in which free PCSK9 plummets to non-detectable levels within 1 hour of dosing. LDL-c was lowered to ~50% baseline as a result of PCSK9 inhibition, with maximum inhibition being observed in the 2-5 day time frame. Additionally, total PCSK9 rises as the PCSK9-PKE2 Adnectin:PCSK9 complex accumulates. Upon complex dissociation and drug clearance, PCSK9 and LDL-c levels return to baseline ~15 days into the study. A similar trend is observed with the PEGylated PCSK9 Adnectin comparator. As shown in FIG. 13, 5190_E01 exhibited similar robust LDL-c lowering at 10 mg/kg as the molar dose equivalent of the PEGylated PCSK9 Adnectin comparator.

Example 20: Dose Dependency in PCSK9 Target Engagement

Figure 14:
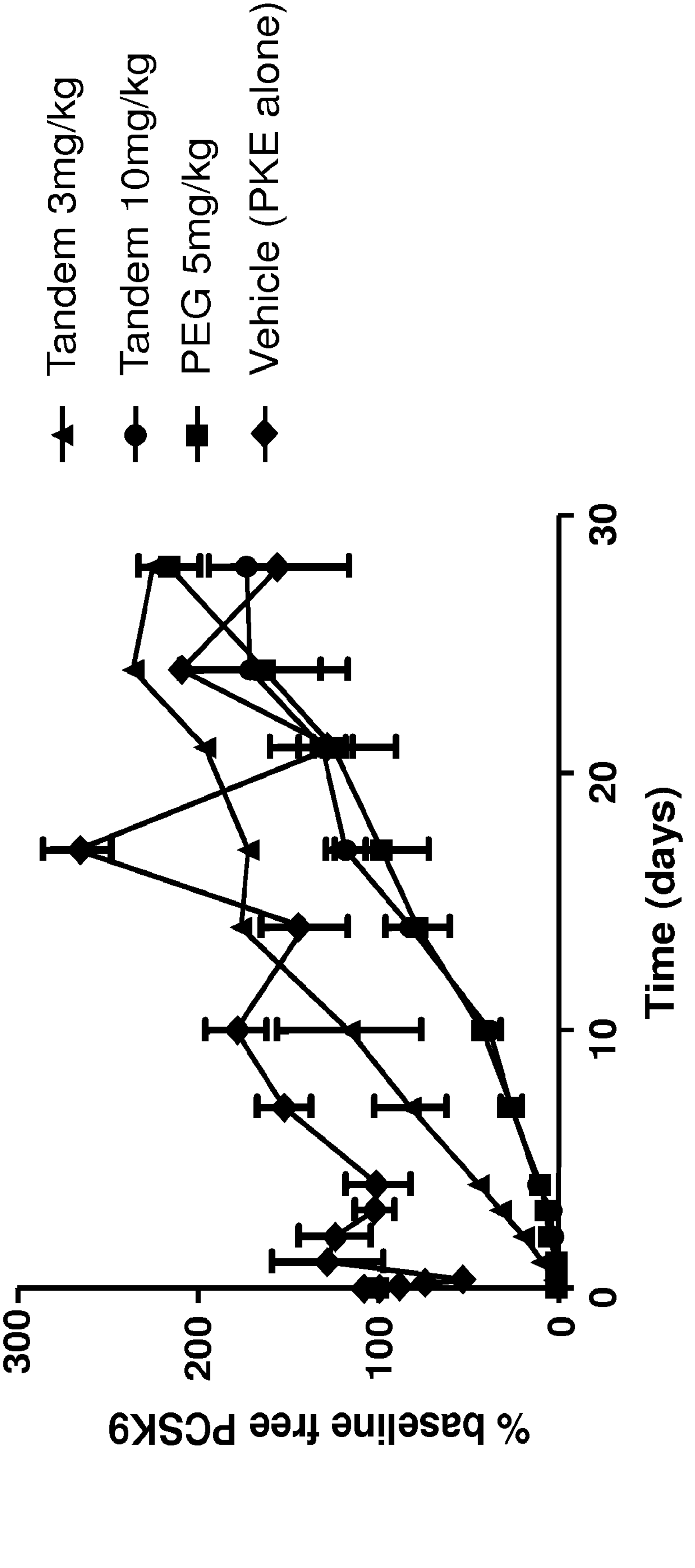
FIG. 14 shows target engagement by the tandem PCSK9-PKE2 Adnectin at two different concentrations compared to PEGylated PCSK9 adnectin and PKE2 Adnectin 2629_E06 in cynomolgus monkeys.

A dose dependent response of free PCSK9 inhibition was observed in the 3 and 10 mg/kg doses of the 5190_E01 as shown in FIG. 14. The 10 mg/kg dose exhibits a longer duration of PCSK9 target engagement than the 3 mg/kg dose. This figure also illustrates equivalent PCSK9 target engagement for the molar dose equivalents of the tandem and PEGylated Adnectins. As expected, 2629_E06 does not modulate free PCSK9; any observed variation in free PCSK9 is likely due to diurnal rhythms and baseline variability.

Figure 15:
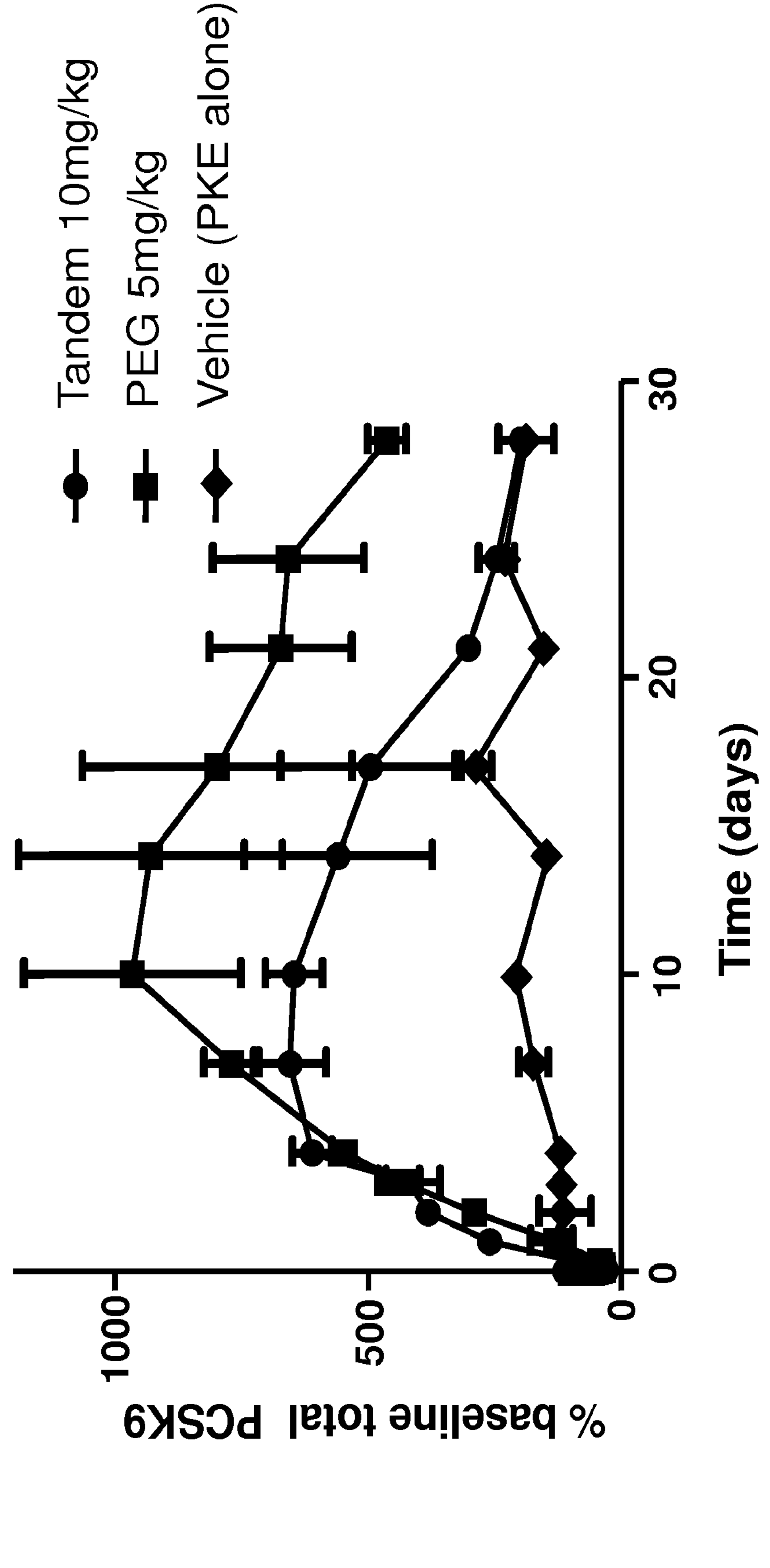
FIG. 15 shows total PCSK9 levels over time in cynomolgus monkeys after administration of the tandem PCSK9-PKE2 Adnectin, pegylated PCSK9 adnectin or PKE2 Adnectin 2629_E06.

FIG. 15 illustrates the difference in effects of the tandem and PEGylated PCSK9 Adnectins on total PCSK9. Although the general trend is the same, total PCSK9 peaks and returns to baseline more quickly in the 5190_E01 dosed cynos relative to the PEGylated PCSK9 Adnectin comparator, suggesting different clearance mechanisms for the PCSK9: Adnectin drug complex depending on the PK enhancement method employed (renal clearance for the tandem vs. macrophage uptake for the PEGylated Adnectin). Again, 2629_E06 shows no pharmacodynamic effect in this assay as expected.

Example 21: Tandem Format Exhibits Equivalent In Vitro Immunogenicity Response Relative to Components In vitro assessment of potential immunogenicity was evaluated for several tandem PCSK9-PKE2 Adnectins using the T-cell proliferation assay, as described in Example 8.

Figure 16:
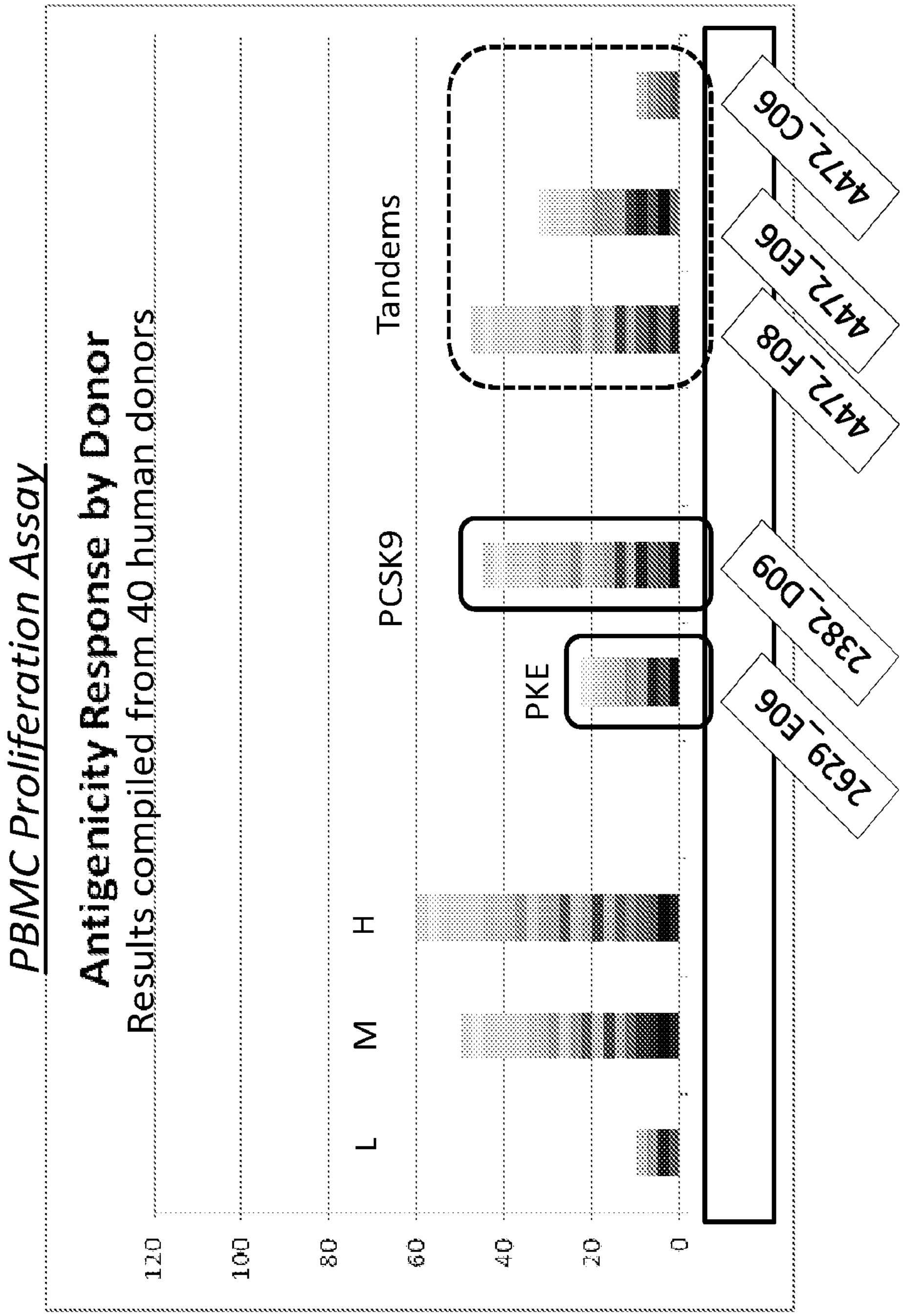
FIG. 16 is a graph depicting T-cell proliferation results for the percent and strength of proliferative responses for the PCSK9-PKE2 tandem Adnectins 4472_F08, 4472_E06, and 4472_C06, as well as the component PKE2 Adnectin 2629_E06 and the component PCSK9 Adnectin 2382_D09. The bars on the far left of the graph correspond to control proteins with low, medium, and high antigenicity.

As shown in FIG. 16, the percentage and magnitude of the immunogenicity response to tandem Adnectins is similar to the mono-Adnectin components (i.e., PCSK9 or PKE2; middle of FIG. 16). These results suggest minimal/no additional immunogenicity risk of tandem Adnectins vs. mono-Adnectins. Additionally, differences in the proliferative response to the tandems are observed as a function of linker sequence joining the PCSK9 and PKE2 Adnectins. Relative to 4472_F08 and 4472_E06 tandem PCSK9-PKE2 Adnectins, the 4472_C06 tandem Adnectin showed the lowest immunogenicity. One potential mechanism for these observed differences could be differences in protein processing by the T-cells in response to the linker sequences.

A summary of the properties of 4472_C06 is presented in Table 19 below.

TABLE 19

| Property | System | 4472_C06 |
|---|---|---|
| Molecular Weight | | 25 kD protein |
| Biophysical | Thermal stability, $T_m$ | 55° C. |
| | Monomericity | >99% |
| PCSK9 $K_D$ (37° C.) | Human, cyno | 0.14 nM, 39 nM (core, Octet Red) |
| Albumin $K_D$ (37° C.) | Human, cyno, mouse, rat | 57 nM, 51 nM, 43 nM, 200 nM |
| Biochemical Activity | PCSK9:EGFA FRET, human | 1.5 nM |
| Cell-based Activity | PCSK9 Uptake | 19 nM (core) 21 nM (tandem) |
| | LDLR Depletion | 9.4 nM (tandem) |
| Predicted immunogenicity | PBMC proliferation | Mid/low (core tandem) |
| | Epimatrix | Low |
| | WT 10Fn3 seq content | Higher |
| PK | Transgenic or WT mouse | 17-24 hr |
| | Cynomolgus monkey | 82 hr |
| Viscosity | At required concentration | Low |

EXEMPLARY EMBODIMENTS

1. A polypeptide comprising a fibronectin type III tenth domain ($^{10}$Fn3) wherein the $^{10}$Fn3 domain comprises a) AB, BC, CD, DE, EF, and FG loops, b) a CD loop with an altered amino acid sequence relative to the sequence of the corresponding CD loop of the human $^{10}$Fn3 domain, and c) wherein the polypeptide binds to human serum albumin with a $K_D$ of less than 500 nM.

2. The polypeptide of embodiment 1, wherein the $^{10}$Fn3 domain further binds to one or more of rhesus serum albumin, cynomolgus serum albumin, mouse serum albumin, and rat serum albumin.

3. The polypeptide of embodiment 2, wherein the $^{10}$Fn3 domain binds to rhesus serum albumin and cynomolgus serum albumin.

4. The polypeptide of embodiment 3, wherein the $^{10}$Fn3 domain binds rhesus serum albumin and cynomolgus serum albumin with a $K_D$ of less than 500 nM.

5. The polypeptide of embodiment 4, wherein the $^{10}$Fn3 domain binds rhesus serum albumin and cynomolgus serum albumin with a $K_D$ of less than 100 nM.

6. The polypeptide of embodiment 5, wherein the $^{10}$Fn3 domain binds rhesus serum albumin and cynomolgus serum albumin with a $K_D$ of less than 10 nM.

7. The polypeptide of any of the preceding embodiments, wherein the $^{10}$Fn3 domain binds to mouse and rat serum albumin.

8. The polypeptide of embodiment 7, wherein the $^{10}$Fn3 domain binds rhesus serum albumin and cynomolgus serum albumin with a $K_D$ of less than 500 nM.

9. The polypeptide of embodiment 8, wherein the $^{10}$Fn3 domain binds rhesus serum albumin and cynomolgus serum albumin with a $K_D$ of less than 100 nM.

10. The polypeptide of embodiment 9, wherein the $^{10}$Fn3 domain binds rhesus serum albumin and cynomolgus serum albumin with a $K_D$ of less than 10 nM.

11. The polypeptide of any one of the preceding embodiments, wherein the $^{10}$Fn3 domain binds to serum albumin at a pH range of 5.5 to 7.4.

12. The polypeptide of any one of the preceding embodiments, wherein the $^{10}$Fn3 domain binds to domain I-II of HSA.

13. The polypeptide of any one of the preceding embodiments, wherein the serum half-life of the polypeptide in the presence of human serum albumin is at least 30 hours.

14. The polypeptide of any one of the preceding embodiments, wherein the CD loop comprises an amino acid sequence according to the formula G-$X_1$-$X_2$-V-$X_3$-$X_4$-$X_5$-S-$X_6$-$X_7$-G-$X_8$-$X_9$-Y-$X_{10}$-$X_{11}$-$X_{12}$-E, wherein, (a) $X_1$ is selected from the group consisting of R or W;

(b) $X_2$ is selected from the group consisting of H, E, D, Y, or Q;

(c) $X_3$ is selected from the group consisting of Q or H;

(d) $X_4$ is selected from the group consisting of I, K, M, Q, L, or V;

(e) $X_5$ is selected from the group consisting of Y, F, or N;

(f) $X_6$ is selected from the group consisting of D, V, or E;

(g) $X_7$ is selected from the group consisting of L, W, or F;

(h) $X_8$ is selected from the group consisting of P or T;

(i) $X_9$ is selected from the group consisting of L or M;

(j) $X_{10}$ is selected from the group consisting of I or V;

(k) $X_{11}$ is selected from the group consisting of Y or F; and (l) $X_{12}$ is selected from the group consisting of T, S, Q, N, or A.

15. The polypeptide of embodiment 14, wherein:

(a) $X_1$ is R;

(b) $X_2$ is E;

(c) $X_3$ is Q;

(d) $X_4$ is K;

(e) $X_5$ is Y;

(f) $X_6$ is D;

(g) $X_7$ is L or W;

(h) $X_8$ is P;

(i) $X_9$ is L;

(j) $X_{10}$ is I;

(k) $X_{11}$ is Y; and (l) $X_{12}$ is Q or N.

16. The polypeptide of embodiment 15, wherein $X_{10}$ is L and $X_{12}$ is Q.

17. The polypeptide of embodiment 15, wherein $X_{10}$ is W and $X_{12}$ is N.

18. The polypeptide of embodiment 14, wherein the CD loop comprises an amino acid sequence selected from the group consisting of SEQ ID NOs: 101-125.

19. The polypeptide of any one of the preceding embodiments, wherein the CD loop comprises the amino acid sequence set forth in SEQ ID NO: 106.

20. The polypeptide of any one of the preceding embodiments, wherein the CD loop comprises the amino acid sequence set forth in SEQ ID NO: 113.

21. A polypeptide of any one of the preceding embodiments, wherein the polypeptide comprises an amino acid sequence at least 80%, 85%, 90%, 95%, 96%, 97%, 98%, 99% or 100% identical to the non-CD loop regions of SEQ ID NOs: 23-100, 184-209 and 235-260.

22. The polypeptide of any one of the preceding embodiments, wherein the polypeptide comprises an amino acid sequence that is at least 80%, 85%, 90%, 95%, 96%, 97%, 98%, 99% or 100% identical to any one of SEQ ID NOs: 23-100, 184-209 and 235-260.

23. A fusion polypeptide comprising a fibronectin type III tenth ($^{10}$Fn3) domain and a heterologous protein, wherein the $^{10}$Fn3 domain comprises a) AB, BC, CD, DE, EF, and FG loops, b) a CD loop with an altered amino acid sequence relative to the sequence of the corresponding loop of the human $^{10}$Fn3 domain, and c) wherein the polypeptide binds to human serum albumin with a $K_D$ of less than 500 nM.

24. The fusion polypeptide of embodiment 23, wherein the $^{10}$Fn3 domain comprises an amino acid sequence at least 70%, 75%, 80%, 85%, 90%, 95%, 96%, 97%, 98%, 99% or 100% identical to any one of SEQ ID NOs: 23-100, 184-209 and 235-260.

25. The fusion polypeptide of embodiment 24, wherein the $^{10}$Fn3 domain comprises an amino acid sequence at least 70%, 75%, 80%, 85%, 90%, 95%, 96%, 97%, 98%, 99% or 100% identical to SEQ ID NO: 55, 81, 190 or 241.

26. The fusion polypeptide of embodiment 25, wherein the $^{10}$Fn3 domain comprises an amino acid sequence of SEQ ID NO: 55, 81,190 or 241.

27. The fusion polypeptide of embodiment 24, wherein the $^{10}$Fn3 domain comprises an amino acid sequence at least 70%, 75%, 80%, 85%, 90%, 95%, 96%, 97%, 98%, 99% or 100% identical to SEQ ID NO: 62, 88, 197 or 248.

28. The fusion polypeptide of embodiment 27, wherein the $^{10}$Fn3 domain comprises an amino acid sequence of SEQ ID NO: 62, 88, 197 or 248.

29. The fusion polypeptide of embodiment 23, wherein the heterologous protein is a therapeutic moiety.

30. The fusion polypeptide of embodiment 23, wherein the heterologous protein is a polypeptide comprising a $^{10}$Fn3 domain.

31. The fusion polypeptide of embodiment 30, wherein the $^{10}$Fn3 domain binds to a target protein other than serum albumin.

32. The fusion polypeptide of embodiment 31, wherein the $^{10}$Fn3 domain binds to PCSK9.

33. The fusion polypeptide of embodiment 32, wherein the $^{10}$Fn3 domain comprises an amino acid sequence at least 70%, 75%, 80%, 85%, 90%, 95%, 96%, 97%, 98%, 99% or 100% identical to SEQ ID NO: 167.

34. The fusion polypeptide of embodiment 33, wherein the $^{10}$Fn3 domain comprises the amino acid sequence of SEQ ID NO: 167.

35. The fusion polypeptide of embodiment 23, wherein the fusion polypeptide comprises an amino acid sequence at least 70%, 75%, 80%, 85%, 90%, 95%, 96%, 97%, 98%, 99% or 100% identical to SEQ ID NO: 168, 169 or 261.

36. The fusion polypeptide of embodiment 35, wherein the fusion polypeptide comprises the amino acid sequence set forth in SEQ ID NO 168, 169 or 261.

37. The fusion polypeptide of any one of embodiments 23-36, wherein the serum half-life of the polypeptide in the presence of mouse serum albumin is at least 10 hours.

38. The fusion polypeptide of any one of embodiments 23-36, wherein the serum half-life of the polypeptide in the presence of cynomolgus serum albumin is at least 50 hours.

39. A polypeptide comprising an amino acid sequence selected from the group consisting of SEQ ID NOs: 23-125, 184-209 and 235-260, 168, and 169.

40. A composition comprising a polypeptide of any one of the preceding embodiments and a carrier.

41. An isolated nucleic acid molecule encoding the polypeptide of any one of embodiments 1-39.

42. The isolated nucleic acid molecule of embodiment 41, wherein the nucleic acid molecule has a sequence selected from the group consisting of SEQ ID NOs: 126-151 and 172 or a nucleotide sequence that is at least 70%, 75%, 80%, 85%. 90%, 95%, 96%, 97%, 98%, or 99% identical thereto.

43. An expression vector comprising the nucleotide sequence of embodiments 41 or 42.

44. A cell comprising a nucleic acid molecule of embodiment 41 or 42 or an expression vector of embodiment 43.

45. A method of producing the polypeptides of any one of embodiments 1-39 comprising culturing the cell of embodiment 44 under conditions suitable for expressing the polypeptide, and purifying the polypeptide.

TABLE 20

SUMMARY OF SEQUENCES

| SEQ ID | Description | Sequence |
|---|---|---|
| 1 | Wild-type human $^{10}$Fn3 domain | VSDVPRDLEVVAATPTSLLISW**DAPAVTVR**YYRITYGETGGNSPVQEF TV**PGSKST**ATISGLKPGVDYTITVYAV**TGRGDSPASSKP**ISINYRT |
| 2 | Wild-type human $^{10}$Fn3 domain w/ loop sequences generically defined | VSDVPRDLEVVAA(X)$_u$LLISW(X)$_v$YYRITY(X)$_w$FTV(X)$_x$ATISGL (X)$_y$YTITVYAV(X)$_z$ISINYRT |
| 3 | N-terminal leader | MGVSDVPRDL |
| 4 | N-terminal leader | GVSDVPRDL |
| 5 | N-terminal leader | $X_n$SDVPRDL |
| 6 | N-terminal leader | $X_n$DVPRDL |
| 7 | N-terminal leader | $X_n$VPRDL |
| 8 | N-terminal leader | $X_n$PRDL |
| 9 | N-terminal leader | $X_n$RDL |

TABLE 20-continued

| SUMMARY OF SEQUENCES | | |
|---|---|---|
| SEQ ID | Description | Sequence |
| 10 | N-terminal leader | $X_n$DL |
| 11 | N-terminal leader | MASTSG |
| 12 | C-terminal tail | EIEK |
| 13 | C-terminal tail | EGSGC |
| 14 | C-terminal tail | EIEKPCQ |
| 15 | C-terminal tail | EIEKPSQ |
| 16 | C-terminal tail | EIEKP |
| 17 | C-terminal tail | EIEKPS |
| 18 | C-terminal tail | EIEKPC |
| 19 | C-terminal tail | EIDK |
| 20 | C-terminal tail | EIDKPCQ |
| 21 | C-terminal tail | EIDKPSQ |
| 22 | 6X His tail | HHHHHH |
| 23 | PKE2 Adnectin 2270_C01 (amino acid sequence) | MASTSGVPRDLEVVAATPTSLLISWDAPAVTVRYYRITYGWQVQMYSD<br>WGPLYIYKEFTVPGSKSTATISGLKPGVDYTITVYAVTGSGESPASSK<br>PISINYRTEGDKPSQHHHHHH |
| 24 | PKE2 Adnectin 2629_A09 (amino acid sequence) | MGVSDVPRDLEVVAATPTSLLISWDAPAVTVRYYRITYGRHVQIYSDL<br>GPLYIYTEFTVPGSKSTATISGLKPGVDYTITVYAVTGSGESPASSKP<br>ISINYRTEIDKPSQHHHHHH |
| 25 | PKE2 Adnectin 2629_A11 (amino acid sequence) | MGVSDVPRDLEVVAATPTSLLISWDAPAVTVRYYRITYGRHVHIYSDW<br>GPMYIYTEFTVPGSKSTATISGLKPGVDYTITVYAVTGSGESPASSKP<br>ISINYRTEIDKPSQHHHHHH |
| 26 | PKE2 Adnectin 2629_C10 (amino acid sequence) | MGVSDVPRDLEVVAATPTSLLISWDAPAVTVRYYRITYGREVQKYSVL<br>GPLYIYTEFTVPGSKSTATISGLKPGVDYTITVYAVTGSGESPASSKP<br>ISINYRTEIDKPSQHHHHHH |
| 27 | PKE2 Adnectin 2629_D09 (amino acid sequence) | MGVSDVPRDLEVVAATPTSLLISWDAPAVTVRYYRITYGREVQMYSDL<br>GPLYVYSEFTVPGSKSTATISGLKPGVDYTITVYAVTGSGESPASSKP<br>ISINYRTEIDKPSQHHHHHH |
| 28 | PKE2 Adnectin 2629_E05 (amino acid sequence) | MGVSDVPRDLEVVAATPTSLLISWDAPAVTVRYYRITYGREVQKFSDW<br>GPLYIYTEFTVPGSKSTATISGLKPGVDYTITVYAVTGSGESPASSKP<br>ISINYRTEIDKPSQHHHHHH |
| 29 | PKE2 Adnectin 2629_E06 (amino acid sequence) (also referred to as ATI-1490) | MGVSDVPRDLEVVAATPTSLLISWDAPAVTVRYYRITYGREVQKYSDL<br>GPLYIYQEFTVPGSKSTATISGLKPGVDYTITVYAVTGSGESPASSKP<br>ISINYRTEIDKPSQHHHHHH |
| 30 | PKE2 Adnectin 2629 F04 (amino acid sequence) | MGVSDVPRDLEVVAATPTSLLISWDAPAVTVRYYRITYGREVHQYSDW<br>GPMYIYNEFTVPGSKSTATISGLKPGVDYTITVYAVTGSGESPASSKP<br>ISINYRTEIDKPSQHHHHHH |
| 31 | PKE2 Adnectin 2629_H01 (amino acid sequence) | MGVSDVPRDLEVVAATPTSLLISWDAPAVTVXYYRITYGREVHKNSDW<br>GTLYIYTEFTVPGSKSTATISGLKPGVDYTITVXAVTGSGEXPASSKP<br>ISINYRTEIDKXSQHHHHHH |
| 32 | PKE2 Adnectin 2629_H06 (amino acid sequence) | MGVSDVPRDLEVVAATPTSLLISWDAPAVTVRYYRITYGREVQKYSDL<br>GPLYIYAEFTVPGSKSTATISGLKPGVDYTITVYAVTGSGESPASSKP<br>ISINYRTEIDKPSQHHHHHH |
| 33 | PKE2 Adnectin 2629_H07 (amino acid sequence) | MGVSDVPRDLEVVAATPTSLLISWDAPAVTVRYYRITYGREVHLYSDW<br>GPMYIYTEFTVPGSKSTATISGLKPGVDYTITVYAVTGSGESPASSKP<br>ISINYRTEIDKPSQHHHHHH |

TABLE 20-continued

SUMMARY OF SEQUENCES

| SEQ ID | Description | Sequence |
|---|---|---|
| 34 | PKE2 Adnectin 2630_A02 (amino acid sequence) | MGVSDVPRDLEVVATTPTSLLISWDAPAVTVRYYRITYGRHVQMYSDLGPLYIFSEFTVPGSKSTATISGLKPGVDYTITVYAVTGSGESPASSKPISINYRTEIDKPSQHHHHHH |
| 35 | PKE2 Adnectin 2630_A11 (amino acid sequence) | MGVSDVPRDLEVVAATPTSLLISWDAPAVTVRYYRITYGREVHMYSDFGPMYIYTEFTVPGSKSTATISGLKPGVDYTITVYAVTGSGESPASSKPISINYRTEIDKPSQHHHHHH |
| 36 | PKE2 Adnectin 2630_D02 (amino acid sequence) | MGVSDVPRDLEVVAATPTSLLISWDAPAVTVRYYRITYGREVQKYSDWGPLYIYNEFTVPGSKSTATISGLKPGVDYTITVYAVTGSGESPASSKPISINYRTEIDKPSQHHHHHH |
| 37 | PKE2 Adnectin 2630_D10 (amino acid sequence) | MGVSDVPRDLEVVAATPTSLLISWDAPAVTVRYYRITYGREVQMYSDLGPLYIYNEFTVPGSKSTATISGLKPGVDYTITVYAVTGSGESPASSKPISINYRTEIDKPSQHHHHHH |
| 38 | PKE2 Adnectin 2630_F04 (amino acid sequence) | MGVSDVPRDLEVVAATPTSLLISWDAPAVTVRYYRITYGREVQMYSDLGPLYIYTEFTVPGSKSTATISGLKPGVGYTITVYAVTGSGESPASSKPISINYRTEIDKPSQHHHHHH |
| 39 | PKE2 Adnectin 2630_G03 (amino acid sequence) | MGVSDVPRDLEVVAATPTSLLISWDAPAVTVRYYRITYGRHVQIYSDLGPLYIYNEFTVPGSKSTATISGLKPGVDYTITVYAVTGSGESPASSKPISINYRTEIDKPSQHHHHHH |
| 40 | PKE2 Adnectin 2630_G10 (amino acid sequence) | MGVSDVPRDLEVVAATPTSLLISWDAPAVTVRYYRITYGREVQIYSDWGPLYIYNEFTVPGSKSTATISGLKPGVDYTITVYAVTGSGESPASSKPISINYRTEIDKPSQHHHHHH |
| 41 | PKE2 Adnectin 2630_H03 (amino acid sequence) | MGVSDVPRDLEVVAATXTSLLISWDAPAVTVXYYRITYGREVQKYSDWGPLYIYQEFTVPGSXSTATISGLKPGVDYTITVYAVTGSGESPASSKPISINYRTEIDKXSQHHHHHH |
| 42 | PKE2 Adnectin 2631_B04 (amino acid sequence) | MGVSDVPRDLEVVAATPTSLLISWDVPAVTVRYYRITYGRHVHLYSEFGPMYIYNEFTVPGSKSTATISGLKPGVDYTITVYAVTGSGESPASSKPISINYRTEIDKPSQHHHHHH |
| 43 | PKE2 Adnectin 2631_E03 (amino acid sequence) | MGVSDVPRDLEVVAATPTSLLISWDAPAVTVRYYRITYGRDVHMYSDWGPMYIYQEFTVPGSKSTATISGLKPGVDYTITVYAVTGSGESPASSKPISINYRTEIDKPSQHHHHHH |
| 44 | PKE2 Adnectin 2631_G01 (amino acid sequence) | MGVSDVPRDLEVVAATPTSLLISWDAPAVTVRYYRITYGRHVQIYSDWGPLYIYNEFTVPGSKSTATISGLKPGVDYTITVYAVTGSGESPASSKPISINYRTEIDKPSQHHHHHH |
| 45 | PKE2 Adnectin 2631_G03 (amino acid sequence) | MGVSDVPRDLEVVAATPTSLLISWDAPAVTVRYYRITYGRYVQLYSDWGPMYIYTEFTVPGSKSTATISGLKPGVDYTITVYAVTGSGESPASSKPISINYRTEIDKPSQHHHHHH |
| 46 | PKE2 Adnectin 2631_H09 (amino acid sequence) | MGVSDVPRDLEVVAATPTSLLISWDAPAVTVRYYRITYGRQVQVFSDLGPLYIYNEFTVPGSKSTATISGLKPGVDYTITVYAVTGSGESPASSKPISINYRTEIDKPSQHHHHHH |
| 47 | PKE2 Adnectin 2632_G01 (amino acid sequence) | MGVSDVPRDLEVVAATPTSLLISWDAPAVTVRYYRITYGRQVQIYSDWGPLYIYNEFTVPGSKSTATISGLKPGVDYTITVYAVTGSGESPASSKPISINYRTEIDKPSQHHHHHH |
| 48 | PKE2 Adnectin 4079_A04 (amino acid sequence) | MGVSDVPRDLEVVAATPTSLLISWDAPAVTVRYYRITYGRQVQMYSDWGPLYIYAEFTVPGSKSTATISGLKPGVDYTITVYAVTGSGESPASSKPISINYRTEIDKPSQHHHHHH |
| 49 | 2270_C01 w/o his tag (amino acid sequence) | MASTSGVPRDLEVVAATPTSLLISWDAPAVTVRYYRITYGWQVQMYSDWGPLYIYKEFTVPGSKSTATISGLKPGVDYTITVYAVTGSGESPASSKPISINYRTEGDKPSQ |
| 50 | 2629_A09 w/o his tag (amino acid sequence) | MGVSDVPRDLEVVAATPTSLLISWDAPAVTVRYYRITYGRHVQIYSDLGPLYIYTEFTVPGSKSTATISGLKPGVDYTITVYAVTGSGESPASSKPISINYRTEIDKPSQ |
| 51 | 2629_A11 w/o his tag (amino acid sequence) | MGVSDVPRDLEVVAATPTSLLISWDAPAVTVRYYRITYGRHVHIYSDWGPMYIYTEFTVPGSKSTATISGLKPGVDYTITVYAVTGSGESPASSKPISINYRTEIDKPSQ |
| 52 | 2629_C10 w/o his tag (amino acid sequence) | MGVSDVPRDLEVVAATPTSLLISWDAPAVTVRYYRITYGREVQKYSVLGPLYIYTEFTVPGSKSTATISGLKPGVDYTITVYAVTGSGESPASSKPISINYRTEIDKPSQ |

TABLE 20-continued

SUMMARY OF SEQUENCES

| SEQ ID | Description | Sequence |
|---|---|---|
| 53 | 2629_D09 w/o his tag (amino acid sequence) | MGVSDVPRDLEVVAATPTSLLISWDAPAVTVRYYRITYGREVQMYSDL GPLYVYSEFTVPGSKSTATISGLKPGVDYTITVYAVTGSGESPASSKP ISINYRTEIDKPSQ |
| 54 | 2629_E05 w/o his tag (amino acid sequence) | MGVSDVPRDLEVVAATPTSLLISWDAPAVTVRYYRITYGREVQKFSDW GPLYIYTEFTVPGSKSTATISGLKPGVDYTITVYAVTGSGESPASSKP ISINYRTEIDKPSQ |
| 55 | 2629_E06 w/o his tag (amino acid sequence) | MGVSDVPRDLEVVAATPTSLLISWDAPAVTVRYYRITYGREVQKYSDL GPLYIYQEFTVPGSKSTATISGLKPGVDYTITVYAVTGSGESPASSKP ISINYRTEIDKPSQ |
| 56 | 2629_F04 w/o his tag (amino acid sequence) | MGVSDVPRDLEVVAATPTSLLISWDAPAVTVRYYRITYGREVHQYSDW GPMYIYNEFTVPGSKSTATISGLKPGVDYTITVYAVTGSGESPASSKP ISINYRTEIDKPSQ |
| 57 | 2629_H01 w/o his tag (amino acid sequence) | MGVSDVPRDLEVVAATPTSLLISWDAPAVTVXYYRITYGREVHKNSDW GTLYIYTEFTVPGSKSTATISGLKPGVDYTITVXAVTGSGEXPASSKP ISINYRTEIDKXSQ |
| 58 | 2629_H06 w/o his tag (amino acid sequence) | MGVSDVPRDLEVVAATPTSLLISWDAPAVTVRYYRITYGREVQKYSDL GPLYIYAEFTVPGSKSTATISGLKPGVDYTITVYAVTGSGESPASSKP ISINYRTEIDKPSQ |
| 59 | 2629_H07 w/o his tag (amino acid sequence) | MGVSDVPRDLEVVAATPTSLLISWDAPAVTVRYYRITYGREVHLYSDW GPMYIYTEFTVPGSKSTATISGLKPGVDYTITVYAVTGSGESPASSKP ISINYRTEIDKPSQ |
| 60 | 2630_A02 w/o his tag (amino acid sequence) | MGVSDVPRDLEVVATTPTSLLISWDAPAVTVRYYRITYGRHVQMYSDL GPLYIFSEFTVPGSKSTATISGLKPGVDYTITVYAVTGSGESPASSKP ISINYRTEIDKPSQ |
| 61 | 2630_A11 w/o his tag (amino acid sequence) | MGVSDVPRDLEVVAATPTSLLISWDAPAVTVRYYRITYGREVHMYSDF GPMYIYTEFTVPGSKSTATISGLKPGVDYTITVYAVTGSGESPASSKP ISINYRTEIDKPSQ |
| 62 | 2630_D02 w/o his tag (amino acid sequence) | MGVSDVPRDLEVVAATPTSLLISWDAPAVTVRYYRITYGREVQKYSDW GPLYIYNEFTVPGSKSTATISGLKPGVDYTITVYAVTGSGESPASSKP ISINYRTEIDKPSQ |
| 63 | 2630_D10 w/o his tag (amino acid sequence) | MGVSDVPRDLEVVAATPTSLLISWDAPAVTVRYYRITYGREVQMYSDL GPLYIYNEFTVPGSKSTATISGLKPGVDYTITVYAVTGSGESPASSKP ISINYRTEIDKPSQ |
| 64 | 2630_F04 w/o his tag (amino acid sequence) | MGVSDVPRDLEVVAATPTSLLISWDAPAVTVRYYRITYGREVQMYSDL GPLYIYTEFTVPGSKSTATISGLKPGVGYTITVYAVTGSGESPASSKP ISINYRTEIDKPSQ |
| 65 | 2630_G03 w/o his tag (amino acid sequence) | MGVSDVPRDLEVVAATPTSLLISWDAPAVTVRYYRITYGRHVQIYSDL GPLYIYNEFTVPGSKSTATISGLKPGVDYTITVYAVTGSGESPASSKP ISINYRTEIDKPSQ |
| 66 | 2630_G10 w/o his tag (amino acid sequence) | MGVSDVPRDLEVVAATPTSLLISWDAPAVTVRYYRITYGREVQIYSDW GPLYIYNEFTVPGSKSTATISGLKPGVDYTITVYAVTGSGESPASSKP ISINYRTEIDKPSQ |
| 67 | 2630_H03 w/o his tag (amino acid sequence) | MGVSDVPRDLEVVAATXTSLLISWDAPAVTVXYYRITYGREVQKYSDW GPLYIYQEFTVPGSXSTATISGLKPGVDYTITVYAVTGSGESPASSKP ISINYRTEIDKXSQ |
| 68 | 2631_B04 w/o his tag (amino acid sequence) | MGVSDVPRDLEVVAATPTSLLISWDVPAVTVRYYRITYGRHVHLYSEF GPMYIYNEFTVPGSKSTATISGLKPGVDYTITVYAVTGSGESPASSKP ISINYRTEIDKPSQ |
| 69 | 2631_E03 w/o his tag (amino acid sequence) | MGVSDVPRDLEVVAATPTSLLISWDAPAVTVRYYRITYGRDVHMYSDW GPMYIYQEFTVPGSKSTATISGLKPGVDYTITVYAVTGSGESPASSKP ISINYRTEIDKPSQ |
| 70 | 2631_G01 w/o his tag (amino acid sequence) | MGVSDVPRDLEVVAATPTSLLISWDAPAVTVRYYRITYGRHVQIYSDW GPLYIYNEFTVPGSKSTATISGLKPGVDYTITVYAVTGSGESPASSKP ISINYRTEIDKPSQ |
| 71 | 2631_G03 w/o his tag (amino acid sequence) | MGVSDVPRDLEVVAATPTSLLISWDAPAVTVRYYRITYGRYVQLYSDW GPMYIYTEFTVPGSKSTATISGLKPGVDYTITVYAVTGSGESPASSKP ISINYRTEIDKPSQ |

TABLE 20-continued

| SUMMARY OF SEQUENCES | | |
|---|---|---|
| SEQ ID | Description | Sequence |
| 72 | 2631_H09 w/o his tag (amino acid sequence) | MGVSDVPRDLEVVAATPTSLLISWDAPAVTVRYYRITYGRQVQVFSDLGPLYIYNEFTVPGSKSTATISGLKPGVDYTITVYAVTGSGESPASSKPISINYRTEIDKPSQ |
| 73 | 2632_G01 w/o his tag (amino acid sequence) | MGVSDVPRDLEVVAATPTSLLISWDAPAVTVRYYRITYGRQVQIYSDWGPLYIYNEFTVPGSKSTATISGLKPGVDYTITVYAVTGSGESPASSKPISINYRTEIDKPSQ |
| 74 | 4079_A04 w/o his tag (amino acid sequence) | MGVSDVPRDLEVVAATPTSLLISWDAPAVTVRYYRITYGRQVQMYSDWGPLYIYAEFTVPGSKSTATISGLKPGVDYTITVYAVTGSGESPASSKPISINYRTEIDKPSQ |
| 75 | 2270_C01 core (amino acid sequence) | EVVAATPTSLLISWDAPAVTVRYYRITYGWQVQMYSDWGPLYIYKEFTVPGSKSTATISGLKPGVDYTITVYAVTGSGESPASSKPISINYRT |
| 76 | 2629_A09 core (amino acid sequence) | EVVAATPTSLLISWDAPAVTVRYYRITYGRHVQIYSDLGPLYIYTEFTVPGSKSTATISGLKPGVDYTITVYAVTGSGESPASSKPISINYRT |
| 77 | 2629_A11 core (amino acid sequence) | EVVAATPTSLLISWDAPAVTVRYYRITYGRHVHIYSDWGPMYIYTEFTVPGSKSTATISGLKPGVDYTITVYAVTGSGESPASSKPISINYRT |
| 78 | 2629_C10 core (amino acid sequence) | EVVAATPTSLLISWDAPAVTVRYYRITYGREVQKYSVLGPLYIYTEFTVPGSKSTATISGLKPGVDYTITVYAVTGSGESPASSKPISINYRT |
| 79 | 2629_D09 core (amino acid sequence) | EVVAATPTSLLISWDAPAVTVRYYRITYGREVQMYSDLGPLYVYSEFTVPGSKSTATISGLKPGVDYTITVYAVTGSGESPASSKPISINYRT |
| 80 | 2629_E05 core (amino acid sequence) | EVVAATPTSLLISWDAPAVTVRYYRITYGREVQKFSDWGPLYIYTEFTVPGSKSTATISGLKPGVDYTITVYAVTGSGESPASSKPISINYRT |
| 81 | 2629_E06 core (amino acid sequence) | EVVAATPTSLLISWDAPAVTVRYYRITYGREVQKYSDLGPLYIYQEFTVPGSKSTATISGLKPGVDYTITVYAVTGSGESPASSKPISINYRT |
| 82 | 2629_F04 core (amino acid sequence) | EVVAATPTSLLISWDAPAVTVRYYRITYGREVHQYSDWGPMYIYNEFTVPGSKSTATISGLKPGVDYTITVYAVTGSGESPASSKPISINYRT |
| 83 | 2629_H01 core (amino acid sequence) | EVVAATPTSLLISWDAPAVTVXYYRITYGREVHKNSDWGTLYIYTEFTVPGSKSTATISGLKPGVDYTITVXAVTGSGEXPASSKPISINYRT |
| 84 | 2629_H06 core (amino acid sequence) | EVVAATPTSLLISWDAPAVTVRYYRITYGREVQKYSDLGPLYIYAEFTVPGSKSTATISGLKPGVDYTITVYAVTGSGESPASSKPISINYRT |
| 85 | 2629_H07 core (amino acid sequence) | EVVAATPTSLLISWDAPAVTVRYYRITYGREVHLYSDWGPMYIYTEFTVPGSKSTATISGLKPGVDYTITVYAVTGSGESPASSKPISINYRT |
| 86 | 2630_A02 core (amino acid sequence) | EVVATTPTSLLISWDAPAVTVRYYRITYGRHVQMYSDLGPLYIFSEFTVPGSKSTATISGLKPGVDYTITVYAVTGSGESPASSKPISINYRT |
| 87 | 2630_A11 core (amino acid sequence) | EVVAATPTSLLISWDAPAVTVRYYRITYGREVHMYSDFGPMYIYTEFTVPGSKSTATISGLKPGVDYTITVYAVTGSGESPASSKPISINYRT |
| 88 | 2630_D02 core (amino acid sequence) | EVVAATPTSLLISWDAPAVTVRYYRITYGREVQKYSDWGPLYIYNEFTVPGSKSTATISGLKPGVDYTITVYAVTGSGESPASSKPISINYRT |
| 89 | 2630_D10 core (amino acid sequence) | EVVAATPTSLLISWDAPAVTVRYYRITYGREVQMYSDLGPLYIYNEFTVPGSKSTATISGLKPGVDYTITVYAVTGSGESPASSKPISINYRT |
| 90 | 2630_F04 core (amino acid sequence) | EVVAATPTSLLISWDAPAVTVRYYRITYGREVQMYSDLGPLYIYTEFTVPGSKSTATISGLKPGVGYTITVYAVTGSGESPASSKPISINYRT |

TABLE 20-continued

| SEQ ID | Description | Sequence |
|---|---|---|
| | SUMMARY OF SEQUENCES | |
| 91 | 2630_G03 core (amino acid sequence) | EVVAATPTSLLISWDAPAVTVRYYRITYGRHVQIYSDLGPLYIYNEFT VPGSKSTATISGLKPGVDYTITVYAVTGSGESPASSKPISINYRT |
| 92 | 2630_G10 core (amino acid sequence) | EVVAATPTSLLISWDAPAVTVRYYRITYGREVQIYSDWGPLYIYNEFT VPGSKSTATISGLKPGVDYTITVYAVTGSGESPASSKPISINYRT |
| 93 | 2630_H03 core (amino acid sequence) | EVVAATXTSLLISWDAPAVTVXYYRITYGREVQKYSDWGPLYIYQEFT VPGSXSTATISGLKPGVDYTITVYAVTGSGESPASSKPISINYRT |
| 94 | 2631_B04 core (amino acid sequence) | EVVAATPTSLLISWDVPAVTVRYYRITYGRHVHLYSEFGPMYIYNEFT VPGSKSTATISGLKPGVDYTITVYAVTGSGESPASSKPISINYRT |
| 95 | 2631_E03 core (amino acid sequence) | EVVAATPTSLLISWDAPAVTVRYYRITYGRDVHMYSDWGPMYIYQEFT VPGSKSTATISGLKPGVDYTITVYAVTGSGESPASSKPISINYRT |
| 96 | 2631_G01 core (amino acid sequence) | EVVAATPTSLLISWDAPAVTVRYYRITYGRHVQIYSDWGPLYIYNEFT VPGSKSTATISGLKPGVDYTITVYAVTGSGESPASSKPISINYRT |
| 97 | 2631_G03 core (amino acid sequence) | EVVAATPTSLLISWDAPAVTVRYYRITYGRYVQLYSDWGPMYIYTEFT VPGSKSTATISGLKPGVDYTITVYAVTGSGESPASSKPISINYRT |
| 98 | 2631_H09 core (amino acid sequence) | EVVAATPTSLLISWDAPAVTVRYYRITYGRQVQVFSDLGPLYIYNEFT VPGSKSTATISGLKPGVDYTITVYAVTGSGESPASSKPISINYRT |
| 99 | 2632_G01 core (amino acid sequence) | EVVAATPTSLLISWDAPAVTVRYYRITYGRQVQIYSDWGPLYIYNEFT VPGSKSTATISGLKPGVDYTITVYAVTGSGESPASSKPISINYRT |
| 100 | 4079_A04 core (amino acid sequence) | EVVAATPTSLLISWDAPAVTVRYYRITYGRQVQMYSDWGPLYIYAEFT VPGSKSTATISGLKPGVDYTITVYAVTGSGESPASSKPISINYRT |
| 101 | 2629_A09 CD loop | GRHVQIYSDLGPLYIYTE |
| 102 | 2629_A11 CD loop | GRHVHIYSDWGPMYIYTE |
| 103 | 2629_C10 CD loop | GREVQKYSVLGPLYIYTE |
| 104 | 2629_D09 CD loop | GREVQMYSDLGPLYVYSE |
| 105 | 2629_E05 CD loop | GREVQKFSDWGPLYIYTE |
| 106 | 2629_E06 CD loop | GREVQKYSDLGPLYIYQE |
| 107 | 2629_F04 CD loop | GREVHQYSDWGPMYIYNE |
| 108 | 2629_H01 CD loop | GREVHKNSDWGTLYIYTE |
| 109 | 2629_H06 CD loop | GREVQKYSDLGPLYIYAE |
| 110 | 2629_H07 CD loop | GREVHLYSDWGPMYIYTE |
| 111 | 2630_A02 CD loop | GRHVQMYSDLGPLYIFSE |
| 112 | 2630_A11 CD loop | GREVHMYSDFGPMYIYTE |

TABLE 20-continued

SUMMARY OF SEQUENCES

| SEQ ID | Description | Sequence |
|---|---|---|
| 113 | 2630_D02 CD loop | GREVQKYSDWGPLYIYNE |
| 114 | 2630_D10 CD loop | GREVQMYSDLGPLYIYNE |
| 115 | 2630_F04 CD loop | GREVQMYSDLGPLYIYTE |
| 116 | 2630_G03 CD loop | GRHVQIYSDLGPLYIYNE |
| 117 | 2630_G10 CD loop | GREVQIYSDWGPLYIYNE |
| 118 | 2630_H03 CD loop | GREVQKYSDWGPLYIYQE |
| 119 | 2631_B04 CD loop | GRHVHLYSEFGPMYIYNE |
| 120 | 2631_E03 CD loop | GRDVHMYSDWGPMYIYQE |
| 121 | 2631_G01 CD loop | GRHVQIYSDWGPLYIYNE |
| 122 | 2631_G03 CD loop | GRYVQLYSDWGPMYIYTE |
| 123 | 2631_H09 CD loop | GRQVQVFSDLGPLYIYNE |
| 124 | 2632_G01 CD loop | GRQVQIYSDWGPLYIYNE |
| 125 | 4079_A04 CD loop | GRQVQMYSDWGPLYIYAE |
| 126 | 2270_C01 (nucleic acid sequence) | ATGGCTAGCACTAGTGGCGTGCCGCGCGACTTGGAAGTGGTTGCCGCG ACCCCGACGTCTCTGCTTATTAGCTGGGATGCACCTGCCGTCACAGTG AGATATTATCGCATTACATATGGTTGGCAGGTTCAGATGTACTCTGAC TGGGGTCCGCTGTACATCTACAAAGAGTTCACGGTACCTGGGAGCAAG TCCACAGCTACCATCAGCGGTCTCAAACCTGGAGTTGATTACACCATT ACGGTATACGCAGTCACCGGCTCTGGAGAGAGCCCCGCAAGCAGCAAG CCAATTTCCATTAATTATCGGACCGAAGGCGACAAACCATCCCAGCAC CATCACCACCACCACTGA |
| 127 | 2629_A09 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGACGGCATGTTCAGATCTATTCTGACTTA GGCCCGCTGTACATCTACACAGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 128 | 2629_A11 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGTAGACACGTTCATATCTACTCAGACTGG GGTCCGATGTACATCTACACAGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 129 | 2629_C10 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGGAGAGAGGTTCAGAAATACTCTGTCTTG GGTCCACTGTACATATACACGGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |

TABLE 20-continued

| SUMMARY OF SEQUENCES | | |
|---|---|---|
| SEQ ID | Description | Sequence |
| 130 | 2629_D09 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGGAGGGAGGTTCAGATGTACTCTGACTTG GGTCCATTGTACGTATACAGCGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 131 | 2629_E05 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGTCGGGAGGTACAGAAGTTCTCGGACTGG GGTCCGCTGTACATCTACACAGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 132 | 2629_E06 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGCAGGGAGGTTCAGAAGTACTCGGACTTG GGTCCGTTGTACATCTACCAAGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 133 | 2629_F04 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGTAGGGAGGTTCATCAATACTCTGACTGG GGTCCGATGTACATCTACAACGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 134 | 2629_H01 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCRA TATTACCGCATCACTTACGGTCGGGAGGTTCATAAGAACTCAGACTGG GGTACGCTGTACATCTACACAGAGTTCACTGTGCCTGGGAGCAAGTCC ACAGCTACCATCAGCGGCCTTAAACCTGGCGTTGATTATACCATCACT GTGTRTGCTGTCACTGGCTCTGGAGAGARCCCCGCAAGCAGCAAGCCA ATTTCCATTAATTACCGCACAGAAATTGACAAAMCATCCCAGCACCAT CACCACCACCACTGA |
| 135 | 2629_H06 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGACGGGAGGTTCAGAAGTATTCAGACTTG GGTCCACTGTACATCTACGCAGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 136 | 2629_H07 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGGCGGGAGGTCCACCTGTACTCCGACTGG GGGCCGATGTACATCTACACAGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 137 | 2630_A02 (nucleic acid sequence) | ATGGGAGTTTCTGATGTGCCGCGCGACCTGGAAGTGGTTGCTACCACC CCCACCAGCCTGCTGATCAGCTGGGATGCACCTGCCGTCACAGTGCGA TATTACCGCATCACTTACGGTAGGCACGTTCAAATGTACTCTGACCTT GGTCCGTTGTACATCTTCAGTGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 138 | 2630_A11 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGACGGGAGGTTCATATGTACTCTGACTTC GGTCCGATGTACATATACACAGAGTTCACTGTGCCTGGGAGCAAGTCC |

TABLE 20-continued

| SUMMARY OF SEQUENCES | | |
|---|---|---|
| SEQ ID | Description | Sequence |
| | | ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 139 | 2630_D02 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGTAGAGAAGTTCAGAAATACTCTGACTGG GGCCCGCTCTACATCTACAATGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 140 | 2630_D10 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGTCGGGAGGTTCAGATGTACTCGGACTTG GGTCCGCTCTACATCTACAACGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 141 | 2630_F04 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGTAGAGAGGTCCAGATGTACTCAGACTTG GGGCCGCTGTACATCTATACAGAGTTCACTGTGCCTGGGAGCAAGTCC ACAGCTACCATCAGCGGCCTTAAACCTGGCGTTGGTTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 142 | 2630_G03 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGACGGCATGTTCAGATCTACTCCGACTTG GGTCCTCTGTATATCTACAATGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 143 | 2630_G10 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGTCGGGAGGTTCAAATATACTCTGACTGG GGTCCGCTGTATATATACAACGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 144 | 2630_H03 (nucleic acid sequence) | ATGGGAGTTTCTGATGTGCCGCGCGACCTGGAAGTGGTTGCTGCCACC SCCACCAGCCTGCTGATCAGCTGGGATGCACCTGCCGTCACAGTGCSA TATTACCGCATCACTTACGGACGTGAAGTRCAGAAATACTCTGACTGG GGCCCGCTGTACATCTACCAAGAGTTCACTGTGCCTGGGAGCRAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAAMCATCCCAGCACCAT CACCACCACCACTGA |
| 145 | 2631_B04 (nucleic acid sequence) | ATGGGAGTTTCTGATGTGCCGCGCGACCTGGAAGTGGTTGCTGCCACC CCCACCAGCCTGCTGATCAGCTGGGATGTACCTGCCGTTACAGTGCGA TATTACCGCATCACTTACGGCAGGCACGTACATTTGTACTCGGAGTTC GGTCCGATGTATATCTACAACGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 146 | 2631_E03 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGTAGGGATGTCCACATGTACTCTGACTGG GGTCCGATGTACATATACCAAGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |

TABLE 20-continued

| SUMMARY OF SEQUENCES | | |
|---|---|---|
| SEQ ID | Description | Sequence |
| 147 | 2631_G01 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGTAGGCATGTTCAGATATACTCGGACTGG GGTCCGCTGTACATCTACAATGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 148 | 2631_G03 (nucleic acid sequence) | ATGGGAGTTTCTGATGTGCCGCGCGACCTGGAAGTGGTTGCTGCCACC CCCACCAGCCTACTGATCAGCTGGGATGCACCTGCCGTCACAGTGCGA TATTACCGCATCACTTACGGAAGGTATGTTCAGCTATACTCTGACTGG GGTCCGATGTACATCTACACGGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 149 | 2631_H09 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGACGGCAAGTGCAAGTGTTCTCAGACTTG GGTCCGCTGTACATATACAACGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 150 | 2632_G01 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGTAGACAGGTGCAGATCTACTCTGACTGG GGACCGCTGTACATCTACAATGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 151 | 4079_A04 (nucleic acid sequence) | ATGGGAGTTTCTGATGTGCCGCGCGACCTGGAAGTGGTTGCTGCCACC CCCACCAGCCTGCTGATCAGCTGGGATGCACCTGCCGTCACAGTGCGA TATTACCGCATCACTTACGGTAGGCAGGTACAGATGTACTCTGACTGG GGTCCACTTTACATCTACGCCGAGTTCACTGTGCCTGGGAGCAAGTCC ACAGCTACCATCAGCGGCCTTAAACCTGGCGTTGATTATACCATCACT GTGTATGCTGTCACTGGCTCTGGAGAGAGCCCCGCAAGCAGCAAGCCA ATTTCCATTAATTACCGCACAGAAATTGACAAACCATCCCAGCACCAT CACCACCACCACTGA |
| 152 | Linker | PSTPPTPSPSTPPTPSPS |
| 153 | Linker | GSGSGSGSGSGSGS |
| 154 | Linker | GGSGSGSGSGSGS |
| 155 | Linker | GGSGSGSGSGSGSGSG |
| 156 | Linker | GSEGSEGSEGSEGSE |
| 157 | Linker | GGSEGGSE |
| 158 | Linker | GSGSGSGS |
| 159 | Linker | GGGGSGGGGSGGGGSGGGGSGGGGSGGGGSGGGGS |
| 160 | Linker | GGGGSGGGGSGGGGSGGGGSGGGGS |
| 161 | Linker | GGGGSGGGGSGGGGSG |
| 162 | Linker | GPGPGPG |
| 163 | Linker | GPGPGPGPGPG |
| 164 | Linker | PAPAPA |
| 165 | Linker | PAPAPAPAPAPA |
| 166 | Linker | PAPAPAPAPAPAPAPA |

TABLE 20-continued

| SUMMARY OF SEQUENCES | | |
|---|---|---|
| SEQ ID | Description | Sequence |
| 167 | PCSK9 $^{10}$Fn3 domain | MGVSDVPRDLEVVAATPTSLLISWDAPAEGYGYYRITYGETGGNSPVQ<br>EFTVPVSKGTATISGLKPGVDYTITVYAVEFDFPGAGYYHRPISINYR<br>T |
| 168 | PCSK9-PKE2 tandem Adnectin w/o his tag 5190_E01 (ATI-1676) | MGVSDVPRDLEVVAATPTSLLISWDAPAEGYGYYRITYGETGGNSPVQ<br>EFTVPVSKGTATISGLKPGVDYTITVYAVEFDFPGAGYYHRPISINYR<br>TEPSTPPTPSPSTPPTPSPSGVSDVPRDLEVVAATPTSLLISWDAPAV<br>TVRYYRITYGREVQKYSDLGPLYIYQEFTVPGSKSTATISGLKPGVDY<br>TITVYAVTGSGESPASSKPISINYRTP |
| 169 | PCSK9-PKE2 tandem Adnectin w/ his tag 4472_C06 (ATI-1574) | MGVSDVPRDLEVVAATPTSLLISWDAPAEGYGYYRITYGETGGNSPVQ<br>EFTVPVSKGTATISGLKPGVDYTITVYAVEFDFPGAGYYHRPISINYR<br>TEPSTPPTPSPSTPPTPSPSGVSDVPRDLEVVAATPTSLLISWDAPAV<br>TVRYYRITYGREVQKYSDLGPLYIYQEFTVPGSKSTATISGLKPGVDY<br>TITVYAVTGSGESPASSKPISINYRTEHHHHHH |
| 170 | CD loop consensus | $G\text{-}X_1\text{-}X_2\text{-}V\text{-}X_3\text{-}X_4\text{-}X_5\text{-}S\text{-}X_6\text{-}X_7\text{-}G\text{-}X_8\text{-}X_9\text{-}Y\text{-}X_{10}\text{-}X_{11}\text{-}X_{12}\text{-}E$ |
| 171 | 3852_F10 | ATGGGAGTTTCTGATGTGCCGCGCGACCTGGAAGTGGTTGCTGCCACC<br>CCCACCAGCCTGCTGATCAGCTGGGACGCTCCGGCTGTTGACGGTCGA<br>TATTACCGCATCACTTACGGCGAAACAGGAGGCAATAGCCCTGTCCAG<br>GAGTTCACTGTGCCTGGTTCTAAATCTACAGCTACCATCAGCGGCCTT<br>AAACCTGGCGTTGATTATACCATCACTGTGTATGCTGTCACTCCGTAC<br>GAATTCCATTTCCCGTACACTCATTACTCTTCTAAACCAATTTCCATT<br>AATTACCGCACAGAAATTGACAAACCATCCCAGCACCATCACCACCAC<br>CACTGA |
| 172 | PCSK9-PKE2 tandem Adnectin nucleic acid sequence 5190_E01 (ATI-1676) | ATGGGAGTTTCTGATGTGCCGCGCGACCTGGAAGTGGTTGCTGCCACC<br>CCCACCAGCCTGCTGATCAGCTGGGACGCTCCGGCTGAAGGGTACGGT<br>TATTACCGCATCACTTACGGCGAAACAGGAGGCAATAGCCCTGTCCAG<br>GAGTTCACTGTGCCTGTTTCTAAAGGTACAGCTACCATCAGCGGCCTT<br>AAACCTGGCGTTGATTATACCATCACTGTGTATGCTGTCGAATTCGAC<br>TTCCCCGGCGCCGGTTACTACCATCGTCCAATTTCCATTAATTACCGG<br>ACCGAACCGAGCACACCTCCGACCCCGAGTCCGTCAACACCACCGACA<br>CCGTCACCGAGCGGAGTTTCTGACGTCCCGCGCGACCTGGAAGTGGTT<br>GCTGCCACCCCCACCAGCCTGCTGATCAGCTGGGATGCACCTGCCGTC<br>ACAGTGCGATATTACCGCATCACTTACGGCAGGGAGGTTCAGAAGTAC<br>TCGGACTTGGGTCCGTTGTACATCTACCAAGAGTTCACTGTGCCTGGG<br>AGCAAGTCCACAGCTACCATCAGCGGCCTTAAACCTGGCGTTGATTAT<br>ACCATCACTGTGTATGCTGTCACTGGCTCTGGAGAGAGCCCCGCAAGC<br>AGCAAGCCAATTTCCATTAATTACCGCACACCGTGA |
| 173 | Linker | PSPEPPTPEP |
| 174 | Linker | PSPEPPTPEPPSPEPPTPEP |
| 175 | Linker | PSPEPPTPEPPSPEPPTPEPPSPEPPTPEP |
| 176 | Linker | PSPEPPTPEPPSPEPPTPEPPSPEPPTPEPPSPEPPTPEP |
| 177 | Linker | EEEEDE |
| 178 | Linker | EEEEDEEEEDE |
| 179 | Linker | EEEEDEEEEDEEEEDEEEEDE |
| 180 | Linker | EEEEDEEEEDEEEEDEEEEDEEEEDEEEEDE |
| 181 | Linker | RGGEEKKKEKEKEEQEERETKTP |
| 182 | Exemplary use of linker | NYRTPGPSPEPPTPEP |
| 183 | Exemplary use of linker | PSPEPPTPEPGVSDV |
| 184 | 2270_C01 core (amino acid sequence) with C-terminal proline | EVVAATPTSLLISWDAPAVTVRYYRITYGWQVQMYSDWGPLYIYKEFT<br>VPGSKSTATISGLKPGVDYTITVYAVTGSGESPASSKPISINYRTP |
| 185 | 2629_A09 core (amino acid sequence) with C-terminal proline | EVVAATPTSLLISWDAPAVTVRYYRITYGRHVQIYSDLGPLYIYTEFT<br>VPGSKSTATISGLKPGVDYTITVYAVTGSGESPASSKPISINYRTP |

TABLE 20-continued

| SEQ ID | Description | Sequence |
|---|---|---|
| SUMMARY OF SEQUENCES | | |
| 186 | 2629_A11 core (amino acid sequence) with C-terminal proline | EVVAATPTSLLISWDAPAVTVRYYRITYGRHVHIYSDWGPMYIYTEFT VPGSKSTATISGLKPGVDYTITVYAVTGSGESPASSKPISINYRTP |
| 187 | 2629_C10 core (amino acid sequence) with C-terminal proline | EVVAATPTSLLISWDAPAVTVRYYRITYGREVQKYSVLGPLYIYTEFT VPGSKSTATISGLKPGVDYTITVYAVTGSGESPASSKPISINYRTP |
| 188 | 2629_D09 core (amino acid sequence) with C-terminal proline | EVVAATPTSLLISWDAPAVTVRYYRITYGREVQMYSDLGPLYVYSEFT VPGSKSTATISGLKPGVDYTITVYAVTGSGESPASSKPISINYRTP |
| 189 | 2629_E05 core (amino acid sequence) with C-terminal proline | EVVAATPTSLLISWDAPAVTVRYYRITYGREVQKFSDWGPLYIYTEFT VPGSKSTATISGLKPGVDYTITVYAVTGSGESPASSKPISINYRTP |
| 190 | 2629_E06 core (amino acid sequence) with C-terminal proline | EVVAATPTSLLISWDAPAVTVRYYRITYGREVQKYSDLGPLYIYQEFT VPGSKSTATISGLKPGVDYTITVYAVTGSGESPASSKPISINYRTP |
| 191 | 2629_F04 core (amino acid sequence) with C-terminal proline | EVVAATPTSLLISWDAPAVTVRYYRITYGREVHQYSDWGPMYIYNEFT VPGSKSTATISGLKPGVDYTITVYAVTGSGESPASSKPISINYRTP |
| 192 | 2629_H01 core (amino acid sequence) with C-terminal proline | EVVAATPTSLLISWDAPAVTVXYYRITYGREVHKNSDWGTLYIYTEFT VPGSKSTATISGLKPGVDYTITVXAVTGSGEXPASSKPISINYRTP |
| 193 | 2629_H06 core (amino acid sequence) with C-terminal proline | EVVAATPTSLLISWDAPAVTVRYYRITYGREVQKYSDLGPLYIYAEFT VPGSKSTATISGLKPGVDYTITVYAVTGSGESPASSKPISINYRTP |
| 194 | 2629_H07 core (amino acid sequence) with C-terminal proline | EVVAATPTSLLISWDAPAVTVRYYRITYGREVHLYSDWGPMYIYTEFT VPGSKSTATISGLKPGVDYTITVYAVTGSGESPASSKPISINYRTP |
| 195 | 2630_A02 core (amino acid sequence) with C-terminal proline | EVVATTPTSLLISWDAPAVTVRYYRITYGRHVQMYSDLGPLYIFSEFT VPGSKSTATISGLKPGVDYTITVYAVTGSGESPASSKPISINYRTP |
| 196 | 2630_A11 core (amino acid sequence) with C-terminal proline | EVVAATPTSLLISWDAPAVTVRYYRITYGREVHMYSDFGPMYIYTEFT VPGSKSTATISGLKPGVDYTITVYAVTGSGESPASSKPISINYRTP |
| 197 | 2630_D02 core (amino acid sequence) with C-terminal proline | EVVAATPTSLLISWDAPAVTVRYYRITYGREVQKYSDWGPLYIYNEFT VPGSKSTATISGLKPGVDYTITVYAVTGSGESPASSKPISINYRTP |
| 198 | 2630_D10 core (amino acid sequence) with C-terminal proline | EVVAATPTSLLISWDAPAVTVRYYRITYGREVQMYSDLGPLYIYNEFT VPGSKSTATISGLKPGVDYTITVYAVTGSGESPASSKPISINYRTP |
| 199 | 2630_F04 core (amino acid sequence) with C-terminal proline | EVVAATPTSLLISWDAPAVTVRYYRITYGREVQMYSDLGPLYIYTEFT VPGSKSTATISGLKPGVGYTITVYAVTGSGESPASSKPISINYRTP |
| 200 | 2630_G03 core (amino acid sequence) with C-terminal proline | EVVAATPTSLLISWDAPAVTVRYYRITYGRHVQIYSDLGPLYIYNEFT VPGSKSTATISGLKPGVDYTITVYAVTGSGESPASSKPISINYRTP |

TABLE 20-continued

| SUMMARY OF SEQUENCES | | |
|---|---|---|
| SEQ ID | Description | Sequence |
| 201 | 2630_G10 core (amino acid sequence) with C-terminal proline | EVVAATPTSLLISWDAPAVTVRYYRITYGREVQIYSDWGPLYIYNEFT VPGSKSTATISGLKPGVDYTITVYAVTGSGESPASSKPISINYRTP |
| 202 | 2630_H03 core (amino acid sequence) with C-terminal proline | EVVAATXTSLLISWDAPAVTVXYYRITYGREVQKYSDWGPLYIYQEFT VPGSXSTATISGLKPGVDYTITVYAVTGSGESPASSKPISINYRTP |
| 203 | 2631_B04 core (amino acid sequence) with C-terminal proline | EVVAATPTSLLISWDVPAVTVRYYRITYGRHVHLYSEFGPMYIYNEFT VPGSKSTATISGLKPGVDYTITVYAVTGSGESPASSKPISINYRTP |
| 204 | 2631_E03 core (amino acid sequence) with C-terminal proline | EVVAATPTSLLISWDAPAVTVRYYRITYGRDVHMYSDWGPMYIYQEFT VPGSKSTATISGLKPGVDYTITVYAVTGSGESPASSKPISINYRTP |
| 205 | 2631_G01 core (amino acid sequence) with C-terminal proline | EVVAATPTSLLISWDAPAVTVRYYRITYGRHVQIYSDWGPLYIYNEFT VPGSKSTATISGLKPGVDYTITVYAVTGSGESPASSKPISINYRTP |
| 206 | 2631_G03 core (amino acid sequence) with C-terminal proline | EVVAATPTSLLISWDAPAVTVRYYRITYGRYVQLYSDWGPMYIYTEFT VPGSKSTATISGLKPGVDYTITVYAVTGSGESPASSKPISINYRTP |
| 207 | 2631_H09 core (amino acid sequence) with C-terminal proline | EVVAATPTSLLISWDAPAVTVRYYRITYGRQVQVFSDLGPLYIYNEFT VPGSKSTATISGLKPGVDYTITVYAVTGSGESPASSKPISINYRTP |
| 208 | 2632_G01 core (amino acid sequence) with C-terminal proline | EVVAATPTSLLISWDAPAVTVRYYRITYGRQVQIYSDWGPLYIYNEFT VPGSKSTATISGLKPGVDYTITVYAVTGSGESPASSKPISINYRTP |
| 209 | 4079_A04 core (amino acid sequence) with C-terminal proline | EVVAATPTSLLISWDAPAVTVRYYRITYGRQVQMYSDWGPLYIYAEFT VPGSKSTATISGLKPGVDYTITVYAVTGSGESPASSKPISINYRTP |
| 210 | C-terminal tail | EIEPKSS |
| 211 | C-terminal tail | EIDKPC |
| 212 | C-terminal tail | EIDKP |
| 213 | C-terminal tail | EIDKPS |
| 214 | C-terminal tail | EIDKPSQLE |
| 215 | C-terminal tail | EIEDEDEDEDED |
| 216 | C-terminal tail | EGSGS |
| 217 | C-terminal tail | EIDKPCQLE |
| 218 | C-terminal tail | EIDKPSQHHHHHH |
| 219 | C-terminal tail | GSGCHHHHHH |
| 220 | C-terminal tail | EGSGCHHHHHH |
| 221 | C-terminal tail | PIDK |
| 222 | C-terminal tail | PIEK |
| 223 | C-terminal tail | PIDKP |
| 224 | C-terminal tail | PIEKP |
| 225 | C-terminal tail | PIDKPS |

TABLE 20-continued

SUMMARY OF SEQUENCES

| SEQ ID | Description | Sequence |
|---|---|---|
| 226 | C-terminal tail | PIEKPS |
| 227 | C-terminal tail | PIDKPC |
| 228 | C-terminal tail | PIEKPC |
| 229 | C-terminal tail | PIDKPSQ |
| 230 | C-terminal tail | PIEKPSQ |
| 231 | C-terminal tail | PIDKPCQ |
| 232 | C-terminal tail | PIEKPCQ |
| 233 | C-terminal tail | PHHHHHH |
| 234 | C-terminal tail | PCHHHHHH |
| 235 | 2270_C01 w/o his tag and N-terminal methionine and w/ C-terminal proline | ASTSGVPRDLEVVAATPTSLLISWDAPAVTVRYYRITYGWQVQMYSDWGPLYIYKEFTVPGSKSTATISGLKPGVDYTITVYAVTGSGESPASSKPISINYRTEGDKPSQP |
| 236 | 2629_A09 w/o his tag and N-terminal methionine and w/ C-terminal proline | GVSDVPRDLEVVAATPTSLLISWDAPAVTVRYYRITYGRHVQIYSDLGPLYIYTEFTVPGSKSTATISGLKPGVDYTITVYAVTGSGESPASSKPISINYRTEIDKPSQP |
| 237 | 2629_A11 w/o his tag and N-terminal methionine and w/ C-terminal proline | GVSDVPRDLEVVAATPTSLLISWDAPAVTVRYYRITYGRHVHIYSDWGPMYIYTEFTVPGSKSTATISGLKPGVDYTITVYAVTGSGESPASSKPISINYRTEIDKPSQP |
| 238 | 2629_C10 w/o his tag and N-terminal methionine and w/ C-terminal proline | GVSDVPRDLEVVAATPTSLLISWDAPAVTVRYYRITYGREVQKYSVLGPLYIYTEFTVPGSKSTATISGLKPGVDYTITVYAVTGSGESPASSKPISINYRTEIDKPSQP |
| 239 | 2629_D09 w/o his tag and N-terminal methionine and w/ C-terminal proline | GVSDVPRDLEVVAATPTSLLISWDAPAVTVRYYRITYGREVQMYSDLGPLYVYSEFTVPGSKSTATISGLKPGVDYTITVYAVTGSGESPASSKPISINYRTEIDKPSQP |
| 240 | 2629_E05 w/o his tag and N-terminal methionine and w/ C-terminal proline | GVSDVPRDLEVVAATPTSLLISWDAPAVTVRYYRITYGREVQKFSDWGPLYIYTEFTVPGSKSTATISGLKPGVDYTITVYAVTGSGESPASSKPISINYRTEIDKPSQP |
| 241 | 2629_E06 w/o his tag and N-terminal methionine and w/ C-terminal proline | GVSDVPRDLEVVAATPTSLLISWDAPAVTVRYYRITYGREVQKYSDLGPLYIYQEFTVPGSKSTATISGLKPGVDYTITVYAVTGSGESPASSKPISINYRTEIDKPSQP |
| 242 | 2629_F04 w/o his tag and N-terminal methionine and w/ C-terminal proline | GVSDVPRDLEVVAATPTSLLISWDAPAVTVRYYRITYGREVHQYSDWGPMYIYNEFTVPGSKSTATISGLKPGVDYTITVYAVTGSGESPASSKPISINYRTEIDKPSQP |
| 243 | 2629_H01 w/o his tag and N-terminal methionine and w/ C-terminal proline | GVSDVPRDLEVVAATPTSLLISWDAPAVTVXYYRITYGREVHKNSDWGTLYIYTEFTVPGSKSTATISGLKPGVDYTITVXAVTGSGEXPASSKPISINYRTEIDKXSQP |
| 244 | 2629_H06 w/o his tag and N-terminal methionine and w/ C-terminal proline | GVSDVPRDLEVVAATPTSLLISWDAPAVTVRYYRITYGREVQKYSDLGPLYIYAEFTVPGSKSTATISGLKPGVDYTITVYAVTGSGESPASSKPISINYRTEIDKPSQP |
| 245 | 2629_H07 w/o his tag and N-terminal methionine and w/ C-terminal proline | GVSDVPRDLEVVAATPTSLLISWDAPAVTVRYYRITYGREVHLYSDWGPMYIYTEFTVPGSKSTATISGLKPGVDYTITVYAVTGSGESPASSKPISINYRTEIDKPSQP |

TABLE 20-continued

SUMMARY OF SEQUENCES

| SEQ ID | Description | Sequence |
|---|---|---|
| 246 | 2630_A02 w/o his tag and N-terminal methionine and w/ C-terminal proline | GVSDVPRDLEVVATTPTSLLISWDAPAVTVRYYRITYGRHVQMYSDLGPLYIFSEFTVPGSKSTATISGLKPGVDYTITVYAVTGSGESPASSKPISINYRTEIDKPSQP |
| 247 | 2630_A11 w/o his tag and N-terminal methionine and w/ C-terminal proline | GVSDVPRDLEVVAATPTSLLISWDAPAVTVRYYRITYGREVHMYSDFGPMYIYTEFTVPGSKSTATISGLKPGVDYTITVYAVTGSGESPASSKPISINYRTEIDKPSQP |
| 248 | 2630_D02 w/o his tag and N-terminal methionine and w/ C-terminal proline | GVSDVPRDLEVVAATPTSLLISWDAPAVTVRYYRITYGREVQKYSDWGPLYIYNEFTVPGSKSTATISGLKPGVDYTITVYAVTGSGESPASSKPISINYRTEIDKPSQP |
| 249 | 2630_D10 w/o his tag and N-terminal methionine and w/ C-terminal proline | GVSDVPRDLEVVAATPTSLLISWDAPAVTVRYYRITYGREVQMYSDLGPLYIYNEFTVPGSKSTATISGLKPGVDYTITVYAVTGSGESPASSKPISINYRTEIDKPSQP |
| 250 | 2630_F04 w/o his tag and N-terminal methionine and w/ C-terminal proline | GVSDVPRDLEVVAATPTSLLISWDAPAVTVRYYRITYGREVQMYSDLGPLYIYTEFTVPGSKSTATISGLKPGVGYTITVYAVTGSGESPASSKPISINYRTEIDKPSQP |
| 251 | 2630_G03 w/o his tag and N-terminal methionine and w/ C-terminal proline | GVSDVPRDLEVVAATPTSLLISWDAPAVTVRYYRITYGRHVQIYSDLGPLYIYNEFTVPGSKSTATISGLKPGVDYTITVYAVTGSGESPASSKPISINYRTEIDKPSQP |
| 252 | 2630_G10 w/o his tag and N-terminal methionine and w/ C-terminal proline | GVSDVPRDLEVVAATPTSLLISWDAPAVTVRYYRITYGREVQIYSDWGPLYIYNEFTVPGSKSTATISGLKPGVDYTITVYAVTGSGESPASSKPISINYRTEIDKPSQP |
| 253 | 2630_H03 w/o his tag and N-terminal methionine and w/ C-terminal proline | GVSDVPRDLEVVAATXTSLLISWDAPAVTVXYYRITYGREVQKYSDWGPLYIYQEFTVPGSXSTATISGLKPGVDYTITVYAVTGSGESPASSKPISINYRTEIDKXSQP |
| 254 | 2631_B04 w/o his tag and N-terminal methionine and w/ C-terminal proline | GVSDVPRDLEVVAATPTSLLISWDVPAVTVRYYRITYGRHVHLYSEFGPMYIYNEFTVPGSKSTATISGLKPGVDYTITVYAVTGSGESPASSKPISINYRTEIDKPSQP |
| 255 | 2631_E03 w/o his tag and N-terminal methionine and w/ C-terminal proline | GVSDVPRDLEVVAATPTSLLISWDAPAVTVRYYRITYGRDVHMYSDWGPMYIYQEFTVPGSKSTATISGLKPGVDYTITVYAVTGSGESPASSKPISINYRTEIDKPSQP |
| 256 | 2631_G01 w/o his tag and N-terminal methionine and w/ C-terminal proline | GVSDVPRDLEVVAATPTSLLISWDAPAVTVRYYRITYGRHVQIYSDWGPLYIYNEFTVPGSKSTATISGLKPGVDYTITVYAVTGSGESPASSKPISINYRTEIDKPSQP |
| 257 | 2631_G03 w/o his tag and N-terminal methionine and w/ C-terminal proline | GVSDVPRDLEVVAATPTSLLISWDAPAVTVRYYRITYGRYVQLYSDWGPMYIYTEFTVPGSKSTATISGLKPGVDYTITVYAVTGSGESPASSKPISINYRTEIDKPSQP |
| 258 | 2631_H09 w/o his tag and N-terminal methionine and w/ C-terminal proline | GVSDVPRDLEVVAATPTSLLISWDAPAVTVRYYRITYGRQVQVFSDLGPLYIYNEFTVPGSKSTATISGLKPGVDYTITVYAVTGSGESPASSKPISINYRTEIDKPSQP |
| 259 | 2632_G01 w/o his tag and N-terminal methionine and w/ C-terminal proline | GVSDVPRDLEVVAATPTSLLISWDAPAVTVRYYRITYGRQVQIYSDWGPLYIYNEFTVPGSKSTATISGLKPGVDYTITVYAVTGSGESPASSKPISINYRTEIDKPSQP |
| 260 | 4079_A04 w/o his tag and N-terminal methionine and w/ C-terminal proline | GVSDVPRDLEVVAATPTSLLISWDAPAVTVRYYRITYGRQVQMYSDWGPLYIYAEFTVPGSKSTATISGLKPGVDYTITVYAVTGSGESPASSKPISINYRTEIDKPSQP |

TABLE 20-continued

| SEQ ID | Description | Sequence |
|---|---|---|
| | SUMMARY OF SEQUENCES | |
| 261 | PCSK9-PKE2 tandem Adnectin w/o his tag and N-terminal methionine 5190_E01 (ATI-1676) | GVSDVPRDLEVVAATPTSLLISWDAPAEGYGYYRITYGETGGNSPVQE FTVPVSKGTATISGLKPGVDYTITVYAVEFDFPGAGYYHRPISINYRT EPSTPPTPSPSTPPTPSPSGVSDVPRDLEVVAATPTSLLISWDAPAVT VRYYRITYGREVQKYSDLGPLYIYQEFTVPGSKSTATISGLKPGVDYT ITVYAVTGSGESPASSKPISINYRTP |
| 262 | Exemplary linker | (PSPEPPTPEP)$_n$ n = 1-10 |
| 263 | Exemplary linker | (EEEEDE)$_n$E n = 1-10 |

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A polypeptide comprising a fibronectin type III tenth domain ($^{10}$Fn3) wherein the amino acid sequence of the CD loop of the wild-type $^{10}$Fn3 domain set forth in SEQ ID NO: 1 is replaced by an amino acid sequence selected from the group consisting of SEQ ID NOs: 101-125, and wherein the polypeptide binds to human serum albumin, and to one or more of rhesus serum albumin, cynomolgus serum albumin, mouse serum albumin, and rat serum albumin.

2. The polypeptide of claim 1, wherein the polypeptide is a fusion polypeptide comprising a heterologous protein.

3. The fusion polypeptide of claim 2, wherein the heterologous protein is a therapeutic moiety.

4. The fusion polypeptide of claim 2, wherein the heterologous protein is a polypeptide comprising a $^{10}$Fn3 domain.

5. The fusion polypeptide of claim 4, wherein the $^{10}$Fn3 domain of the heterologous protein binds to a target protein other than serum albumin.

6. A polypeptide comprising an amino acid sequence selected from the group consisting of SEQ ID NOs: 23-30, 32-40, 42-56, 58-66, 68-82, 84-92, 94-100, 184-191, 193-201, 203-209, 235-242, 243-252 and 254-260, wherein the polypeptide binds to human serum albumin, and to one or more of rhesus serum albumin, cynomolgus serum albumin, mouse serum albumin, and rat serum albumin.

7. The polypeptide of claim 6, wherein the polypeptide is a fusion polypeptide comprising a heterologous protein.

8. The fusion polypeptide of claim 7, wherein the heterologous protein is a therapeutic moiety.

9. The fusion polypeptide of claim 7, wherein the heterologous protein is a polypeptide comprising a $^{10}$Fn3 domain.

10. The fusion polypeptide of claim 8, wherein the $^{10}$Fn3 domain of the heterologous protein binds to a target protein other than serum albumin.

11. A composition comprising the polypeptide of claim 1 and a carrier.

12. A composition comprising the polypeptide of claim 6 and a carrier.

* * * * *